(12) United States Patent
Shalwitz et al.

(10) Patent No.: US 9,096,555 B2
(45) Date of Patent: Aug. 4, 2015

(54) METHODS FOR TREATING VASCULAR LEAK SYNDROME

(71) Applicant: Aerpio Therapeutics, Inc., Cincinnati, OH (US)

(72) Inventors: Robert Shalwitz, Bexley, OH (US); Kevin Gene Peters, Cincinnati, OH (US)

(73) Assignee: AERPIO THERAPEUTICS, INC., Cincinnati, OH (US)

(*) Notice: Subject to any disclaimer, the term of this patent is extended or adjusted under 35 U.S.C. 154(b) by 139 days.

(21) Appl. No.: 13/724,396

(22) Filed: Dec. 21, 2012

(65) Prior Publication Data

US 2014/0179693 A1 Jun. 26, 2014
US 2014/0378445 A9 Dec. 25, 2014

Related U.S. Application Data

(62) Division of application No. 12/677,512, filed as application No. PCT/US2010/020817 on Jan. 12, 2010, now abandoned.

(60) Provisional application No. 61/144,022, filed on Jan. 12, 2009, provisional application No. 61/184,986, filed on Jun. 8, 2009.

(51) Int. Cl.

| | |
|---|---|
| *A61K 31/425* | (2006.01) |
| *A61K 31/426* | (2006.01) |
| *A61K 31/41* | (2006.01) |
| *C07D 277/28* | (2006.01) |
| *A61K 45/06* | (2006.01) |
| *C07D 263/32* | (2006.01) |
| *C07D 277/30* | (2006.01) |
| *C07D 277/60* | (2006.01) |
| *C07D 277/64* | (2006.01) |
| *C07D 413/04* | (2006.01) |
| *C07D 413/14* | (2006.01) |
| *C07D 417/04* | (2006.01) |
| *C07D 417/06* | (2006.01) |
| *C07D 417/10* | (2006.01) |
| *C07D 417/12* | (2006.01) |
| *C07D 417/14* | (2006.01) |
| *G01N 33/68* | (2006.01) |
| *A61K 31/422* | (2006.01) |
| *A61K 31/427* | (2006.01) |
| *A61K 31/428* | (2006.01) |
| *A61K 31/433* | (2006.01) |
| *A61K 31/4439* | (2006.01) |
| *A61K 31/496* | (2006.01) |
| *A61K 31/497* | (2006.01) |
| *A61K 31/506* | (2006.01) |

(Continued)

(52) U.S. Cl.
CPC ............ *C07D 277/28* (2013.01); *A61K 31/422* (2013.01); *A61K 31/426* (2013.01); *A61K 31/427* (2013.01); *A61K 31/428* (2013.01); *A61K 31/433* (2013.01); *A61K 31/4439* (2013.01); *A61K 31/496* (2013.01); *A61K 31/497* (2013.01); *A61K 31/506* (2013.01); *A61K 31/513* (2013.01); *A61K 31/538* (2013.01); *A61K 45/06* (2013.01); *C07D 263/32* (2013.01); *C07D 277/30* (2013.01); *C07D 277/60* (2013.01); *C07D 277/64* (2013.01); *C07D 413/04* (2013.01); *C07D 413/14* (2013.01); *C07D 417/04* (2013.01); *C07D 417/06* (2013.01); *C07D 417/10* (2013.01); *C07D 417/12* (2013.01); *C07D 417/14* (2013.01); *G01N 33/68* (2013.01); *G01N 33/6893* (2013.01); *G01N 2800/7095* (2013.01)

(58) Field of Classification Search
CPC ... A61K 31/426; A61K 31/427; A61K 31/41; A61K 31/428; A61K 31/433; A61K 31/4439; A61K 31/497; A61K 31/538; A61K 45/06; A61K 31/4245; A61K 31/422; A61K 31/496; A61K 31/506; A61K 31/513
USPC ............... 514/230.5, 254.02, 255.02, 255.05, 514/272, 274, 275, 342, 361, 363, 364, 365, 514/366, 367, 369
See application file for complete search history.

(56) References Cited

U.S. PATENT DOCUMENTS

| | | | |
|---|---|---|---|
| 4,673,641 | A | 6/1987 | George et al. |
| 5,424,398 | A | 6/1995 | Middeldorp et al. |

(Continued)

FOREIGN PATENT DOCUMENTS

| | | |
|---|---|---|
| WO | WO 00/65085 | 11/2000 |
| WO | WO 00/65088 A1 | 11/2000 |

(Continued)

OTHER PUBLICATIONS

Canadian Patent Application No. 2,657,096; Response to Office Action, Jun. 20, 2011.

(Continued)

*Primary Examiner* — My-Chau T Tran
(74) *Attorney, Agent, or Firm* — Wilson Sonsini Goodrich & Rosati

(57) ABSTRACT

Disclosed are methods for treating Vascular Leak Syndrome. Further disclosed are methods for treating vascular leakage due to inflammatory diseases, inter alia, sepsis, lupus, inflammatory bowel disease. Yet further disclosed are methods for treating renal cell carcinoma and melanoma. Still further disclosed are methods for reducing metastasis of malignant cells and/or preventing the proliferation of carcinoma cells via spreading due to vascular leakage.

2 Claims, 7 Drawing Sheets

(51) Int. Cl.
*A61K 31/513* (2006.01)
*A61K 31/538* (2006.01)

(56) References Cited

U.S. PATENT DOCUMENTS

| | | | |
|---|---|---|---|
| 5,585,089 A | 12/1996 | Queen et al. | |
| 5,688,878 A | 11/1997 | Decker et al. | |
| 5,807,819 A | 9/1998 | Cheng et al. | |
| 5,994,128 A | 11/1999 | Fallaux et al. | |
| 6,033,908 A | 3/2000 | Bout et al. | |
| 6,432,219 B1 | 8/2002 | Wijngaard et al. | |
| 6,589,758 B1 | 7/2003 | Zhu | |
| 6,596,722 B2 | 7/2003 | Moltzen et al. | |
| 7,226,755 B1 | 6/2007 | Peters | |
| 7,507,568 B2 | 3/2009 | Evdokimov | |
| 7,588,924 B2 | 9/2009 | Evdokimov et al. | |
| 7,589,212 B2 | 9/2009 | Gray et al. | |
| 7,622,593 B2 | 11/2009 | Gray et al. | |
| 7,795,444 B2 | 9/2010 | Gray et al. | |
| 8,106,078 B2 | 1/2012 | Gray et al. | |
| 8,188,125 B2 | 5/2012 | Gray et al. | |
| 8,258,311 B2 | 9/2012 | Gray et al. | |
| 8,329,916 B2 | 12/2012 | Amarasinghe et al. | |
| 8,338,615 B2 | 12/2012 | Gray et al. | |
| 2004/0167183 A1 | 8/2004 | Klopfenstein et al. | |
| 2004/0204863 A1 | 10/2004 | Kim et al. | |
| 2007/0299116 A1 | 12/2007 | Gray | |
| 2008/0004267 A1 | 1/2008 | Gray | |
| 2008/0076764 A1 | 3/2008 | Peters et al. | |
| 2008/0108631 A1 | 5/2008 | Gray et al. | |
| 2009/0227639 A1 | 9/2009 | Gray et al. | |
| 2010/0016336 A1 | 1/2010 | Gray et al. | |
| 2011/0268694 A1* | 11/2011 | Shalwitz et al. | 424/85.2 |
| 2012/0128625 A1 | 5/2012 | Shalwitz et al. | |
| 2012/0129847 A1 | 5/2012 | Peters et al. | |
| 2013/0095065 A1* | 4/2013 | Peters et al. | 424/85.2 |
| 2013/0331386 A1* | 12/2013 | Shalwitz et al. | 514/230.5 |
| 2014/0066458 A1* | 3/2014 | Shalwitz et al. | 514/255.05 |

FOREIGN PATENT DOCUMENTS

| | | | | |
|---|---|---|---|---|
| WO | WO 02/26774 A1 | 4/2002 | | |
| WO | WO 2008002569 A2 * | 1/2008 | | C07D 277/28 |

OTHER PUBLICATIONS

Canadian Patent Application No. 2,657,096; Amended Claims in Response to Office Action, Jun. 20, 2011.
Canadian Patent Application No. 2,657,096; Office Action, Feb. 27, 2012.
Canadian Patent Application No. 2,657,096; Response to Office Action, Mar. 26, 2012.
Canadian Patent Application No. 2,657,096; Further Response to Office Action, Dec. 27, 2012.
Canadian Patent Application No. 2,657,107; Office Action, May 25, 2011.
Canadian Patent Application No. 2,657,107; Office Action, Mar. 7, 2012.
Canadian Patent Application No. 2,656,915; Office Action, Oct. 26, 2011.
Canadian Patent Application No. 2,656,915; Response to Office Action, Nov. 25, 2011.
Canadian Patent Application No. 2,656,915; Further Response to Office Action, Nov. 27, 2011.
Canadian Patent Application No. 2,656,915; Notice of Acceptance, Mar. 28, 2012.
Canadian Patent Application No. 2,748,814; Office Action, Sep. 6, 2012.
Canadian Patent Application No. 2,748,814; Response to Office Action, Oct. 23, 2012.
Canadian Patent Application No. 2,748,814; Office Action, Mar. 26, 2013.
Canadian Patent Application No. 2,748,814; Response to Office Action, May 14, 2013.
Canadian Patent Application No. 2,748,765; Office Action, Sep. 5, 2012.
Canadian Patent Application No. 2,748,765; Response to Office Action, Oct. 15, 2012.
Canadian Patent Application No. 2,748,765; Office Action, Mar. 26, 2013.
Canadian Patent Application No. 2,748,765; Response to Office Action, May 14, 2013.
Chinese Patent Application No. 200780030939.0; Response to Office Action, Jul. 12, 2011.
Chinese Patent Application No. 200780030939.0; Patent Issued, Aug. 8, 2012.
Chinese Patent Application No. 200780030984.6; Office Action, Nov. 3, 2010.
Chinese Patent Application No. 200780030984.6; Response to Office Action, Dec. 16, 2010.
Chinese Patent Application No. 200780030984.6; Office Action, May 30, 2011.
Chinese Patent Application No. 200780030984.6; Office Action, May 23, 2012.
Russian Patent Application No. 2009102538; Response to Office Action dated May 4, 2011.
Russian Patent Application No. 2009102538; Response to Examiner proposal dated May 27, 2011.
Russian Patent Application No. 2009102538; Decision to Grant dated Jul. 7, 2011.
Russian Patent Application No. 2009102537; Office Action, Oct. 21, 2010.
Russian Patent Application No. 2009102537; Response to Office Action, Nov. 2, 2010.
Russian Patent Application No. 2011133833, Response to Office Action dated May 2, 2013.
Singapore Patent Application No. 200809619-0; Office Action, Dec. 28, 2009.
Singapore Patent Application No. 200809619-0; Response to Office Action, Jan. 28, 2010.
Singapore Patent Application No. 200809619-0; Notice of Allowance, Jun. 6, 2011.
Singapore Patent Application No. 200809621-6; Response to Office Action, 2010.
Singapore Patent Application No. 200809621-6; Decision to Grant, Jul. 29, 2011.
Singapore Patent Application No. 200800622; Office Action, Feb. 19, 2010.
Singapore Patent Application No. 200800622; Office Action, Sep. 9, 2010.
Singapore Patent Application No. 201104563-0; Response to Office Action, Oct. 24, 2012.
Siddiqui et al., "Combination of angiopoietin-1 and vascular endothelial growth factor gene therapy enhances arteriogenesis in the ischemic myocardium," Biochem. Biophys. Res. Comm., 310:1002-1009 (2003).
Simons, "Angiogenesis: Where Do We Stand Now?," Circulation, 111:1556-1566 (2005).
Simons et al., "Clinical Trials in Coronary Angiogenesis," Circulation, 102:73-86 (2000).
Stal et al., "Detailed Analysis of Scoring Functions for Virtual Screening," J. Med. Chem., 44:1035-1042 (2001).
Stetler-Stevenson, "The Role of Matrix Metalloproteinases in Tumor Invasion, Metastasis, and Angiogenesis," Surg. Oncol. Clin. N. Am., 10(2):383-392 (2001).
Suggitt et al., "50 Years of Preclinical Anticancer Drug Screening: Empirical to Target-Drive Approaches," Clinical Cancer Research, 11:971-981 (2005).
Suri et al., "Increased Vascularization in Mice Overexpressing Angiopoietin-1," Science, 282:468-471 (1998).
Takahashi et al.,"Adenoviral-Delivered Angiopoietin-1 Reduces the Infarction and Attenuates the Progression of Cardiace Dysfunction in the Rate Model of Acute Myocardial Infarction," Molecular Therapy, 8(4):584-592 (2003).

(56) References Cited

OTHER PUBLICATIONS

Teischer, "Potentiation of cytotoxic cancer therapies by TNP-470 alone and with other anti-angiogenic agents," Int. J. Cancer, 57(6)920-925 (1994).
Thurston, "Complimentary Actions of VEGF and Angiopoietin-1 on Blood Vessel Growth and Leakage," J. Anat., 200:575-580 (2002).
Thurston et al., "Angiopoietin-1 Protects the Adult Vasculature Against Plasma Leakage," Nature Medicine, 6 (4):460-463 (2000).
Vailhe et al., "In Vitro Models of Vasculogenesis and Angiogenesis," Laboratory Investigation, 81:439-452 (2001).
Wang et al., "Expressions and Characterization of Wild Type, Truncated, and Mutant Forms of the Intracellular Region of the Receptor-Like Protein Tyrosine Phosphatase HPTPß," J. of Bio. Chem., 267(23):16696-16702 (1992).
Weidner, "Tumor Angiogenesis and Metastasis Correlation in Invasive Breast Carcinoma," New Eng. J. Med., 324 (1):108 (1991).
Whitaker et al., "Vascular Endothelial Growth Factor Receptor-2 and Neuropilin-1 Form a Receptor Complex That Is Responsible for the Differential Signaling Potency of VEGF165 and VEGF121," Journal of Biological Chemistry, 276 (27):25520-25531 (2001).
Wright et al., "Protein-Tyrosine Phosphatases in the Vessel Wall Differential Expression After Actue Arterial Injury," Arterioscler Thromb. Vasc., 1189-1198 (2000).
Yancopoulos et al., "Vascular-Specific Growth Factors and Blood Vessel Formation," Nature, 407(6801):242-248 (2000).
Zhang et al., "Vascular Endothelial Growth Factor and Angiopoietins in Focal Cerebral Ischemia," Trends Cardiovascular Med., 12(2):62-66 (2002).
Collaborative Computational Project, No. 4, "The CCP4 Suite: Programs for Protein Crystallography," Acta Cryst., D50:760-763 (1994).
Australian Patent Application No. 2007265453; Office Action, Dec. 15, 2010.
Australian Patent Application No. 2007265453; Response to Office Action, Feb. 8, 2011.
Australian Patent Application No. 2007265453; Response to Office Action, Aug. 1, 2011.
Australian Patent Application No. 2007265453; Office Action, Oct. 26, 2011.
Australian Patent Application No. 2007265453; Response to Office Action, Nov. 23, 2011.
Australian Patent Application No. 2007265453; Notice of Acceptance, Dec. 21, 2011.
Australian Patent Application No. 2007265454; Office Action, Feb. 25, 2011.
Australian Patent Application No. 2007265454; Response to Office Action, Mar. 25, 2011.
Australian Patent Application No. 2007265454; Office Action, Jul. 25, 2011.
Australian Patent Application No. 2007265454; Notice of Acceptance, Nov. 16, 2011.
Australian Patent Application No. 2007265455; Office Action, Feb. 8, 2011.
Australian Patent Application No. 2012200253; Office Action, Apr. 16, 2012.
Australian Patent Application No. 2012200253; Response to Office Action, Jun. 12, 2012.
Australian Patent Application No. 2012200253; Notice of Acceptance, Jun. 20, 2012.
Australian Patent Application No. 2010203352; Office Action dated Aug. 20, 2012.
Australian Patent Application No. 2010203352; Response to Office Action dated Feb. 17, 2013.
Australian Patent Application No. 2010271105; Office Action dated Aug. 14, 2012.
Australian Patent Application No. 2010271105; Response to Office Action dated Feb. 5, 2013.
Gallagher et al., "Angiopoietin 2 is a Potential Mediator of High-Dose Interleutkin 2-Induced Vascular Leak," Clin Cancer REs (2007);13:2115-2120.
Kumpers et al., "Ecxess circulating angiopoietin-2 is a strong predictor of mortality in critically ill medical patients," Clinical Care (2008), Vol-12, No. 6.
Kumpers et al., "The Tie2 receptor antagonist angiopoietin 2 facilitates vascular inflammation in systemic lupus erythematosus," Ann. Rheum Dis 2009;68:1638-1643.
Milner et al., "Roles of the receptor tyrosine kinases Tie1 and Tie2 in mediating the effects of angiopoietin-1 on endothelial permeability and apoptosis," Microvascular Research; 77(2009) pp. 187-191.
Roviezzo et al., "Angiopoietin-2 Causes Inflammation in Vivo by promoting Vascular Leakage," J. Pharmacology and Experimental Therapeutics; vol. 314, No. 2, (2005).
Colombian Patent Application No. 0900733; Decision to Grant, dated Jun. 12, 2013.
European Patent Application No. 07 809 907.4; communication under Article 94(3) EPC, Jul. 5, 2013.
European Patent Application No. 07809 908.2; Communication under 94(3) EPC, Jul. 12, 2013.
European Patent Application No. 07 809 909.0; Response to Communication under 94(3) EPC, Aug. 27, 2013.
Chinese Patent Application No. 201080011867.7, Response to Office Action dated Jun. 25, 2013.
Chinese Patent Application No. 201080012192.8, Office Action dated Mar. 5, 2013.
Chinese Patent Application No. 201080012192.8, Response to Office Action dated Jul. 7, 2013.
Israeli Patent Application No. 214,048, Response to Communication under Section 18, dated Jul. 10, 2013.
Japanese Patent Application No. 2011-545536, Office Action, dated Jun. 24, 2013.
Japanese Patent Application No. 2011-554058, Office Action, dated Jun. 14, 2013.
Japanese Patent Application No. 2011-554058, Response to Office Action, dated Sep. 1, 2013.
Philippine Patent Application No. 1-2009500032, Office Action dated Jul. 8, 2013.
Russian Patent Application No. 2011133835, Response to Office Action, dated Jun. 24, 2013.
New Zealand Patent Application No. 574407; Notice of Acceptance, Jan. 16, 2012.
New Zealand Patent Application No. 574406; Notice of Acceptance, Jan. 12, 2012.
New Zealand Patent Application No. 574405; Office Action, Jun. 14, 2010.
New Zealand Patent Application No. 574405; Response to Office Action, Apr. 20, 2011.
New Zealand Patent Application No. 574405; Office Action, Jun. 2, 2011.
New Zealand Patent Application No. 574405; Response to Office Action, Sep. 2, 2011.
New Zealand Patent Application No. 574405; Further Response to Office Action, Nov. 27, 2011.
New Zealand Patent Application No. 594535, Office Action, dated May 15, 2012.
New Zealand Patent Application No. 594535, Response to Office Action, dated Jul. 13, 2012.
New Zealand Patent Application No. 594535, Office Action, dated Dec. 12, 2012.
New Zealand Patent Application No. 594535, Response to Office Action, dated Feb. 3, 2013.
New Zealand Patent Application No. 594535, Office Action, dated Mar. 11, 2013.
New Zealand Patent Application No. 594535, Response to Office Action, dated Mar. 21, 2013.
New Zealand Patent Application No. 594537, Office Action dated Oct. 3, 2012.
New Zealand Patent Application No. 594537, Response to Office Action dated Feb. 5, 2013.
New Zealand Patent Application No. 594537, Office Action dated Apr. 15, 2013.

(56) References Cited

OTHER PUBLICATIONS

New Zealand Patent Application No. 594537, Response to Office Action dated Jun. 2, 2013.
Philippine Application No. 12009500031; Office Action, Mar. 15, 2012.
Philippine Application No. 12009500031; Notice of Allowance, May 30, 2012.
Philippine Patent Application No. 1-2009500032, Office Action dated Jun. 5, 2012.
Philippine Patent Application No. 12009500033, Notice of Allowance dated Jun. 21, 2012.
Russian Patent Application No. 2009102516; Response to Office Action, Dec. 29, 2010.
Russian Patent Application No. 2009102516; Examiner suggested amendments, Jul. 21, 2011.
Russian Patent Application No. 2009102516; Notice of Grant dated Oct. 27, 2011.
Russian Patent Application No. 2009102538; Office Action, dated Mar. 1, 2010.
Russian Patent Application No. 2009102538; Response to Office Action dated Mar. 5, 2011.
Russian Patent Application No. 2009102538; Response to Office Action dated Apr. 28, 2011.
Van Hijsduijnen, et al., "Protein tyrosine phosphatatses as drug targets: PTP1B and beyond," Expert Opinion Thera. Targets (2002) 6(6):637-647.
Altschul et al., "Gapped BLAST and PSI-BLAST: A New Generation of Protein Database Search Programs," Nucleic Acids Res., 25(27):3389-3402 (1997).
Annex et al., "Growth Factor-Induced Therapeutic Angiogenesis in the Heart: Protein Therapy," Cardiovascular Research, 65(3):649-655 (2005).
Ardelt et al., "Estradiol Regulates Angiopoietin-1 mRNA Expression Through Estrogen Receptor-α in a Rodent Experimental Stroke Model," Stroke, 36:337-341 (2005).
Barnay et al., "Solid-phase Peptide Synthesis: A Silver Anniversary Report," Int. J. Peptide Protein Res., 30 (6):705-739 (1987).
Bartlett et al., "Molecular Recognition in Chemical and Biological Problems; Cavet: A Program to Facilitate the Structure-Derived Design of Biologically Active Molecules," Special Pub., Royal Chem. Soc., 78:182-196 (1989).
Bohm, "The Computer Program LUDI: A New Method for the De Novo Design of Enzyme Inhibitors," J. Comuter-Aided. Molec. Design, 6(1):61-78 (1992).
Bussolino, et al., "Molecular mechanisms of blood vessel formation," Trends Biochem Sci. 22(7):251-256 (1997).
Carano et al., "Angiogenesis and Bone Repair," Drug Discovery Today, 8(21):980-989 (2003).
Chanteau et al., "Synthesis of Anthropomorphic Molecules: The NanoPutians," J. Org. Chem., 68:8750-8766 (2003).
Cohen et al., "Molecular Modeling Software and Methods for Medicinal Chemistry," J. Med. Chem., 33(3):883-894 (1990).
Daar, "Perspective: Emerging Resistance Profiles of Newly Approved Antiretroviral Drugs," Topics in HIV Medicine, 16(4):110-116 (2008).
Dean, "Recent Advances in Drug Design Methods: Where Will They Lead?" BioEssays, 16(9):683-687 (1994).
Fachinger et al., "Functional Interaction of Vascular Endothelial-Protein-Tyrosine Phosphatase with the Angiopoietin Receptor Tie-2," Oncogene, 18:5948-5953 (1999).
Flower, "Modelling G-Protein-Coupled Receptors for Drug Design," Biochimica et Biophysica Acta, 1422:207-234 (1999).
Folkman, J., "Tumor angiogenesis," The Molecular Basis of Cancer (eds. Mendelsohn, J., Howley, P. M., Israel, M. A. & Liotta, L. A.) 206-232 (1995).
Gaits et al., "Increase in Receptor-like Protein Tyrosine Phosphatase Activity and Express Level on Density-Dependent Growth Arrest of Endothelial Cells," Biochem J., 311:97-103 (1995).

Goodford, "A Computational Procedure for Determining Energetically Favorable Binding Sites on Biologically Important Macromolecules," J. Med. Chem., 28(7):849-57 (1985).
Goodsell et al., "Automated Docking of Substrates to Proteins by Simulated Annealing," Proteins Struct. Funct. Genet. 8:195-202 (1990).
Harder et al., "Characterization and Kinetic Analysis of the Intracellular Domain of Human Protein Tyrosine Phosphatase ß (HPTPß) Using Synthetic Phosphopeptides," Biochem. J., 296:395-401 (1994).
Henikoff et al., "Amino Acid Substitution Matrices from Protein Blocks," Proc. Natl. Acad. Sci. USA 89:10915-10919 (1992).
Hopkins et al., "Inhibitors of Kinesin Activity from Structure-Based Computer Screening," Biochemistry, 39:2805-2814 (2000).
Huang et al., "HCPTPA, a Protein Tyrosine Phosphatase that Regulates Vascular Endothelial Growth Factor Receptor-Mediated Signal Transduction and Biological Activity," J. Biol. Chem., 53:38183-38188 (1999).
Itoh et al., "Purification and Characterization of the Catalytic Domains of the Human Receptor-Linked Protein Tyrosine Phosphatases HPTPß, Leukocyte Common Antigen (LCA), and Leukocyte Common Antigen-Related Molecule (LAR)," Journal of Biological Chemistry, 267(17):12356-12363 (1992).
Jones et al., "Development and Validation of a Genetic Algorithm for Flexible Docking," J. Mol. Biol., 267:727-748 (1997).
Jones et al., "Molecular Recognition of Receptor Sites Using a Genetic Algorithm with a Description of Desolvation," J. Mol. Biol., 245:43-53 (1995).
Keen, "Radioligand Binding Methods for Membrane Preparations and Intact cells," Methods in Molecular Biology, 83: Receptor Signal Transduction Protocols, edited Humana Press Inc., Totoway N.J. (1997).
Köhler et al., "Continuous Cultures of Fused Cells Secreting Antibody of Predefined Specificity," Biotechnology, 24:524-526 (1992).
Krueger et al., "Structural Diversity and evolution of Human Receptor-Like Protein Tyrosine Phosphatases," The EMBO Journal, 9(10):3241-3252 (1990).
Kugathasan et al., "Role of Angiopoietin-1 in Experimental and Human Pulmonary Arterial Hpertension," Chest, 128:633-642 (2005).
Kuntz et al., "A Geometric Approach to Macromolecule—Ligand Interactions," J. Mol. Biol. 161:269-288 (1982).
Lin et al., "Inhibition of Tumor Angiogenesis Using a Soluble Receptor Establishes a Role for Tie2 in Pathologic Vascular Growth," J. Clinical Invest.,100(8):2072-–2078 (1997).
Ma et al., "RNase Protection Assay," Methods, 10(3):273-8 (1996).
Martin, "3D Database Searching in Drug Design," J. of Medicinal Chemistry, 35(12):2145-2154 (1992).
Meadows, "Keeping Up with Drug Safety Information," 2006: FDA Consumer Magazine: http://www.fda.gov/fdac/features/2006/306_drugsafety.html, accessed Mar. 17, 2008.
Merrifield, "Solid Phase Peptide Synthesism. I. The Synthesis of a Tetrapeptide," J. Am. Chem. Soc., 85:2149-2154 (1963).
Miranker et al., "Functionality Maps of Binding Sites: A Multiple Copy Simultaneous Search Method," Proteins: Struc. Func. and Genectics, 11(1):29-34 (1991).
Navaza, "AMoRe: An Automated Package for Molecular Replacement," J. Acta Cryst. A50:157-163 (1994).
Nguyen et al., "Cellular Interactions in Vascular Growth and Differentiation," Int. Rev. Cytol., 204:1-48 (2001).
Nishibata et al., "Automatic Creation of Drug Candidate Structures Based on Receptor Structure. Starting Point for Artificial Lead Generation," Tetrahedron, 47(43):8985-8990 (1991).
O'Reilly, "Angiostatin: a novel angiogenesis inhibitor that mediates the suppression of metastases by a Lewis lung carcinoma," Cell, 79(2):315-28 (1994).
O'Reilly, "Endostatin: an endogenous inhibitor of angiogenesis and tumor growth," Cell, 88(2):277-85 (1997).
Rarey et al., "A Fast Flexible Docking Method Using an Incremental Construction Algorithm," J. Mol. Biol., 261:470-489 (1996).
Riechmann et al., "Reshaping Human Antibodies for Therapy," Nature, 332:323-327 (1988).

(56) References Cited

OTHER PUBLICATIONS

Saliba, "Heparin in the Treatment of Burns: A Review," May 2001; Burn 27(4):349-358; full text edition, pp. 1-16.
Schöneberg et al., "Structural basis of G protein-coupled receptor function," Molecular and Cellular Endocrinology, 151:181-193 (1999).
Sexton, "Recent advances in our understanding of peptide hormone receptors and RAMPS," Current Opinion in Drug Discovery and Development, 2(5):440-448 (1999).
Shiojima et al., "Disruption of Coordinated Cardiac Hypertrophy and Angiogenesis Contributes to the Transition to Heart Failure," Journal of Clinical Invest., 115(8):2108-2118 (2005).
Shoichet et al., "Lead Discovery Using Molecular Docking," Chem. Biology, 6:439-446 (2002).
Brindle et al., "Signaling and Functions of Angiopoietin-1 in Vascular Protection," Circ. Res. (2006) 98:1014-1023.
Jain et al., "Leaky vessels? Call Ang1!" Mat. Med. (2000) 6(2): 131-132.
Mellberg et al., "Transcriptional profiling reveals a critical role for tyrosine phosphatase VE-PTP in regulation of VEGFR2 activity and endothelial cell morphogenesis," FASEB Journal, May 2009, 1490-1502.
Nottebaum et al., "VE-PTP maintains the edothelial barrier via plakoglobin and becomes dissociated from VE-cadherin by leukocyttes and by VEGF," J. Ex. Med. vol. 205:No. 12, 2929-2945 (2008).
Israeli Patent Application No. 196128; Office Action (Communication), Apr. 8, 2012.
Israeli Patent Application No. 196128; Response to Office Action (Communication), Apr. 11, 2012.
Israeli Patent Application No. 196128; Office Action (Communication), Aug. 20, 2012.
Israeli Patent Application No. 196128; Response to Office Action (Communication), Sep. 26, 2012.
Israeli Patent Application No. 196129; Office Action (Communication), Apr. 8, 2012.
Israeli Patent Application No. 196129; Response to Office Action (Communication), Apr. 16, 2012.
Israeli Patent Application No. 196129; Office Action (Communication), Aug. 16, 2012.
Israeli Patent Application No. 196130; Office Action (Communication), Aug. 15, 2012.
Israeli Patent Application No. 196130; Response to Office Action (Communication), Sep. 4, 2012.
Israeli Patent Application No. 196130; Office Action (Communication), Feb. 7, 2013.
Israeli Patent Application No. 196130; Response to Office Action (Communication), Apr. 24, 2013.
Japanese Patent Application No. 2009-518226; Office Action, May 30, 2012.
Japanese Patent Application No. 2009-518226; Response to Office Action, Jul. 5, 2012.
Japanese Patent Application No. 2009-518226; Office Action, Sep. 6, 2012.
Japanese Patent Application No. 2009-518226; Office Action, Nov. 3, 2012.
Japanese Patent Application No. 2009-518227, Office Action, Sep. 12, 2012.
Japanese Patent Application No. 2009-518227; Response to Office Action, Nov. 7, 2012.
Japanese Patent Application No. 2009-518227, Response to Office Action, dated Feb. 2, 2013.
Japanese Patent Application No. 2009-518228; Office Action, Sep. 4, 2012.
Japanese Patent Application No. 2009-518228, Notice of Allowance, dated Feb. 6, 2013.
Korean Patent Application No. 2009-7001678: Office Action, Apr. 6, 2011.
Korean Patent Application No. 2009-7001678: Office Action, May 10, 2011.
Korean Patent Application No. 2009-7001678: Office Action, Dec. 23, 2011.
Korean Patent Application No. 2009-7001678: Further Response to Office Action, Dec. 29, 2011.
2000 Korean Patent Application No. 2009-7001694; Response to Office Action, Jun. 9, 2011.
Korean Patent Application No. 2009-7001694; Further Response to Office Action, Oct. 17, 2011.
Korean Patent Application No. 2009-7001694; Response to Office Action, Apr. 5, 2012.
Korean Patent Application No. 2009-7001694; Notice of Allowance, Jul. 10, 2012.
Korean Patent Application No. 2009-7001692; Office Action, May 14, 2011.
Korean Patent Application No. 2009-7001692; Response to Office Action, May 25, 2011.
Korean Patent Application No. 2009-7001692; Notice of Allowance, Jun. 13, 2012.
Korean Patent Application No. 2011-701878, Office Action dated Apr. 8, 2013.
Korean Patent Application No. 2011-701878, Response to Office Action dated Jun. 7, 2013.
Korean Patent Application No. 2011-7018742, Office Action dated Apr. 8, 2013.
Korean Patent Application No. 2011-7018742, Response to Office Action dated Jun. 6, 2013.
Mexican Patent Application No. MX/A/2009/000288, Office Action dated Apr. 2, 2013.
Mexican Patent Application No. MX/A/2009/000288, Response to Office Action dated Jun. 9, 2013.
Mexican Patent Application No. MX/A/2009/000289; Office Action (Correspondence), Apr. 23, 2012.
Mexican Patent Application No. MX/A/2009/000289; Response to Office Action, May 7, 2012.
Mexican Patent Application No. MX/A/2009/000289; Communication re Issuance of Patent, Sep. 14, 2012.
Mexican Patent Application No. MX/A/2009/000290; Office Action (Correspondence), Jun. 18, 2010.
Mexican Patent Application No. MX/A/2009/000290; Office Action (Correspondence), Jul. 27, 2010.
New Zealand Patent Application No. 574407; Office Action, Jun. 14, 2010.
New Zealand Patent Application No. 574407; Further Response to Office Action, May 3, 2011.
New Zealand Patent Application No. 574407; Office Action, Jun. 8, 2011.
New Zealand Patent Application No. 574407; Response to Office Action, Oct. 25, 2011.
New Zealand Patent Application No. 574407; Office Action, Nov. 29, 2011.
New Zealand Patent Application No. 574407; Response to Office Action, Dec. 14, 2011.
Chinese Patent Application No. 201080011867.7, Office Action dated Mar. 5, 2013.
Colombian Patent Application No. 0900733; Office Action dated Mar. 20, 2013.
Colombian Patent Application No. 0900733; Response to Office Action dated Apr. 30, 2013.
Colombian Patent Application No. 09007334; Office Action, Sep. 7, 2012.
Colombian Patent Application No. 09007334; Response to Office Action, Sep. 24, 2012.
Colombian Patent Application No. 09007337; Office Action, Sep. 24, 2012.
European Patent Application No. 07 809 907.4; Office Action, Nov. 30, 2010.
European Patent Application No. 07 809 907.4; Response to Office Action, Jan. 19, 2011.
European Patent Application No. 07 809 907.4; Further Response to Office Action, Mar. 30, 2011.
European Patent Application No. 07 809 907.4; communication under Article 94(3) EPC, Oct. 19, 2012.

(56) References Cited

OTHER PUBLICATIONS

European Patent Application No. 12 196 174.2; Extended European Search Report dated Apr. 25, 2013.
European Patent Application No. 07809 908.2; Office Action, Nov. 30, 2010.
European Patent Application No. 07809 908.2; Response to Office Action, Jan. 11, 2011.
European Patent Application No. 07809 908.2; Further Response to Office Action, Apr. 4, 2011.
European Patent Application No. 07809 908.2; Communication under 94(3) EPC, Oct. 19, 2012.
European Patent Application No. 07 809 909.0; Office Action, Nov. 30, 2010.
European Patent Application No. 07 809 909.0; Response to Office Action, Jan. 14, 2011.
European Patent Application No. 07 809 909.0; Further Response to Office Action, Nov. 27, 2011.
European Patent Application No. 10 729 682.4; Extended European Search Report, dated Feb. 6, 2013.
European Patent Application No. 10 729 682.4; Response to European Search Report, dated Feb. 25, 2013.
European Patent Application No. 10 797 461.0, Extended European Search Report, dated Feb. 22, 2013.
European Patent Application No. 10 797 461.0, Response to European Search Report, dated Mar. 24, 2013.
Indonesian Patent Application No. W-00200804210; Response to Office Action, Jul. 5, 2011.
Indonesian Patent Application No. W-00200804213; Office Action, May 26, 2011.
Indonesian Patent Application No. W-00200804213; Response to Office Action, Aug. 2, 2011.

* cited by examiner

METHODS FOR TREATING VASCULAR LEAK SYNDROME

CROSS REFERENCE TO RELATED APPLICATIONS

This application is a Divisional Application of application Ser. No. 12/677,512 filed Mar. 22, 2010, which is a U.S. National Stage Application under 35 U.S.C. 371(c) of PCT/US2010/020817, filed Jan. 12, 2010, which claims the benefit of Provisional Application Ser. No. 61/144,022 filed on Jan. 12, 2009 and Provisional Application Ser. No. 61/184,985 filed on Jun. 8, 2009. The entire disclosure of these referenced applications is incorporated herein by reference.

FIELD

Disclosed are methods for treating Vascular Leak Syndrome. Further disclosed are methods for treating vascular leakage due to inflammatory diseases, inter alia, sepsis, lupus, inflammatory bowel disease. Also disclosed are methods for treating vascular leakage due to the presence of pathogens. Yet further disclosed are methods for treating metastatic renal cell carcinoma and metastatic melanoma.

BACKGROUND

Vascular leak is characterized by hypotension, peripheral edema, and hypoalbuminemia. Vascular leak can occur as a side effect of illness especially illnesses due to pathogens, inter alia, viruses and bacteria. Vascular leak complicates the healing process and can itself be a direct result of certain therapies. For example, patients suffering from malignant renal carcinoma are given Interleukin-2 to help boost their immune system; however, this treatment must be withdrawn in many patients due to the onset of severe vascular leak well before the full course of treatment can be administered. Therefore, the cancer treatment is withdrawn earlier than desired and usually before the therapy is maximally effective. VLS restricts the doses of IL-2 which can be administered to humans and, in some cases, necessitates the cessation of therapy.

VLS is characterized by an increase in vascular permeability accompanied by extravasation of fluids and proteins resulting in interstitial edema and organ failure. Manifestations of VLS include fluid retention, increase in body weight, peripheral edema, pleural and pericardial effusions, ascites, anasarca and, in severe form, signs of pulmonary and cardiovascular failure. Symptoms are highly variable among patients and the causes are poorly understood. Endothelial cell modifications or damage are thought to be important is vascular leak. The pathogenesis of endothelial cell (EC) damage is complex and can involve activation or damage to ECs and leukocytes, release of cytokines and of inflammatory mediators, alteration in cell-cell and cell-matrix adhesion and in cytoskeleton function.

During the course of antiviral and antibacterial infections, patients can develop vascular leak that is induced as result of the initial infection. There is now a long felt need for a method of preventing vascular leak due to viral or bacterial infection, and therefore provide a method of increasing the survival of humans or other mammals infected with one or more pathogens. In addition, there is a long felt need for a method of preventing vascular leakage due to certain anticancer drugs or other anticancer therapies such that the administration of anticancer drugs or anticancer therapies can be given to humans or other mammals for a longer course of treatment or therapy.

SUMMARY

Disclosed herein are compounds that inhibit the intracellular catalytic site of human protein tyrosine phosphatase beta (HPTP-β) molecule. HPTP-β is known only to be expressed in vascular endothelial cells. Inhibition of HPTP-β reduces the rate of dephosphorylation of the Tie-2 receptor tyrosine kinase. This inhibition results in amplification of the Angiopoietin 1 (Ang-1) signal through Tie-2, and effectively counters the inhibitory effects of Angiopoietin 2 (Ang-2) on Tie-2. Because Tie-2 is critical to maintaining vascular endothelial integrity, the disclosed HPTP-β inhibitors provide a method for providing vascular stabilization in humans and mammals. As such, the disclosed HPTP-β inhibitors provide Tie-2 signal amplification. One important manifestation of vascular de-stabilization is vascular leak syndrome (VLS) which has many causes, for example, infection of a human or mammal by a pathogen. Another common cause of vascular leak syndrome is the use of certain chemotherapeutic agents, inter alia, IL-2 which is used in treating certain forms of cancer.

Disclosed herein are methods for stabilizing human and mammalian vasculature. The stabilization of vasculature in patients compromised with an infection due to the presence of pathogens, inter alia, bacteria, viruses, yeasts, and fungi, provide a method for preventing complications due to infection such as sepsis, pulmonary edema, and the like. Subjects suffering from or diagnosed with certain cancers are given chemotherapeutic agents that result in vascular leak syndrome as a primary side effect causing cessation of treatment before the desired full course has been achieved. For weakened humans and mammals, the onset of vascular leak syndrome due to one or more compromising events can be avoided by the disclosed methods for monitoring the level of Ang-2 and administering the appropriate amount of HPTP-β inhibitor, either alone, or as part of a prophylactic combination therapy.

BRIEF DESCRIPTION OF THE FIGURES

FIG. 10c is a micrograph showing that vascular integrity is preserved as compared to LPS treatment for cells in a renal section from a mouse treated with LPS and D91 that is subsequently injected with 70 kDa of fluorescent fixable dextran by intravenous catheter 2 minutes prior to sacrifice. The pattern of staining in this section is similar to 10a.

DETAILED DESCRIPTION

Figure 1:
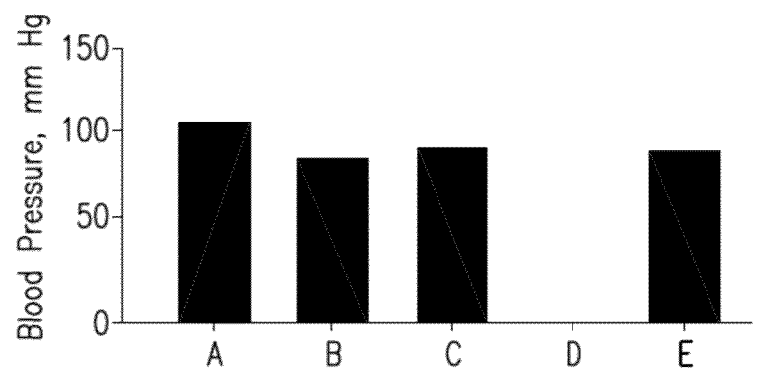
FIG. 1 depicts the effect of 4-{(S)-2-[(S)-2-(methoxycarbonylamino)-3-phenyl-propanamido]-2-[2-(thiophen-2-yl)thiazol-4-yl]ethyl}phenylsulfamic acid ammonium salt (inhibitor) on murine blood pressure during IL-2 induced VLS at low and high IL-2 dosing. As depicted, High IL-2 dosing in the absence of a Tie-2 signal amplifier resulted in death. A depicts the control sample; B depicts mice treated with 180,000 IU of IL-2 for 5 days; C depicts mice treated with 180,000 IU of IL-2 for 5 days and 40 mg/kg of D91 for the first 2 days, then at 20 mg/kg for 3 days; D depicts mice treated with 400,000 IU of IL-2 for 5 days; E depicts mice treated with 400,000 IU of IL-2 for 5 days and 40 mg/kg of D91 for the first 2 days, then at 20 mg/kg for 3 days.

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "effective amount" as used herein means "an amount of one or more of the disclosed Tie-2 signal amplifiers, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, breakdown, or eliminate a particular characteristic or event (e.g., vascular leakge). The disclosed compounds affect vascular leakage by inhibiting HPTP-β (and the rodent equivalent, VE-PTP) which enhances or amplifies Tie-2 signaling.

By "chemotherapeutic agent" is meant any drug, pharmaceutical or otherwise, that can be given to a subject as part of a combination therapy. Non-limiting examples of chemotherapeutic agents include anticancer drugs, for example, IL-2, taxol, and the like, antimicrobials, anti-virals, anti-fungicides, and the like.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (i.e., carbocyclic and aryl rings) or can comprise one or more heteroatoms in the ring (i.e., heterocyclic and heteroaryl rings). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and unsubstituted acyclic hydrocarbyl:

For the purposes of the present disclosure the term "substituted and unsubstituted acyclic hydrocarbyl" encompasses 3 categories of units:

1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminoethyl ($C_1$), 1-chloroethyl ($C_2$), 2-hydroxyethyl ($C_2$), 1,2-difluoroethyl ($C_2$), 3-carboxypropyl ($C_3$), and the like.

2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and unsubstituted cyclic hydrocarbyl:
For the purposes of the present disclosure the term "substituted and unsubstituted cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:
   i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).
   ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).
   iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:
   i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).
   ii) $C_6$ or $C_{10}$ aryl rings fused with 1 or 2 saturated rings to afford $C_8$-$C_{20}$ ring systems, non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which contains the heteroatom is also not an aromatic ring." The following are non-limiting examples of "substituted and unsubstituted heterocyclic rings" which encompass the following categories of units:
   i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydroquinoline ($C_9$).
   ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:
   i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$)
   ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

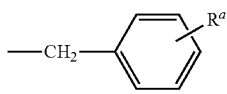

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxyphenyl)ethyl $C_2$-($C_6$), as well as substituted and unsubstituted $C_3$-$C_{10}$ alkylenecarbocyclic units, for example, cyclopropylmethyl $C_1$-($C_3$), cyclopentylethyl $C_2$-($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

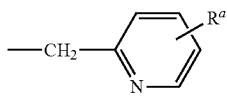

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

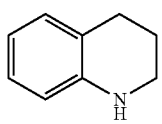

is, for the purposes of the present disclosure, considered a heterocyclic unit. 6,7-Dihydro-5H-cyclopentapyrimidine having the formula:

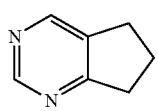

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the invention. For example, 1,2,3,4-tetrahydro-[1,8]naphthpyridine having the formula:

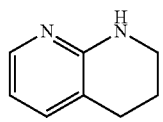

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_6$ or $C_{10}$ alkylenearyl; for example, benzyl, 2-phenylethyl, naphthylen-2-ylmethyl;

iv) substituted or unsubstituted $C_1$-$C_9$ heterocyclic rings; as described herein below;

v) substituted or unsubstituted $C_1$-$C_9$ heteroaryl rings; as described herein below;

vi) —$(CR^{102a}R^{102b})_aOR^{101}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) —(CR$^{102a}$R$^{102b}$)$_a$C(O)R$^{101}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;

viii) —(CR$^{102a}$R$^{102b}$)$_a$C(O)OR$^{101}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;

ix) —(CR$^{102a}$R$^{102b}$)$_a$C(O)N(R$^{101}$)$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;

x) —(CR$^{102a}$R$^{102b}$)$_a$N(R$^{101}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;

xi) halogen; —F, —Cl, —Br, and —I;

xii) —(CR$^{102a}$R$^{102b}$)$_a$CN;

xiii) —(CR$^{102a}$R$^{102b}$)$_a$NO$_2$;

xiv) —CH$_j$X$_k$; wherein X is halogen, the index j is an integer from 0 to 2, j+k=3; for example, —CH$_2$F, —CHF$_2$, —CF$_3$, —CCl$_3$, or —CBr$_3$;

xv) —(CR$^{102a}$R$^{102b}$)$_a$SR$^{101}$; —SH, —CH$_2$SH, —SCH$_3$, —CH$_2$SCH$_3$, —SC$_6$H$_5$, and —CH$_2$SC$_6$H$_5$;

xvi) —(CR$^{102a}$R$^{102b}$)$_a$SO$_2$R$^{101}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xvii) —(CR$^{102a}$R$^{102b}$)$_a$SO$_3$R$^{101}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{101}$ is independently hydrogen, substituted or unsubstituted C$_1$-C$_6$ linear, branched, or cyclic alkyl, phenyl, benzyl, heterocyclic, or heteroaryl; or two R$^{101}$ units can be taken together to form a ring comprising 3-7 atoms; R$^{102a}$ and R$^{102b}$ are each independently hydrogen or C$_1$-C$_4$ linear or branched alkyl; the index "a" is from 0 to 4.

For the purposes of the present disclosure the terms "compound," "analog," and "composition of matter" stand equally well for each other and are used interchangeably throughout the specification. The disclosed compounds include all enantiomeric forms, diastereomeric forms, salts, and the like.

The compounds disclosed herein include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The disclosed compounds have Formula (I):

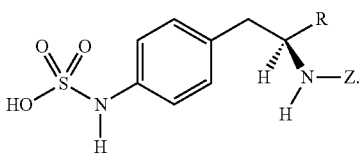

(I)

wherein the carbon atom having the amino unit has the (S) stereochemistry as indicated in the following formula:

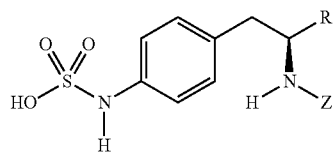

The units which comprise R and Z can comprise units having any configuration, and, as such, the disclosed compounds can be single enantiomers, diastereomeric pairs, or combinations thereof. In addition, the compounds can be isolated as salts or hydrates. In the case of salts, the compounds can comprises more than one cation or anion. In the case of hydrates, any number of water molecules, or fractional part thereof (for example, less than 1 water molecule present for each molecule of analog) can be present.

R Units

R is a substituted or unsubstituted thiazolyl unit having the formula:

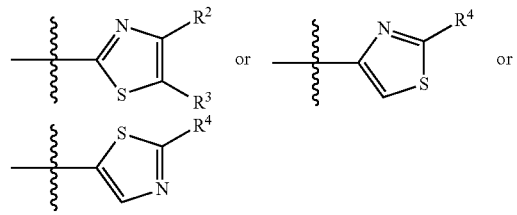

R$^2$, R$^3$, and R$^4$ are substituent groups that can be independently chosen from a wide variety of non-carbon atom containing units (for example, hydrogen, hydroxyl, amino, halogen, nitro, and the like) or organic substituent units, such as substituted and unsubstituted acyclic hydrocarbyl and cyclic hydrocarbyl units as described herein. The carbon comprising units can comprise from 1 to 12 carbon atoms, or 1 to 10 carbon atoms, or 1 to 6 carbon atoms.

An example of compounds of Formula (I) include compounds wherein R units are thiazol-2-yl units having the formula:

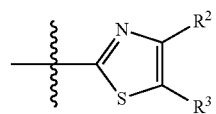

wherein R$^2$ and R$^3$ are each independently chosen from:
  i) hydrogen;
  ii) substituted or unsubstituted C$_1$-C$_6$ linear, branched, or cyclic alkyl;
  iii) substituted or unsubstituted C$_2$-C$_6$ linear, branched, or cyclic alkenyl;
  iv) substituted or unsubstituted C$_2$-C$_6$ linear or branched alkynyl;
  v) substituted or unsubstituted C$_6$ or C$_{10}$ aryl;
  vi) substituted or unsubstituted C$_1$-C$_9$ heteroaryl;
  vii) substituted or unsubstituted C$_1$-C$_9$ heterocyclic; or
  viii) R$^2$ and R$^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the R$^2$ and R$^3$ units. The following substituents, as well as others not herein described, are each independently chosen:

i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_6$ or $C_{10}$ alkylenearyl; for example, benzyl, 2-phenylethyl, naphthylen-2-ylmethyl;

iv) substituted or unsubstituted $C_1$-$C_9$ heterocyclic rings; as described herein;

v) substituted or unsubstituted $C_1$-$C_9$ heteroaryl rings; as described herein;

vi) —$(CR^{21a}R^{21b})_pOR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) —$(CR^{21a}R^{21b})_pC(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;

viii) —$(CR^{21a}R^{21b})_pC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

x) —$(CR^{21a}R^{21b})_pC(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

x) —$(CR^{21a}R^{21b})_pN(R^{20})_2$; for example, —$NH_2$, —$CH_2NH_2$, —$NHCH_3$, —$CH_2NHCH_3$, —$N(CH_3)_2$, and —$CH_2N(CH_3)_2$;

xi) halogen; —F, —Cl, —Br, and —I;

xii) —$(CR^{21a}R^{21b})_pCN$;

xiii) —$(CR^{21a}R^{21b})_pNO_2$;

xiv) —$(CH_jX_k)_hCH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;

xv) —$(CR^{21a}R^{21b})_pSR^{20}$; —SH, —$CH_2SH$, —$SCH_3$, —$CH_2SCH_3$, —$SC_6H_5$, and —$CH_2SC_6H_5$;

xvi) —$(CR^{21a}R^{21b})_pSO_2R^{20}$, for example, —$SO_2H$, —$CH_2SO_2H$, —$SO_2CH_3$, —$CH_2SO_2CH_3$, —$SO_2C_6H_5$, and —$CH_2SO_2C_6H_5$; and xvii) —$(CR^{21a}R^{21b})_pSO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{20}$ is independently hydrogen, substituted or unsubstituted $C_1$-$C_4$ linear, branched, or cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or branched alkyl; the index p is from 0 to 4.

An example of compounds of Formula (I) includes R units having the formula:

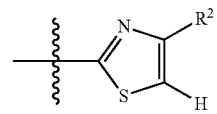

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), cyclopropyl ($C_3$), n-hexyl ($C_6$), 4-methylpentyl ($C_6$), and cyclohexyl ($C_6$).

Another example of compounds of Formula (I) include R units having the formula:

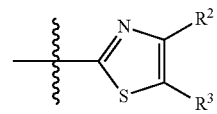

wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylthiazol-2-yl, 4-ethyl-5-methylthiazol-2-yl, 4-methyl-5-ethylthiazol-2-yl, and 4,5-diethylthiazol-2-yl.

A further example of compounds of Formula (I) includes R units wherein $R^3$ is hydrogen and $R^2$ is a substituted alkyl unit, said substitutions chosen from:
i) halogen: —F, —Cl, —Br, and —I;
ii) —$N(R^{11})_2$; and
iii) —$OR^{11}$;

wherein each $R^{11}$ is independently hydrogen or $C_1$-$C_4$ linear or branched alkyl. Non-limiting examples of units that can be a substitute for a $R^2$ or $R^3$ hydrogen atom on R units include —$CH_2F$, —$CHF_2$, —$CF_3$, —$CH_2CF_3$, —$CH_2CH_2CF_3$, —$CH_2Cl$, —$CH_2OH$, —$CH_2OCH_3$, —$CH_2CH_2OH$, —$CH_2CH_2OCH_3$, —$CH_2NH_2$, —$CH_2NHCH_3$, —$CH_2N(CH_3)_2$, and —$CH_2NH(CH_2CH_3)$.

Further non-limiting examples of units that can be a substitute for a $R^2$ or $R^3$ hydrogen atom on R units include 2,2-difluorocyclopropyl, 2-methoxycyclohexyl, and 4-chlorocyclohexyl.

A yet further example of compounds of Formula (I), R units include units wherein $R^3$ is hydrogen and $R^2$ is phenyl or substituted phenyl, wherein non-limiting examples of $R^2$ units include phenyl, 3,4-dimethylphenyl, 4-tert-butylphenyl, 4-cyclopropylphenyl, 4-diethylaminophenyl, 4-(trifluoromethyl)phenyl, 4-methoxyphenyl, 4-(difluoromethoxy)phenyl, 4-(trifluoromethoxy)phenyl, 3-chloropheny, 4-chlorophenyl, and 3,4-dichlorophenyl, which when incorporated into the definition of R affords the following R units 4-phenylthiazol-2-yl, 3,4-dimethylphenylthiazol-2-yl, 4-tert-butylphenylthiazol-2-yl, 4-cyclopropylphenylthiazol-2-yl, 4-diethylaminophenylthiazol-2-yl, 4-(trifluoromethyl)phenylthiazol-2-yl, 4-methoxyphenylthiazol-2-yl, 4-(difluoromethoxy)phenylthiazol-2-yl, 4-(trifluoromethoxy)phenylthiazol-2-yl, 3-chlorophenylthiazol-2-yl, 4-chlorophenylthiazol-2-yl, and 3,4-dichlorophenylthiazol-2-yl.

A still further example of compounds of Formula (I) includes R units wherein $R^2$ is chosen from hydrogen, methyl, ethyl, n-propyl, and iso-propyl and $R^3$ is phenyl or substituted phenyl. A non-limiting example of a R unit according to the fifth aspect of the first category of R units includes 4-methyl-5-phenylthiazol-2-yl and 4-ethyl-5-phenylthiazol-2-yl.

Another further example of compounds of Formula (I) includes R units wherein $R^3$ is hydrogen and $R^2$ is a substituted or unsubstituted heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Further non-limiting example of compounds of Formula (I) includes R units wherein $R^2$ is substituted or unsubstituted thiophen-2-yl, for example thiophen-2-yl, 5-chlorothiophen-2-yl, and 5-methylthiophen-2-yl.

A still further example of compounds of Formula (I) includes R units wherein $R^2$ is substituted or unsubstituted thiophen-3-yl, for example thiophen-3-yl, 5-chlorothiophen-3-yl, and 5-methylthiophen-3-yl.

Another example of compounds of Formula (I) includes R units wherein $R^2$ and $R^3$ are taken together to form a saturated or unsaturated ring having from 5 to 7 atoms. Non-limiting examples of the sixth aspect of the first category of R units include 5,6-dihydro-4H-cyclopenta[d]thiazol-2-yl and 4,5,6,7-tetrahydrobenzo[d]thiazol-2-yl.

Further examples of compounds of Formula (I) include R units that are thiazol-4-yl units having the formula:

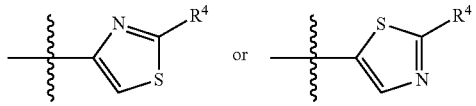

wherein $R^4$ is a unit chosen from:
i) hydrogen;
ii) substituted or unsubstituted $C_1$-$C_6$ linear, branched, or cyclic alkyl;
iii) substituted or unsubstituted $C_2$-$C_6$ linear, branched, or cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl; or
vii) substituted or unsubstituted $C_1$-$C_9$ heterocyclic.

The following are non-limiting examples of units that can substitute for one or more hydrogen atoms on the $R^4$ units. The following substituents, as well as others not herein described, are each independently chosen:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein below;
v) substituted or unsubstituted $C_1$-$C_9$ heteroaryl rings; as described herein below;
vi) $-(CR^{21a}R^{21b})_pOR^{20}$; for example, $-OH$, $-CH_2OH$, $-OCH_3$, $-CH_2OCH_3$, $-OCH_2CH_3$, $-CH_2OCH_2CH_3$, $-OCH_2CH_2CH_3$, and $-CH_2OCH_2CH_2CH_3$;
vii) $-(CR^{21a}R^{21b})_pC(O)R^{20}$; for example, $-COCH_3$, $-CH_2COCH_3$, $-COCH_2CH_3$, $-CH_2COCH_2CH_3$, $-COCH_2CH_2CH_3$, and $-CH_2COCH_2CH_2CH_3$;
viii) $-(CR^{21a}R^{21b})_pC(O)OR^{20}$; for example, $-CO_2CH_3$, $-CH_2CO_2CH_3$, $-CO_2CH_2CH_3$, $-CH_2CO_2CH_2CH_3$, $-CO_2CH_2CH_2CH_3$, and $-CH_2CO_2CH_2CH_2CH_3$;
xi) $-(CR^{21a}R^{21b})_pC(O)N(R^{20})_2$; for example, $-CONH_2$, $-CH_2CONH_2$, $-CONHCH_3$, $-CH_2CONHCH_3$, $-CON(CH_3)_2$, and $-CH_2CON(CH_3)_2$;
x) $-(CR^{21a}R^{21b})_pN(R^{20})_2$; for example, $-NH_2$, $-CH_2NH_2$, $-NHCH_3$, $-CH_2NHCH_3$, $-N(CH_3)_2$, and $-CH_2N(CH_3)_2$;
xi) halogen; $-F$, $-Cl$, $-Br$, and $-I$;
xii) $-(CR^{21a}R^{21b})_pCN$;
xiii) $-(CR^{21a}R^{21b})_pNO_2$;
xiv) $-(CH_jX_k)_hCH_jX_k$; wherein X is halogen, the index j is an integer from 0 to 2, j+k=3, the index j' is an integer from 0 to 2, j'+k'=2, the index h is from 0 to 6; for example, $-CH_2F$, $-CHF_2$, $-CF_3$, $-CH_2CF_3$, $-CHFCF_3$, $-CCl_3$, or $-CBr_3$;
xv) $-(CR^{21a}R^{21b})_pSR^{20}$; $-SH$, $-CH_2SH$, $-SCH_3$, $-CH_2SCH_3$, $-SC_6H_5$, and $-CH_2SC_6H_5$;
xvi) $-(CR^{21a}R^{21b})_pSO_2R^{20}$; for example, $-SO_2H$, $-CH_2SO_2H$, $-SO_2CH_3$, $-CH_2SO_2CH_3$, $-SO_2C_6H_5$, and $-CH_2SO_2C_6H_5$; and
xvii) $-(CR^{21a}R^{21b})_pSO_3R^{20}$; for example, $-SO_3H$, $-CH_2SO_3H$, $-SO_3CH_3$, $-CH_2SO_3CH_3$, $-SO_3C_6H_5$, and $-CH_2SO_3C_6H_5$;

wherein each $R^{20}$ is independently hydrogen, substituted or unsubstituted $C_1$-$C_4$ linear, branched, or cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or branched alkyl; the index p is from 0 to 4.

An example of compounds of Formula (I) includes R units wherein $R^4$ is hydrogen.

A further example of compounds of Formula (I) includes R units wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methylthiazol-4-yl, 2-ethylthiazol-4-yl, 2-(n-propyl)thiazol-4-yl, and 2-(iso-propyl)thiazol-4-yl.

A still further example of compounds of Formula (I) includes R units wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

Yet further example of compounds of Formula (I) includes R units wherein $R^4$ is substituted or unsubstituted heteroaryl, non-limiting examples of which include thiophen-2-yl, thiophen-3-yl, thiazol-2-yl, thiazol-4-yl, thiazol-5-yl, 2,5- dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Another example of 5-member ring R units includes substituted or unsubstituted imidazolyl units having the formula:

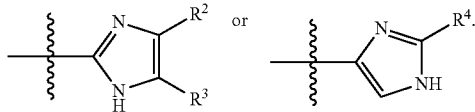

One example of imidazolyl R units includes imidazol-2-yl units having the formula:

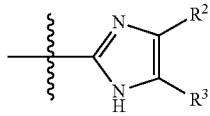

wherein $R^2$ and $R^3$ are each independently chosen from:
  i) hydrogen;
  ii) substituted or unsubstituted $C_1$-$C_6$ linear, branched, or cyclic alkyl;
  iii) substituted or unsubstituted $C_2$-$C_6$ linear, branched, or cyclic alkenyl;
  iv) substituted or unsubstituted $C_2$-$C_6$ linear or branched alkynyl;
  v) substituted or unsubstituted $C_6$ or $C_{10}$ aryl;
  vi) substituted or unsubstituted $C_1$-$C_9$ heteroaryl;
  vii) substituted or unsubstituted $C_1$-$C_9$ heterocyclic; or
  viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the $R^2$ and $R^3$ units. The following substituents, as well as others not herein described, are each independently chosen:
  i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
  ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
  iii) substituted or unsubstituted $C_6$ or $C_{10}$ alkylenearyl; for example, benzyl, 2-phenylethyl, naphthylen-2-ylmethyl;
  iv) substituted or unsubstituted $C_1$-$C_9$ heterocyclic rings; as described herein;
  v) substituted or unsubstituted $C_1$-$C_9$ heteroaryl rings; as described herein;
  vi) —$(CR^{21a}R^{21b})_zOR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
  vii) —$(CR^{21a}R^{21b})_zC(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
  viii) —$(CR^{21a}R^{21b})_zC(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
  xii) —$(CR^{21a}R^{21b})_zC(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
  x) —$(CR^{21a}R^{21b})_zN(R^{20})_2$; for example, —$NH_2$, —$CH_2NH_2$, —$NHCH_3$, —$CH_2NHCH_3$, —$N(CH_3)_2$, and —$CH_2N(CH_3)_2$;
  xi) halogen; —F, —Cl, —Br, and —I;
  xii) —$(CR^{21a}R^{21b})_zCN$;
  xiii) —$(CR^{21a}R^{21b})_zNO_2$;
  xiv) —$(CH_jX_k)_hCH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
  xv) —$(CR^{21a}R^{21b})_zSR^{20}$; —SH, —$CH_2SH$, —$SCH_3$, —$CH_2SCH_3$, —$SC_6H_5$, and —$CH_2SC_6H_5$;
  xvi) —$(CR^{21a}R^{21b})_zSO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
  xvii) —$(CR^{21a}R^{21b})_zSO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;
wherein each $R^{20}$ is independently hydrogen, substituted or unsubstituted $C_1$-$C_4$ linear, branched, or cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or branched alkyl; the index p is from 0 to 4.

One example of R units includes compounds wherein R units have the formula:

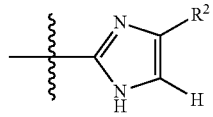

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

Another example of R units includes compounds wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylimidazol-2-yl, 4-ethyl-5-methylimidazol-2-yl, 4-methyl-5-ethylimidazol-2-yl, and 4,5-diethylimidazol-2-yl.

An example of R units includes compounds wherein $R^3$ is hydrogen and $R^2$ is a substituted alkyl unit chosen, said substitutions chosen from:
  i) halogen: —F, —Cl, —Br, and —I;
  ii) —$N(R^{11})_2$; and
  iii) —$OR^{11}$;
wherein each $R^{11}$ is independently hydrogen or $C_1$-$C_4$ linear or branched alkyl.

Non-limiting examples of units comprising this embodiment of R includes: —$CH_2F$, —$CHF_2$, —$CF_3$, —$CH_2CF_3$, —$CH_2Cl$, —$CH_2OH$, —$CH_2OCH_3$, —$CH_2CH_2OH$, —$CH_2CH_2OCH_3$, —$CH_2NH_2$, —$CH_2NHCH_3$, —$CH_2N(CH_3)_2$, and —$CH_2NH(CH_2CH_3)$.

A yet further example of R units include units wherein $R^3$ is hydrogen and $R^2$ is phenyl.

A still further example of R units include units wherein $R^3$ is hydrogen and $R^2$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Z Units

Z is a unit having the formula:

$-(L)_n-R^1$ $R^1$ is chosen from:
i) hydrogen;
ii) hydroxyl;
iii) amino;
iv) substituted or unsubstituted $C_1$-$C_6$ linear, branched or cyclic alkyl;
v) substituted or unsubstituted $C_1$-$C_6$ linear, branched or cyclic alkoxy;
vi) substituted or unsubstituted $C_6$ or $C_{10}$ aryl;
vii) substituted or unsubstituted $C_1$-$C_9$ heterocyclic rings; or
viii) substituted or unsubstituted $C_1$-$C_9$ heteroaryl rings.

The following are non-limiting examples of units that can substitute for one or more hydrogen atoms on the $R^1$ units. The following substituents, as well as others not herein described, are each independently chosen:

i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein;
v) substituted or unsubstituted $C_1$-$C_9$ heteroaryl rings; as described herein;
vi) $-(CR^{31a}R^{31b})_qOR^{30}$; for example, $-OH$, $-CH_2OH$, $-OCH_3$, $-CH_2OCH_3$, $-OCH_2CH_3$, $-CH_2OCH_2CH_3$, $-OCH_2CH_2CH_3$, and $-CH_2OCH_2CH_2CH_3$;
vii) $-(CR^{31a}R^{31b})_qC(O)R^{30}$; for example, $-COCH_3$, $-CH_2COCH_3$, $-COCH_2CH_3$, $-CH_2COCH_2CH_3$, $-COCH_2CH_2CH_3$, and $-CH_2COCH_2CH_2CH_3$;
viii) $-(CR^{31a}R^{31b})_qC(O)OR^{30}$; for example, $-CO_2CH_3$, $-CH_2CO_2CH_3$, $-CO_2CH_2CH_3$, $-CH_2CO_2CH_2CH_3$, $-CO_2CH_2CH_2CH_3$, and $-CH_2CO_2CH_2CH_2CH_3$;
xiii) $-(CR^{31a}R^{31b})_qC(O)N(R^{30})_2$; for example, $-CONH_2$, $-CH_2CONH_2$, $-CONHCH_3$, $-CH_2CONHCH_3$, $-CON(CH_3)_2$, and $-CH_2CON(CH_3)_2$;
x) $-(CR^{31a}R^{31b})_qN(R^{30})_2$; for example, $-NH_2$, $-CH_2NH_2$, $-NHCH_3$, $-CH_2NHCH_3$, $-N(CH_3)_2$, and $-CH_2N(CH_3)_2$;
xi) halogen; $-F$, $-Cl$, $-Br$, and $-I$;
xii) $-(CR^{31a}R^{31b})_qCN$;
xiii) $-(CR^{31a}R^{31b})_qNO_2$;
xiv) $-(CH_jX_k)_hCH_{j'}X_{k'}$; wherein X is halogen, the index j is an integer from 0 to 2, j+k=3, the index j' is an integer from 0 to 2, j'+k'=2, the index h is from 0 to 6; for example, $-CH_2F$, $-CHF_2$, $-CF_3$, $-CH_2CF_3$, $-CHFCF_3$, $-CCl_3$, or $-CBr_3$;
xv) $-(CR^{31a}R^{31b})_qSR^{30}$; $-SH$, $-CH_2SH$, $-SCH_3$, $-CH_2SCH_3$, $-SC_6H_5$, and $-CH_2SC_6H_5$;
xvi) $-(CR^{31a}R^{31b})_qSO_2R^{30}$; for example, $-SO_2H$, $-CH_2SO_2H$, $-SO_2CH_3$, $-CH_2SO_2CH_3$, $-SO_2C_6H_5$, and $-CH_2SO_2C_6H_5$; and
xvii) $-(CR^{31a}R^{31b})_qSO_3R^{30}$; for example, $-SO_3H$, $-CH_2SO_3H$, $-SO_3CH_3$, $-CH_2SO_3CH_3$, $-SO_3C_6H_5$, and $-CH_2SO_3C_6H_5$;

wherein each $R^{30}$ is independently hydrogen, substituted or unsubstituted $C_1$-$C_6$ linear, branched, or cyclic alkyl, phenyl, benzyl, heterocyclic, or heteroaryl; or two $R^{30}$ units can be taken together to form a ring comprising 3-7 atoms; $R^{31a}$ and $R^{31b}$ are each independently hydrogen or $C_1$-$C_4$ linear or branched alkyl; the index q is from 0 to 4.

One example of $R^1$ units includes substituted or unsubstituted phenyl ($C_6$ aryl) units, wherein each substitution is independently chosen from: halogen, $C_1$-$C_4$ linear, branched alkyl, or cyclic alkyl, $-OR^{11}$, $-CN$, $-N(R^{11})_2$, $-CO_2R^{11}$, $-C(O)N(R^{11})_2$, $-NR^{11}C(O)R^{11}$, $-NO_2$, and $-SO_2R^{11}$; each $R^{11}$ is independently hydrogen; substituted or unsubstituted $C_1$-$C_4$ linear, branched, cyclic alkyl, alkenyl, or alkynyl; substituted or unsubstituted phenyl or benzyl; or two $R^{11}$ units can be taken together to form a ring comprising from 3-7 atoms.

Another example of $R^1$ units includes substituted $C_6$ aryl units chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl.

A further example of $R^1$ units includes substituted or unsubstituted $C_6$ aryl units chosen from 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, and 2,4,6-trichlorophenyl.

A yet further example of $R^1$ units includes substituted $C_6$ aryl units chosen from 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Another still further example of $R^1$ units includes substituted $C_6$ aryl units chosen from 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

$R^1$ can comprise heteroaryl units. Non-limiting examples of heteroaryl units include:

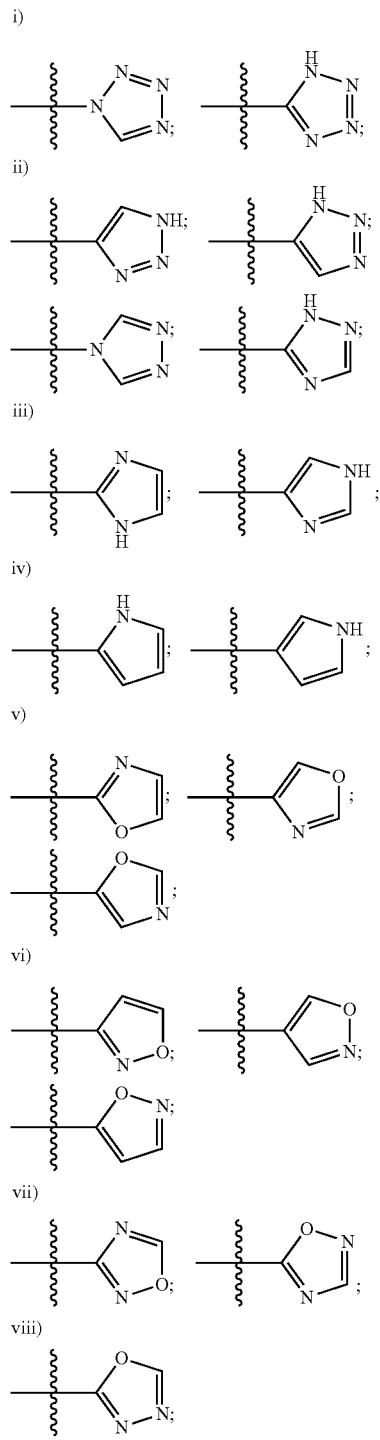
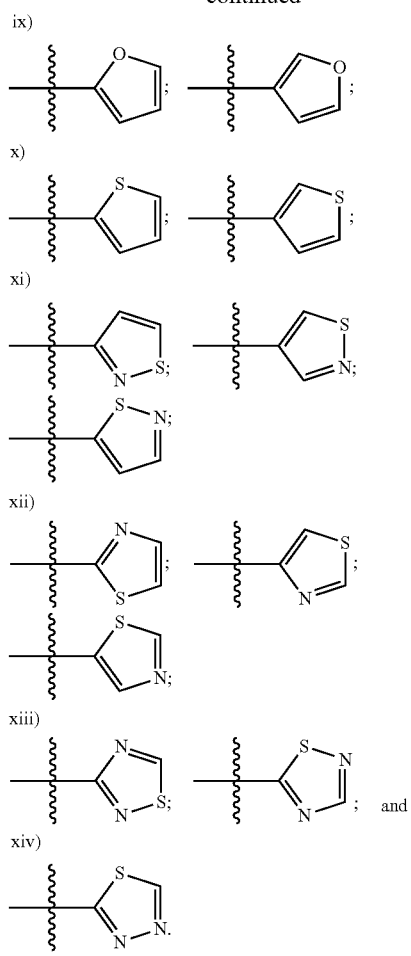

$R^1$ heteroaryl units can be substituted or unsubstituted. Non-limiting examples of units that can substitute for hydrogen include units chosen from:
  i) $C_1$-$C_6$ linear, branched, and cyclic alkyl;
  ii) substituted or unsubstituted phenyl and benzyl;
  iii) substituted of unsubstituted $C_1$-$C_9$ heteroaryl;
  iv) —C(O)$R^9$; and
  v) —NHC(O)$R^9$;
wherein $R^9$ is $C_1$-$C_6$ linear and branched alkyl; $C_1$-$C_6$ linear and branched alkoxy; or —NHCH$_2$C(O)$R^{10}$; $R^{10}$ is chosen from hydrogen, methyl, ethyl, and tert-butyl.

An example of $R^1$ relates to units substituted by an alkyl unit chosen from methyl, ethyl, n-propyl, iso-propyl, n-butyl, iso-butyl, sec-butyl, and tert-butyl.

Another example of $R^1$ includes units that are substituted by substituted or unsubstituted phenyl and benzyl, wherein the phenyl and benzyl substitutions are chosen from one or more:
  i) halogen;
  ii) $C_1$-$C_3$ alkyl;
  iii) $C_1$-$C_3$ alkoxy;
  iv) —CO$_2R^{11}$; and
  v) —NHCOR$^{16}$;
wherein $R^{11}$ and $R^{16}$ are each independently hydrogen, methyl, or ethyl.

Another example of $R^1$ relates to phenyl and benzyl units substituted by a carboxy unit having the formula —C(O)$R^9$; $R^9$ is chosen from methyl, methoxy, ethyl, and ethoxy.

A further example of $R^1$ includes phenyl and benzyl units substituted by an amide unit having the formula —NHC(O)$R^9$; $R^9$ is chosen from methyl, methoxy, ethyl, ethoxy, tert-butyl, and tert-butoxy.

A yet further example of $R^1$ includes phenyl and benzyl units substituted by one or more fluoro or chloro units.

L Units

L is a linking unit which is present when the index n is equal to 1, but is absent when the index n is equal to 0. L units have the formula:

$$-[Q]_y[C(R^{5a}R^{5b})]_x[Q^1]_z[C(R^{6a}R^{6b})]_w-$$

wherein Q and $Q^1$ are each independently:
i) —C(O)—;
ii) —NH—;
iii) —C(O)NH—;
iv) —NHC(O)—;
v) —NHC(O)NH—;
vi) —NHC(O)O—;
vii) —C(O)O—;
viii) —C(O)NHC(O)—;
ix) —O—;
x) —S—;
xi) —SO$_2$—;
xii) —C(=NH)—;
xiii) —C(=NH)NH—;
xiv) —NHC(=NH)—; or
xv) —NHC(=NH)NH—.

When the index y is equal to 1, Q is present. When the index y is equal to 0, Q is absent.

When the index z is equal to 1, $Q^1$ is present. When the index z is equal to 0, $Q^1$ is absent.

$R^{5a}$ and $R^{5b}$ are each independently:
i) hydrogen;
ii) hydroxy;
iii) halogen;
iv) $C_1$-$C_6$ substituted or unsubstituted linear or branched alkyl; or
v) a unit having the formula:

$$-[C(R^{7a}R^{7b})]_tR^8$$

wherein $R^{7a}$ and $R^{7b}$ are each independently:
i) hydrogen; or
ii) substituted or unsubstituted $C_1$-$C_6$ linear, branched, or cyclic alkyl.

$R^8$ is:
i) hydrogen;
ii) substituted or unsubstituted $C_1$-$C_6$ linear, branched, or cyclic alkyl;
iii) substituted or unsubstituted $C_6$ or $C_{10}$ aryl;
iv) substituted or unsubstituted $C_1$-$C_9$ heteroaryl; or
v) substituted or unsubstituted $C_1$-$C_9$ heterocyclic.

$R^{6a}$ and $R^{6b}$ are each independently:
i) hydrogen; or
ii) $C_1$-$C_4$ linear or branched alkyl.

The indices t, w and x are each independently from 0 to 4.

The following are non-limiting examples of units that can substitute for one or more hydrogen atoms on $R^{5a}$, $R^{5b}$, $R^{7a}$, $R^{7b}$, and $R^8$ units. The following substituents, as well as others not herein described, are each independently chosen:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein below;
v) substituted or unsubstituted $C_1$-$C_9$ heteroaryl rings; as described herein below;
vi) —(CR$^{41a}$R$^{41b}$)$_r$OR$^{40}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;
vii) —(CR$^{41a}$R$^{41b}$)$_r$C(O)R$^{40}$; for example, —COCH$_3$, —CH$_2$COCH$_3$, —COCH$_2$CH$_3$, —CH$_2$COCH$_2$CH$_3$, —COCH$_2$CH$_2$CH$_3$, and —CH$_2$COCH$_2$CH$_2$CH$_3$;
viii) —(CR$^{41a}$R$^{41b}$)$_r$C(O)OR$^{40}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;
xiv) —(CR$^{41a}$R$^{41b}$)$_r$C(O)N(R$^{40}$)$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;
x) —(CR$^{41a}$R$^{41b}$)$_r$N(R$^{40}$)$_2$; for example, —NH$_2$, —CH$_2$NH$_2$, —NHCH$_3$, —CH$_2$NHCH$_3$, —N(CH$_3$)$_2$, and —CH$_2$N(CH$_3$)$_2$;
xi) halogen; —F, —Cl, —Br, and —I;
xii) —(CR$^{41a}$R$^{41b}$)$_r$CN;
xiii) —(CR$^{41a}$R$^{41b}$)$_r$NO$_2$;
xiv) —(CH$_j$X$_k$)$_h$CH$_{j'}$X$_{k'}$; wherein X is halogen, the index j is an integer from 0 to 2, j+k=3, the index j' is an integer from 0 to 2, j'+k'=2, the index h is from 0 to 6; for example, —CH$_2$F, —CHF$_2$, —CF$_3$, —CH$_2$CF$_3$, —CHFCF$_3$, —CCl$_3$, or —CBr$_3$;
xv) —(CR$^{41a}$R$^{41b}$)$_r$SR$^{40}$; —SH, —CH$_2$SH, —SCH$_3$, —CH$_2$SCH$_3$, —SC$_6$H$_5$, and —CH$_2$SC$_6$H$_5$;
xvi) —(CR$^{41a}$R$^{41b}$)$_r$SO$_2$R$^{40}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and
xvii) —(CR$^{41a}$R$^{41b}$)$^r$SO$_3$R$^{40}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each $R^{40}$ is independently hydrogen, substituted or unsubstituted $C_1$-$C_6$ linear, branched, or cyclic alkyl, phenyl, benzyl, heterocyclic, or heteroaryl; or two $R^{40}$ units can be taken together to form a ring comprising 3-7 atoms; $R^{41a}$ and $R^{41b}$ are each independently hydrogen or $C_1$-$C_4$ linear or branched alkyl; the index r is from 0 to 4.

One aspect of L units relates to units having the formula:

$$-C(O)[C(R^{5a}R^{5b})]_xNHC(O)-$$

wherein $R^{5a}$ is hydrogen, substituted or unsubstituted $C_1$-$C_4$ alkyl, substituted or unsubstituted phenyl, and substituted or unsubstituted heteroaryl; and the index x is 1 or 2. One embodiment relates to linking units having the formula:

$$-C(O)[C(R^{5a}H)]NHC(O)O-\qquad\text{i)}$$

$$-C(O)[C(R^{5a}H)][CH_2]NHC(O)O-\qquad\text{ii)}$$

$$-C(O)[CH_2][C(R^{5a}H)]NHC(O)O-\qquad\text{iii)}$$

$$-C(O)[C(R^{5a}H)]NHC(O)-\qquad\text{iv)}$$

—C(O)[C(R$^{5a}$H)][CH$_2$]NHC(O)—; or    v)

—C(O)[CH$_2$][C(R$^{5a}$H)]NHC(O)—;    vi)

wherein R$^{5a}$ is:
i) hydrogen;
ii) methyl;
iii) ethyl;
iv) isopropyl;
v) phenyl;
vi) benzyl;
vii) 4-hydroxybenzyl;
viii) hydroxymethyl; or
ix) 1-hydroxyethyl.

When the index x is equal to 1, this embodiment provides the following non-limiting examples of L units:

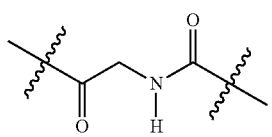

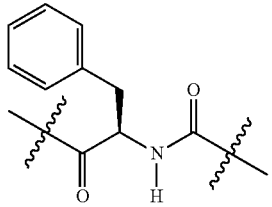

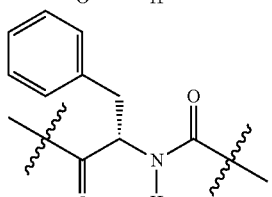

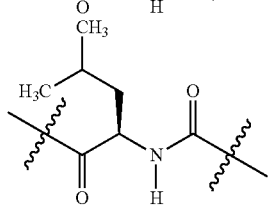

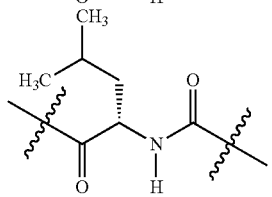

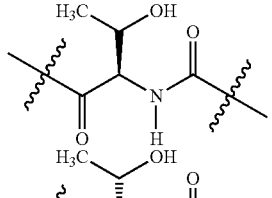
; and

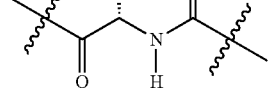

When the index x is equal to 2, this embodiment provides the following non-limiting examples of L units:

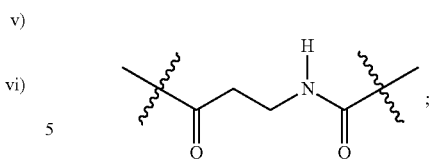

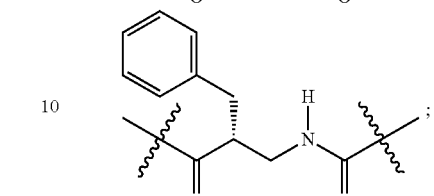

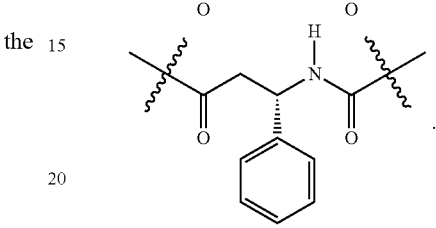

Another embodiment of L units includes units wherein Q is —C(O)—, the indices x and z are equal to 0, w is equal to 1 or 2, a first R$^{6a}$ unit chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl; a second R$^{6a}$ unit is hydrogen and R$^{6b}$ units are hydrogen. For example a linking unit having the formula:

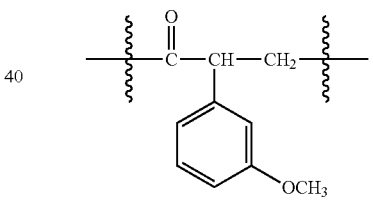

A further example of this embodiment of L includes a first R$^{6a}$ unit as depicted herein above that is a substituted or unsubstituted heteroaryl unit as described herein above.

A yet further example of this embodiment of L includes units having the formula:

—C(O)[C(R$^{6a}$R$^{6b}$)]$_w$—;

wherein R$^{6a}$ and R$^{6b}$ are hydrogen and the index w is equal to 1 or 2; said units chosen from:
i) —C(O)CH$_2$—; and
ii) —C(O)CH$_2$CH$_2$—.

Another embodiment of L units includes units having the formula:

—C(O)[C(R$^{5a}$R$^{5b}$)]$_x$C(O)—;

wherein R$^{5a}$ and R$^{5b}$ are hydrogen and the index x is equal to 1 or 2; said units chosen from:
i) —C(O)CH$_2$C(O)—; and
ii) —C(O)CH$_2$CH$_2$C(O)—.

A still further embodiment of L units includes units having the formula:

wherein $R^{5a}$ and $R^{5b}$ are hydrogen and the index w is equal to 0, 1 or 2; said units chosen from:
 ii) —C(O)NH—;
 ii) —C(O)NHCH$_2$—; and
 iii) —C(O)NHCH$_2$CH$_2$—.

A yet still further example of L units includes units having the formula:

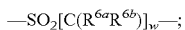

wherein $R^{8a}$ and $R^{8b}$ are hydrogen or methyl and the index w is equal to 0, 1 or 2; said units chosen from:
 i) —SO$_2$—;
 ii) —SO$_2$CH$_2$—; and
 iii) —SO$_2$CH$_2$CH$_2$—.

Tie-2 Signal Amplifiers

The disclosed compounds (analogs) are arranged into several Categories to assist the formulator in applying a rational synthetic strategy for the preparation of analogs which are not expressly exampled herein. The arrangement into categories does not imply increased or decreased efficacy for any of the compositions of matter described herein.

A described herein above the disclosed compounds include all pharmaceutically acceptable salt forms. A compound having the formula:

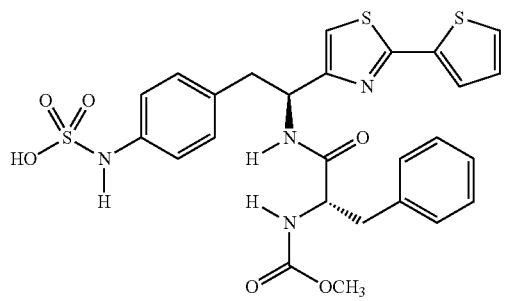 [SMILES: COC(=O)N[C@@H](Cc1ccccc1)C(=O)N[C@@H](Cc1ccc(NS(=O)(=O)O)cc1)c1csc(-c2cccs2)n1]

can form salts, for example, a salt of the sulfamic acid:

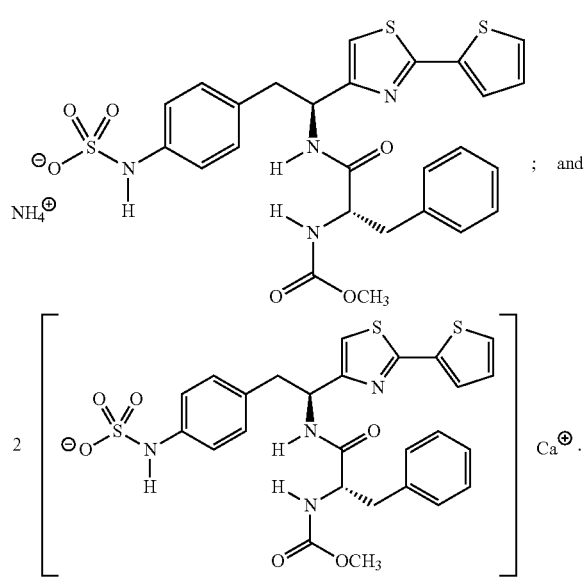

The compounds can also exist in a zwitterionic form, for example:

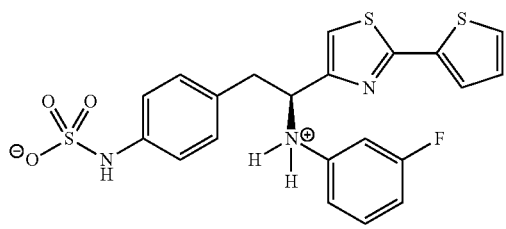

or
as a salt of a strong acid, for example:

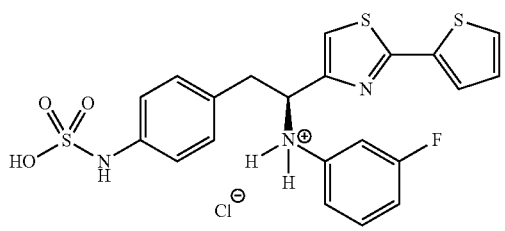

The first aspect of Category I of the present disclosure relates to compounds wherein R is a substituted or unsubstituted thiazol-2-yl unit having the formula:

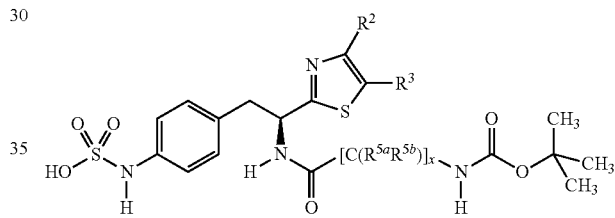

one embodiment of which relates to inhibitors having the formula:

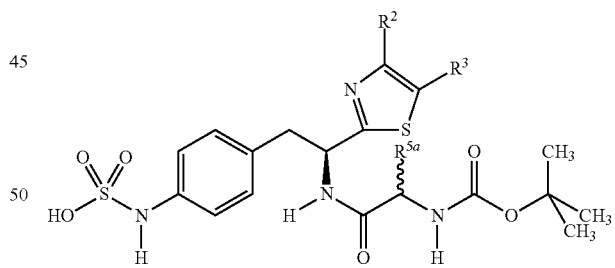

wherein R units are thiazol-2-yl units, that when substituted, are substituted with $R^2$ and $R^3$ units. R and $R^{5a}$ units are further described in Table I.

TABLE I

| No. | R | $R^{5a}$ |
|-----|---|----------|
| A1 | thiazol-2-yl | (S)-benzyl |
| A2 | 4-methylthiazol-2-yl | (S)-benzyl |
| A3 | 4-ethylthiazol-2-yl | (S)-benzyl |
| A4 | 4-propylthiazol-2-yl | (S)-benzyl |
| A5 | 4-iso-propylthiazol-2-yl | (S)-benzyl |
| A6 | 4-cyclopropylthiazol-2-yl | (S)-benzyl |

TABLE I-continued

| No. | R | R$^{5a}$ |
|---|---|---|
| A7 | 4-butylthiazol-2-yl | (S)-benzyl |
| A8 | 4-tert-butylthiazol-2-yl | (S)-benzyl |
| A9 | 4-cyclohexylthiazol-2-yl | (S)-benzyl |
| A10 | 4-(2,2,2-trifluoroethyl)thiazol-2-yl | (S)-benzyl |
| A11 | 4-(3,3,3-trifluoropropyl)thiazol-2-yl | (S)-benzyl |
| A12 | 4-(2,2-difluorocyclopropyl)thiazol-2-yl | (S)-benzyl |
| A13 | 4-(methoxymethyl)thiazol-2-yl | (S)-benzyl |
| A14 | 4-(carboxylic acid ethyl ester)thiazol-2-yl | (S)-benzyl |
| A15 | 4,5-dimethylthiazol-2-yl | (S)-benzyl |
| A16 | 4-methyl-5-ethylthiazol-2-yl | (S)-benzyl |
| A17 | 4-phenylthiazol-2-yl | (S)-benzyl |
| A18 | 4-(4-chlorophenyl)thiazol-2-yl | (S)-benzyl |
| A19 | 4-(3,4-dimethylphenyl)thiazol-2-yl | (S)-benzyl |
| A20 | 4-methyl-5-phenylthiazol-2-yl | (S)-benzyl |
| A21 | 4-(thiophen-2-yl)thiazol-2-yl | (S)-benzyl |
| A22 | 4-(thiophen-3-yl)thiazol-2-yl | (S)-benzyl |
| A23 | 4-(5-chlorothiophen-2-yl)thiazol-2-yl | (S)-benzyl |
| A24 | 5,6-dihydro-4H-cyclopenta[d]thiazol-2-yl | (S)-benzyl |
| A25 | 4,5,6,7-tetrahydrobenzo[d]thiazol-2-yl | (S)-benzyl |

The compounds encompassed within the first aspect of Category I of the present disclosure can be prepared by the procedure outlined in Scheme I and described in Example 1 herein below.

Scheme I

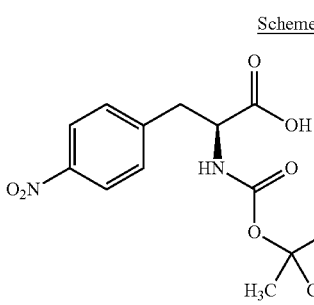

Reagents and conditions: (a) (i) (iso-butyl) OCOCl, NMM, DMF; 0° C., 20 min. (ii) NH$_3$; 0° C. for 30 min.

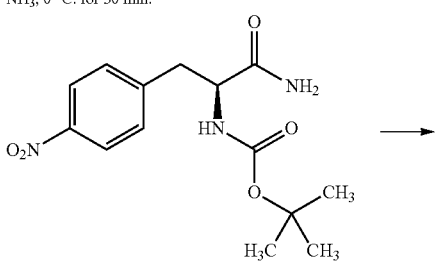

1

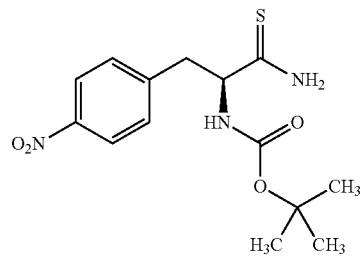

2

Reagents and conditions: (b) Lawesson's reagent, THF; rt, 3 hr.

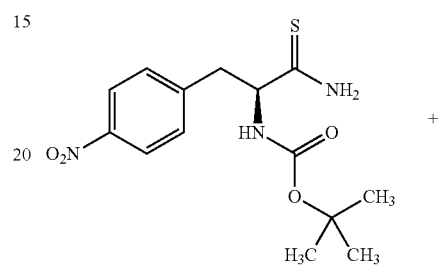

2

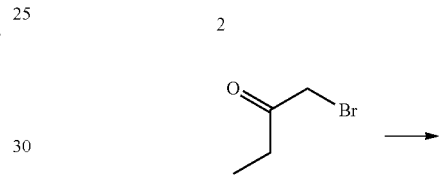

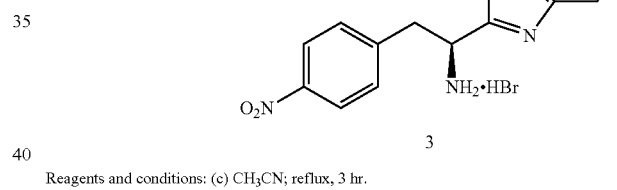

3

Reagents and conditions: (c) CH$_3$CN; reflux, 3 hr.

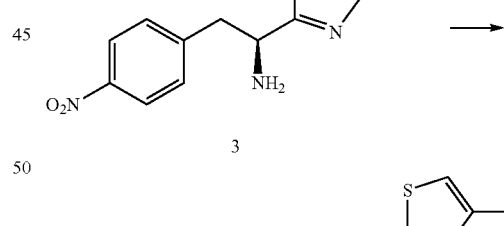

3

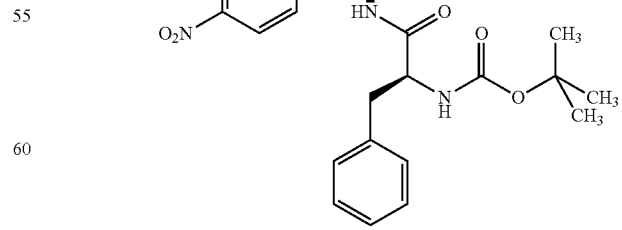

4

Reagents and conditions: (d) Boc-Phe, EDCI, HOBt, DIPEA, DMF; rt, 18 hr.

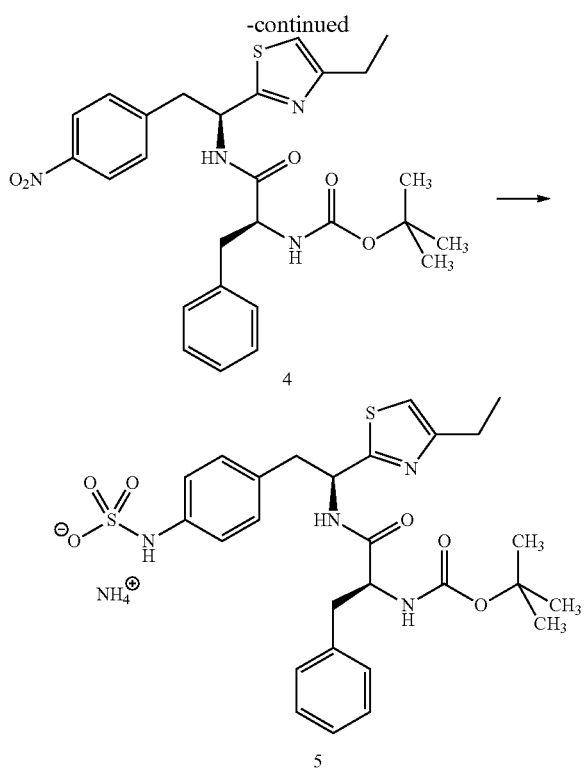

Reagents and conditions: (e) (i) H₂:Pd/C, MeOH; (ii) SO₂-pyridine, NH₄OH; rt, 2 hr.

EXAMPLE 1

4-{(S)-2-[(S)-2-(tert-Butoxycarbonylamino)-3-phenylpropanamido]-2-(4-ethylthiazol-2-yl)ethyl}phenylsulfamic acid (5)

Preparation of [1-(S)-carbamoyl-2-(4-nitrophenyl)ethyl-carbamic acid tert-butyl ester (1): To a 0° C. solution of 2-(S)-tert-butoxycarbonylamino-3-(4-nitrophenyl)-propionic acid and N-methylmorpholine (1.1 mL, 9.65 mmol) in DMF (10 mL) is added dropwise iso-butyl chloroformate (1.25 mL, 9.65 mmol). The mixture is stirred at 0° C. for 20 minutes after which NH₃ (g) is passed through the reaction mixture for 30 minutes at 0° C. The reaction mixture is concentrated and the residue dissolved in EtOAc, washed successively with 5% citric acid, water, 5% NaHCO₃, water and brine, dried (Na₂SO₄), filtered and concentrated in vacuo to a residue that is triturated with a mixture of EtOAc/petroleum ether to provide 2.2 g (74%) of the desired product as a white solid.

Preparation of [2-(4-nitrophenyl)-1-(S)-thiocarbamoyl-ethyl]carbamic acid tert-butyl ester (2): To a solution of [1-(S)-carbamoyl-2-(4-nitrophenyl)ethyl-carbamic acid tert-butyl ester, 1, (0.400 g, 1.29 mmol) in THF (10 mL) is added Lawesson's reagent (0.262 g. 0.65 mmol). The reaction mixture is stirred for 3 hours and concentrated to a residue which is purified over silica to provide 0.350 g (83%) of the desired product. ¹H NMR (300 MHz, CDCl₃) δ 8.29 (s, 1H), 8.10 (d. J=8.4 Hz, 2H), 8.01 (s, 1H), 7.42 (d, J=8.4 Hz, 2H), 5.70 (d, J=7.2 Hz, 1H), 4.85 (d, J=7.2 Hz, 1H), 3.11-3.30 (m, 1H), 1.21 (s, 9H).

Preparation of 1-(S)-(4-ethylthiazol-2-yl)-2-(4-nitrophenyl)ethyl amine (3): A mixture of [2-(4-nitrophenyl)-1-(S)-thiocarbamoylethyl]-carbamic acid tert-butyl ester, 2, (0.245 g, 0.753 mmol), 1-bromo-2-butanone (0.125 g, 0.828 mmol) in CH₃CN (5 mL) is refluxed 3 hours. The reaction mixture is cooled to room temperature and diethyl ether is added to the solution and the precipitate which forms is removed by filtration. The solid is dried under vacuum to afford 0.242 g (90% yield) of the desired product. ESI+ MS 278 (M+1).

Preparation of {1-[1-(4-ethylthiazol-2-yl)-2-(4-nitrophenyl)ethylcarbamoyl]-2-phenylethyl}carbamic acid tert-butyl ester (4): To a solution of 1-(S)-(4-ethylthiazol-2-yl)-2-(4-nitrophenyl)ethyl amine hydrobromide, 3, (0.393 g, 1.1 mmol), (S)-(2-tert-butoxycarbonylamino)-3-phenylpropionic acid (0.220 g, 0.828 mmol) and 1-hydroxybenzotriazole (HOBt) (0.127 g, 0.828 mmol) in DMF (10 mL) at 0° C., is added 1-(3-dimethylaminopropyl)-3-ethylcarbodiimide (EDCI) (0.159 g, 0.828 mmol) followed by diisopropylamine (0.204 g, 1.58 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.345 g of the desired product which is used without further purification. LC/MS ESI+ 525 (M+1).

Preparation of 4-{(S)-2-[(S)-2-(tert-butoxycarbonylamino)-3-phenylpropanamido]-2-(4-ethylthiazol-2-yl)ethyl}phenylsulfamic acid ammonium salt (5): {1-[1-(4-ethylthiazol-2-yl)-2-(4-nitrophenyl)ethylcarbamoyl]-2-phenylethyl}carbamic acid tert-butyl ester, 4, (0.345 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO₃-pyridine (0.314 g). The reaction is stirred at room temperature for 5 minutes after which a 7% solution of NH₄OH (50 mL) is added. The mixture is then concentrated and the resulting residue is purified by reverse phase chromatography to afford 0.222 g of the desired product as the ammonium salt. ¹H NMR (CD₃OD): δ 7.50-6.72 (m, 10H), 5.44-5.42 (d, 1H, J=6.0 Hz), 4.34 (s, 1H), 3.34-2.79 (m, 4H), 2.83-2.76 (q, 2H, J=7.2 Hz), 1.40 (s, 9H), 1.31 (t, 3H, J=7.5 Hz).

The disclosed inhibitors can also be isolated as the free acid. A non-limiting example of this procedure is described herein below in Example 4.

The following is a non-limiting example of compounds encompassed within this embodiment of the first aspect of Category I of the present disclosure.

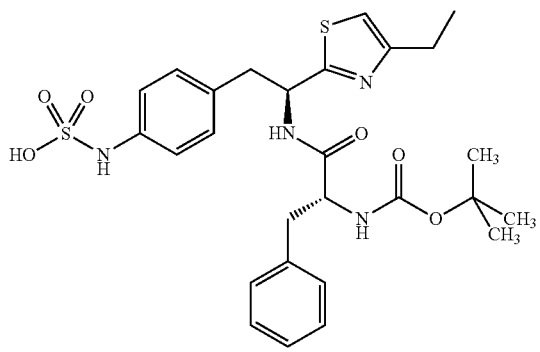 [SMILES: CCc1csc([C@H](Cc2ccc(NS(=O)(=O)O)cc2)NC(=O)[C@@H](Cc2ccccc2)NC(=O)OC(C)(C)C)n1]

4-{(S)-2-[(R)-2-(tert-butoxycarbonylamino)-3-phenylpropanamido]-2-(4-ethylthiazol-2-yl)ethyl}phenylsulfamic acid: $^1$H NMR (CD$_3$OD): δ 7.22-7.02 (m, 10H), 5.39 (s, 1H), 4.34 (s, 1H), 3.24-2.68 (m, 6H), 1.37 (s, 9H), 1.30 (t, 3H, J=7.5 Hz).

Another embodiment of this aspect of Category I relates to inhibitors having the formula:

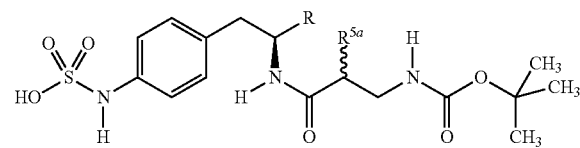

wherein R units and R$^{5a}$ units further described in Table II.

TABLE II

| No. | R | R$^{5a}$ |
|---|---|---|
| B26 | thiazol-2-yl | (S)-benzyl |
| B27 | 4-methylthiazol-2-yl | (S)-benzyl |
| B28 | 4-ethylthiazol-2-yl | (S)-benzyl |
| B29 | 4-propylthiazol-2-yl | (S)-benzyl |
| B30 | 4-iso-propylthiazol-2-yl | (S)-benzyl |
| B31 | 4-cyclopropylthiazol-2-yl | (S)-benzyl |
| B32 | 4-butylthiazol-2-yl | (S)-benzyl |
| B33 | 4-tert-butylthiazol-2-yl | (S)-benzyl |
| B34 | 4-cyclohexylthiazol-2-yl | (S)-benzyl |
| B35 | 4-(2,2,2-trifluoroethyl)thiazol-2-yl | (S)-benzyl |
| B36 | 4-(3,3,3-trifluoropropyl)thiazol-2-yl | (S)-benzyl |
| B37 | 4-(2,2-difluorocyclopropyl)thiazol-2-yl | (S)-benzyl |
| B38 | 4-(methoxymethyl)thiazol-2-yl | (S)-benzyl |
| B39 | 4-(carboxylic acid ethyl ester)thiazol-2-yl | (S)-benzyl |
| B40 | 4,5-dimethylthiazol-2-yl | (S)-benzyl |
| B41 | 4-methyl-5-ethylthiazol-2-yl | (S)-benzyl |
| B42 | 4-phenylthiazol-2-yl | (S)-benzyl |
| B43 | 4-(4-chlorophenyl)thiazol-2-yl | (S)-benzyl |
| B44 | 4-(3,4-dimethylphenyl)thiazol-2-yl | (S)-benzyl |
| B45 | 4-methyl-5-phenylthiazol-2-yl | (S)-benzyl |
| B46 | 4-(thiophen-2-yl)thiazol-2-yl | (S)-benzyl |
| B47 | 4-(thiophen-3-yl)thiazol-2-yl | (S)-benzyl |
| B48 | 4-(5-chlorothiophen-2-yl)thiazol-2-yl | (S)-benzyl |
| B49 | 5,6-dihydro-4H-cyclopenta[d]thiazol-2-yl | (S)-benzyl |
| B50 | 4,5,6,7-tetrahydrobenzo[d]thiazol-2-yl | (S)-benzyl |

The compounds of this embodiment can be prepared according to the procedure outlined above in Scheme I and described in Example 1 by substituting the appropriate Boc-β-amino acid for (S)-(2-tert-butoxycarbonylamino)-3-phenylpropionic acid in step (d).

The following are non-limiting examples of compounds according to this embodiment.

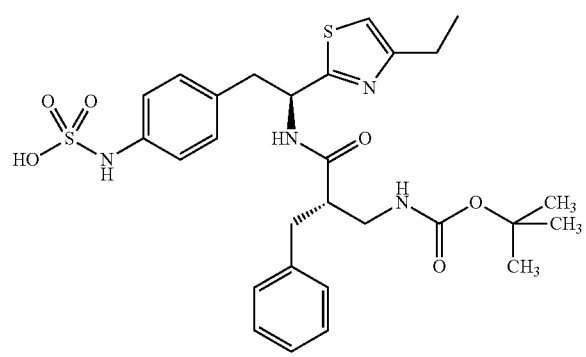 [SMILES: CCc1csc([C@H](Cc2ccc(NS(=O)(=O)O)cc2)NC(=O)[C@H](CNC(=O)OC(C)(C)C)Cc2ccccc2)n1]

{1-[1-(4-Ethylthiazol-2-yl)-(S)-2-(4-sulfoaminophenyl) ethylcarbamoyl]-(S)-2-phenylethyl}methyl carbamic acid tert-butyl ester: $^1$H NMR (300 MHz, MeOH-d$_4$) δ 8.36 (d, J=8.1 Hz, 1H), 7.04-7.22 (m, 9H), 5.45 (s, 1H), 3.01-3.26 (m, 2H), 2.60-2.88 (m, 4H), 2.33 (s, 3H), 1.30 (s, 9H).

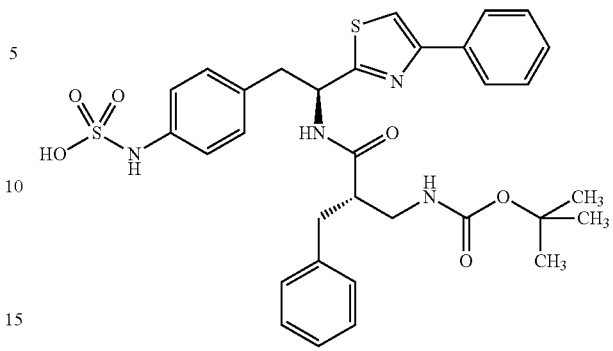

{1-[1-(4-Phenylthiazol-2-yl)-(S)-2-(4-sulfoaminophenyl) ethylcarbamoyl]-(S)-2-phenylethyl}methyl carbamic acid tert-butyl ester: $^1$H NMR (300 MHz, MeOH-d$_4$) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The second aspect of Category I of the present disclosure relates to compounds wherein R is a substituted or unsubstituted thiazol-4-yl having the formula:

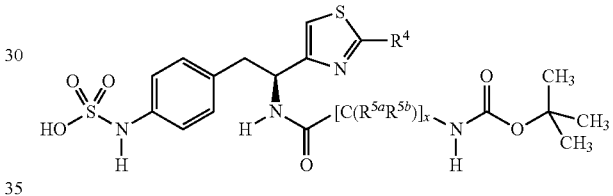

one embodiment of which relates to inhibitors having the formula:

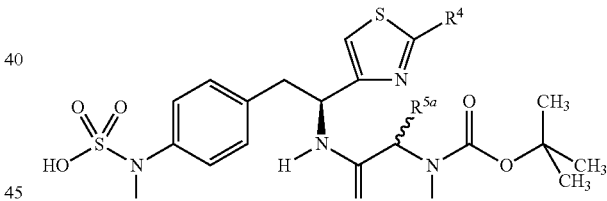

wherein R units and R$^{5a}$ units further described in Table III.

TABLE III

| No. | R | R$^{5a}$ |
|---|---|---|
| C51 | thiazol-4-yl | (S)-benzyl |
| C52 | 2-methylthiazol-4-yl | (S)-benzyl |
| C53 | 2-ethylthiazol-4-yl | (S)-benzyl |
| C54 | 2-propylthiazol-4-yl | (S)-benzyl |
| C55 | 2-iso-propylthiazol-4-yl | (S)-benzyl |
| C56 | 2-cyclopropylthiazol-4-yl | (S)-benzyl |
| C57 | 2-butylthiazol-4-yl | (S)-benzyl |
| C58 | 2-tert-butylthiazol-4-yl | (S)-benzyl |
| C59 | 2-cyclohexylthiazol-4-yl | (S)-benzyl |
| C60 | 2-(2,2,2-trifluoroethyl)thiazol-4-yl | (S)-benzyl |
| C61 | 2-(3,3,3-trifluoropropyl)thiazol-4-yl | (S)-benzyl |
| C62 | 2-(2,2-difluorocyclopropyl)thiazol-4-yl | (S)-benzyl |
| C63 | 2-phenylthiazol-4-yl | (S)-benzyl |
| C64 | 2-(4-chlorophenyl)thiazol-4-yl | (S)-benzyl |
| C65 | 2-(3,4-dimethylphenyl)thiazol-4-yl | (S)-benzyl |
| C66 | 2-(thiophen-2-yl)thiazol-4-yl | (S)-benzyl |
| C67 | 2-(thiophen-3-yl)thiazol-4-yl | (S)-benzyl |
| C68 | 2-(3-chlorothiophen-2-yl)thiazol-4-yl | (S)-benzyl |

TABLE III-continued

| No. | R | R5a |
|---|---|---|
| C69 | 2-(3-methylthiophen-2-yl)thiazol-4-yl | (S)-benzyl |
| C70 | 2-(2-methylthiazol-4-yl)thiazol-4-yl | (S)-benzyl |
| C71 | 2-(furan-2-yl)thiazol-4-yl | (S)-benzyl |
| C72 | 2-(pyrazin-2-yl)thiazol-4-yl | (S)-benzyl |
| C73 | 2-[(2-methyl)pyridin-5-yl]thiazol-4-yl | (S)-benzyl |
| C74 | 2-(4-chlorobenzenesulfonylmethyl)thiazol-4-yl | (S)-benzyl |
| C75 | 2-(tert-butylsulfonylmethyl)thiazol-4-yl | (S)-benzyl |

The compounds encompassed within the second aspect of Category I of the present disclosure can be prepared by the procedure outlined in Scheme II and described in Example 2 herein below.

Scheme II

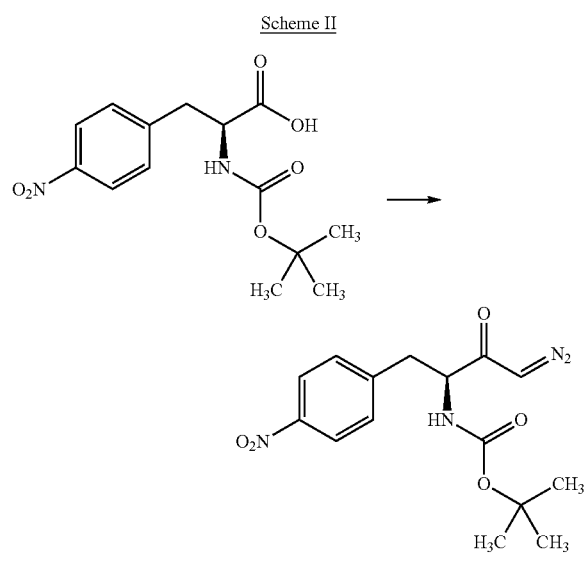

Reagents and conditions: (a) (i) (iso-butyl) OCOCl, Et3N, THF; 0° C., 20 min. (ii) CH2N2; room temp for 3 hours.

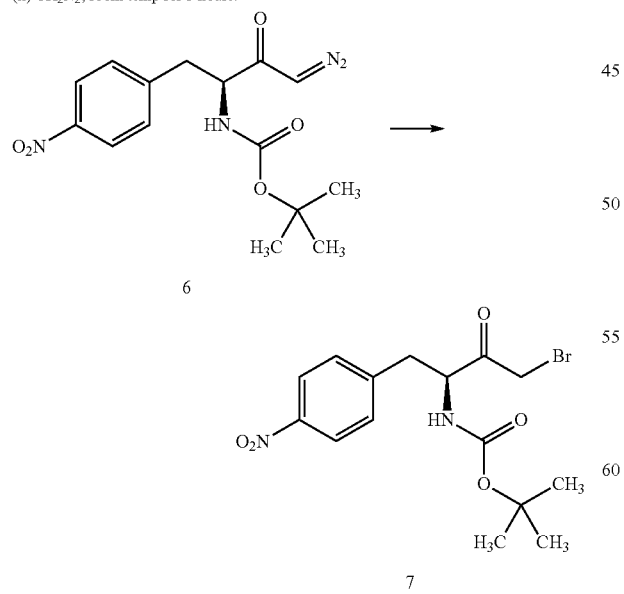

Reagents and conditions: (b) 48% HBr, THF; 0° C., 1.5 hr.

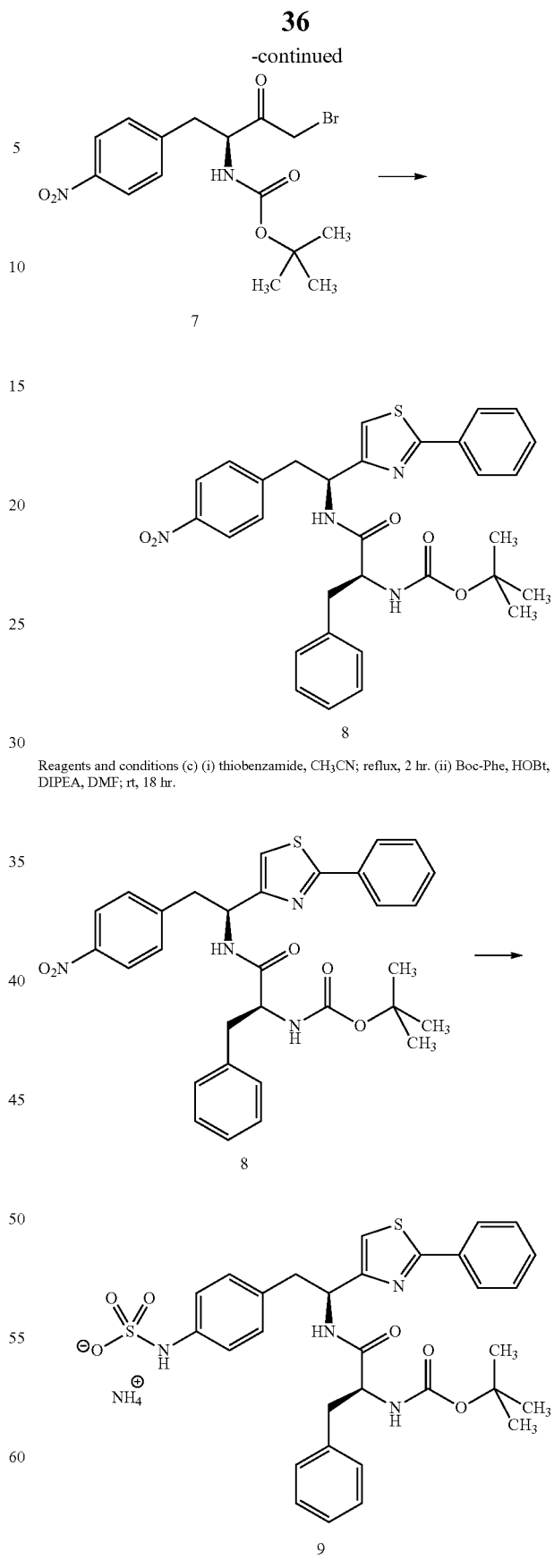

Reagents and conditions (c) (i) thiobenzamide, CH3CN; reflux, 2 hr. (ii) Boc-Phe, HOBt, DIPEA, DMF; rt, 18 hr.

Reagents and conditions: (d) (i) H2:Pd/C, MeOH; (ii) SO3-pyridine, NH4OH; rt, 12 hr.

EXAMPLE 2

(4-((S)-2-((S)-2-((tert-Butoxycarbonyl)amino)-3-phenylpropanamido)-2-(2-phenylthiazol-4-yl)ethyl)phenyl)sulfamic acid (9)

Preparation of (S)-[3-diazo-1-(4-nitrobenzyl)-2-oxo-propyl]-carbamic acid tert-butyl ester (6): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by isobutyl chloroformate (0.57 mL, 4.4 mmol). The reaction mixture is stirred at 0° C. for 20 minutes and filtered. The filtrate is treated with an ether solution of diazomethane (~16 mmol) at 0° C. The reaction mixture is stirred at room temperature for 3 hours then concentrated in vacuo. The resulting residue is dissolved in EtOAc and washed successively with water and brine, dried ($Na_2SO_4$), filtered and concentrated. The residue is purified over silica (hexane/EtOAc 2:1) to afford 1.1 g (82% yield) of the desired product as a slightly yellow solid. $^1$H NMR (300 MHz, $CDCl_3$) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of (S)-tert-butyl 4-bromo-1-(4-nitrophenyl)-3-oxobutan-2-ylcarbamate (7): To a 0° C. solution of (S)-[3-diazo-1-(4-nitrobenzyl)-2-oxo-propyl]-carbamic acid tert-butyl ester, 6, (0.350 g, 1.04 mmol) in THF (5 mL) is added dropwise 48% aq. HBr (0.14 mL, 1.25 mmol). The reaction mixture is stirred at 0° C. for 1.5 hours then the reaction is quenched at 0° C. with sat. $Na_2CO_3$. The mixture is extracted with EtOAc (3×25 mL) and the combined organic extracts are washed with brine, dried ($Na_2SO_4$), filtered and concentrated to obtain 0.400 g of the product which is used in the next step without further purification. $^1$H NMR (300 MHz, $CDCl_3$) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of tert-butyl (S)-1-(S)-2-(4-nitrophenyl)-1-(2-phenylthiazole-4-yl)ethylamino-1-oxo-3-phenylpropan-2-ylcarbamate (8): A mixture of thiobenzamide (0.117 g, 0.85 mmol) and (S)-tert-butyl 4-bromo-1-(4-nitrophenyl)-3-oxobutan-2-ylcarbamate, 7, (0.300 g, 0.77 mmol) in $CH_3CN$ (4 mL) is refluxed 2 hours. The reaction mixture is cooled to room temperature and diethyl ether is added to precipitate the intermediate 2-(nitrophenyl)-(S)-1-(4-phenylthiazol-2-yl)ethylamine which is isolated by filtration as the hydrobromide salt. The hydrobromide salt is dissolved in DMF (3 mL) together with diisoproylethylamine (0.42 mL, 2.31 mmol), 1-hydroxybenzotriazole (0.118 g, 0.79 mmol) and (S)-(2-tert-butoxycarbonyl-amino)-3-phenylpropionic acid (0.212 g, 0.80 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous $NaHCO_3$, water and brine, and dried over $Na_2SO_4$. The solvent is removed in vacuo to afford 0.395 g (90% yield) of the desired product which is used without further purification. LC/MS ESI+ 573 (M+1).

Preparation of (4-((S)-2-((S)-2-((tert-Butoxycarbonyl)amino)-3-phenyl-propanamido)-2-(2-phenylthiazol-4-yl)ethyl)phenyl)sulfamic acid (9): tert-butyl (S)-1-(S)-2-(4-nitrophenyl)-1-(2-phenylthiazole-4-yl)ethylamino-1-oxo-3-phenylpropan-2-ylcarbamate, 8, (0.360 g) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with $SO_3$-pyridine (0.296 g). The reaction is stirred at room temperature for 5 minutes after which a 7% solution of $NH_4OH$ (10 mL) is added. The mixture is then concentrated and the resulting residue is purified by reverse phase chromatography to afford 0.050 g of the desired product as the ammonium salt. $^1$H NMR (300 MHz, MeOH-$d_4$) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The first aspect of Category II of the present disclosure relates to compounds wherein R is a substituted or unsubstituted thiazol-4-yl unit having the formula:

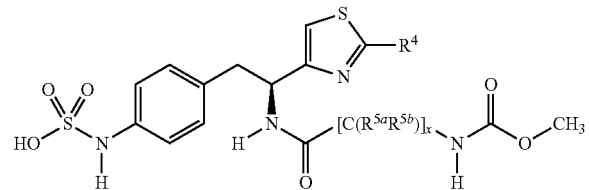

one embodiment of which relates to inhibitors having the formula:

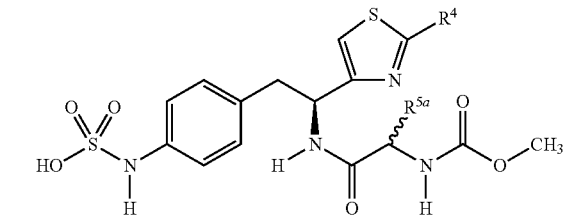

wherein R units are thiazol-4-yl units, that when substituted, are substituted with $R^4$ units. R and $R^{5a}$ units are further described in Table IV.

TABLE IV

| No. | R | $R^{5a}$ |
|---|---|---|
| D76 | thiazol-4-yl | (S)-benzyl |
| D77 | 2-methylthiazol-4-yl | (S)-benzyl |
| D78 | 2-ethylthiazol-4-yl | (S)-benzyl |
| D79 | 2-propylthiazol-4-yl | (S)-benzyl |
| D80 | 2-iso-propylthiazol-4-yl | (S)-benzyl |
| D81 | 2-cyclopropylthiazol-4-yl | (S)-benzyl |
| D82 | 2-butylthiazol-4-yl | (S)-benzyl |
| D83 | 2-tert-butylthiazol-4-yl | (S)-benzyl |
| D84 | 2-cyclohexylthiazol-4-yl | (S)-benzyl |
| D85 | 2-(2,2,2-trifluoroethyl)thiazol-4-yl | (S)-benzyl |
| D86 | 2-(3,3,3-trifluoropropyl)thiazol-4-yl | (S)-benzyl |
| D87 | 2-(2,2-difluorocyclopropyl)thiazol-4-yl | (S)-benzyl |
| D88 | 2-phenylthiazol-4-yl | (S)-benzyl |
| D89 | 2-(4-chlorophenyl)thiazol-4-yl | (S)-benzyl |
| D90 | 2-(3,4-dimethylphenyl)thiazol-4-yl | (S)-benzyl |
| D91 | 2-(thiophen-2-yl)thiazol-4-yl | (S)-benzyl |
| D92 | 2-(thiophen-3-yl)thiazol-4-yl | (S)-benzyl |
| D93 | 2-(3-chlorothiophen-2-yl)thiazol-4-yl | (S)-benzyl |
| D94 | 2-(3-methylthiophen-2-yl)thiazol-4-yl | (S)-benzyl |
| D95 | 2-(2-methylthiazol-4-yl)thiazol-4-yl | (S)-benzyl |
| D96 | 2-(furan-2-yl)thiazol-4-yl | (S)-benzyl |
| D97 | 2-(pyrazin-2-yl)thiazol-4-yl | (S)-benzyl |
| D98 | 2-[(2-methyl)pyridin-5-yl]thiazol-4-yl | (S)-benzyl |
| D99 | 2-(4-chlorobenzenesulfonylmethyl)thiazol-4-yl | (S)-benzyl |
| D100 | 2-(tert-butylsulfonylmethyl)thiazol-4-yl | (S)-benzyl |

The compounds encompassed within the second aspect of Category II of the present disclosure can be prepared by the procedure outlined in Scheme III and described in Example 3 herein below.

Scheme III

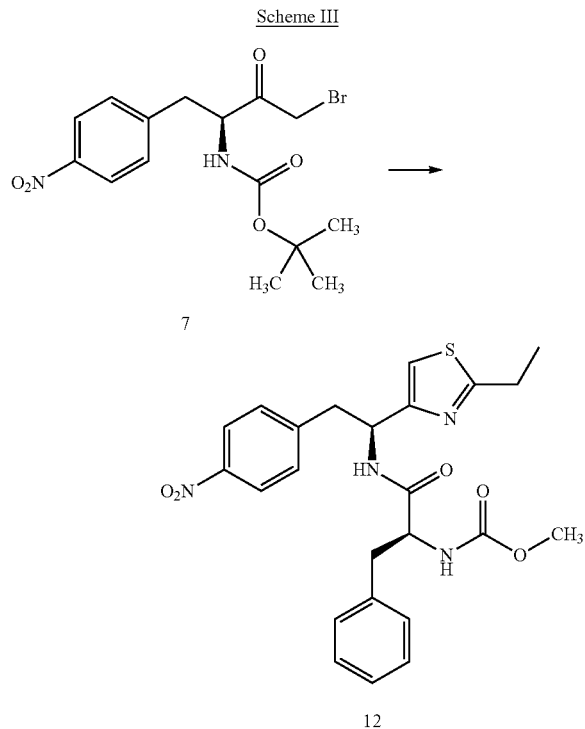

7

12

Reagents and conditions: (a) (i) propanethioamide, CH₃CN; reflux, 2 hr. (ii) Boc-Phe, HOBt, DIPEA, DMF; rt, 18 hr.

12

13

Reagents and conditions: (b) (i) H₂:Pd/C, MeOH; (ii) SO₃-pyridine, NH₄OH; rt, 18 hr.

EXAMPLE 3

4-{(S)-2-[(S)-2-(Methoxycarbonylamino)-3-phenyl-propanamido]-2-(2-ethylthiazol-4-yl) ethyl}phenylsulfamic acid (13)

Preparation of methyl (S)-1-[(S)-1-(2-ethylthiazole-4-yl)-2-(4-nitrophenyl)-ethyl]amino-1-oxo-3-phenylpropane-2-ylcarbamate (12): A mixture of propanethioamide (69 mg, 0.78 mmol) and (S)-tert-butyl 4-bromo-1-(4-nitrophenyl)-3-oxobutan-2-ylcarbamate, 7, (0.300 g, 0.77 mmol) in CH₃CN (4 mL) is refluxed for 2 hours. The reaction mixture is cooled to room temperature and diethyl ether is added to precipitate the intermediate 2-(nitrophenyl)-(S)-1-(4-ethylthiazol-2-yl) ethylamine which is isolated by filtration as the hydrobromide salt. The hydrobromide salt is dissolved in DMF (8 mL) together with diisoproylethylamine (0.38 mL, 2.13 mmol), 1-hydroxybenzotriazole (107 mg, 0.71 mmol) and (S)-(2-methoxycarbonyl-amino)-3-phenylpropionic acid (175 mg, 0.78 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.300 g (81% yield) of the desired product which is used without further purification. LC/MS ESI+ MS 483 (M+1).

Preparation of 4-((S)-2-((S)-2-(methoxycarbonylamino)-3-phenylpropanamido)-2-(2-ethylthiazol-4-yl)ethyl)phenyl-sulfamic acid ammonium salt (13): tert-Butyl (S)-1-(S)-2-(4-nitrophenyl)-1-(2-ethylthiazole-4-yl)ethylamino-1-oxo-3-phenylpropan-2-ylcarbamate, 12, (0.300 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (223 mg, 1.40 mmol). The reaction is stirred at room temperature for 5 minutes after which a 7% solution of NH₄OH (12 mL) is added. The mixture is then concentrated and the resulting residue is purified by reverse phase chromatography to afford 25 mg of the desired product as the ammonium salt. ¹H NMR (300 MHz, MeOH-d₄) δ 7.14-7.24 (m, 6H), 6.97-7.0 (m, 4H), 6.62 (s, 1H), 5.10-5.30 (m, 1H), 4.36 (t, J=7.2 Hz, 1H), 3.63 (s, 3H), 3.14 (dd, J=13.5 and 6.3 Hz, 1H), 2.93-3.07 (m, 5H), 2.81 (dd, J=13.5 and 6.3 HZ, 1H), 1.39 (t, J=7.8 Hz, 3H).

In another iteration of the process of the present disclosure, compound 13, as well as the other analogs which comprise the present disclosure, can be isolated as the free acid by adapting the procedure described herein below.

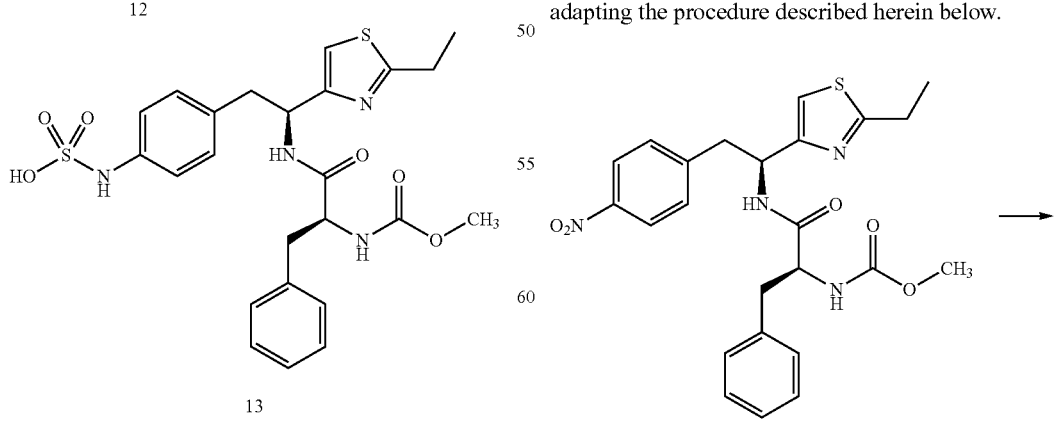

12

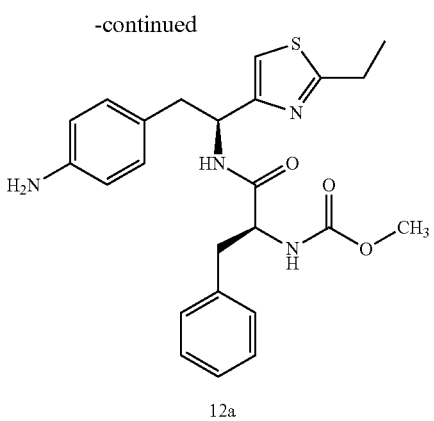

12a

Reagents and conditions: (a) H₂:Pd/C, MeOH; rt, 40 hr.

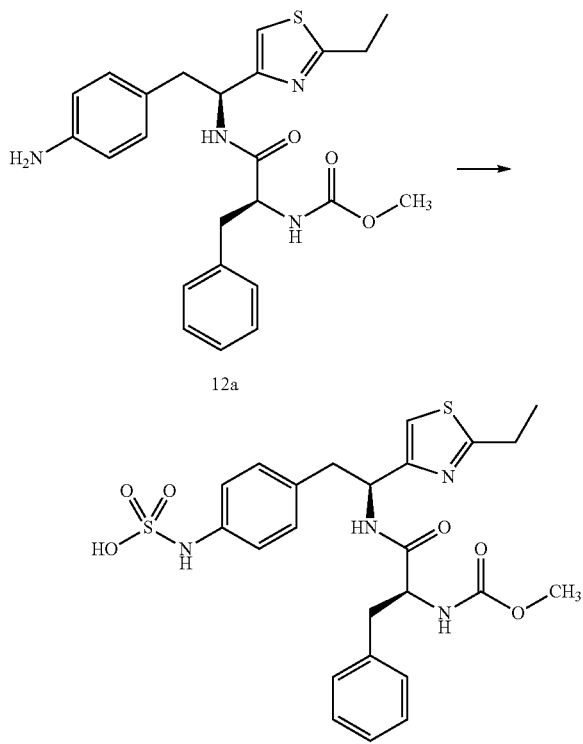

12a

13

Reagents and conditions: (b) SO₃-pyridine, CH₃CN; heat, 45 min.

EXAMPLE 4

4-((S)-2-((S)-2-(Methoxycarbonylamino)-3-phenyl-propanamido)-2-(2-ethylthiazol-4-yl) ethyl)phenyl-sulfamic acid [Free Acid Form] (13)

Preparation of {1-[2-(S)-(4-(S)-aminophenyl)-1-(2-ethylthiazol-4-yl)ethyl-carbamoyl]-2-phenylethyl}-carbamic acid methyl ester (12a): A Parr hydrogenation vessel is charged with tert-butyl (S)-1-(S)-2-(4-nitrophenyl)-1-(2-ethylthiazole-4-yl)ethylamino-1-oxo-3-phenylpropan-2-ylcarbamate, 12, (18.05 g, 37.4 mmol, 1.0 eq) and Pd/C (10% Pd on C, 50% wet, Degussa-type E101 NE/W, 2.68 g, 15 wt %) as solids. MeOH (270 mL, 15 mL/g) is added to provide a suspension. The vessel is put on a Parr hydrogenation apparatus. The vessel is submitted to a fill/vacuum evacuate process with N₂ (3×20 psi) to inert, followed by the same procedure with H₂ (3×40 psi). The vessel is filled with H₂ and the vessel is shaken under 40 psi H₂ for ~40 hr. The vessel is evacuated and the atmosphere is purged with N₂ (5×20 psi). An aliquot is filtered and analyzed by HPLC to insure complete conversion. The suspension is filtered through a pad of celite to remove the catalyst, and the homogeneous yellow filtrate is concentrated by rotary evaporation to afford 16.06 g (95% yield) of the desired product as a tan solid, which is used without further purification.

Preparation of 4-((S)-2-((S)-2-(methoxycarbonyl)-3-phenylpropanamido)-2-(2-ethylthiazol-4-yl)ethyl)phenylsulfamic acid (13): A 100 mL RBF is charged with {1-[2-(S)-(4-(S)-aminophenyl)-1-(2-ethylthiazol-4-yl)ethyl-carbamoyl]-2-phenylethyl}-carbamic acid methyl ester, 12a, (10.36 g, 22.9 mmol, 1.0 eq.) prepared in the step described herein above. Acetonitrile (50 mL, 5 mL/g) is added and the yellow suspension is stirred at room temperature. A second 3-necked 500 mL RBF is charged with SO₃.pyr (5.13 g, 32.2 mmol, 1.4 eq.) and acetonitrile (50 mL 5 mL/g) and the white suspension is stirred at room temperature. Both suspensions are gently heated until the reaction solution containing {1-[2-(S)-(4-(S)-aminophenyl)-1-(2-ethylthiazol-4-yl)ethyl-carbamoyl]-2-phenylethyl}-carbamic acid methyl ester becomes red-orange in color (typically for this example about 44° C.). This substrate containing solution is poured in one portion into the stirring suspension of SO₃.pyr at 35° C. The resulting opaque mixture (39° C.) is stirred vigorously while allowed to slowly cool to room temperature. After stirring for 45 min, the reaction is determined to be complete by HPLC. H₂O (200 mL, 20 mL/g) is added to the orange suspension to provide a yellow-orange homogeneous solution having a pH of approximately 2.4. Concentrated H₃PO₄ is added slowly over 12 minutes to lower the pH to approximately 1.4. During this pH adjustment, an off-white precipitate is formed and the solution is stirred at room temperature for 1 hr. The suspension is filtered and the filter cake is washed with the filtrate. The filter cake is air-dried on the filter overnight to afford 10.89 g (89% yield) of the desired product as a tan solid.

The following are further non-limiting examples of the second aspect of Category II of the present disclosure.

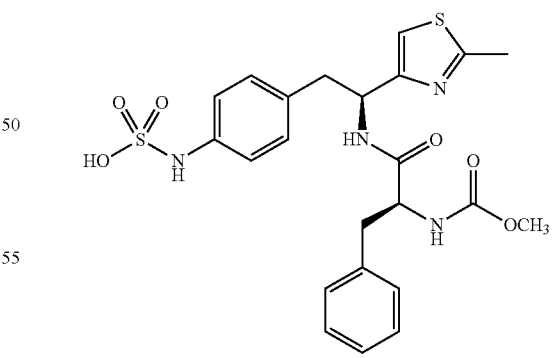

4-{(S)-2-[(S)-2-(Methoxycarbonylamino)-3-phenylpropanamido]-2-(2-methylthiazol-4-yl)ethyl}phenylsulfamic acid: ¹H NMR (300 MHz, MeOH-d₄) δ 8.15 (d, J=8.4 Hz, 1H), 7.16-7.25 (m, 5H), 6.97-7.10 (m, 4H), 6.61 (s, 1H), 5.00-5.24 (m, 1H), 4.36 (t, J=7.2 Hz, 1H), 3.64 (s, 2H), 3.11-3.19 (s, 1H), 2.92-3.04 (s, 2H), 2.81 (dd, J=13.5 and 8.1 Hz, 1H), 2.75 (s, 3H).

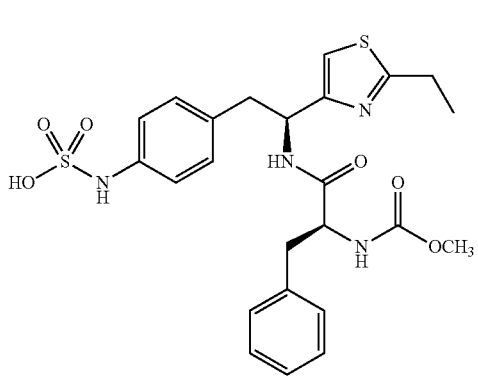 [SMILES: CCc1nc([C@H](Cc2ccc(NS(=O)(=O)O)cc2)NC(=O)[C@H](Cc2ccccc2)NC(=O)OC)cs1]

4-{(S)-2-(2-Ethylthiazole-4-yl)-2-[(S)-2-(methoxycarbonylamino)-3-phenylpropan-amido]ethyl}phenylsulfamic acid: $^1$H NMR (300 MHz, MeOH-d$_4$) δ 7.16-7.29 (m, 5H), 7.02-7.12 (m, 4H), 6.83 (s, 1H), 5.10-5.35 (m, 1H), 3.52-3.67 (m, 3H), 3.18-3.25 (m, 2H), 3.05 (q, J=7.5 Hz, 2H), 2.82-2.95 (m, 2H), 2.65 (s, 3H), 1.39 (t, J=7.5 Hz, 3H).

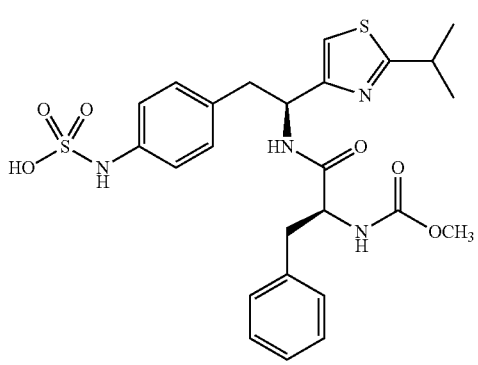 [SMILES: COC(=O)N[C@@H](Cc1ccccc1)C(=O)N[C@@H](Cc1ccc(NS(=O)(=O)O)cc1)c1csc(C(C)C)n1]

4-{(S)-2-(2-Isopropylthiazol-4-yl)-2-[(S)-2-(methoxycarbonylamino)-3-phenylpropan-amido]ethyl}phenylsulfamic acid: $^1$H NMR (CD$_3$OD) δ 8.16 (d, 1H, J=8.7Hz), 7.22-7.13 (m, 3H), 7.07 (d, 1H, J=8.4 Hz), 6.96 (d, 1H, J=8.1Hz), 6.62 (s, 1H), 5.19 (t, 1H, J=7.2Hz), 4.36 (t, 1H, J=7.8Hz), 3.63 (s, 3H), 3.08 (1H, A of ABX, J=3.6, 14.5Hz), 2.99 (1H, B of ABX, J=7.2, 13.8Hz), 2.85-2.78 (m, 1H), 1.41 (d, 6H, J=6.9Hz).

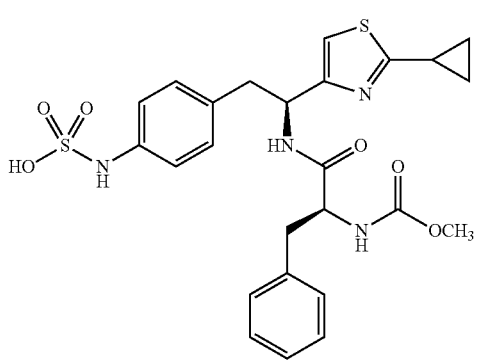 [SMILES: COC(=O)N[C@@H](Cc1ccccc1)C(=O)N[C@@H](Cc1ccc(NS(=O)(=O)O)cc1)c1csc(C2CC2)n1]

4-{(S)-2-(2-Cyclopropylthiazol-4-yl)-2-[(S)-2-(methoxycarbonylamino)-3-phenylpropanamido]ethyl}phenylsulfamic acid: $^1$H NMR (CD$_3$OD): δ 7.15-7.02 (m, 5H), 6.96-6.93 (d, 2H, J=8.4 Hz), 6.86-6.83 (d, 2H, J=8.3 Hz), 6.39 (s, 1H), 5.01 (t, 1H, J=5.0 Hz), 4.22 (t, 1H, J=7.4 Hz), 3.51 (s, 3H), 2.98-2.69 (m, 2H), 2.22-2.21 (m, 1H), 1.06-1.02 (m, 2H), 0.92-0.88 (m, 2H).

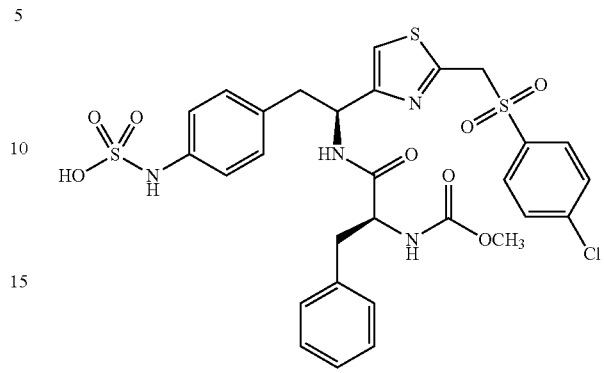

4-{(S)-2-{2-[(4-Chlorophenylsulfonyl)methyl]thiazol-4-yl}-2-[(S)-2-(methoxy-carbonylamino)-3-phenylpropanamido]ethyl}phenylsulfamic acid: $^1$H NMR (CD$_3$OD): δ 7.96-7.93 (d, 2H, J=8.6 Hz), 7.83-7.80 (d, 2H, J=8.6 Hz), 7.44-7.34 (m, 5H), 7.29-7.27 (d, 2H, J=8.4 Hz), 7.14-7.11 (d, 2H, J=8.4 Hz), 6.97 (s, 1H), 5.31 (t, 1H, J=6.8 Hz), 5.22-5.15 (m, 2H), 4.55 (t, 1H, J=7.3 Hz), 3.84 (s, 3H), 3.20-2.96 (m, 4H).

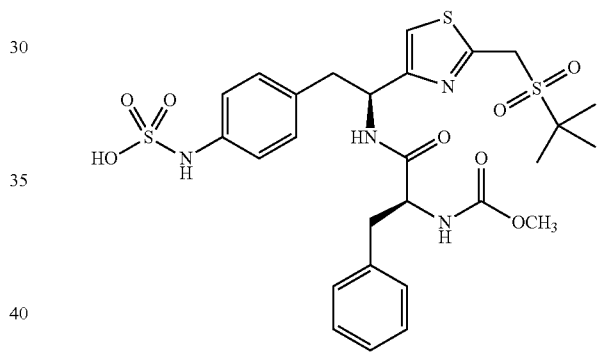

4-{(S)-2-[2-(tert-Butylsulfonylmethyl)thiazol-4-yl]-2-[(S)-2-(methoxycarbonylamino)-3-phenylpropanamido]ethyl}phenylsulfamic acid: $^1$H NMR (CD$_3$OD): δ 7.40-7.30 (m, 5H), 7.21-7.10 (m, 4H), 7.02 (s, 1H), 5.37 (t, 1H, J=6.9 Hz), 5.01-4.98 (m, 2H), 4.51 (t, 1H, J=7.1 Hz), 3.77 (s, 3H), 3.34-2.91 (m, 4H), 1.58 (s, 9H).

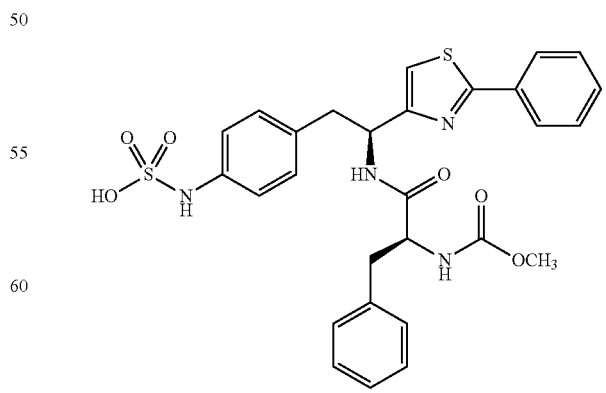

4-{(S)-2-[(S)-2-(Methoxycarbonylamino)-3-phenylpropionamido]-2-(2-phenylthiazol-4-yl)ethyl}phenylsulfamic acid: ¹H NMR (300 MHz, DMSO-d₆) δ 7.96-7.99 (m, 2H), 7.51-7.56 (m, 3H), 7.13-7.38 (m, 6H), 6.92-6.95 (m, 4H), 5.11-5.16 (m, 1H), 4.32-4.35 (m, 1H), 3.51 (s, 3H), 3.39-3.40 (m, 2H), 3.09-3.19 (m, 1H), 2.92-3.02 (m, 2H), 2.75 (dd, J=10.5 Hz and 9.9 Hz, 1H).

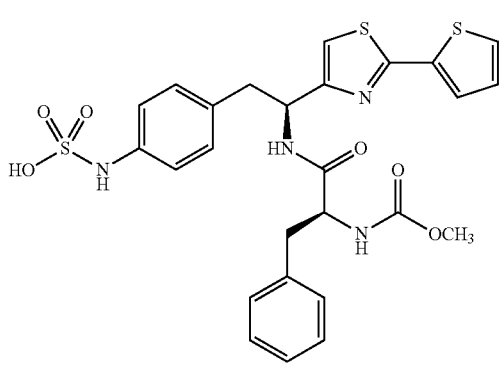 [SMILES: COC(=O)N[C@@H](Cc1ccccc1)C(=O)N[C@@H](Cc1ccc(NS(=O)(=O)O)cc1)c1csc(-c2cccs2)n1]

4-{(S)-2-[(S)-2-(Methoxycarbonylamino)-3-phenylpropanamido]-2-[2-(thiophen-2-yl)thiazol-4-yl]ethyl}phenylsulfamic acid: ¹H NMR (CD₃OD): δ 7.61-7.56 (m, 2H), 7.25-7.01 (m, 10H), 6.75 (s, 1H), 5.24-5.21 (q, 1H, J=7.2 Hz), 4.38 (t, 1H, J=7.2 Hz), 3.60 (s, 3H), 3.23-3.14 (m, 1H), 3.08-3.00 (m, 2H), 2.87-2.80 (m, 1H).

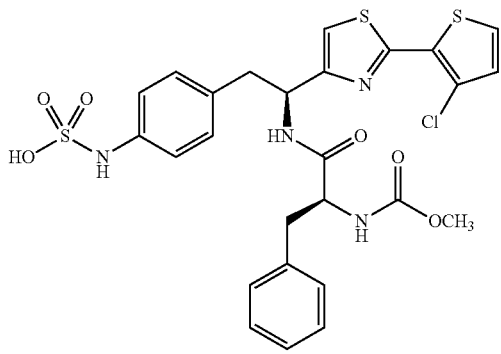 [SMILES: COC(=O)N[C@@H](Cc1ccccc1)C(=O)N[C@@H](Cc1ccc(NS(=O)(=O)O)cc1)c1csc(-c2sccc2Cl)n1]

4-{(S)-2-[2-(3-Chlorothiophen-2-yl)thiazol-4-yl]-2-[(S)-2-(methoxycarbonylamino)-3-phenylpropanamido]ethyl}phenylsulfamic acid: ¹H NMR (CD₃OD): δ 7.78-7.76 (d, 1H, J=5.4 Hz), 7.36-7.14 (m, 10H), 7.03 (s, 1H), 5.39 (t, 1H, J=6.9 Hz), 4.54 (t, 1H, J=7.3 Hz), 3.80 (s, 3H), 3.39-2.98 (m, 4H).

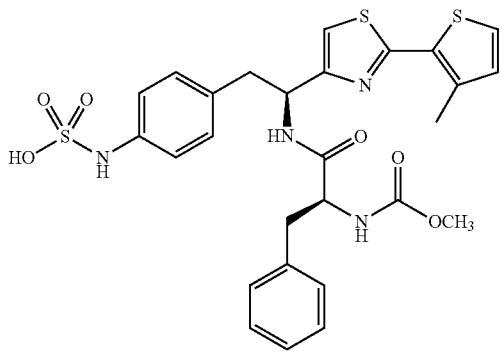 [SMILES: COC(=O)N[C@@H](Cc1ccccc1)C(=O)N[C@@H](Cc1ccc(NS(=O)(=O)O)cc1)c1csc(-c2sccc2C)n1]

4-{(S)-2-[(S)-2-(Methoxycarbonylamino)-3-phenylpropanamido]-2-[2-(3-methylthiophen-2-yl)thiazol-4-yl]ethyl}phenylsulfamic acid: ¹H NMR (CD₃OD): δ 7.38 (d, 1H, J=5.1 Hz), 7.15-6.93 (m, 10H), 6.73 (s, 1H), 5.17 (t, 1H, J=6.9 Hz), 4.31 (t, 1H, J=7.3 Hz), 3.57 (s, 3H), 3.18-3.11 (m, 1H), 3.02-2.94 (m, 2H), 2.80-2.73 (m, 1H), 2.46 (s, 3H).

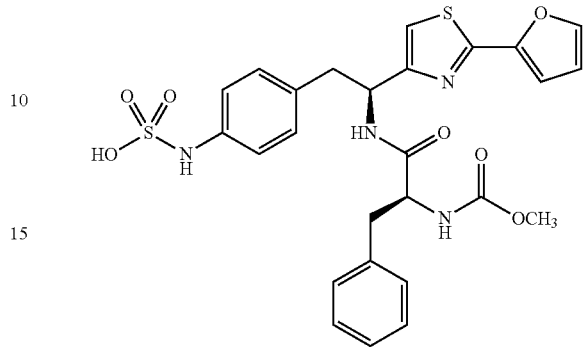

4-((S)-2-(2-(Furan-2-yl)thiazol-4-yl)-2-((S)-2-((methoxycarbonyl)amino)-3-phenylpropanamido)ethyl)phenylsulfamic acid: ¹H NMR (CD₃OD): δ 7.54-7.46 (m, 1H), 7.02-6.79 (m, 10H), 6.55-6.51 (m, 1H), 6.44-6.41 (m, 1H), 5.02-5.00 (q, 1H, J=6.4 Hz), 4.16-4.14 (q, 1H, J=7.1 Hz), 3.43 (s, 3H), 2.96-2.58 (m, 4H).

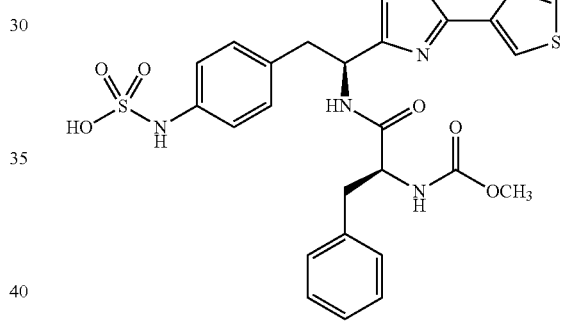

4-{(S)-2-[(S)-2-(Methoxycarbonylamino)-3-phenylpropanamido]-2-[2-(2-methylthiazole-4-yl)thiazol-4yl]ethyl}phenylsulfamic acid: ¹H NMR (300 MHz, MeOH-d₄) δ 8.27 (d, J=5.4 Hz, 1H), 7.97 (s, 1H), 6.99-7.21 (m, 8H), 5.18-5.30 (m, 1H), 4.30-4.39 (m, 1H), 3.64 (s, 3H), 3.20 (dd, J=14.1 and 6.6 Hz, 1H), 2.98-3.08 (m, 2H), 2.84 (dd, J=14.1 and 6.6 Hz, 1H), 2.78 (s, 3H).

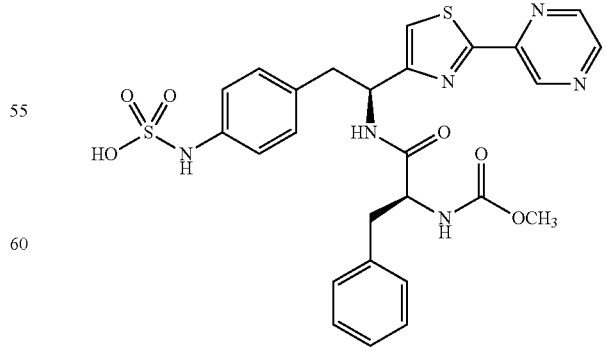

4-{(S)-2-[(S)-2-(Methoxycarbonylamino)-3-phenylpropanamido]-2-[(2-pyrazin-2-yl)thiazol-4-yl]

ethyl}phenylsulfamic acid: $^1$H NMR (300 MHz, MeOH-d$_4$) δ 9.34 (s, 1H), 8.65 (s, 2H), 8.34 (d, J=8.1 Hz, 1H), 7.00-5.16 (m. 9H), 5.30 (q, J=7.2 Hz, 1H), 4.41 (t, J=7.2 Hz, 1H), 3.65 (s, 3H), 3.23 (dd, J=13.8 and 6.9 Hz, 1H), 2.98-3.13 (m, 2H), 2.85 (dd, J=13.8 and 6.9 Hz, 1H).

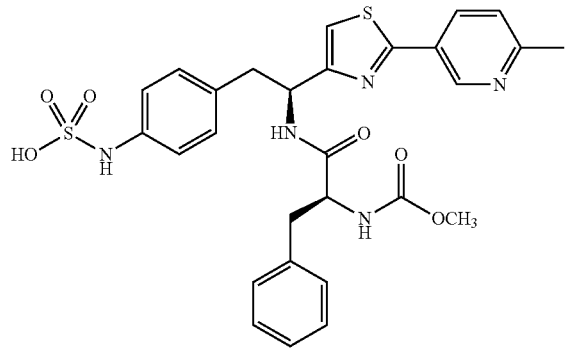 [SMILES: COC(=O)N[C@@H](Cc1ccccc1)C(=O)N[C@@H](Cc1ccc(NS(=O)(=O)O)cc1)c1csc(-c2ccc(C)nc2)n1]

4-{(S)-2-[(S)-2-(Methoxycarbonylamino)-3-phenylpropanamido]-2-[2-(6-methylpyridin-3-yl)thiazol-4-yl]ethyl}phenylsulfamic acid: $^1$H NMR (CD$_3$OD): δ 8.90 (s, 1H), 8.19-8.13 (m, 1H), 7.39-7.36 (d, 1H, J=8.2 Hz), 7.07-6.88 (m, 9H), 6.79 (s, 1H), 5.17 (t, 1H, J=7.0 Hz), 4.29 (t, 1H, J=7.4 Hz), 3.54 (s, 3H), 3.10-2.73 (m, 4H), 2.53 (s, 3H).

Category III of the present disclosure relates to compounds wherein R is a substituted or unsubstituted thiazol-2-yl unit having the formula:

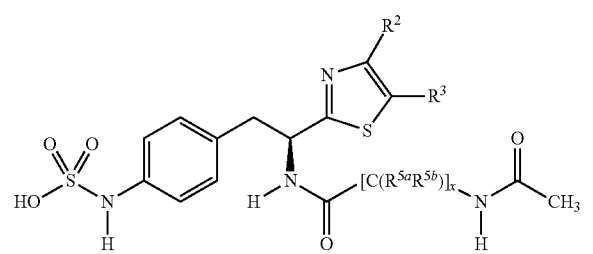

one embodiment of which relates to inhibitors having the formula:

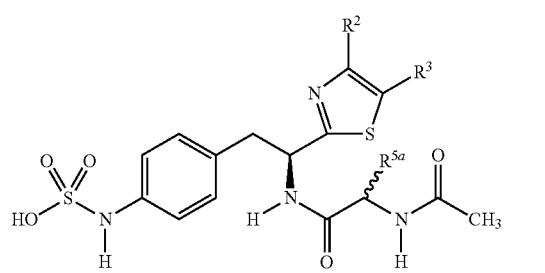

wherein R units are thiazol-2-yl units, that when substituted, are substituted with $R^2$ and $R^3$ units. R and $R^{5a}$ units are further described in Table V.

TABLE V

| No. | R | $R^{5a}$ |
|---|---|---|
| E101 | thiazol-2-yl | (S)-benzyl |
| E102 | 4-methylthiazol-2-yl | (S)-benzyl |
| E103 | 4-ethylthiazol-2-yl | (S)-benzyl |

TABLE V-continued

| No. | R | $R^{5a}$ |
|---|---|---|
| E104 | 4-propylthiazol-2-yl | (S)-benzyl |
| E105 | 4-iso-propylthiazol-2-yl | (S)-benzyl |
| E106 | 4-cyclopropylthiazol-2-yl | (S)-benzyl |
| E107 | 4-butylthiazol-2-yl | (S)-benzyl |
| E108 | 4-tert-butylthiazol-2-yl | (S)-benzyl |
| E109 | 4-cyclohexylthiazol-2-yl | (S)-benzyl |
| E110 | 4-(2,2,2-trifluoroethyl)thiazol-2-yl | (S)-benzyl |
| E111 | 4-(3,3,3-trifluoropropyl)thiazol-2-yl | (S)-benzyl |
| E112 | 4-(2,2-difluorocyclopropyl)thiazol-2-yl | (S)-benzyl |
| E113 | 4-(methoxymethyl)thiazol-2-yl | (S)-benzyl |
| E114 | 4-(carboxylic acid ethyl ester)thiazol-2-yl | (S)-benzyl |
| E115 | 4,5-dimethylthiazol-2-yl | (S)-benzyl |
| E116 | 4-methyl-5-ethylthiazol-2-yl | (S)-benzyl |
| E117 | 4-phenylthiazol-2-yl | (S)-benzyl |
| E118 | 4-(4-chlorophenyl)thiazol-2-yl | (S)-benzyl |
| E119 | 4-(3,4-dimethylphenyl)thiazol-2-yl | (S)-benzyl |
| E120 | 4-methyl-5-phenylthiazol-2-yl | (S)-benzyl |
| E121 | 4-(thiophen-2-yl)thiazol-2-yl | (S)-benzyl |
| E122 | 4-(thiophen-3-yl)thiazol-2-yl | (S)-benzyl |
| E123 | 4-(5-chlorothiophen-2-yl)thiazol-2-yl | (S)-benzyl |
| E124 | 5,6-dihydro-4H-cyclopenta[d]thiazol-2-yl | (S)-benzyl |
| E125 | 4,5,6,7-tetrahydrobenzo[d]thiazol-2-yl | (S)-benzyl |

The compounds encompassed within Category III of the present disclosure can be prepared by the procedure outlined in Scheme IV and described in Example 5 herein below.

Scheme IV

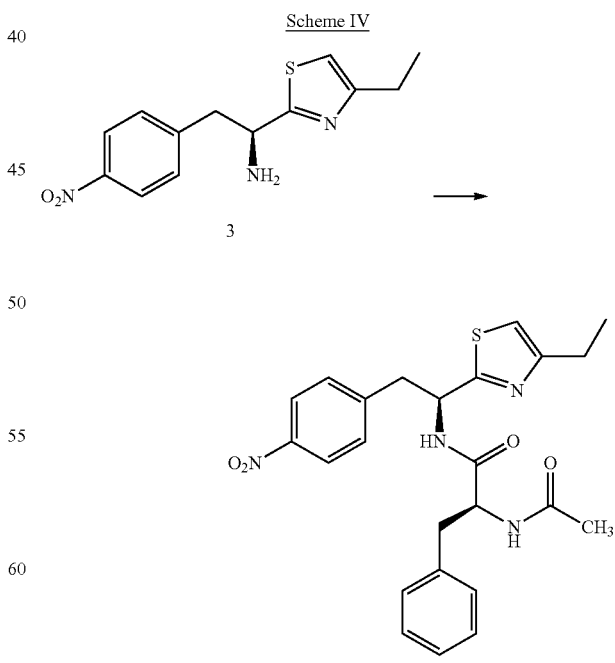

Reagents and conditions: (a) Ac-Phe, EDCI, HOBt, DIPEA, DMF; rt, 18 hr.

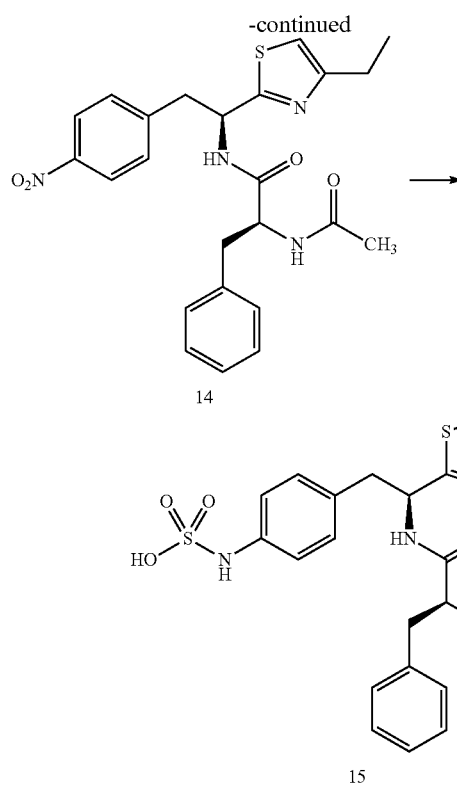

Reagents and conditions: (b) (i) H₂:Pd/C, MeOH; (ii) SO₃-pyridine, NH₄OH.

EXAMPLE 5

4-[(S)-2-((S)-2-Acetamido-3-phenylpropanamido)-2-(4-ethylthiazol-2-yl)ethyl]phenylsulfamic acid (15)

Preparation of (S)-2-acetamido-N-[(S)-1-(4-ethylthiazol-2-yl)-2-(4-nitrophenyl)-ethyl]-3-phenylpropanamide (14): To a solution of 1-(S)-(4-ethylthiazol-2-yl)-2-(4-nitrophenyl) ethyl amine hydrobromide, 3, (0.343 g, 0.957 mmol), N-acetyl-L-phenylalanine (0.218 g), 1-hydroxybenzotriazole (HOBt) (0.161 g), diisopropyl-ethylamine (0.26 g), in DMF (10 mL) at 0°, is added 1-(3-dimethylaminopropyl)-3-ethyl-carbodiimide (EDCI) (0.201 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.313 g (70% yield) of the desired product which is used without further purification. LC/MS ESI+ 467 (M+1).

Preparation of 4-((S)-2-((S)-2-acetamido-3-phenylpropanamido)-2-(4-ethylthiazol-2-yl)ethyl)phenylsulfamic acid (15): (S)-2-Acetamido-N—[(S)-1-(4-ethylthiazol-2-yl)-2-(4-nitrophenyl)ethyl]-3-phenylpropanamide, 14, (0.313 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO₃-pyridine (0.320 g). The reaction is stirred at room temperature for 5 minutes after which a 7% solution of NH₄OH (30 mL) is added. The mixture is then concentrated and the resulting residue is purified by reverse phase chromatography to afford 0.215 g of the desired product as the ammonium salt. ¹H NMR (CD₃OD): δ 7.23-6.98 (m, 10H), 5.37 (t, 1H), 4.64 (t, 1H, J=6.3 Hz), 3.26-2.74 (m, 6H), 1.91 (s, 3H), 1.29 (t, 3H, J=7.5 Hz).

The following are further non-limiting examples of compounds encompassed within Category III of the present disclosure.

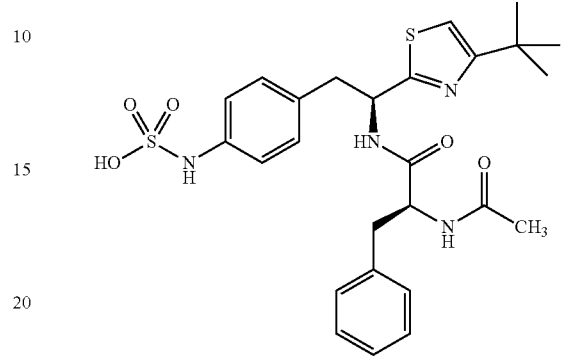

4-[(S)-2-((S)-2-Acetamido-3-phenylpropanamido)-2-(4-tert-butylthiazol-2-yl)ethyl]phenylsulfamic acid: ¹H NMR (300 MHz, CD₃OD): δ 7.22-7.17 (m, 5H), 7.06 (dd, J=14.1, 8.4 Hz, 4H), 6.97 (d, J=0.9 Hz, 1H), 5.39 (dd, J=8.4, 6.0 Hz, 1H), 4.65 (t, J=7.2 Hz, 1H), 3.33-3.26 (m, 1H), 3.13-3.00 (m, 3H), 2.80 (dd, J=13.5, 8.7 Hz, 1H), 1.91 (s, 3H), 1.36 (s, 9H).

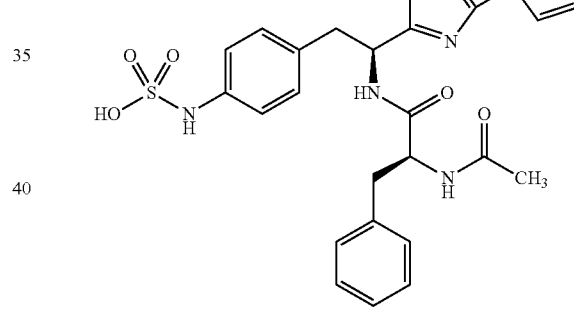

4-{(S)-2-((S)-2-Acetamido-3-phenylpropanamido)-2-[4-(thiophen-3-yl)thiazol-2-yl]ethyl)phenylsulfamic acid: ¹H NMR (300 MHz, CD₃OD): δ 8.58 (d, J=8.1 Hz, 1H), 7.83-7.82 (m, 1H), 7.57-7.46 (m, 3H), 7.28-6.93 (m, 11H), 5.54-5.43 (m, 1H), 4.69-4.55 (m, 2H), 3.41-3.33 (m, 1H), 3.14-3.06 (3H), 2.86-2.79 (m, 1H), 1.93 (s, 3H).

The first aspect of Category IV of the present disclosure relates to compounds wherein R is a substituted or unsubstituted thiazol-2-yl unit having the formula:

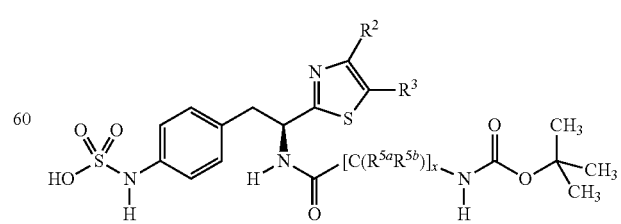

one embodiment of which relates to inhibitors having the formula:

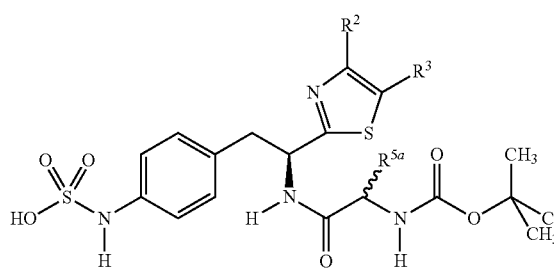

wherein R units and $R^{5a}$ units further described in Table VI.

TABLE VI

| No. | R | $R^{5a}$ |
|---|---|---|
| F126 | thiazol-2-yl | hydrogen |
| F127 | 4-methylthiazol-2-yl | hydrogen |
| F128 | 4-ethylthiazol-2-yl | hydrogen |
| F129 | 4-propylthiazol-2-yl | hydrogen |
| F130 | 4-iso-propylthiazol-2-yl | hydrogen |
| F131 | 4-cyclopropylthiazol-2-yl | hydrogen |
| F132 | 4-butylthiazol-2-yl | hydrogen |
| F133 | 4-tert-butylthiazol-2-yl | hydrogen |
| F134 | 4-cyclohexylthiazol-2-yl | hydrogen |
| F135 | 4,5-dimethylthiazol-2-yl | hydrogen |
| F136 | 4-methyl-5-ethylthiazol-2-yl | hydrogen |
| F137 | 4-phenylthiazol-2-yl | hydrogen |
| F138 | thiazol-2-yl | (S)-iso-propyl |
| F139 | 4-methylthiazol-2-yl | (S)-iso-propyl |
| F140 | 4-ethylthiazol-2-yl | (S)-iso-propyl |
| F141 | 4-propylthiazol-2-yl | (S)-iso-propyl |
| F142 | 4-iso-propylthiazol-2-yl | (S)-iso-propyl |
| F143 | 4-cyclopropylthiazol-2-yl | (S)-iso-propyl |
| F144 | 4-butylthiazol-2-yl | (S)-iso-propyl |
| F145 | 4-tert-butylthiazol-2-yl | (S)-iso-propyl |
| F146 | 4-cyclohexylthiazol-2-yl | (S)-iso-propyl |
| F147 | 4,5-dimethylthiazol-2-yl | (S)-iso-propyl |
| F148 | 4-methyl-5-ethylthiazol-2-yl | (S)-iso-propyl |
| F149 | 4-phenylthiazol-2-yl | (S)-iso-propyl |
| F150 | 4-(thiophen-2-yl)thiazol-2-yl | (S)-iso-propyl |

The compounds encompassed within Category IV of the present disclosure can be prepared by the procedure outlined in Scheme V and described in Example 6 herein below.

Scheme V

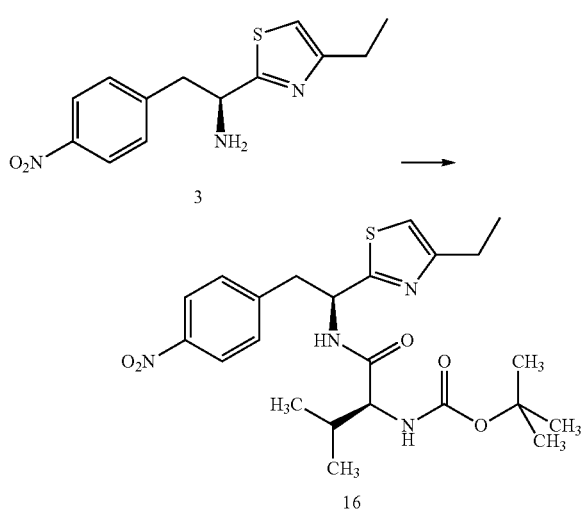

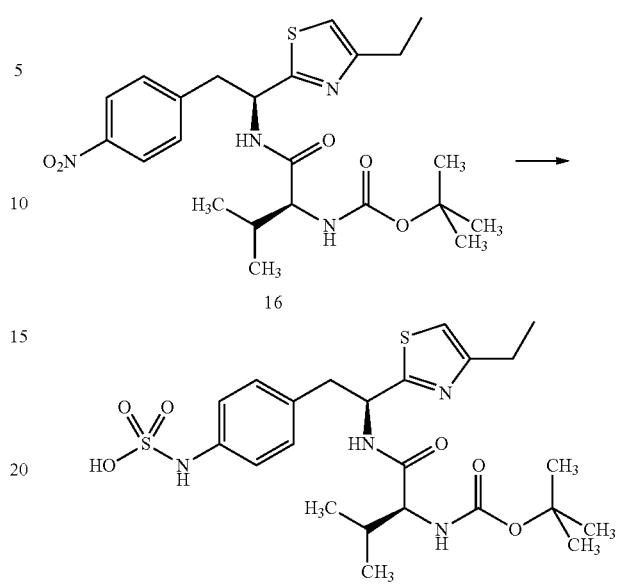

Reagents and conditions (a): Boc-Val; EDCI, HOBt, DIPEA, DMF; rt, 18 hr.

Reagents and conditions: (b) (i) $H_2$:Pd/C, MeOH; (ii) $SO_3$-pyridine, $NH_4OH$, rt, 2 hr..

EXAMPLE 6

4-{(S)-2-[(S)-2-(tert-Butoxycarbonylamino)-3-methylbutanamido]-2-(4-ethylthiazol-2-yl) ethyl}phenylsulfamic acid (17)

Preparation of tert-butyl (S)-1-[(S)-(4-ethylthiazol-2-yl)-2-(4-nitrophenyl)ethylamino]-3-methyl-1-oxobutan-2-yl-carbamate (16): To a solution of 1-(5)-(4-ethylthiazol-2-yl)-2-(4-nitrophenyl)ethyl amine hydrobromide, 3, (0.200 g, 0.558 mmol), (S)-(2-tert-butoxycarbonylamino)-3-methylbutyric acid (0.133 g) and 1-hydroxybenzo-triazole (HOBt) (0.094 g) in DMF (5 mL) at 0°, is added 1-(3-dimethylaminopropyl)-3-ethylcarbodiimide (EDCI) (0.118 g) followed by diisopropylamine (0.151 g). The mixture is stirred at 0° C. for 30 minutes then at room temperature overnight. The reaction mixture is diluted with water and extracted with EtOAc. The combined organic phase is washed with 1 N aqueous HCl, 5% aqueous $NaHCO_3$, water and brine, and dried over $Na_2SO_4$. The solvent is removed in vacuo to afford 0.219 g (82% yield) of the desired product which is used without further purification. LC/MS ESI+ 477 (M+1).

Preparation of 4-{(S)-2-[(S)-2-(tert-butoxycarbonylamino)-3-methylbutanamido]-2-(4-ethylthiazol-2-yl) ethyl}phenylsulfamic acid (17): tert-Butyl (S)-1-[(S)-(4-ethylthiazol-2-yl)-2-(4-nitrophenyl)ethylamino]-3-methyl-1-oxobutan-2-ylcarbamate, 16, (0.219 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (5 mL) and treated with $SO_3$-pyridine (0.146 g). The reaction is stirred at room temperature for 5 minutes after which a 7% solution of $NH_4OH$ (30 mL) is added. The mixture is then concentrated and the resulting residue is purified by reverse phase chromatography to afford 0.148 g of the desired product as the ammonium salt.

¹H NMR (CD₃OD): δ 7.08 (s, 4H), 7.02 (s, 1H), 5.43 (s, 1H), 3.85 (s, 1H), 3.28-2.77 (m, 4H), 1.94 (s, 1H), 1.46 (s, 9H), 1.29 (s, 3H, J=7.3 Hz), 0.83 (s, 6H).

The following are further non-limiting examples of the second aspect of Category IV of the present disclosure.

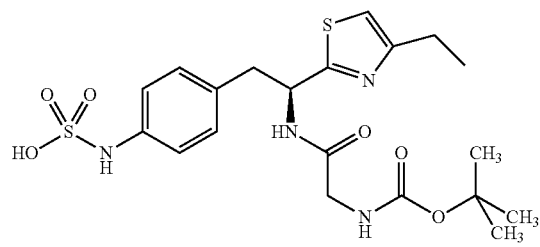 [SMILES: CCc1csc([C@H](Cc2ccc(NS(=O)(=O)O)cc2)NC(=O)CNC(=O)OC(C)(C)C)n1]

(S)-4-{2-[2-(tert-Butoxycarbonyl)acetamide]-2-(4-ethylthiazol-2-yl)ethyl}phenyl-sulfamic acid: ¹H NMR (CD₃OD): δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

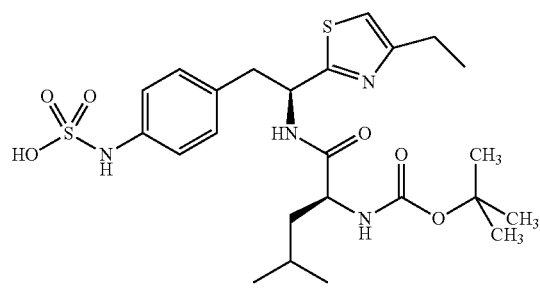 [SMILES: CCc1csc([C@H](Cc2ccc(NS(=O)(=O)O)cc2)NC(=O)[C@H](CC(C)C)NC(=O)OC(C)(C)C)n1]

4-{(S)-2-[(S)-2-(tert-Butoxycarbonylamino)-4-methylpentanamido]-2-(4-ethylthiazol-2-yl)ethyl}phenylsulfamic acid: ¹H NMR (CD3OD) δ 7.19-7.00 (m, 4H), 5.50-5.40 (m, 1H), 4.13-4.06 (m, 1H), 3.32 (1H, A of ABX,J=7.5, 18Hz), 3.12 (1H, B of ABX, J=8.1, 13.8Hz), 2.79 (q, 2H, J=7.8, 14.7Hz), 1.70-1.55 (m, 1H), 1.46 (s, 9H), 1.33 (t, 3H, J=2.7Hz), 0.92 (q, 6H, J=6, 10.8Hz).

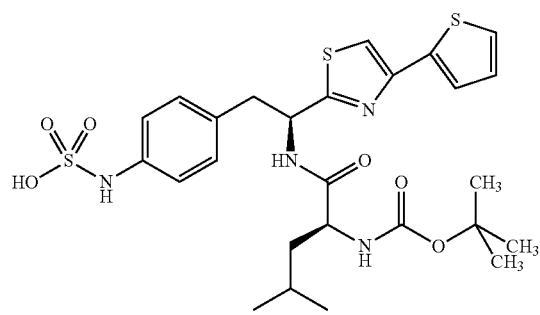 [SMILES: CC(C)C[C@H](NC(=O)OC(C)(C)C)C(=O)N[C@@H](Cc1ccc(NS(=O)(=O)O)cc1)c1nc(-c2cccs2)cs1]

4-{(S)-2-[(S)-2-(tert-Butoxycarbonylamino)-4-methylpentanamido]-2-[2-(thiophen-2-yl)thiazol-4-yl]ethyl}phenylsulfamic acid: ¹H NMR (CD3OD) δ 8.06 (d, 1H, J=84 Hz), 7.61-7.58 (m, 1H), 7.57 (s, 1H), 7.15 (t, 1H, J=0.6Hz), 7.09-6.98 (m, 6H), 5.30-5.20 (m, 1H), 4.10-4.00 (m, 1H), 3.19-3.13 (m, 2H), 1.63-1.55 (m, 2H), 1.48-1.33 (m, 10H), 0.95-0.89 (m, 6H).

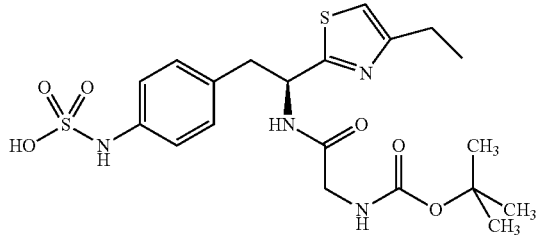 [SMILES: CCc1csc([C@H](Cc2ccc(NS(=O)(=O)O)cc2)NC(=O)CNC(=O)OC(C)(C)C)n1]

(S)-4-{2-[2-(tert-Butoxycarbonyl)acetamide]-2-(4-ethylthiazol-2-yl)ethyl}-phenylsulfamic acid: ¹H NMR (CD₃OD): δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

A further embodiment of Category IV relates to inhibitors having the formula:

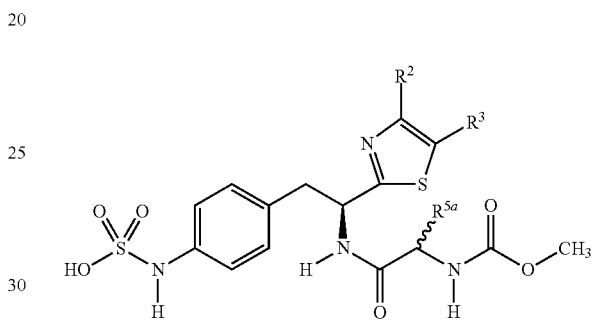

wherein R units and R⁵ᵃ units further described in Table VII.

TABLE VII

| No. | R | R⁵ᵃ |
|---|---|---|
| G151 | thiazol-2-yl | hydrogen |
| G152 | 4-methylthiazol-2-yl | hydrogen |
| G153 | 4-ethylthiazol-2-yl | hydrogen |
| G154 | 4-propylthiazol-2-yl | hydrogen |
| G155 | 4-iso-propylthiazol-2-yl | hydrogen |
| G156 | 4-cyclopropylthiazol-2-yl | hydrogen |
| G157 | 4-butylthiazol-2-yl | hydrogen |
| G158 | 4-tert-butylthiazol-2-yl | hydrogen |
| G159 | 4-cyclohexylthiazol-2-yl | hydrogen |
| G160 | 4,5-dimethylthiazol-2-yl | hydrogen |
| G161 | 4-methyl-5-ethylthiazol-2-yl | hydrogen |
| G162 | 4-phenylthiazol-2-yl | hydrogen |
| G163 | thiazol-2-yl | (S)-iso-propyl |
| G164 | 4-methylthiazol-2-yl | (S)-iso-propyl |
| G165 | 4-ethylthiazol-2-yl | (S)-iso-propyl |
| G166 | 4-propylthiazol-2-yl | (S)-iso-propyl |
| G167 | 4-iso-propylthiazol-2-yl | (S)-iso-propyl |
| G168 | 4-cyclopropylthiazol-2-yl | (S)-iso-propyl |
| G169 | 4-butylthiazol-2-yl | (S)-iso-propyl |
| G170 | 4-tert-butylthiazol-2-yl | (S)-iso-propyl |
| G171 | 4-cyclohexylthiazol-2-yl | (S)-iso-propyl |
| G172 | 4,5-dimethylthiazol-2-yl | (S)-iso-propyl |
| G173 | 4-methyl-5-ethylthiazol-2-yl | (S)-iso-propyl |
| G174 | 4-phenylthiazol-2-yl | (S)-iso-propyl |
| G175 | 4-(thiophen-2-yl)thiazol-2-yl | (S)-iso-propyl |

The compounds encompassed within this embodiment of Category IV can be made according to the procedure outlined in Scheme V and described in Example 6 by substituting the corresponding methylcarbamate for the Boc-protected reagent. The following are non-limiting examples of this embodiment.

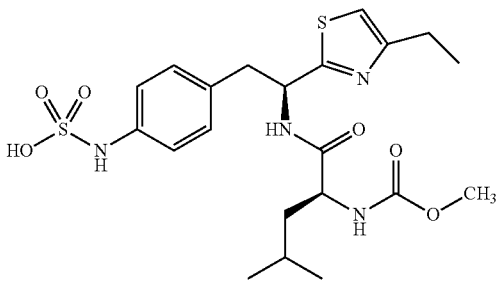 [SMILES: CCc1csc([C@H](Cc2ccc(NS(=O)(=O)O)cc2)NC(=O)[C@H](CC(C)C)NC(=O)OC)n1]

4-{(S)-2-(4-Ethylthiazol-2-yl)-2-[(S)-2-(methoxycarbonylamino)-4-methylpentan-amido]ethyl}phenylsulfamic acid: $^1$H NMR (CD3OD) δ 7.12-7.03 (m, 5H), 6.84 (d, 1H, J=8.4Hz), 5.40 (t, 1H, J=5.7Hz), 4.16 (t, 1H, J=6.3Hz), 3.69 (s, 3H), 3.61-3.55 (m, 1H), 3.29-3.27 (m, 1H), 3.14-3.07 (m, 1H), 2.81 (q, 2H, J=3.9, 11.2Hz), 1.66-1.59 (m, 1H), 1.48-1.43 (m, 2H), 1.31 (t, 3H, J=4.5Hz), 0.96-0.90 (m, 6H).

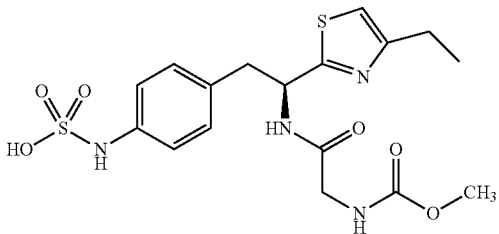 [SMILES: CCc1csc([C@H](Cc2ccc(NS(=O)(=O)O)cc2)NC(=O)CNC(=O)OC)n1]

(S)-4-{2-(4-Ethylthiazol-2-yl)-2-[2-(methoxycarbonylamino)acetamido]ethyl}-phenylsulfamic acid: $^1$H NMR (CD$_3$OD): δ 7.12-7.07 (m, 4H), 7.03 (s, 1H), 5.42 (t, 1H, J=5.7 Hz), 3.83-3.68 (q, 2H, J=11.4 Hz), 3.68 (s, 3H), 3.34-3.04 (m, 2H), 2.83-2.76 (q, 2H, J=7.8 Hz), 1.31 (t, 3H, J=7.5 Hz).

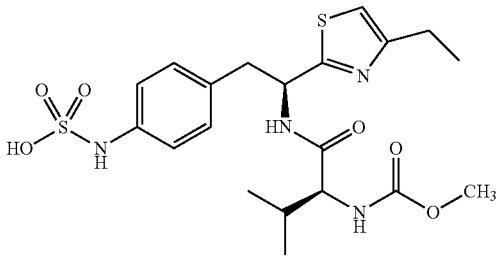 [SMILES: CCc1csc([C@H](Cc2ccc(NS(=O)(=O)O)cc2)NC(=O)[C@@H](NC(=O)OC)C(C)C)n1]

4-{(S)-2-(4-Ethylthiazol-2-yl)-2-[(S)-2-(methoxycarbonylamino)-3-methylbutanamido]-ethyl}phenylsulfamic acid: $^1$H NMR (CD$_3$OD) δ 8.56 (d, 1H, J=7.8Hz), 7.09 (s, 4H), 7.03 (s, 1H), 5.26-5.20 (m, 1H), 3.90 (d, 1H, J=7.8Hz), 3.70 (s, 3H), 3.30 (1H, A of ABX, obscured by solvent), 3.08 (1H, B of ABX, J=9.9, 9Hz), 2.79 (q, 2H, J=11.1, 7.2Hz), 2.05-1.97 (m, 1H), 1.31 (t, 3H, J=7.5Hz), 0.88 (s, 3H), 0.85 (s, 3H), 0.79-0.75 (m, 1H).

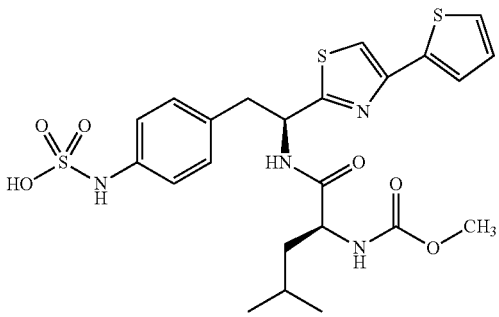 [SMILES: COC(=O)N[C@@H](CC(C)C)C(=O)N[C@@H](Cc1ccc(NS(=O)(=O)O)cc1)c1nc(-c2cccs2)cs1]

4-{(S)-2-[(S)-2-(Methoxycarbonylamino)-4-methylpentanamido]-2-[2-(thiophen-2-yl)thiazol-4-yl]ethyl}phenylsulfamic acid: $^1$H NMR (CD$_3$OD) δ 8.22 (d, 1H, J=9Hz), 7.62-7.57 (m, H), 7.15 (t, 1H, J=0.6Hz), 7.10-6.97 (m, 4H), 5.30-5.20 (m, 1H), 4.16-4.11 (m, 1H), 3.67 (s, 2H), 3.22 (1H, A of ABX, J=6.9, 13.5Hz), 3.11 (1H, B of ABX, J=7.8, 13.6Hz), 1.65-1.58 (m, 1H), 1.50-1.45 (m, 2H), 0.95-0.88 (m, 6H).

Category IV of the present disclosure relates to compounds having the formula:

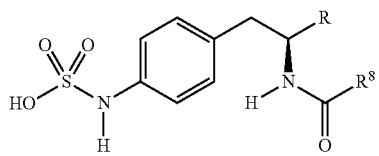

wherein R is a substituted or unsubstituted thiophen-2-yl or thiophen-4-yl unit and non-limiting examples of R$^2$ are further described in Table VIII.

TABLE VIII

| No. | R | R$^8$ |
| --- | --- | --- |
| H176 | thiazol-2-yl | —OC(CH$_3$)$_3$ |
| H177 | 4-methylthiazol-2-yl | —OC(CH$_3$)$_3$ |
| H178 | 4-ethylthiazol-2-yl | —OC(CH$_3$)$_3$ |
| H179 | 4-cyclopropylthiazol-2-yl | —OC(CH$_3$)$_3$ |
| H180 | 4-tert-butylthiazol-2-yl | —OC(CH$_3$)$_3$ |
| H181 | 4-cyclohexylthiazol-2-yl | —OC(CH$_3$)$_3$ |
| H182 | 4-(2,2,2-trifluoroethyl)thiazol-2-yl | —OC(CH$_3$)$_3$ |
| H183 | 4-(3,3,3-trifluoropropyl)thiazol-2-yl | —OC(CH$_3$)$_3$ |
| H184 | 4-(2,2-difluorocyclopropyl)thiazol-2-yl | —OC(CH$_3$)$_3$ |
| H185 | 4,5-dimethylthiazol-2-yl | —OC(CH$_3$)$_3$ |
| H186 | 4-methyl-5-ethylthiazol-2-yl | —OC(CH$_3$)$_3$ |
| H187 | 4-phenylthiazol-2-yl | —OC(CH$_3$)$_3$ |
| H188 | 4-(4-chlorophenyl)thiazol-2-yl | —OC(CH$_3$)$_3$ |
| H189 | 4-(3,4-dimethylphenyl)thiazol-2-yl | —OC(CH$_3$)$_3$ |
| H190 | 4-methyl-5-phenylthiazol-2-yl | —OC(CH$_3$)$_3$ |
| H191 | 4-(thiophen-2-yl)thiazol-2-yl | —OC(CH$_3$)$_3$ |
| H192 | thiazol-4-yl | —OC(CH$_3$)$_3$ |
| H193 | 4-methylthiazol-4-yl | —OC(CH$_3$)$_3$ |
| H194 | 4-ethylthiazol-4-yl | —OC(CH$_3$)$_3$ |
| H195 | 4-cyclopropylthiazol-4-yl | —OC(CH$_3$)$_3$ |
| H196 | 4-tert-butylthiazol-4-yl | —OC(CH$_3$)$_3$ |
| H197 | 4-cyclohexylthiazol-4-yl | —OC(CH$_3$)$_3$ |
| H198 | 4-(2,2,2-trifluoroethyl)thiazol-4-yl | —OC(CH$_3$)$_3$ |
| H199 | 4-(3,3,3-trifluoropropyl)thiazol-4-yl | —OC(CH$_3$)$_3$ |
| H200 | 4-(2,2-difluorocyclopropyl)thiazol-4-yl | —OC(CH$_3$)$_3$ |
| H201 | 4,5-dimethylthiazol-4-yl | —OC(CH$_3$)$_3$ |
| H202 | 4-methyl-5-ethylthiazol-4-yl | —OC(CH$_3$)$_3$ |
| H203 | 4-phenylthiazol-4-yl | —OC(CH$_3$)$_3$ |
| H204 | 4-(4-chlorophenyl)thiazol-4-yl | —OC(CH$_3$)$_3$ |
| H205 | 4-(3,4-dimethylphenyl)thiazol-4-yl | —OC(CH$_3$)$_3$ |
| H206 | 4-methyl-5-phenylthiazol-4-yl | —OC(CH$_3$)$_3$ |
| H207 | 4-(thiophen-2-yl)thiazol-4-yl | —OC(CH$_3$)$_3$ |
| H208 | thiazol-2-yl | —OCH$_3$ |
| H209 | 4-methylthiazol-2-yl | —OCH$_3$ |
| H210 | 4-ethylthiazol-2-yl | —OCH$_3$ |
| H211 | 4-cyclopropylthiazol-2-yl | —OCH$_3$ |
| H212 | 4-tert-butylthiazol-2-yl | —OCH$_3$ |
| H213 | 4-cyclohexylthiazol-2-yl | —OCH$_3$ |
| H214 | 4-(2,2,2-trifluoroethyl)thiazol-2-yl | —OCH$_3$ |
| H215 | 4-(3,3,3-trifluoropropyl)thiazol-2-yl | —OCH$_3$ |
| H216 | 4-(2,2-difluorocyclopropyl)thiazol-2-yl | —OCH$_3$ |
| H217 | 4,5-dimethylthiazol-2-yl | —OCH$_3$ |
| H218 | 4-methyl-5-ethylthiazol-2-yl | —OCH$_3$ |
| H219 | 4-phenylthiazol-2-yl | —OCH$_3$ |
| H220 | 4-(4-chlorophenyl)thiazol-2-yl | —OCH$_3$ |
| H221 | 4-(3,4-dimethylphenyl)thiazol-2-yl | —OCH$_3$ |
| H222 | 4-methyl-5-phenylthiazol-2-yl | —OCH$_3$ |
| H223 | 4-(thiophen-2-yl)thiazol-2-yl | —OCH$_3$ |
| H224 | thiazol-4-yl | —OCH$_3$ |
| H225 | 4-methylthiazol-4-yl | —OCH$_3$ |

TABLE VIII-continued

| No. | R | R[8] |
|---|---|---|
| H226 | 4-ethylthiazol-4-yl | —OCH₃ |
| H227 | 4-cyclopropylthiazol-4-yl | —OCH₃ |
| H228 | 4-tert-butylthiazol-4-yl | —OCH₃ |
| H229 | 4-cyclohexylthiazol-4-yl | —OCH₃ |
| H230 | 4-(2,2,2-trifluoroethyl)thiazol-4-yl | —OCH₃ |
| H231 | 4-(3,3,3-trifluoropropyl)thiazol-4-yl | —OCH₃ |
| H232 | 4-(2,2-difluorocyclopropyl)thiazol-4-yl | —OCH₃ |
| H233 | 4,5-dimethylthiazol-4-yl | —OCH₃ |
| H234 | 4-methyl-5-ethylthiazol-4-yl | —OCH₃ |
| H235 | 4-phenylthiazol-4-yl | —OCH₃ |
| H236 | 4-(4-chlorophenyl)thiazol-4-yl | —OCH₃ |
| H237 | 4-(3,4-dimethylphenyl)thiazol-4-yl | —OCH₃ |
| H238 | 4-methyl-5-phenylthiazol-4-yl | —OCH₃ |
| H239 | 4-(thiophen-2-yl)thiazol-4-yl | —OCH₃ |
| H240 | thiazol-2-yl | —CH₃ |
| H241 | 4-methylthiazol-2-yl | —CH₃ |
| H242 | 4-ethylthiazol-2-yl | —CH₃ |
| H243 | 4-cyclopropylthiazol-2-yl | —CH₃ |
| H244 | 4-tert-butylthiazol-2-yl | —CH₃ |
| H245 | 4-cyclohexylthiazol-2-yl | —CH₃ |
| H246 | 4-(2,2,2-trifluoroethyl)thiazol-2-yl | —CH₃ |
| H247 | 4-(3,3,3-trifluoropropyl)thiazol-2-yl | —CH₃ |
| H248 | 4-(2,2-difluorocyclopropyl)thiazol-2-yl | —CH₃ |
| H249 | 4,5-dimethylthiazol-2-yl | —CH₃ |
| H250 | 4-methyl-5-ethylthiazol-2-yl | —CH₃ |
| H251 | 4-phenylthiazol-2-yl | —CH₃ |
| H252 | 4-(4-chlorophenyl)thiazol-2-yl | —CH₃ |
| H253 | 4-(3,4-dimethylphenyl)thiazol-2-yl | —CH₃ |
| H254 | 4-methyl-5-phenylthiazol-2-yl | —CH₃ |
| H255 | 4-(thiophen-2-yl)thiazol-2-yl | —CH₃ |
| H256 | thiazol-4-yl | —CH₃ |
| H257 | 4-methylthiazol-4-yl | —CH₃ |
| H258 | 4-ethylthiazol-4-yl | —CH₃ |
| H259 | 4-cyclopropylthiazol-4-yl | —CH₃ |
| H260 | 4-tert-butylthiazol-4-yl | —CH₃ |
| H261 | 4-cyclohexylthiazol-4-yl | —CH₃ |
| H262 | 4-(2,2,2-trifluoroethyl)thiazol-4-yl | —CH₃ |
| H263 | 4-(3,3,3-trifluoropropyl)thiazol-4-yl | —CH₃ |
| H264 | 4-(2,2-difluorocyclopropyl)thiazol-4-yl | —CH₃ |
| H265 | 4,5-dimethylthiazol-4-yl | —CH₃ |
| H266 | 4-methyl-5-ethylthiazol-4-yl | —CH₃ |
| H267 | 4-phenylthiazol-4-yl | —CH₃ |
| H268 | 4-(4-chlorophenyl)thiazol-4-yl | —CH₃ |
| H269 | 4-(3,4-dimethylphenyl)thiazol-4-yl | —CH₃ |
| H270 | 4-methyl-5-phenylthiazol-4-yl | —CH₃ |
| H271 | 4-(thiophen-2-yl)thiazol-4-yl | —CH₃ |

The compounds encompassed within Category IV of the present disclosure can be prepared by the procedure outlined in VI and described in Example 7 herein below.

Scheme VI

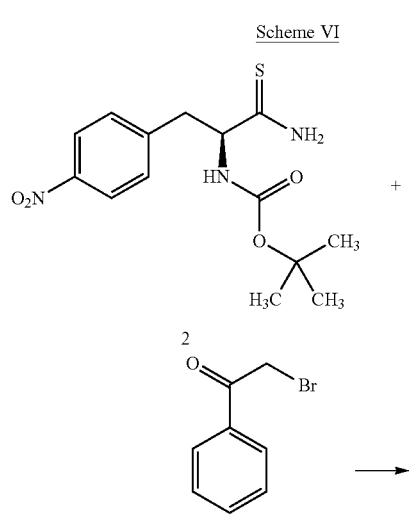

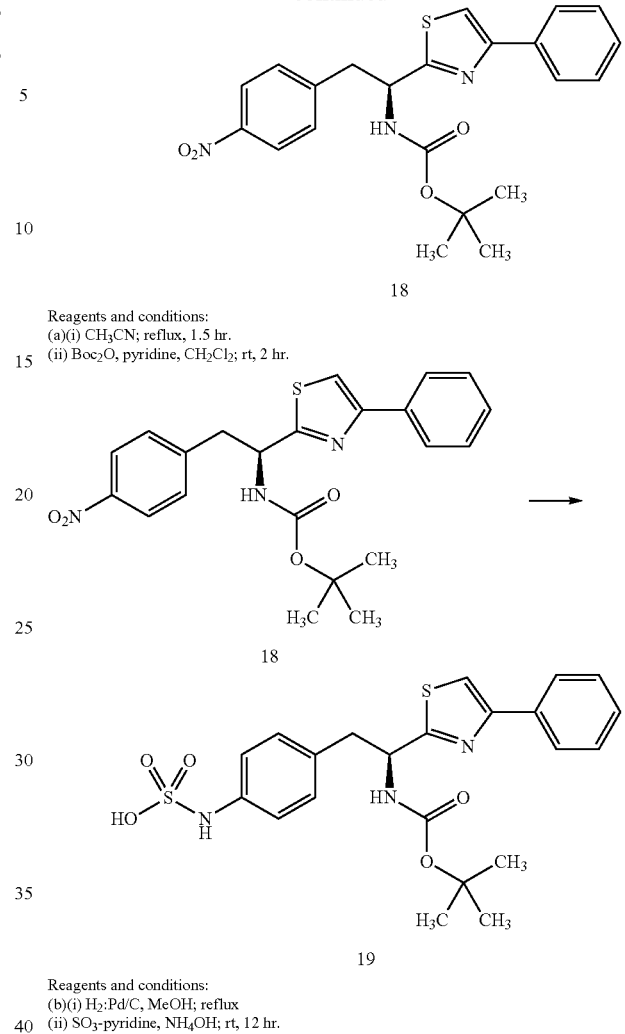

Reagents and conditions:
(a)(i) CH₃CN; reflux, 1.5 hr.
(ii) Boc₂O, pyridine, CH₂Cl₂; rt, 2 hr.

Reagents and conditions:
(b)(i) H₂:Pd/C, MeOH; reflux
(ii) SO₃-pyridine, NH₄OH; rt, 12 hr.

EXAMPLE 7

[1-(S)-(Phenylthiazol-2-yl)-2-(4-sulfoaminophenyl) ethyl]-carbamic acid tert-butyl ester (19)

Preparation of [2-(4-nitrophenyl)-1-(S)-(4-phenylthiazol-2-yl)ethyl]-carbamic acid tert-butyl ester (18): A mixture of [2-(4-nitrophenyl)-1-(S)-thiocarbamoylethyl]-carbamic acid tert-butyl ester, 2, (0.343 g, 1.05 mmol), 2-bromoacetophenone (0.231 g, 1.15 mmol), in CH₃CN (5 mL) is refluxed 1.5 hour. The solvent is removed under reduced pressure and the residue re-dissolved in CH₂Cl₂ then pyridine (0.24 mL, 3.0 mmol) and Boc₂O (0.24 mL, 1.1 mmol) are added. The reaction is stirred for 2 hours and diethyl ether is added to the solution and the precipitate which forms is removed by filtration. The organic layer is dried (Na₂SO₄), filtered, and concentrated to a residue which is purified over silica to afford 0.176 g (39%) of the desired product ESI+ MS 426 (M+1).

Preparation of [1-(S)-(phenylthiazol-2-yl)-2-(4-sulfoaminophenyl)ethyl]-carbamic acid tert-butyl ester (19): [2-(4-nitrophenyl)-1-(S)-(4-phenylthiazol-2-yl)ethyl]-carbamic acid tert-butyl ester, 18, (0.176 g, 0.41 mmol) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with $SO_3$-pyridine (0.195 g, 1.23 mmol). The reaction is stirred at room temperature for 5 minutes after which a 7% solution of $NH_4OH$ (10 mL) is added. The mixture is then concentrated and the resulting residue is purified by reverse phase chromatography to afford 0.080 g of the desired product as the ammonium salt. $^1$H NMR (300 MHz, MeOH-$d_4$) δ 7.93 (d, J=6.0 Hz, 2H), 7.68 (s, 1H), 7.46-7.42 (m, 3H), 7.37-7.32 (m, 1H), 7.14-7.18 (m, 3H), 5.13-5.18 (m, 1H), 3.40 (dd, J=4.5 and 15.0 Hz, 1H), 3.04 (dd, J=9.6 and 14.1 Hz, 1H), 1.43 (s, 9H).

The following are further non-limiting examples of Category IV of the present disclosure.

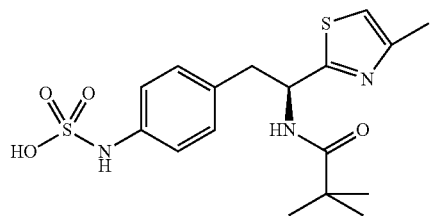 [SMILES: Cc1csc([C@H](Cc2ccc(NS(=O)(=O)O)cc2)NC(=O)C(C)(C)C)n1]

(S)-4-(2-(4-Methylthiazol-2-yl)-2-pivalamidoethyl)phenylsulfamic acid: $^1$H NMR(CD$_3$OD): δ 7.31 (s, 4H), 7.20 (s, 1H), 5.61-5.56 (m, 1H), 3.57-3.22 (m, 2H), 2.62 (s, 3H) 1.31 (s, 3H).

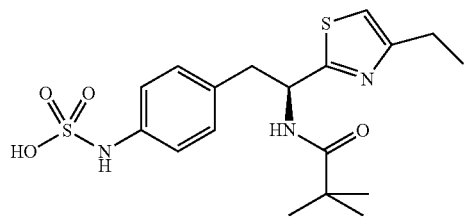 [SMILES: CCc1csc([C@H](Cc2ccc(NS(=O)(=O)O)cc2)NC(=O)C(C)(C)C)n1]

(S)-4-(2-(4-Ethylthiazol-2-yl)-2-pivalamidoethyl)phenylsulfamic acid: $^1$H NMR (300 MHz, MeOH-$d_4$) δ 7.92 (d, J=8.1 Hz, 1H), 7.12-7.14 (m, 4H), 7.03 (s, 1H), 5.38-5.46 (m, 1H), 3.3-3.4 (m, 1H), 3.08 (dd, J=10.2 and 13.8 Hz, 1H), 2.79 (q, J=7.2 Hz, 2H), 1.30 (t, J=7.2 Hz, 3H), 1.13 (s, 9H).

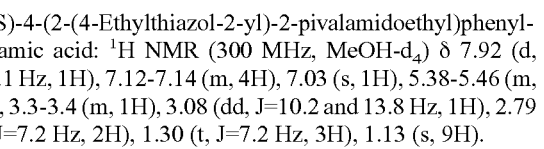

(S)-4-(2-(4-(Hydroxymethyl)thiazol-2-yl)-2-pivalamidoethyl)phenylsulfamic acid: $^1$H NMR (300 MHz, MeOH-$d_4$) δ 7.92 (d, J=8.1 Hz, 1H), 7.24 (s, 1H), 7.08 (d, J=8.7 Hz, 2H), 7.00 (d, J=8.7 Hz, 2H), 5.29-5.37 (m, 1H), 4.55 (s, 2H), 3.30 (dd, J=4.8 and 13.5 Hz, 1H), 2.99 (dd, J=10.5 and 13.5 Hz, 1H), 0.93 (s, 9H).

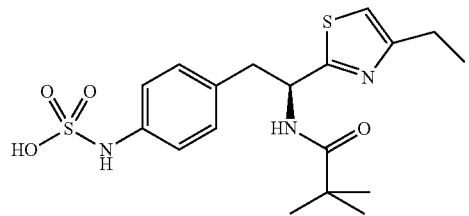 [SMILES: CCc1csc([C@H](Cc2ccc(NS(=O)(=O)O)cc2)NC(=O)C(C)(C)C)n1]

(S)-4-(2-(4-(Ethoxycarbonyl)thiazol-2-yl)-2-pivalamidoethyl)phenylsulfamic acid: $^1$H NMR (300 MHz, MeOH-$d_4$) δ 8.30 (s, 1H), 8.04 (d, J=8.1 Hz, 1H), 7.13 (s, 4H), 5.41-5.49 (m, 1H), 4.41 (q, J=7.2 Hz, 2H), 3.43 (dd, J=5.1 and 13.8 Hz, 1H), 3.14 (dd, J=5.7 and 9.9 Hz, 1H), 1.42 (t, J=7.2 Hz, 3H), 1.14 (s, 9H).

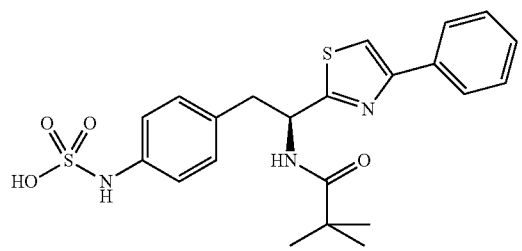 [SMILES: CC(C)(C)C(=O)N[C@@H](Cc1ccc(NS(=O)(=O)O)cc1)c1nc(-c2ccccc2)cs1]

(S)-4-(2-(4-Phenylthiazol-2-yl)-2-pivalamidoethyl)phenylsulfamic acid: $^1$H NMR (300 MHz, MeOH-$d_4$) δ 7.94-8.01 (m, 3H), 7.70 (s, 1H), 7.42-7.47 (m, 2H), 7.32-7.47 (m, 1H), 7.13-7.20 (m, 3H), 5.48-5.55 (m, 1H), 3.50 (dd, J=5.1 and 14.1 Hz, 1H), 3.18 (dd, J=10.2 and 14.1 Hz, 1H), 1.17 (s, 9H).

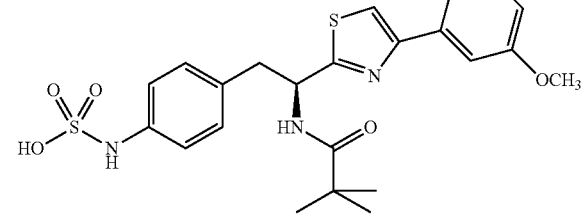

4-((S)-2-(4-(3-Methoxyphenyl)thiazol-2-yl)-2-pivalamidoethyl)phenylsulfamic acid: $^1$H NMR (CD$_3$OD): δ 7.96-7.93 (d, 1H, J=8.1 Hz), 7.69 (s, 1H), 7.51-7.49 (d, 2H, J=7.9 Hz), 7.33 (t, 1H, J=8.0 Hz), 7.14 (s, 4H), 6.92-6.90 (d, 1H, J=7.8 Hz), 5.50 (t, 1H, J=5.1 Hz), 3.87 (s, 3H), 3.50-3.13 (m, 2H), 1.15 (s, 9H).

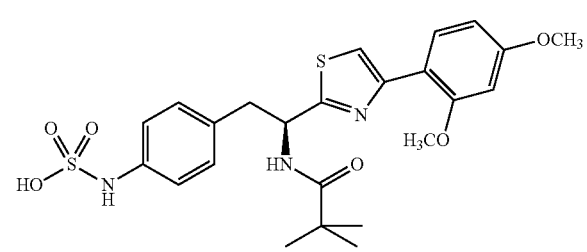 [SMILES: COc1ccc(-c2csc([C@H](Cc3ccc(NS(=O)(=O)O)cc3)NC(=O)C(C)(C)C)n2)c(OC)c1]

4-((S)-2-(4-(2,4-Dimethoxyphenyl)thiazol-2-yl)-2-pivalamidoethyl)phenylsulfamic acid: $^1$H NMR (CD$_3$OD): δ

8.11-8.09 (d, 1H, J=7.8 Hz), 7.96-7.93 (d, 1H, J=8.4 Hz), 7.74 (s, 1H), 7.18-7.16 (m, 4H), 6.67-6.64 (d, 2H, J=9.0 Hz), 5.55-5.47 (m, 1H), 3.95 (s, 3H), 3.87 (s, 3H), 3.52-3.13 (m, 2H), 1.17 (s, 9H).

(CD₃OD): δ 7.53 (s, 1H), 7.45 (s, 1H), 7.42-7.40 (d, 1H, J=8.4 Hz), 7.19-7.15 (m, 4H), 6.91-6.88 (d, 2H, J=8.4 Hz), 5.51-5.46 (m, 1H), 4.30 (s, 4H), 3.51-3.12 (m, 2H), 1.16 (s, 9H).

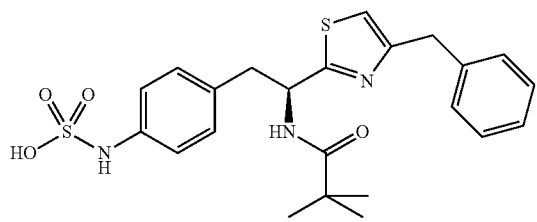 [SMILES: CC(C)(C)C(=O)N[C@@H](Cc1ccc(NS(=O)(=O)O)cc1)c1nc(Cc2ccccc2)cs1]

(S)-4-(2-(4-Benzylthiazol-2-yl)-2-pivalamidoethyl)phenylsulfamic acid: ¹H NMR (CD₃OD) δ 7.85 (d, 1H, J=8.4Hz), 7.38-7.20 (m, 4H), 7.11-7.02 (m, 1H), 7.00 (s, 1H), 5.42-5.37 (m, 1H), 4.13 (s, 2H), 3.13-3.08 (m, 2H), 1.13 (s, 9H).

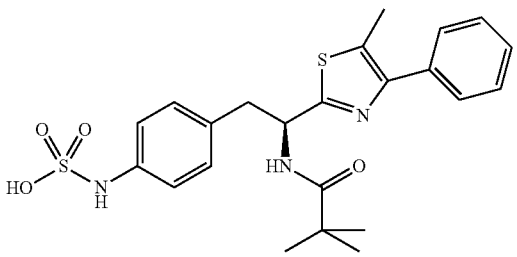

(S)-4-(2-(5-Methyl-4-phenylthiazol-2-yl)-2-pivalamidoethyl)phenylsulfamic acid: ¹H NMR (CD₃OD): δ 7.63-7.60 (d, 2H, J=7.1 Hz), 7.49-7.35 (m, 3H), 7.14 (s, 4H), 5.43-5.38 (m, 1H), 3.42-3.09 (m, 2H), 2.49 (s, 3H), 1.14 (s, 9H).

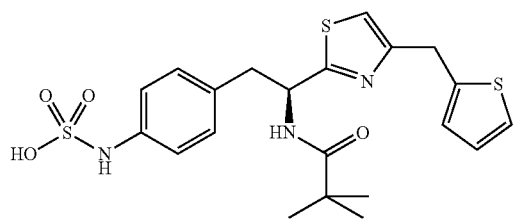 [SMILES: CC(C)(C)C(=O)N[C@@H](Cc1ccc(NS(=O)(=O)O)cc1)c1nc(Cc2cccs2)cs1]

(S)-4-(2-Pivalamido-2-(4-(thiophen-2-ylmethyl)thiazol-2-yl)ethyl)phenylsulfamic acid: ¹H NMR (CD₃OD) δ 7.88-7.85 (d, 1H), 7.38-7.35 (m, 1H), 7.10-7.01 (m, 4H), 7.02 (s, 1H), 5.45-5.38 (m, 1H), 4.13 (s, 2H), 3.13-3.05 (m, 2H), 1.13 (2, 9H).

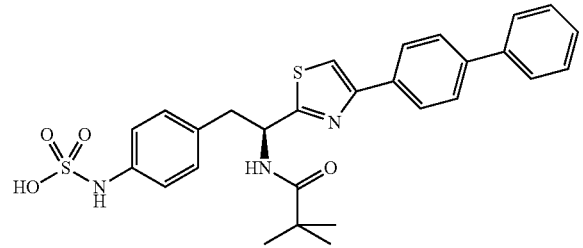

(S)-4-(2-(4-(Biphen-4-yl)thiazol-2-yl)-2-pivalamidoethyl)phenylsulfamic acid: ¹H NMR (CD₃OD): δ 8.04-8.01 (m, 2H), 7.72-7.66 (m, 5H), 7.48-7.35 (m, 3H), 7.15 (s, 4H), 5.50 (t, 1H, J=5.0 Hz), 3.57-3.15 (d, 2H), 1.16 (s, 9H).

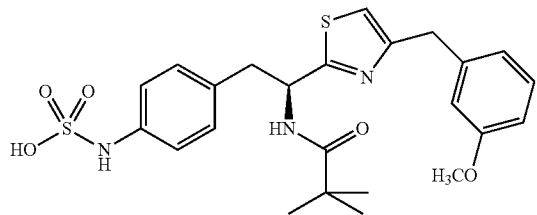 [SMILES: COc1cccc(Cc2csc([C@H](Cc3ccc(NS(=O)(=O)O)cc3)NC(=O)C(C)(C)C)n2)c1]

(S)-4-(2-(4-(3-Methoxybenzyl)thiazol-2-yl)-2-pivalamidoethyl)phenylsulfamic acid: ¹H NMR (CD₃OD) δ 7.85 (d, 1H, J=8.4Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

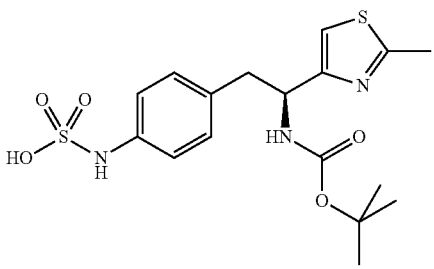

(S)-4-(2-tert-Butoxycarbonyl-2-(2-methylthaizol-4-yl)-phenylsulfamic acid ¹H NMR (300 MHz, D₂O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

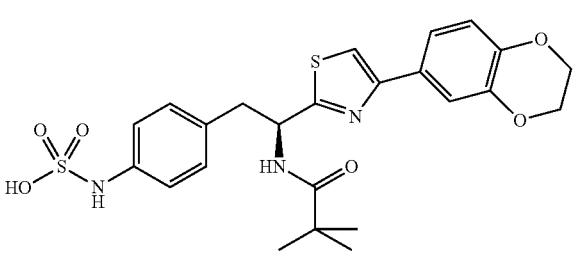 [SMILES: CC(C)(C)C(=O)N[C@@H](Cc1ccc(NS(=O)(=O)O)cc1)c1nc(-c2ccc3c(c2)OCCO3)cs1]

4-((S)-2-(4-(2,3-Dihydrobenzo[b][1,4]dioxin-6-yl)thiazol-2-yl)-2-pivalamidoethyl)-phenylsulfamic acid: ¹H NMR

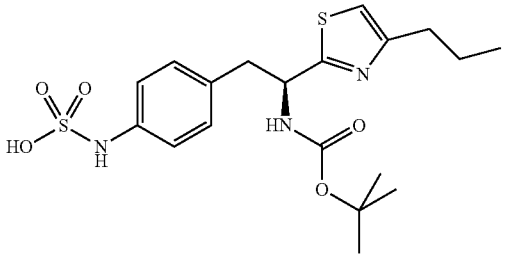 [SMILES: CCCc1csc([C@H](Cc2ccc(NS(=O)(=O)O)cc2)NC(=O)OC(C)(C)C)n1]

(S)-4-(2-(tert-Butoxycarbonyl)-2-(4-propylthiazol-2-yl)ethyl)-phenyl sulfamic acid: ¹H NMR (300 MHz, CD₃OD): δ 7.18-7.02 (m, 5H), 5.06-5.03 (m, 1H), 3.26 (dd, J=13.8, 4.8

Hz, 1H), 2.95 (dd, J=13.8, 9.3 Hz, 1H), 2.74 (dd, J=15.0, 7.2 Hz, 2H), 1.81-1.71 (m, 2H), 1.40 (s, 7H), 1.33 (bs, 2H), 0.988 (t, J=7.5 Hz 3H).

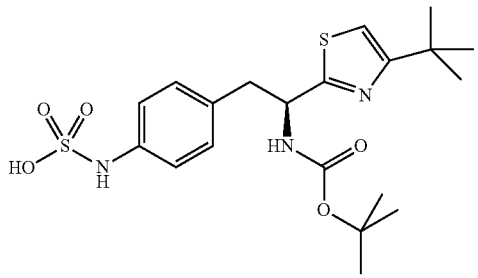 [SMILES: CC(C)(C)OC(=O)N[C@@H](Cc1ccc(NS(=O)(=O)O)cc1)c1nc(C(C)(C)C)cs1]

(S)-4-(2-(tert-Butoxycarbonyl)-2-(4-tert-butylthiazol-2-yl)ethyl)-phenyl sulfamic acid: ¹H NMR (300 MHz, CD₃OD): δ 7.12 (s, 4H), 7.01 (s, 1H), 5.11-5.06 (m, 1H), 3.32-3.25 (m, 1H), 2.96 (m, 1H), 1.42 (s, 8H), 1.38 (s, 9H), 1.32 (s, 1H).

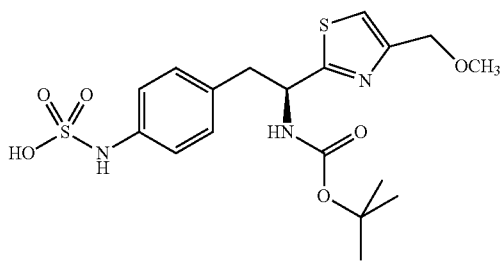

(S)-4-(2-(tert-Butoxycarbonylamino)-2-(4-(methoxymethyl)thiazol-2-yl)ethyl)-phenyl sulfamic acid: ¹H NMR (300 MHz, CD₃OD): δ 7.36 (s, 1H), 7.14-7.05 (m, 4H), 5.06 (dd, J=9.0, 5.1 Hz, 1H), 4.55 (s, 2H), 3.42 (s, 3H), 3.31-3.24 (m, 1H), 2.97 (dd, J=13.8, 9.9 Hz, 1H), 1.47-1.31 (m, 9H).

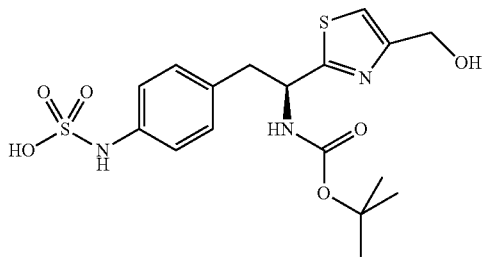 [SMILES: CC(C)(C)OC(=O)N[C@@H](Cc1ccc(NS(=O)(=O)O)cc1)c1nc(CO)cs1]

(S)-4-(2-tert-Butoxycarbonylamino)-2-(4-(2-hydroxymethyl)thiazol-2-yl)ethyl)phenylsulfamic acid: ¹H NMR (300 MHz, MeOH-d₄) δ 7.22-7.25 (m, 1H), 7.09-7.15 (m, 4H), 5.00-5.09 (m, 1H), 4.32-4.35 (m, 1H), 3.87 (t, J=6.6 Hz, 2H), 3.23-3.29 (m, 1H), 3.09-3.18 (m, 1H), 2.98 (t, J=6.6 Hz, 2H), 1.41 (s, 9H).

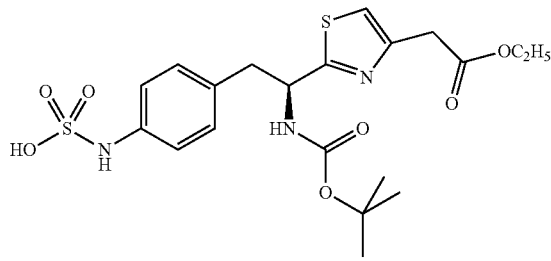 [SMILES: CCOC(=O)Cc1csc([C@H](Cc2ccc(NS(=O)(=O)O)cc2)NC(=O)OC(C)(C)C)n1]

(S)-4-(2-tert-Butoxycarbonylamino)-2-(4-(2-ethoxy-2-oxoethyl)-thiazole-2-yl)-ethyl)phenylsulfamic acid: ¹H NMR (300 MHz, MeOH-d₄) δ 7.29 (s, 1H), 7.09-7.16 (m, 4H), 5.04-5.09 (m, 1H), 4.20 (q, J=6.9 Hz, 2H), 3.84 (s, 2H), 3.30 (dd, J=4.8 and 14.1 HZ, 1H), 2.97 (dd, J=9.6 Hz and 13.8 Hz, 1H), 1.41 (s, 9H), 1.29 (t, J=7.2 Hz, 3H).

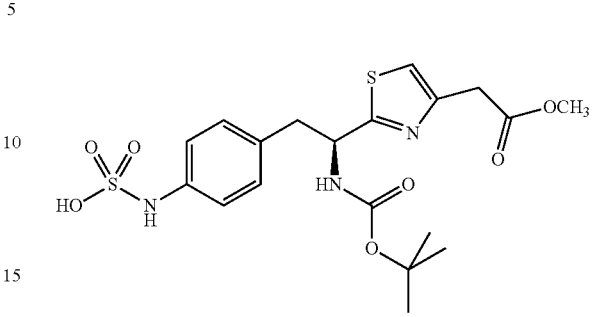

(S)-4-(2-(tert-Butoxycarbonylamino)-2-(4-(2-methoxy-2-oxoethyl)thiazol-2-yl)ethyl)phenylsulfamic acid: ¹H NMR (300 MHz, MeOH-d₄) δ 7.31 (s, 1H), 7.01-7.16 (m, 4H), 5.04-5.09 (m, 1H), 4.01 (s, 2H), 3.78 (s, 2H), 3.74 (s, 3H), 3.29 (dd, J=5.1 and 13.8 Hz, 1H), 2.99 (dd, J=9.3 and 13.8 Hz, 1H), 1.41 (s, 9H).

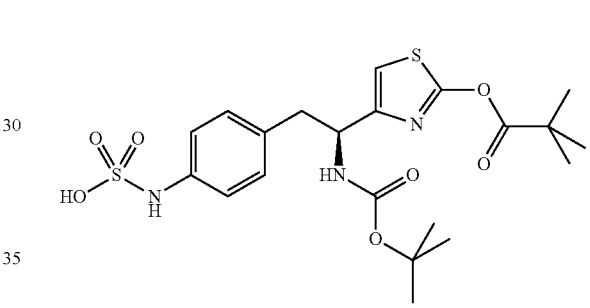

(S)-4-(2-(tert-Butoxycarbonylamino)-2-(2-(pivaloyloxy)thiazol-4-yl)ethyl)-phenylsulfamic acid: ¹H NMR (300 MHz, D₂O) δ 6.95 (s, 4H), 6.63 (s, 1H), 2.94 (dd, J=13.5 and 4.8 Hz, 1H), 2.75 (dd, J=13.5 and 4.8 Hz, 1H), 1.16 (s, 9H), 1.13 (s, 9H).

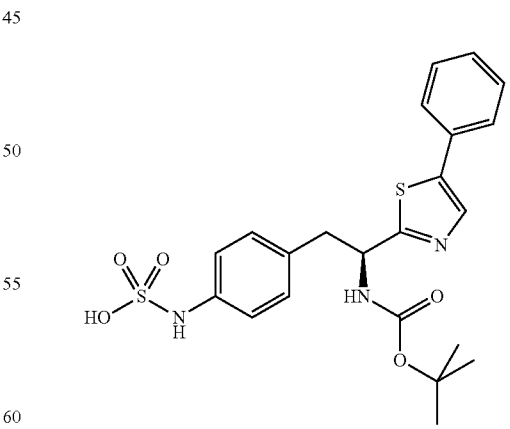

(S)-4-(2-(tert-Butoxycarbonylamino)-2-(5-phenylthiazol-2-yl)ethyl)-phenyl sulfamic acid: ¹H NMR (300 MHz, CD₃OD): δ 7.98 (s, 1H), 7.62 (d, J=7.2 Hz, 2H), 7.46-7.35 (m, 4H), 7.14 (s, 4H), 5.09 (bs, 1H), 3.07-2.99 (m, 2H), 1.43 (s, 9H).

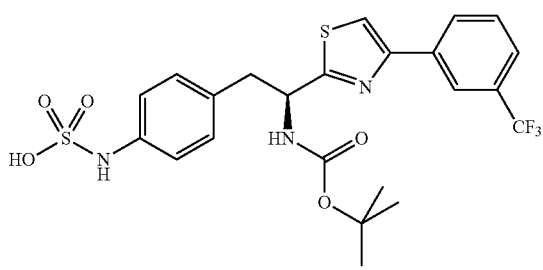 [SMILES: CC(C)(C)OC(=O)N[C@@H](Cc1ccc(NS(=O)(=O)O)cc1)c1nc(-c2cccc(C(F)(F)F)c2)cs1]

4-((S)-2-(tert-Butoxycarbonylamino)-2-(4-(3-(trifluoromethyl)phenyl)thiazol-2-yl)ethyl)phenyl sulfamic acid: $^1$H NMR (300 MHz, CD$_3$OD): δ 8.28 (s, 1H), 8.22-8.19 (m, 1H), 7.89 (s, 1H), 7.65 (d, J=5.1 Hz, 2H), 7.45 (d, J=8.1 Hz, 1H), 7.15 (s, 4H), 5.17-5.14 (m, 1H), 3.43-3.32 (m, 1H), 3.05 (dd, J=14.1, 9.6 Hz, 1H), 1.42 (s, 9H).

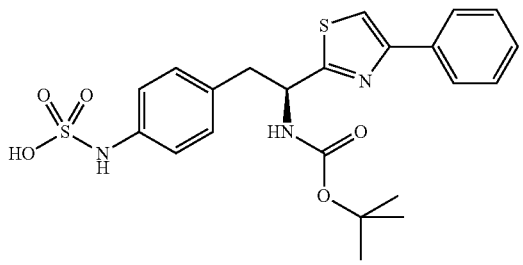 [SMILES: CC(C)(C)OC(=O)N[C@@H](Cc1ccc(NS(=O)(=O)O)cc1)c1nc(-c2ccccc2)cs1]

(S)-4-(2-(tert-Butoxycarbonylamino)-2-(4-phenylthiazol-2-yl)ethyl)-phenyl sulfamic acid: $^1$H NMR (300 MHz, CD$_3$OD): δ 7.98 (s, 1H), 7.94 (d, J=7.2 Hz, 2H), 7.46-7.35 (m, 4H), 7.14 (s, 4H), 5.09 (bs, 1H), 3.07-2.99 (m, 2H), 1.43 (s, 9H).

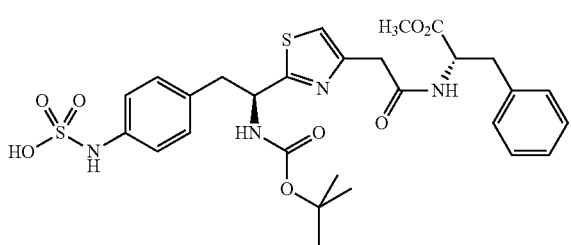 [SMILES: COC(=O)[C@H](Cc1ccccc1)NC(=O)Cc1csc([C@H](Cc2ccc(NS(=O)(=O)O)cc2)NC(=O)OC(C)(C)C)n1]

(S,S)-2-(2-{2-[2-tert-Butoxycarbonylamino-2-(4-sulfoaminophenyl)ethyl]thiazol-4-yl}acetylamido)-3-phenyl-propionic acid methyl ester: $^1$H NMR (300 MHz, MeOH-d$_4$) δ 6.85-6.94 (m, 9H), 6.64 (s, 1H), 4.83 (s, 1H), 4.54-4.58 (m, 1H), 3.49 (s, 3H), 3.39 (s, 2H), 2.80-2.97 (m, 1H), 2.64-2.78 (m, 1H), 1.12 (s, 9H).

(S)-[1-{1-Oxo-4-[2-(1-phenyl-1H-tetrazol-5-sulfonyl)ethyl]-1H-1λ$^4$-thiazol-2-yl}-2-(4-sulfamino-phenyl)-ethyl]-carbamic acid tert-butyl ester: $^1$H NMR (300 MHz, MeOH-d$_4$) δ 7.22-7.75 (m, 2H), 7.62-7.69 (m, 2H), 7.55 (s, 1H), 7.10-7.20 (m, 5H), 5.25 (m, 1H), 4.27-4.36 (m, 1H), 4.11-4.21 (m, 1H), 3.33-3.44 (m, 4H), 2.84-2.90 (m, 1H), 1.33 (s, 9H).

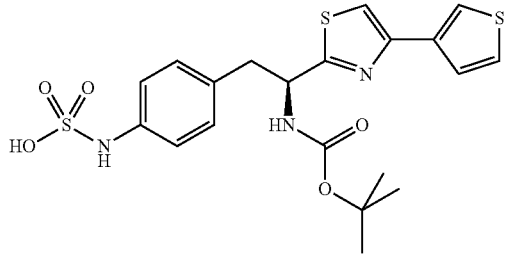 [SMILES: CC(C)(C)OC(=O)N[C@@H](Cc1ccc(NS(=O)(=O)O)cc1)c1nc(-c2ccsc2)cs1]

4-((S)-2-(tert-Butoxycarbonylamino)-2-(4-(thiophen-3-yl)thiazol-2-yl)ethyl)phenyl sulfamic acid: $^1$H NMR (300 MHz, CD$_3$OD): δ 7.84 (dd, J=3.0, 1.5 Hz, 1H), 7.57-7.55 (m, 2H), 7.47 (dd, J=4.8, 3.0 Hz, 1H), 7.15 (s, 4H), 5.15-5.10 (m, 1H), 3.39-3.34 (m, 1H), 3.01 (dd, J=14.1, 9.6 Hz, 1H), 1.42 (s, 8H), 1.32 (s, 1H).

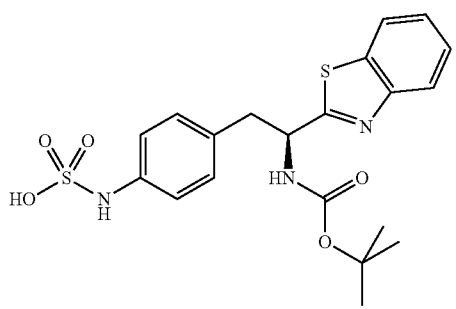 [SMILES: CC(C)(C)OC(=O)N[C@@H](Cc1ccc(NS(=O)(=O)O)cc1)c1nc2ccccc2s1]

(S)-4-(2-(Benzo[d]thiazol-2-ylamino)-2-(tert-butoxycarbonyl)ethyl)phenylsulfamic acid: $^1$H NMR (CD$_3$OD) δ 7.86-7.82 (m, 2H), 7.42 (t, 2H, J=7.1 Hz), 7.33 (t, 1H, J=8.2 Hz), 7.02 (s, 4H), 5.10-5.05 (m, 1H), 2.99-2.91 (m, 2H), 1.29 (s, 9H).

(S)-4-(2-tert-Butoxycarbonylamino-2-(2-methylthiazol-4-yl)-phenylsulfamic acid $^1$H NMR (300 MHz, D$_2$O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

The first aspect of Category V of the present disclosure relates to 2-(thiazol-2-yl) compounds having the formula:

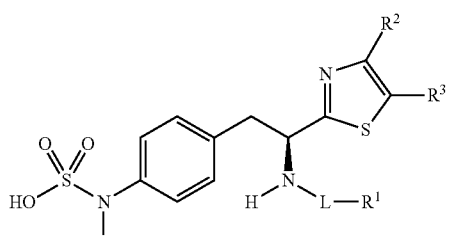

wherein R$^1$, R$^2$, R$^3$, and L are further defined herein in Table IX herein below.

TABLE IX

| No. | L | R$^1$ | R$^2$ | R$^3$ |
|---|---|---|---|---|
| I272 | —C(O)CH$_2$— | phenyl | —CH$_3$ | —H |
| I273 | —C(O)CH$_2$— | 2-fluorophenyl | —CH$_3$ | —H |
| I274 | —C(O)CH$_2$— | 3-fluorophenyl | —CH$_3$ | —H |
| I275 | —C(O)CH$_2$— | 4-fluorophenyl | —CH$_3$ | —H |

TABLE IX-continued

| No. | L | R¹ | R² | R³ |
|---|---|---|---|---|
| I276 | —C(O)CH₂— | 2,3-difluorophenyl | —CH₃ | —H |
| I277 | —C(O)CH₂— | 3,4-difluorophenyl | —CH₃ | —H |
| I278 | —C(O)CH₂— | 3,5-difluorophenyl | —CH₃ | —H |
| I279 | —C(O)CH₂— | 2-chlorophenyl | —CH₃ | —H |
| I280 | —C(O)CH₂— | 3-chlorophenyl | —CH₃ | —H |
| I281 | —C(O)CH₂— | 4-chlorophenyl | —CH₃ | —H |
| I282 | —C(O)CH₂— | 2,3-dichlorophenyl | —CH₃ | —H |
| I283 | —C(O)CH₂— | 3,4-dichlorophenyl | —CH₃ | —H |
| I284 | —C(O)CH₂— | 3,5-dichlorophenyl | —CH₃ | —H |
| I285 | —C(O)CH₂— | 2-hydroxyphenyl | —CH₃ | —H |
| I286 | —C(O)CH₂— | 3-hydroxyphenyl | —CH₃ | —H |
| I287 | —C(O)CH₂— | 4-hydroxyphenyl | —CH₃ | —H |
| I288 | —C(O)CH₂— | 2-methoxyphenyl | —CH₃ | —H |
| I289 | —C(O)CH₂— | 3-methoxyphenyl | —CH₃ | —H |
| I290 | —C(O)CH₂— | 4-methoxyphenyl | —CH₃ | —H |
| I291 | —C(O)CH₂— | 2,3-dimethoxyphenyl | —CH₃ | —H |
| I292 | —C(O)CH₂— | 3,4-dimethoxyphenyl | —CH₃ | —H |
| I293 | —C(O)CH₂— | 3,5-dimethoxyphenyl | —CH₃ | —H |
| I294 | —C(O)CH₂— | phenyl | —CH₂CH₃ | —H |
| I295 | —C(O)CH₂— | 2-fluorophenyl | —CH₂CH₃ | —H |
| I296 | —C(O)CH₂— | 3-fluorophenyl | —CH₂CH₃ | —H |
| I297 | —C(O)CH₂— | 4-fluorophenyl | —CH₂CH₃ | —H |
| I298 | —C(O)CH₂— | 2,3-difluorophenyl | —CH₂CH₃ | —H |
| I299 | —C(O)CH₂— | 3,4-difluorophenyl | —CH₂CH₃ | —H |
| I300 | —C(O)CH₂— | 3,5-difluorophenyl | —CH₂CH₃ | —H |
| I301 | —C(O)CH₂— | 2-chlorophenyl | —CH₂CH₃ | —H |
| I302 | —C(O)CH₂— | 3-chlorophenyl | —CH₂CH₃ | —H |
| I303 | —C(O)CH₂— | 4-chlorophenyl | —CH₂CH₃ | —H |
| I304 | —C(O)CH₂— | 2,3-dichlorophenyl | —CH₂CH₃ | —H |
| I305 | —C(O)CH₂— | 3,4-dichlorophenyl | —CH₂CH₃ | —H |
| I306 | —C(O)CH₂— | 3,5-dichlorophenyl | —CH₂CH₃ | —H |
| I307 | —C(O)CH₂— | 2-hydroxyphenyl | —CH₂CH₃ | —H |
| I308 | —C(O)CH₂— | 3-hydroxyphenyl | —CH₂CH₃ | —H |
| I309 | —C(O)CH₂— | 4-hydroxyphenyl | —CH₂CH₃ | —H |
| I310 | —C(O)CH₂— | 2-methoxyphenyl | —CH₂CH₃ | —H |
| I311 | —C(O)CH₂— | 3-methoxyphenyl | —CH₂CH₃ | —H |
| I312 | —C(O)CH₂— | 4-methoxyphenyl | —CH₂CH₃ | —H |
| I313 | —C(O)CH₂— | 2,3-dimethoxyphenyl | —CH₂CH₃ | —H |
| I314 | —C(O)CH₂— | 3,4-dimethoxyphenyl | —CH₂CH₃ | —H |
| I315 | —C(O)CH₂— | 3,5-dimethoxyphenyl | —CH₂CH₃ | —H |
| I316 | —C(O)CH₂CH₂— | phenyl | —CH₃ | —H |
| I317 | —C(O)CH₂CH₂— | 2-fluorophenyl | —CH₃ | —H |
| I318 | —C(O)CH₂CH₂— | 3-fluorophenyl | —CH₃ | —H |
| I319 | —C(O)CH₂CH₂— | 4-fluorophenyl | —CH₃ | —H |
| I320 | —C(O)CH₂CH₂— | 2,3-difluorophenyl | —CH₃ | —H |
| I321 | —C(O)CH₂CH₂— | 3,4-difluorophenyl | —CH₃ | —H |
| I322 | —C(O)CH₂CH₂— | 3,5-difluorophenyl | —CH₃ | —H |
| I323 | —C(O)CH₂CH₂— | 2-chlorophenyl | —CH₃ | —H |
| I324 | —C(O)CH₂CH₂— | 3-chlorophenyl | —CH₃ | —H |
| I325 | —C(O)CH₂CH₂— | 4-chlorophenyl | —CH₃ | —H |
| I326 | —C(O)CH₂CH₂— | 2,3-dichlorophenyl | —CH₃ | —H |
| I327 | —C(O)CH₂CH₂— | 3,4-dichlorophenyl | —CH₃ | —H |
| I328 | —C(O)CH₂CH₂— | 3,5-dichlorophenyl | —CH₃ | —H |
| I329 | —C(O)CH₂CH₂— | 2-hydroxyphenyl | —CH₃ | —H |
| I330 | —C(O)CH₂CH₂— | 3-hydroxyphenyl | —CH₃ | —H |
| I331 | —C(O)CH₂CH₂— | 4-hydroxyphenyl | —CH₃ | —H |
| I332 | —C(O)CH₂CH₂— | 2-methoxyphenyl | —CH₃ | —H |
| I333 | —C(O)CH₂CH₂— | 3-methoxyphenyl | —CH₃ | —H |
| I334 | —C(O)CH₂CH₂— | 4-methoxyphenyl | —CH₃ | —H |
| I335 | —C(O)CH₂CH₂— | 2,3-dimethoxyphenyl | —CH₃ | —H |
| I336 | —C(O)CH₂CH₂— | 3,4-dimethoxyphenyl | —CH₃ | —H |
| I337 | —C(O)CH₂CH₂— | 3,5-dimethoxyphenyl | —CH₃ | —H |
| I338 | —C(O)CH₂CH₂— | phenyl | —CH₂CH₃ | —H |
| I339 | —C(O)CH₂CH₂— | 2-fluorophenyl | —CH₂CH₃ | —H |
| I340 | —C(O)CH₂CH₂— | 3-fluorophenyl | —CH₂CH₃ | —H |
| I341 | —C(O)CH₂CH₂— | 4-fluorophenyl | —CH₂CH₃ | —H |
| I342 | —C(O)CH₂CH₂— | 2,3-difluorophenyl | —CH₂CH₃ | —H |
| I343 | —C(O)CH₂CH₂— | 3,4-difluorophenyl | —CH₂CH₃ | —H |
| I344 | —C(O)CH₂CH₂— | 3,5-difluorophenyl | —CH₂CH₃ | —H |
| I345 | —C(O)CH₂CH₂— | 2-chlorophenyl | —CH₂CH₃ | —H |
| I346 | —C(O)CH₂CH₂— | 3-chlorophenyl | —CH₂CH₃ | —H |
| I347 | —C(O)CH₂CH₂— | 4-chlorophenyl | —CH₂CH₃ | —H |
| I348 | —C(O)CH₂CH₂— | 2,3-dichlorophenyl | —CH₂CH₃ | —H |
| I349 | —C(O)CH₂CH₂— | 3,4-dichlorophenyl | —CH₂CH₃ | —H |
| I350 | —C(O)CH₂CH₂— | 3,5-dichlorophenyl | —CH₂CH₃ | —H |
| I351 | —C(O)CH₂CH₂— | 2-hydroxyphenyl | —CH₂CH₃ | —H |
| I352 | —C(O)CH₂CH₂— | 3-hydroxyphenyl | —CH₂CH₃ | —H |
| I353 | —C(O)CH₂CH₂— | 4-hydroxyphenyl | —CH₂CH₃ | —H |
| I354 | —C(O)CH₂CH₂— | 2-methoxyphenyl | —CH₂CH₃ | —H |
| I355 | —C(O)CH₂CH₂— | 3-methoxyphenyl | —CH₂CH₃ | —H |
| I356 | —C(O)CH₂CH₂— | 4-methoxyphenyl | —CH₂CH₃ | —H |
| I357 | —C(O)CH₂CH₂— | 2,3-dimethoxyphenyl | —CH₂CH₃ | —H |
| I358 | —C(O)CH₂CH₂— | 3,4-dimethoxyphenyl | —CH₂CH₃ | —H |
| I359 | —C(O)CH₂CH₂— | 3,5-dimethoxyphenyl | —CH₂CH₃ | —H |

The compounds encompassed within the first aspect of Category V of the present disclosure can be prepared by the procedure outlined in Scheme VII and described in Example 8 herein below.

Scheme VII

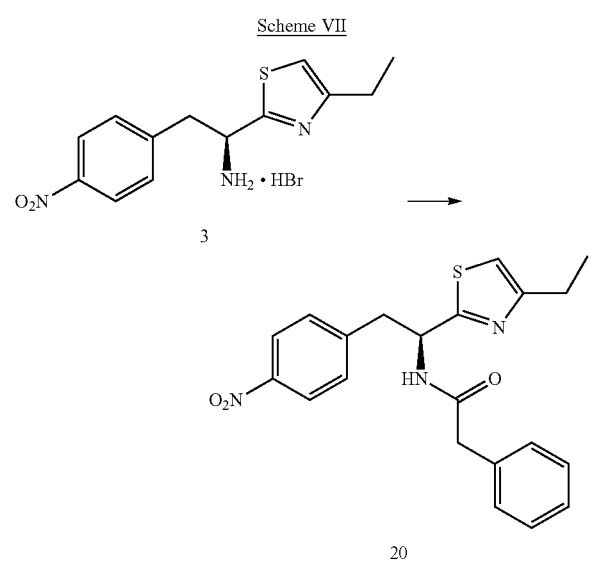

Reagents and conditions: (a) C₆H₄CO₂H, EDCI, HOBt, DIPEA, DMF; rt, 18 hr.

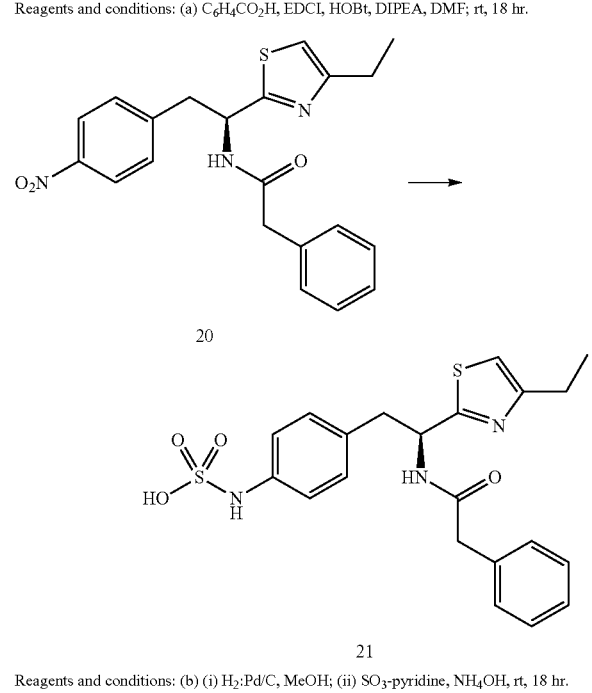

Reagents and conditions: (b) (i) H₂:Pd/C, MeOH; (ii) SO₃-pyridine, NH₄OH, rt, 18 hr.

EXAMPLE 8

{4-[2-(S)-(4-Ethylthiazol-2-yl)-2-(2-phenylacetylamido)ethyl]phenyl}sulfamic acid (21)

Preparation of N-[1-(4-ethylthiazol-2-yl)-2-(4-nitrophenyl)ethyl]-2-phenyl-acetamide (20): To a solution of 1-(S)-(4-ethylthiazol-2-yl)-2-(4-nitrophenyl)ethyl amine hydrobromide, 3, (0.393 g, 1.1 mmol), phenylacetic acid (0.190 g, 1.4 mmol) and 1-hydroxybenzotriazole (HOBt) (0.094 g, 0.70 mmol) in DMF (10 mL) at 0°, is added 1-(3-dimethylaminopropyl)-3-ethylcarbodiimide (EDCI) (0.268 g, 1.4 mmol) followed by triethylamine (0.60 mL, 4.2 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous $NaHCO_3$, water and brine, and dried over $Na_2SO_4$. The solvent is removed in vacuo to afford 0.260 g (60% yield) of the desired product which is used without further purification. ESI+ MS 396 (M+1).

Preparation of {4-[2-(S)-(4-ethylthiazol-2-yl)-2-(2-phenylacetylamido)ethyl]-phenyl}sulfamic acid (21): N-[1-(4-ethylthiazol-2-yl)-2-(4-nitrophenyl)ethyl]-2-phenyl-acetamide, 20, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with $SO_3$-pyridine (0.177 g, 1.23). The reaction is stirred at room temperature for 5 minutes after which a 7% solution of $NH_4OH$ (10 mL) is added. The mixture is then concentrated and the resulting residue is purified by reverse phase chromatography to afford 0.136 g of the desired product as the ammonium salt. $^1$H NMR ($CD_3OD$) δ 8.60 (d, 1H, J=8.1 Hz), 7.33-7.23 (m, 3H), 7.16-7.00 (m, 6H), 5.44-5.41 (m, 1H), 3.28 (1H, A of ABX, obscured by solvent), 3.03 (1H, B of ABX, J=14.1, 9.6Hz), 2.80 (q, 2H, J=10.5, 7.8Hz) 1.31 (t, 3H, J=4.6Hz).

The following are non-limiting examples of the first aspect of Category V of the present disclosure.

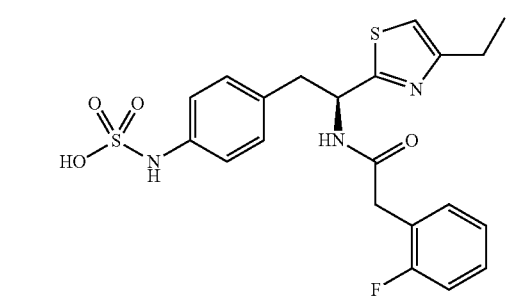 [SMILES: CCc1csc([C@H](Cc2ccc(NS(=O)(=O)O)cc2)NC(=O)Cc2ccccc2F)n1]

(S)-4-(2-(4-Ethylthiazol-2-yl)-2-(2-(2-fluorophenyl)acetamido)ethyl)phenylsulfamic acid: $^1$H NMR ($CD_3OD$) δ 8.65 (d, 1H, J=8.4Hz), 7.29-7.15 (m, 1H), 7.13-7.03 (m, 7H), 5.46-5.42 (m, 1H), 3.64-3.51 (m, 2H), 3.29 (1H), 3.04 (1H, B of ABX, J=13.8, 9.6Hz), 2.81 (q, 2H, J=15.6, 3.9Hz), 1.31 (t, 3H, J=7.8Hz). $^{19}$F NMR ($CD_3OD$) δ 43.64.

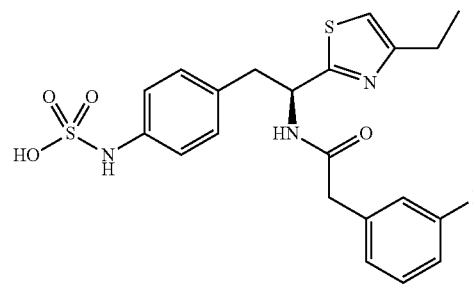

(S)-4-(2-(4-Ethylthiazol-2-yl)-2-(2-(3-fluorophenyl)acetamido)ethyl)phenylsulfamic acid: $^1$H NMR (CD3OD) δ 8.74 (d, 1H, J=8.4Hz), 7.32 (q, 1H, J=6.6, 14.2Hz), 7.10-6.91 (m, 8H), 5.47-5.40 (m, 1H), 3.53 (s, 2H), 3.30 (1H), 3.11 (1H, B of ABX, J=9.6, 14.1Hz), 2.80 (q, 2H, J=6.6, 15.1Hz), 1.31 (t, 3H, J=7.8Hz). 19F NMR δ 47.42.

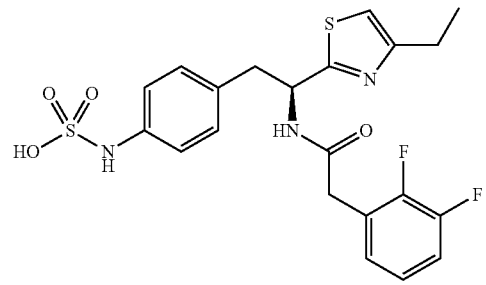 [SMILES: CCc1csc([C@H](Cc2ccc(NS(=O)(=O)O)cc2)NC(=O)Cc2cccc(F)c2F)n1]

(S)-4-(2-(2-(2,3-Difluorophenyl)acetamido)-2-(4-ethylthiazol-2-yl)ethyl)-phenylsulfamic acid: $^1$H NMR ($CD_3OD$) δ 7.16-7.05 (m, 5H), 6.85-6.80 (m, 1H), 5.48-5.43 (m, 1H), 3.63 (s, 2H), 3.38 (1H, A of ABX, obscured by solvent), 3.03 (1H), 2.80 (q, H, J=15.1, 7.8Hz), 1.31 (t, 3H, J=7.5Hz).

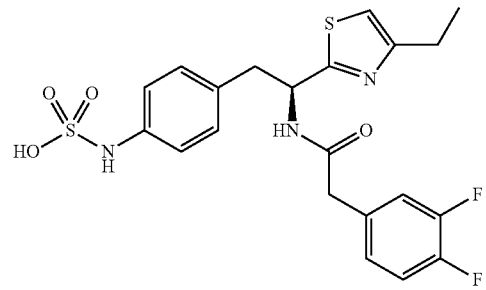 [SMILES: CCc1csc([C@H](Cc2ccc(NS(=O)(=O)O)cc2)NC(=O)Cc2ccc(F)c(F)c2)n1]

(S)-4-(2-(2-(3,4-Difluorophenyl)acetamido)-2-(4-ethylthiazol-2-yl)ethyl)-phenylsulfamic acid: $^1$H NMR ($CD_3OD$) δ 8.75 (d, 1H, J=7.8Hz), 7.23-7.04 (m, 6H), 6.88-6.84 (m, 1H), 5.44-5.40 (m, 1H), 3.49 (s, 2H), 3.34 (1H), 3.02 (1H, B of ABX, J=14.1, 9.9Hz), 2.80 (q, 2H, J=15.1, 7.8Hz), 1.31 (t, 1H, J=7.5Hz). 19F NMR (CD3OD) δ 22.18, 19.45.

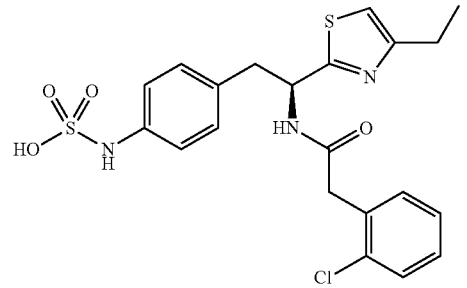 [SMILES: CCc1csc([C@H](Cc2ccc(NS(=O)(=O)O)cc2)NC(=O)Cc2ccccc2Cl)n1]

(S)-4-(2-(2-(2-Chlorophenyl)acetamido)-2-(4-ethylthiazol-2-yl)ethyl)phenylsulfamic acid: $^1$H NMR (CD3OD) δ 7.39-7.36 (m, 1H), 7.27-7.21 (m, 2H), 7.15-6.98 (m, 5H), 5.49-5.44 (m, 1H), 3.69 (d, 2H, J=11.7 Hz), 3.32 (1H), 3.04 (1H, B of ABX, J=9.3, 13.9 Hz), 2.80 (q, 2H, J=7.8, 15.3 Hz), 1.31 (t, 3H, J=7.5 Hz).

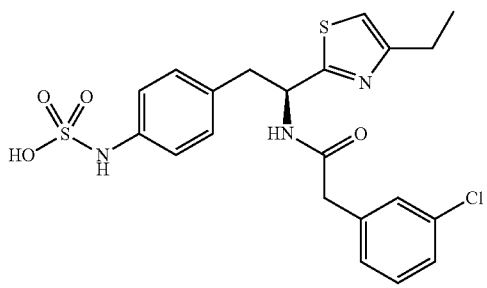 [SMILES: CCc1csc([C@H](Cc2ccc(NS(=O)(=O)O)cc2)NC(=O)Cc2cccc(Cl)c2)n1]

(S)-4-(2-(2-(3-Chlorophenyl)acetamido)-2-(4-ethylthiazol-2-yl)ethyl)phenylsulfamic acid: $^1$H NMR (CD3OD) δ 7.33-7.23 (m, 3H), 7.13-7.03 (m, 5H), 5.43 (q, 1H, J=5.1, 9.6Hz), 3.51 (s, 2H), 3.29 (1H), 3.03 (1H, B of ABX, J=9.9, 14.1Hz), 2.80 (q, 2H, J=7.5, 15Hz), 1.31 (t, 3H, J=7.8Hz).

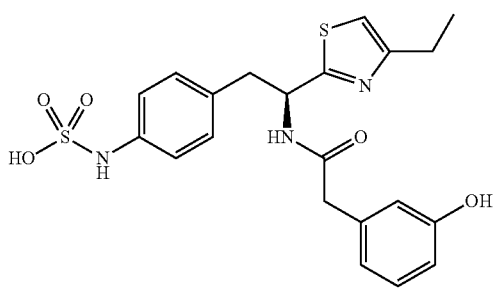 [SMILES: CCc1csc([C@H](Cc2ccc(NS(=O)(=O)O)cc2)NC(=O)Cc2cccc(O)c2)n1]

(S)-4-(2-(4-Ethylthiazol-2-yl)-2-(2-(3-hydroxyphenyl)acetamido)ethyl)-phenylsulfamic acid: $^1$H NMR (CD$_3$OD) δ 7.16-7.08 (m, 3H), 7.03-7.00 (m, 3H), 6.70-6.63 (m, 2H), 5.42-5.40 (m, 1H), 3.44 (s, 2H), 3.28 (1H, A of ABX, obscured by solvent), 3.04 (B of ABX, J=14.1, 9.6Hz), 2.89 (q, 2H, J=15, 7.5Hz), 1.31 (t, 3H, J=7.5Hz).

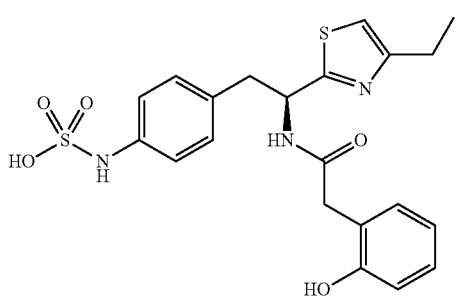 [SMILES: CCc1csc([C@H](Cc2ccc(NS(=O)(=O)O)cc2)NC(=O)Cc2ccccc2O)n1]

(S)-4-(2-(4-Ethylthiazol-2-yl)-2-(2-(2-methoxyphenyl)acetamido)ethyl)-phenylsulfamic acid: $^1$H NMR (CD$_3$OD) δ 8.00 (d, 1H, J=7.8Hz), 7.26 (t, 1H, J=13.2Hz), 7.09-7.05 (m, 4H), 7.01 (s, 1H), 6.91-6.89 (m, 4H), 5.44-5.39 (m, 1H), 3.71 (s, 3H), 3.52 (s, 2H), 3.26 (1H, A of ABX, J=14.1, 5.1Hz), 3.06 (1H B of ABX, J=13.8, 8.4Hz), 2.80 (q, 2H, J=8.1, 15.6Hz), 1.31 (t, 3H, J=1.2Hz).

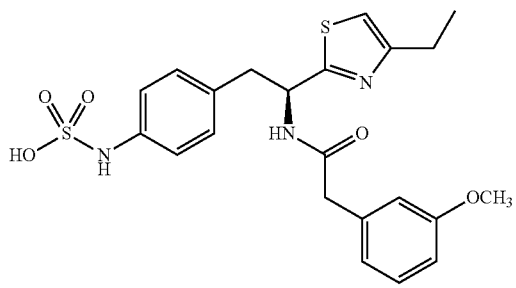 [SMILES: CCc1csc([C@H](Cc2ccc(NS(=O)(=O)O)cc2)NC(=O)Cc2cccc(OC)c2)n1]

(S)-4-{2-(4-Ethylthiazol-2-yl)-2-[2-(3-methoxyphenyl)acetamido]ethyl}-phenylsulfamic acid: $^1$H NMR (CD$_3$OD) δ 8.58 (d, 1H, J=8.1 Hz), 7.21 (t, 1H, J=7.8Hz), 7.12-7.02 (m, 4H), 6.81 (s, 2H), 6.72 (d, 1H, J=7.5Hz), 5.45-5.40 (m, 1H), 3.79 (s, 3H), 3.50 (s, 2H), 3.29 (1H, A of ABX, obscured by solvent), 3.08 (1H, B of ABX, J=11.8, 5.1Hz), 2.80 (q, 2H, J=15, 7.5Hz), 1.31 (t, 3H, J=6.6Hz).

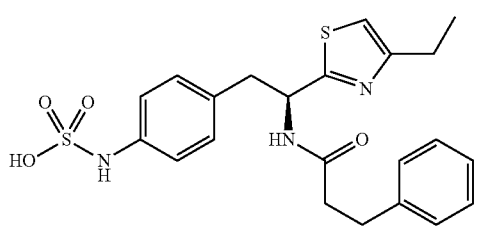 [SMILES: CCc1csc([C@H](Cc2ccc(NS(=O)(=O)O)cc2)NC(=O)CCc2ccccc2)n1]

(S)-4-(2-(4-Ethylthiazol-2-yl)-2-(3-phenylpropanamido)ethyl)phenylsulfamic acid: $^1$H NMR (CD$_3$OD) δ 8.56 (d, 1H, J=8.4Hz), 7.25-6.98 (m, 9H), 5.43-5.38 (m, 1H), 3.26 (1H, A of ABX, J=14.1, 9.6Hz), 2.97 (1H, B of ABX, J=10.9, 3Hz), 2.58-2.76 (m, 3H), 2.98 (q, 2H, J=13.8, 7.2Hz), 1.29 (t, 3H, J=8.7Hz).

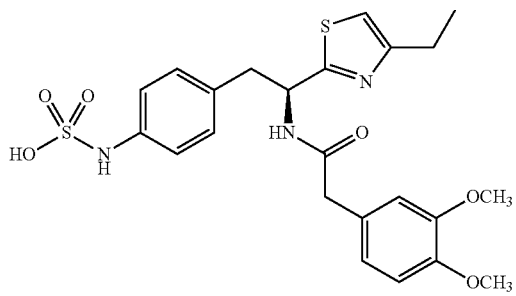 [SMILES: CCc1csc([C@H](Cc2ccc(NS(=O)(=O)O)cc2)NC(=O)Cc2ccc(OC)c(OC)c2)n1]

(S)-4-(2-(2-(3,4-Dimethoxyphenyl)acetamido)-2-(4-ethylthiazol-2-yl)ethyl)-phenylsulfamic acid: $^1$H NMR (CD$_3$OD) δ 7.12-7.03 (m, 3H), 6.91 (d, 1H, J=8.4Hz), 6.82 (s, 1H), 6.66 (d, 1H, J=2.1Hz), 6.63 (d, 1H, J=2.1Hz), 5.43 (m, 1H), 3.84 (s, 3H), 3.80 (s, 3H), 3.45 (s, 2H), 3.30 (1H), 3.03 (1H, B of ABX, J=14.1, 9.6Hz), 2.79 (q, 2H, J=15.1, 7.2Hz), 1.30 (t, 3H, J=7.2Hz).

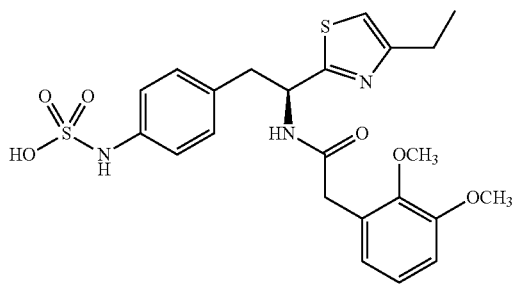 [SMILES: CCc1csc([C@H](Cc2ccc(NS(=O)(=O)O)cc2)NC(=O)Cc2cccc(OC)c2OC)n1]

(S)-4-(2-(2-(2,3-Dimethoxyphenyl)acetamido)-2-(4-ethylthiazol-2-yl)ethyl)-phenylsulfamic acid: ¹H NMR (CD₃OD) δ 8.31 (d, 1H, J=7.8Hz), 7.11-6.93 (m, 6H), 6.68 (d, 1H, J=7.5Hz), 5.49-5.40 (m, 1H), 3.87 (s, 3H), 3.70 (s, 3H), 3.55 (s, 2H), 3.26 (1H, A of ABX, obscured by solvent), 3.06 (1H, B of ABX, J=13.9, 9Hz), 2.80 (q, 2H, J=14.8, 7.5Hz), 1.31 (t, 3H, J=7.5Hz).

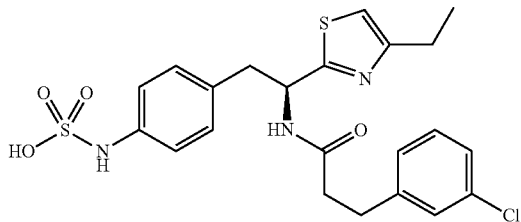 [SMILES: CCc1csc([C@H](Cc2ccc(NS(=O)(=O)O)cc2)NC(=O)CCc2cccc(Cl)c2)n1]

(S)-4-(2-(3-(3-Chlorophenyl)propanamido)-2-(4-ethylthiazol-2-yl)ethyl)phenyl-sulfamic acid: ¹H NMR (CD3OD) δ 7.27-7.18 (m, 3H), 7.13-7.08 (m, 5H), 7.01 (s, 1H), 5.39 (q, 1H, J=5.1, 9.4Hz), 3.28 (1H, A of ABX, J=5.1, 14.1Hz), 2.97 (1H, B of ABX, J=9.3, 13.9Hz), 2.88-2.76 (m, 4H), 2.50 (t, 2H, J=8.1Hz), 1.31 (t, 3H, J=7.8Hz).

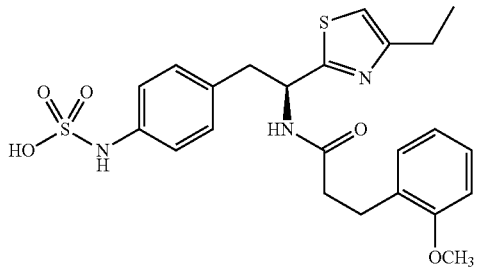 [SMILES: CCc1csc([C@H](Cc2ccc(NS(=O)(=O)O)cc2)NC(=O)CCc2ccccc2OC)n1]

(S)-4-(2-(4-Ethylthiazol-2-yl)-2-(3-(2-methoxyphenyl)propanamido)ethyl)-phenylsulfamic acid: ¹H NMR (CD₃OD) δ 7.18-7.08 (m, 6H), 6.92 (d, 1H, J=8.1Hz), 6.82 (t, 1H, J=7.5Hz), 5.40-5.35 (m, 1H), 3.25 (1H, A of ABX, J=15, 5.4Hz), 3.00 (1H, B of ABX, J=10.5, 7.5Hz), 2.88-2.76 (m, 4H), 2.47 (q, 2H, J=9.1, 6Hz), 1.31 (t, 3H, J=7.8Hz).

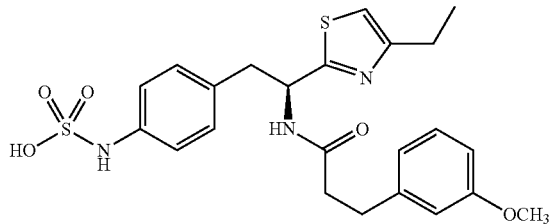 [SMILES: CCc1csc([C@H](Cc2ccc(NS(=O)(=O)O)cc2)NC(=O)CCc2cccc(OC)c2)n1]

(S)-4-(2-(4-Ethylthiazol-2-yl)-2-(3-(3-methoxyphenyl)propanamido)ethyl)-phenylsulfamic acid: ¹H NMR (CD₃OD) δ 7.19-7.00 (m, 5H), 6.75 (s, 1H), 6.73 (s, 1H), 5.42-5.37 (m, 1H), 3.76 (s, 3H), 3.25 (1H, A of ABX, J=13.9, 5.4Hz), 2.98 (1H, B of ABX, J=14.1, 9.6Hz), 2.86-2.75 (m, 4H), 2.48 (q, 2H, J=11.7, 1.2Hz), 1.31 (t, 3H, J=7.5Hz).

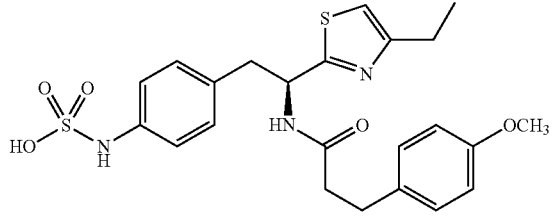 [SMILES: CCc1csc([C@H](Cc2ccc(NS(=O)(=O)O)cc2)NC(=O)CCc2ccc(OC)cc2)n1]

(S)-4-(2-(4-Ethylthiazol-2-yl)-2-(3-(4-methoxyphenyl)propanamido)ethyl)-phenylsulfamic acid: ¹H NMR (CD₃OD) δ 7.13-6.99 (m, 7H), 6.82-6.78 (m, 2H), 5.42-5.37 (m, 1H), 3.33 (s, 3H), 3.23 (1H), 2.97 (1H, B of ABX, J=13.3, 11.4Hz), 2.83-2.75 (m, 4H), 2.49 (q, 2H, J=6.4, 3.3Hz), 1.31 (t, 3H, J=7.5Hz).

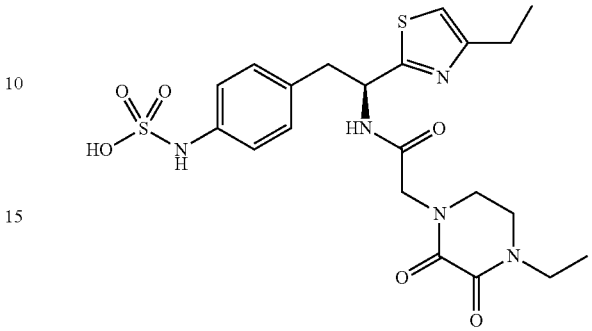

(S)-4-{2-[2-(4-Ethyl-2,3-dioxopiperazin-1-yl)acetamido]-2-(4-ethylthiazol-2-yl)ethyl}phenylsulfamic acid: ¹H NMR (CD₃OD) δ 7.14 (s, 4H), 7.08 (s, 1H), 5.56-5.51 (m, 1H), 4.34 (d, 2H, J=16.2Hz), 3.88 (d, 2H, J=17.6Hz), 3.59-3.40 (m, 3H), 3.26-3.14 (m, 3H), 2.98 (1H, B of ABX, J=10.8, 13.9Hz), 2.82 (q, 2H, J=6.9, 15Hz), 1.32 (t, 3H, J=7.5Hz), 1.21 (t, 3H, J=7.2Hz).

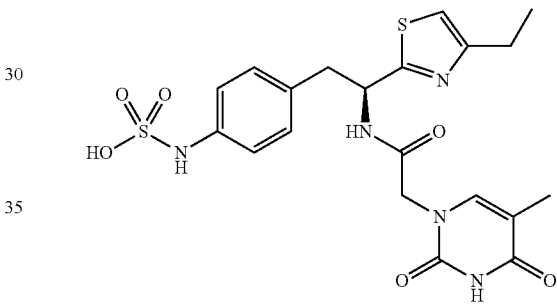

(S)-4-{2-(4-Ethylthiazol-2-yl)-2-[2-(5-methyl-2,4-dioxo-3,4-dihydropyrimidin-1(2H)-yl)acetamido]ethyl}phenylsulfamic acid: ¹H NMR (CD₃OD): δ 7.13 (s, 1H), 7.06-7.02 (m, 4H), 6.95 (s, 1H), 5.42-5.31 (m, 1H), 4.43-4.18 (dd, 2H, J=16.5Hz), 3.24-2.93 (m, 2H), 2.74-2.69 (q, 2H, J=7.3Hz), 1.79 (s, 3H), 1.22 (t, 3H, J=7.5Hz).

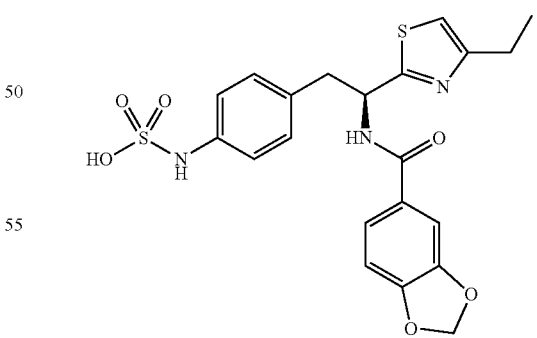

(S)-4-[2-(benzo[d][1,3]dioxole-5-carboxamido)-2-(4-ethylthiazol-2-yl)ethyl]-phenylsulfamic acid: ¹H NMR (CD₃OD) δ 7.25 (d, 1H, J=6.5 Hz), 7.13 (s, 1H), 7.06 (d, 2H, J=8.5 Hz), 7.00 (d, 2H, J=8.5 Hz), 6.91 (s, 1H), 6.76 (d, 1H, J=8.1 Hz), 5.90 (s, 2H), 5.48 (q, 1H, J=5.0 Hz), 3.32-3.24 (m, 2H), 3.07-2.99 (m, 2H), 2.72 (q, 2H, J=7.5 Hz), 1.21 (t, 3H, J=7.5 Hz).

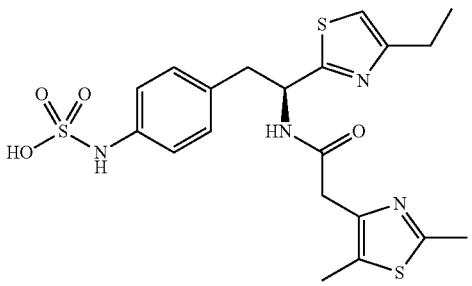 [SMILES: CCc1csc([C@H](Cc2ccc(NS(=O)(=O)O)cc2)NC(=O)Cc2nc(C)sc2C)n1]

(S)-4-{2-[2-(2,5-Dimethylthiazol-4-yl)acetamido]-2-(4-ethylthiazol-2-yl)ethyl}-phenylsulfamic acid: $^1$H NMR (CD$_3$OD): δ 7.10-7.01 (m, 5H), 5.41 (t, 1H, J=6.9 Hz), 3.58 (s, 2H), 3.33-3.01 (m, 2H), 2.82-2.75 (q, 2H, J=7.5 Hz), 2.59 (s, 3H), 2.23 (s, 3H), 1.30 (t, 3H, J=7.5 Hz).

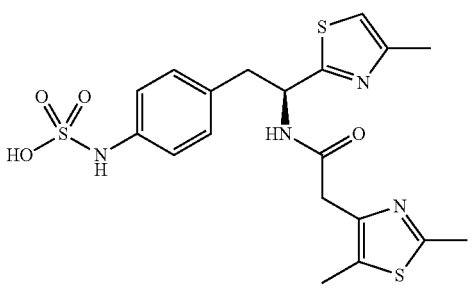 [SMILES: Cc1csc([C@H](Cc2ccc(NS(=O)(=O)O)cc2)NC(=O)Cc2nc(C)sc2C)n1]

(S)-4-{2-[2-(2,4-Dimethylthiazol-5-yl)acetamido]-2-(4-methylthiazol-2-yl)ethyl}-phenylsulfamic acid: $^1$H NMR (CD$_3$OD): δ 8.71-8.68 (d, 1H, J=8.4 Hz), 7.10-7.03 (m, 4H), 7.01 (s, 1H), 5.41 (m, 1H), 3.59 (s, 1H), 3.34-2.96 (m, 2H), 2.59 (s, 3H), 2.40 (s, 3H), 2.23 (s, 3H).

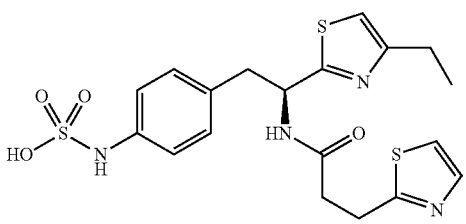 [SMILES: CCc1csc([C@H](Cc2ccc(NS(=O)(=O)O)cc2)NC(=O)CCc2nccs2)n1]

(S)-4-{2-(4-Ethylthiazol-2-yl)-2-[3-(thiazol-2-yl)propanamido]ethyl}phenylsulfamic acid: $^1$H NMR (CD$_3$OD): δ 7.67-7.65 (m, 1H), 7.49-7.47 (m, 1H), 7.14-7.08 (m, 4H), 7.04 (s, 1H), 5.46-5.41 (q, 1H, J=5.1 Hz), 3.58 (s, 2H), 3.30-3.25 (m, 3H), 3.02-2.67 (m, 5H), 1.31 (t, 3H, J=7.5 Hz).

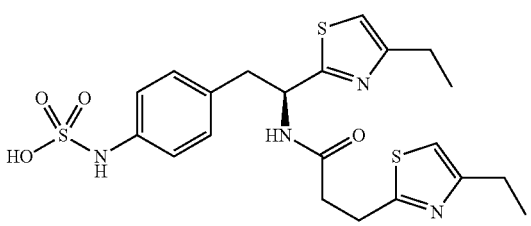 [SMILES: CCc1csc(CCC(=O)N[C@@H](Cc2ccc(NS(=O)(=O)O)cc2)c2nc(CC)cs2)n1]

(S)-4-{2-(4-Ethylthiazol-2-yl)-2-[2-(4-ethylthiazol-2-yl)acetamido]ethyl}-phenylsulfamic acid: $^1$H NMR (CD$_3$OD):
δ 7.04-6.91 (m, 6H), 5.32 (t, 1H, J=5.4 Hz), 3.25-2.90 (m, 2H), 2.71-2.61 (m, 4H) 1.93 (s, 2H) 1.22-1.14 (m, 6H).

The second aspect of Category V of the present disclosure relates to 2-(thiazol-4-yl) compounds having the formula:

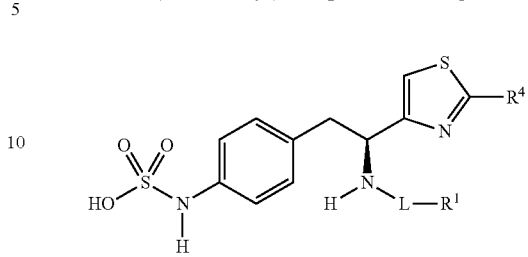

wherein R$^1$, R$^4$, and L are further defined herein in Table X herein below.

TABLE X

| No. | L | R$^1$ | R$^4$ |
|---|---|---|---|
| J360 | —C(O)CH$_2$— | phenyl | methyl |
| J361 | —C(O)CH$_2$— | phenyl | ethyl |
| J362 | —C(O)CH$_2$— | phenyl | phenyl |
| J363 | —C(O)CH$_2$— | phenyl | thiophen-2-yl |
| J364 | —C(O)CH$_2$— | phenyl | thiazol-2-yl |
| J365 | —C(O)CH$_2$— | phenyl | oxazol-2-yl |
| J366 | —C(O)CH$_2$— | phenyl | isoxazol-3-yl |
| J367 | —C(O)CH$_2$— | 3-chlorophenyl | methyl |
| J368 | —C(O)CH$_2$— | 3-chlorophenyl | ethyl |
| J369 | —C(O)CH$_2$— | 3-chlorophenyl | phenyl |
| J370 | —C(O)CH$_2$— | 3-chlorophenyl | thiophen-2-yl |
| J371 | —C(O)CH$_2$— | 3-chlorophenyl | thiazol-2-yl |
| J372 | —C(O)CH$_2$— | 3-chlorophenyl | oxazol-2-yl |
| J373 | —C(O)CH$_2$— | 3-chlorophenyl | isoxazol-3-yl |
| J374 | —C(O)CH$_2$— | 3-methoxyphenyl | methyl |
| J375 | —C(O)CH$_2$— | 3-methoxyphenyl | ethyl |
| J376 | —C(O)CH$_2$— | 3-methoxyphenyl | phenyl |
| J377 | —C(O)CH$_2$— | 3-methoxyphenyl | thiophen-2-yl |
| J378 | —C(O)CH$_2$— | 3-methoxyphenyl | thiazol-2-yl |
| J379 | —C(O)CH$_2$— | 3-methoxyphenyl | oxazol-2-yl |
| J380 | —C(O)CH$_2$— | 3-methoxyphenyl | isoxazol-3-yl |
| J381 | —C(O)CH$_2$— | 3-fluorophenyl | methyl |
| J382 | —C(O)CH$_2$— | 3-fluorophenyl | ethyl |
| J383 | —C(O)CH$_2$— | 3-fluorophenyl | phenyl |
| J384 | —C(O)CH$_2$— | 3-fluorophenyl | thiophen-2-yl |
| J385 | —C(O)CH$_2$— | 3-fluorophenyl | thiazol-2-yl |
| J386 | —C(O)CH$_2$— | 3-fluorophenyl | oxazol-2-yl |
| J387 | —C(O)CH$_2$— | 3-fluorophenyl | isoxazol-3-yl |
| J388 | —C(O)CH$_2$— | 2,5-dimethylthiazol-4-yl | methyl |
| J389 | —C(O)CH$_2$— | 2,5-dimethylthiazol-4-yl | ethyl |
| J390 | —C(O)CH$_2$— | 2,5-dimethylthiazol-4-yl | phenyl |
| J391 | —C(O)CH$_2$— | 2,5-dimethylthiazol-4-yl | thiophen-2-yl |
| J392 | —C(O)CH$_2$— | 2,5-dimethylthiazol-4-yl | thiazol-2-yl |
| J393 | —C(O)CH$_2$— | 2,5-dimethylthiazol-4-yl | oxazol-2-yl |
| J394 | —C(O)CH$_2$— | 2,5-dimethylthiazol-4-yl | isoxazol-3-yl |
| J395 | —C(O)CH$_2$— | 2,4-dimethylthiazol-5-yl | methyl |
| J396 | —C(O)CH$_2$— | 2,4-dimethylthiazol-5-yl | ethyl |
| J397 | —C(O)CH$_2$— | 2,4-dimethylthiazol-5-yl | phenyl |
| J398 | —C(O)CH$_2$— | 2,4-dimethylthiazol-5-yl | thiophen-2-yl |
| J399 | —C(O)CH$_2$— | 2,4-dimethylthiazol-5-yl | thiazol-2-yl |
| J400 | —C(O)CH$_2$— | 2,4-dimethylthiazol-5-yl | oxazol-2-yl |
| J401 | —C(O)CH$_2$— | 2,4-dimethylthiazol-5-yl | isoxazol-3-yl |
| J402 | —C(O)CH$_2$— | 4-ethylthiazol-2-yl | methyl |
| J403 | —C(O)CH$_2$— | 4-ethylthiazol-2-yl | ethyl |
| J404 | —C(O)CH$_2$— | 4-ethylthiazol-2-yl | phenyl |
| J405 | —C(O)CH$_2$— | 4-ethylthiazol-2-yl | thiophen-2-yl |
| J406 | —C(O)CH$_2$— | 4-ethylthiazol-2-yl | thiazol-2-yl |
| J407 | —C(O)CH$_2$— | 4-ethylthiazol-2-yl | oxazol-2-yl |

TABLE X-continued

| No. | L | R¹ | R⁴ |
|---|---|---|---|
| J408 | —C(O)CH₂— | 4-ethylthiazol-2-yl | isoxazol-3-yl |
| J409 | —C(O)CH₂— | 3-methyl-1,2,4-oxadiazol-5-yl | methyl |
| J410 | —C(O)CH₂— | 3-methyl-1,2,4-oxadiazol-5-yl | ethyl |
| J411 | —C(O)CH₂— | 3-methyl-1,2,4-oxadiazol-5-yl | phenyl |
| J412 | —C(O)CH₂— | 3-methyl-1,2,4-oxadiazol-5-yl | thiophen-2-yl |
| J413 | —C(O)CH₂— | 3-methyl-1,2,4-oxadiazol-5-yl | thiazol-2-yl |
| J414 | —C(O)CH₂— | 3-methyl-1,2,4-oxadiazol-5-yl | oxazol-2-yl |
| J415 | —C(O)CH₂— | 3-methyl-1,2,4-oxadiazol-5-yl | isoxazol-3-yl |
| J416 | —C(O)CH₂CH₂— | phenyl | methyl |
| J417 | —C(O)CH₂CH₂— | phenyl | ethyl |
| J418 | —C(O)CH₂CH₂— | phenyl | phenyl |
| J419 | —C(O)CH₂CH₂— | phenyl | thiophen-2-yl |
| J420 | —C(O)CH₂CH₂— | phenyl | thiazol-2-yl |
| J421 | —C(O)CH₂CH₂— | phenyl | oxazol-2-yl |
| J422 | —C(O)CH₂CH₂— | phenyl | isoxazol-3-yl |
| J423 | —C(O)CH₂CH₂— | 3-chlorophenyl | methyl |
| J424 | —C(O)CH₂CH₂— | 3-chlorophenyl | ethyl |
| J425 | —C(O)CH₂CH₂— | 3-chlorophenyl | phenyl |
| J426 | —C(O)CH₂CH₂— | 3-chlorophenyl | thiophen-2-yl |
| J427 | —C(O)CH₂CH₂— | 3-chlorophenyl | thiazol-2-yl |
| J428 | —C(O)CH₂CH₂— | 3-chlorophenyl | oxazol-2-yl |
| J429 | —C(O)CH₂CH₂— | 3-chlorophenyl | isoxazol-3-yl |
| J430 | —C(O)CH₂CH₂— | 3-methoxyphenyl | methyl |
| J431 | —C(O)CH₂CH₂— | 3-methoxyphenyl | ethyl |
| J432 | —C(O)CH₂CH₂— | 3-methoxyphenyl | phenyl |
| J433 | —C(O)CH₂CH₂— | 3-methoxyphenyl | thiophen-2-yl |
| J434 | —C(O)CH₂CH₂— | 3-methoxyphenyl | thiazol-2-yl |
| J435 | —C(O)CH₂CH₂— | 3-methoxyphenyl | oxazol-2-yl |
| J436 | —C(O)CH₂CH₂— | 3-methoxyphenyl | isoxazol-3-yl |
| J437 | —C(O)CH₂CH₂— | 3-fluorophenyl | methyl |
| J438 | —C(O)CH₂CH₂— | 3-fluorophenyl | ethyl |
| J439 | —C(O)CH₂CH₂— | 3-fluorophenyl | phenyl |
| J440 | —C(O)CH₂CH₂— | 3-fluorophenyl | thiophen-2-yl |
| J441 | —C(O)CH₂CH₂— | 3-fluorophenyl | thiazol-2-yl |
| J442 | —C(O)CH₂CH₂— | 3-fluorophenyl | oxazol-2-yl |
| J443 | —C(O)CH₂CH₂— | 3-fluorophenyl | isoxazol-3-yl |
| J444 | —C(O)CH₂CH₂— | 2,5-dimethylthiazol-4-yl | methyl |
| J445 | —C(O)CH₂CH₂— | 2,5-dimethylthiazol-4-yl | ethyl |
| J446 | —C(O)CH₂CH₂— | 2,5-dimethylthiazol-4-yl | phenyl |
| J447 | —C(O)CH₂CH₂— | 2,5-dimethylthiazol-4-yl | thiophen-2-yl |
| J448 | —C(O)CH₂CH₂— | 2,5-dimethylthiazol-4-yl | thiazol-2-yl |
| J449 | —C(O)CH₂CH₂— | 2,5-dimethylthiazol-4-yl | oxazol-2-yl |
| J450 | —C(O)CH₂CH₂— | 2,5-dimethylthiazol-4-yl | isoxazol-3-yl |
| J451 | —C(O)CH₂CH₂— | 2,4-dimethylthiazol-5-yl | methyl |
| J452 | —C(O)CH₂CH₂— | 2,4-dimethylthiazol-5-yl | ethyl |
| J453 | —C(O)CH₂CH₂— | 2,4-dimethylthiazol-5-yl | phenyl |
| J454 | —C(O)CH₂CH₂— | 2,4-dimethylthiazol-5-yl | thiophen-2-yl |
| J455 | —C(O)CH₂CH₂— | 2,4-dimethylthiazol-5-yl | thiazol-2-yl |
| J456 | —C(O)CH₂CH₂— | 2,4-dimethylthiazol-5-yl | oxazol-2-yl |
| J457 | —C(O)CH₂CH₂— | 2,4-dimethylthiazol-5-yl | isoxazol-3-yl |
| J458 | —C(O)CH₂CH₂— | 4-ethylthiazol-2-yl | methyl |
| J459 | —C(O)CH₂CH₂— | 4-ethylthiazol-2-yl | ethyl |
| J460 | —C(O)CH₂CH₂— | 4-ethylthiazol-2-yl | phenyl |
| J461 | —C(O)CH₂CH₂— | 4-ethylthiazol-2-yl | thiophen-2-yl |
| J462 | —C(O)CH₂CH₂— | 4-ethylthiazol-2-yl | thiazol-2-yl |
| J463 | —C(O)CH₂CH₂— | 4-ethylthiazol-2-yl | oxazol-2-yl |
| J464 | —C(O)CH₂CH₂— | 4-ethylthiazol-2-yl | isoxazol-3-yl |
| J465 | —C(O)CH₂CH₂— | 3-methyl-1,2,4-oxadiazol-5-yl | methyl |
| J466 | —C(O)CH₂CH₂— | 3-methyl-1,2,4-oxadiazol-5-yl | ethyl |
| J467 | —C(O)CH₂CH₂— | 3-methyl-1,2,4-oxadiazol-5-yl | phenyl |
| J468 | —C(O)CH₂CH₂— | 3-methyl-1,2,4-oxadiazol-5-yl | thiophen-2-yl |
| J469 | —C(O)CH₂CH₂— | 3-methyl-1,2,4-oxadiazol-5-yl | thiazol-2-yl |
| J470 | —C(O)CH₂CH₂— | 3-methyl-1,2,4-oxadiazol-5-yl | oxazol-2-yl |
| J471 | —C(O)CH₂CH₂— | 3-methyl-1,2,4-oxadiazol-5-yl | isoxazol-3-yl |

The compounds encompassed within the second aspect of Category I of the present disclosure can be prepared by the procedure outlined in Scheme II and described in Example 9 herein below.

Scheme VIII

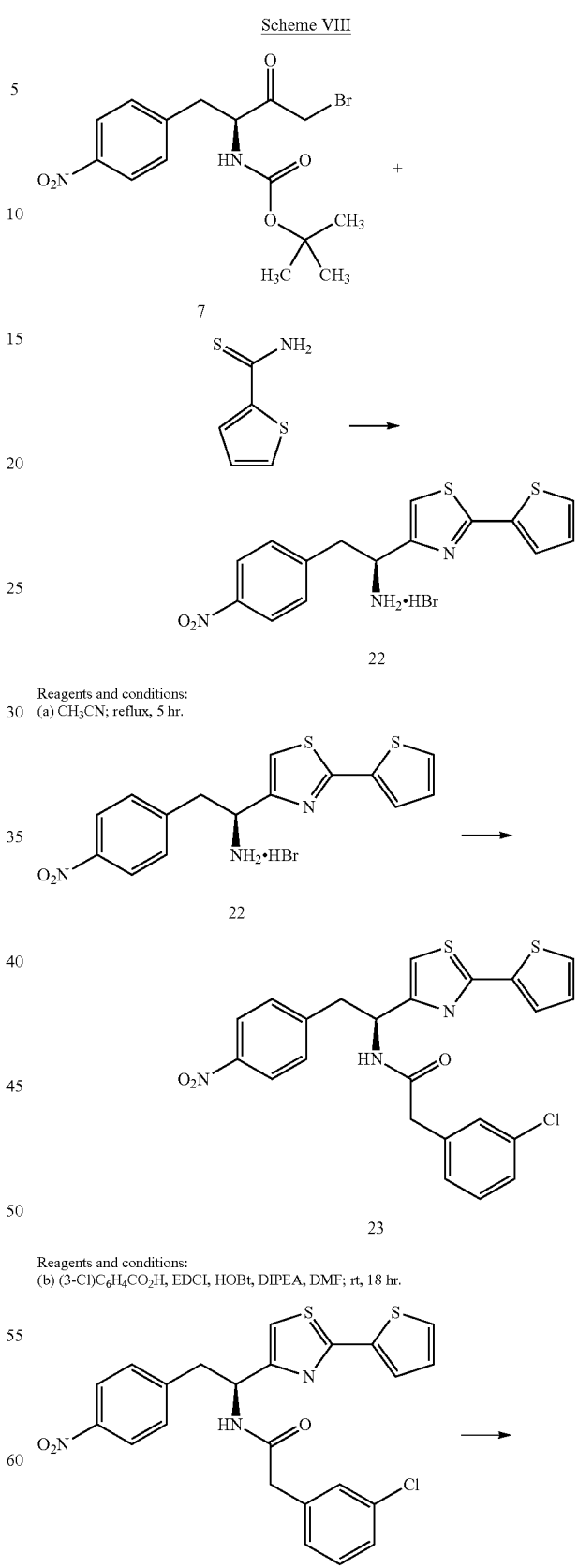

Reagents and conditions:
(a) CH₃CN; reflux, 5 hr.

Reagents and conditions:
(b) (3-Cl)C₆H₄CO₂H, EDCI, HOBt, DIPEA, DMF; rt, 18 hr.

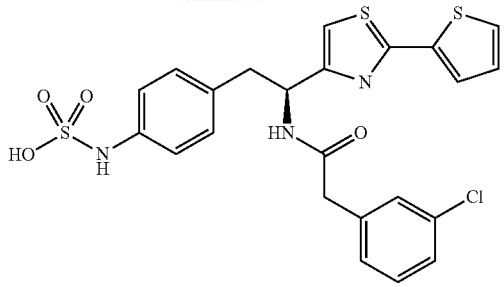 [SMILES: O=C(Cc1cccc(F)c1)N[C@@H](Cc1ccc(NS(=O)(=O)O)cc1)c1csc(-c2cccs2)n1]

24

Reagents and conditions:
(c)(i) H₂:Pd/C, MeOH; (ii) SO₃-pyridine, NH₄OH, rt, 18 hr.

EXAMPLE 9

4-((S)-2-(2-(3-chlorophenyl)acetamido)-2-(2-(thiophen-2-yl)thiazol-4-yl)ethyl)phenylsulfamic acid (23)

Preparation of (S)-2-(4-nitrophenyl)-1-[(thiophen-2-yl)thiazol-4-yl]ethanamine hydrobromide salt (22): A mixture of (S)-tert-butyl 4-bromo-1-(4-nitrophenyl)-3-oxobutan-2-ylcarbamate, 7, (7.74 g, 20 mmol), and thiophen-2-carbothioic acid amide (3.14 g, 22 mmol) in CH₃CN (200 mL) is refluxed for 5 hours. The reaction mixture is cooled to room temperature and diethyl ether (50 mL) is added to the solution. The precipitate which forms is collected by filtration. The solid is dried under vacuum to afford 7.14 g (87% yield) of the desired product. ESI+ MS 332 (M+1).

Preparation of 2-(3-chlorophenyl)-N-{(S)-2-(4-nitrophenyl)-1-[2-(thiophen-2-yl)thiazol-4-yl]ethyl}acetamide (23): To a solution of 2-(4-nitrophenyl)-1-(2-thiophene2-ylthiazol-4-yl)ethylamine, 22, (0.41 g, 1 mmol) 3-chlorophenylacetic acid (0.170 g, 1 mmol) and 1-hydroxybenzotriazole (HOBt) (0.070 g, 0.50 mmol) in DMF (5 mL) at 0° C., is added 1-(3-dimethylaminopropyl)-3-ethylcarbodiimide (EDCI) (0.190 g, 1 mmol) followed by triethylamine (0.42 mL, 3 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.290 g (60% yield) of the desired product which is used without further purification. ESI– MS 482 (M–1).

Preparation of {4-[2-(3-chlorophenyl)acetylamino]-2-(2-thiophen-2-ylthiazol-4-yl)ethyl]phenyl}sulfamic acid (24): 2-(3-chlorophenyl)-N-{(S)-2-(4-nitrophenyl)-1-[2-(thiophene2-yl)thiazol-4-yl]ethyl}acetamide, 23, (0.290 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue is purified by reverse phase chromatography to afford 0.078 g of the desired product as the ammonium salt. ¹H NMR (CD3OD) δ 7.61 (d, 1H, J=3.6Hz), 7.58 (d, 1H, J=5.1Hz), 7.41-7.35 (m, 1H), 7.28-7.22 (m, 2H), 7.18-6.98 (m, 6H), 5.33 (t, 1H, J=6.6Hz), 3.70 (d, 2H, J=3.9 Hz), 3.23 (1H, A of ABX, J=6.6, 13.8Hz), 3.07 (1H, B of ABX, J=8.1, 13.5Hz).

The following are non-limiting examples of compounds encompassed within the second aspect of Category V of the present disclosure.

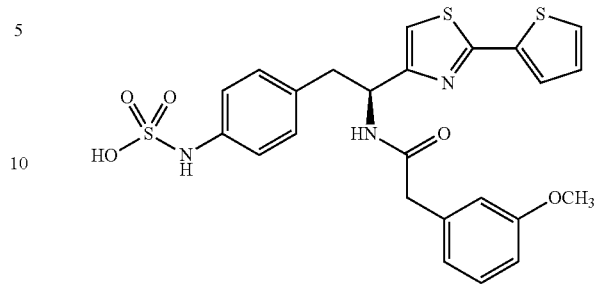

4-((S)-2-(2-(3-Methoxyphenyl)acetamido)-2-(2-(thiophene2-yl)thiazol-4-yl)ethyl)-phenylsulfamic acid: ¹H NMR (CD3OD) δ 8.35 (d, 1H, J=8.7Hz), 7.61-7.57 (m, 2H), 7.25-7.20 (m, 2H), 7.25-7.20 (m, 2H), 7.09 (s, 1H), 7.05 (d, 2H, J=4.2Hz), 6.99 (d, 1H, J=8.7Hz), 6.81 (d, 1H, J=7.8Hz), 6.77 (s, 1H), 5.30-5.28 (m, 1H), 3.76 (s, 3H), 3.51 (s, 2H), 3.20 (1H, A of ABX, J=6.3, 13.6Hz), 3.06 (1H, B of ABX, J=8.1, 13.8Hz).

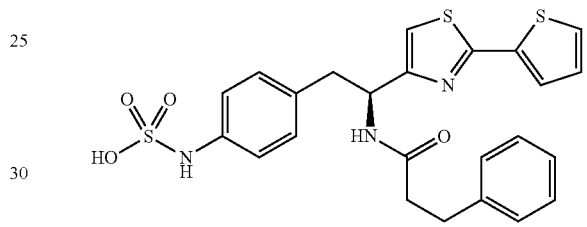

4-{(S)-2-(3-Phenylpropanamido)-2-[2-(thiophene2-yl)thiazol-4-yl]ethyl}-phenylsulfamic acid: ¹H NMR (CD3OD) δ 8.30 (d, 1H, J=9Hz), 7.61-7.56 (m, 2H), 7.26-7.14 (m, 7H), 7.12 (d, 1H, J=1.5Hz), 7.09 (d, 1H, J=2.1Hz), 6.89 (s, 1H), 5.28-5.26 (m, 1H), 3.18 (1H, A of ABX, J=6.2, 13.8Hz), 2.96 (1H, B of ABX, J=8.4, 13.6Hz).

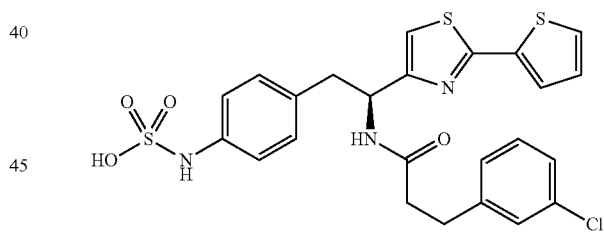

4-{(S)-2-(3-(3-Chlorophenyl)propanamido)-2-[2-(thiophene2-yl)thiazol-4-yl]ethyl}phenylsulfamic acid: ¹H NMR (CD₃OD) δ 7.61-7.56 (m, 3H), 7.22-7.14 (m, 6H), 7.08 (d, 1H), 7.00 (d, 1H, J=77.5Hz), 6.870 (s, 1H), 5.25 (t, 1H, J=7. Hz), 3.18 (1H, A of ABX, J=6.6, 13.8Hz), 2.97 (1H, B of ABX, J=7.8, 13.8Hz), 2.87 (t, 2H, J=7.5Hz), 2.51 (t, 2H, J=7.2 Hz).

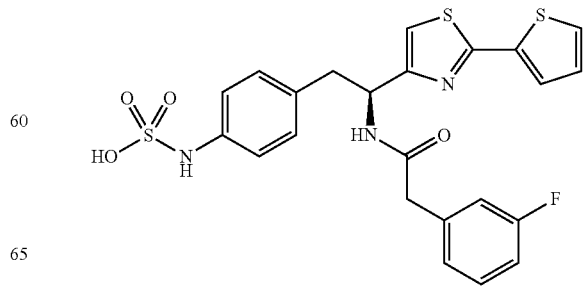

4-{(S)-2-[2-(3-Fluorophenyl)acetamido]-2-[2-(thiophen-2-yl)thiazol-4-yl]ethyl}phenylsulfamic acid: ¹H NMR (CD₃OD) δ 7.61-7.57 (m, 2H), 7.32-7.28 (m, 1H), 7.19-7.16 (m, 2H), 7.08 (t, 1H, J=4.5Hz), 7.02-6.95 (m, 6H), 5.29 (t, 1H, J=8.1Hz), 3.53 (s, 2H), 3.22 (1H, A of ABX, J=6.6, 13.9Hz), 3.06 (1H, B of ABX, J=8.4, 13.6Hz).

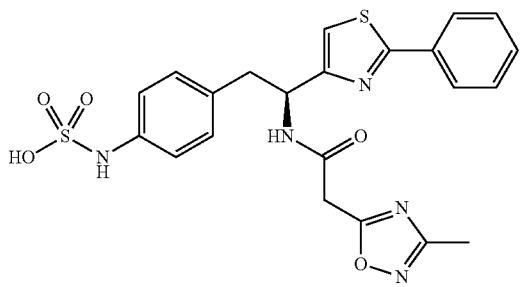 [SMILES: Cc1noc(CC(=O)N[C@@H](Cc2ccc(NS(=O)(=O)O)cc2)c2csc(-c3ccccc3)n2)n1]

(S)-4-{2-[2-(3-Methyl-1,2,4-oxadiazol-5-yl)acetamido]-2-(2-phenylthiazol-4-yl)ethyl}phenylsulfamic acid: ¹H NMR (CD₃OD): δ 7.98-7.95 (m, 2H), 7.48-7.46 (m, 3H), 7.23 (s, 1H), 7.09-7.05 (m, 4H), 5.33 (t, 1H, J=7.2Hz), 3.33-3.06 (m, 2H), 2.35 (s, 3H).

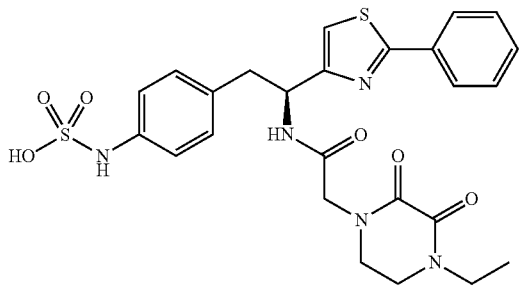 [SMILES: CCN1CCN(CC(=O)N[C@@H](Cc2ccc(NS(=O)(=O)O)cc2)c2csc(-c3ccccc3)n2)C(=O)C1=O]

4-{(S)-2-[2-(4-ethyl-2,3-dioxopiperazin-1-yl)acetamido]-2-[2-(thiophen-2-yl)thiazol-4-yl]ethyl}phenylsulfamic acid: ¹H NMR (CD₃OD) δ 7.62 (d, 1H, J=3Hz), 7.58 (d, 1H, J=15.6Hz), 7.27 (s, 1H), 7.16 (t, 1H, J=1.5Hz), 5.42-5.32 (m, 1H), 4.31 (d, 1H, J=15.6Hz), 3.91 (d, 1H, J=15.9Hz), 3.60-3.50 (m, 4H), 3.30-3.23 (m, 2H), 2.98 (1H, B of ABX, J=9.9, 13.8Hz), 1.21 (t, 3H, J=6.9Hz).

The third aspect of Category V of the present disclosure relates to compounds having the formula:

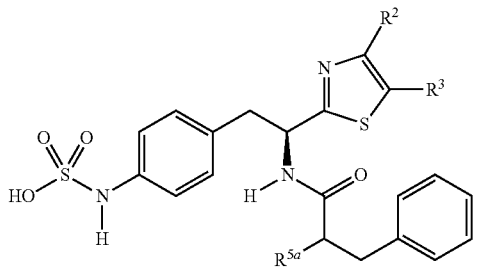

wherein the linking unit L comprises a phenyl unit, said linking group having the formula:

—C(O)[(CR⁵ᵃH)][(CR⁶ᵃH)]—

R¹ is hydrogen, R⁶ᵃ is phenyl, R⁵ᵃ is phenyl or substituted phenyl and non-limiting examples of the units R², R³, and R⁵ᵃ are further exemplified herein below in Table XI.

TABLE XI

| No. | R² | R³ | R⁵ᵃ |
|---|---|---|---|
| K472 | methyl | hydrogen | phenyl |
| K473 | methyl | hydrogen | 2-fluorophenyl |
| K474 | methyl | hydrogen | 3-fluorophenyl |
| K475 | methyl | hydrogen | 4-fluorophenyl |
| K476 | methyl | hydrogen | 3,4-difluorophenyl |
| K477 | methyl | hydrogen | 2-chlorophenyl |
| K478 | methyl | hydrogen | 3-chlorophenyl |
| K479 | methyl | hydrogen | 4-chlorophenyl |
| K480 | methyl | hydrogen | 3,4-dichlorophenyl |
| K481 | methyl | hydrogen | 2-methoxyphenyl |
| K482 | methyl | hydrogen | 3-methoxyphenyl |
| K483 | methyl | hydrogen | 4-methoxyphenyl |
| K484 | ethyl | hydrogen | phenyl |
| K485 | ethyl | hydrogen | 2-fluorophenyl |
| K486 | ethyl | hydrogen | 3-fluorophenyl |
| K487 | ethyl | hydrogen | 4-fluorophenyl |
| K488 | ethyl | hydrogen | 3,4-difluorophenyl |
| K489 | ethyl | hydrogen | 2-chlorophenyl |
| K490 | ethyl | hydrogen | 3-chlorophenyl |
| K491 | ethyl | hydrogen | 4-chlorophenyl |
| K492 | ethyl | hydrogen | 3,4-dichlorophenyl |
| K493 | ethyl | hydrogen | 2-methoxyphenyl |
| K494 | ethyl | hydrogen | 3-methoxyphenyl |
| K495 | ethyl | hydrogen | 4-methoxyphenyl |

The compounds encompassed within the third aspect of Category V of the present disclosure can be prepared by the procedure outlined in Scheme IX and described in Example 10 herein below.

Scheme IX

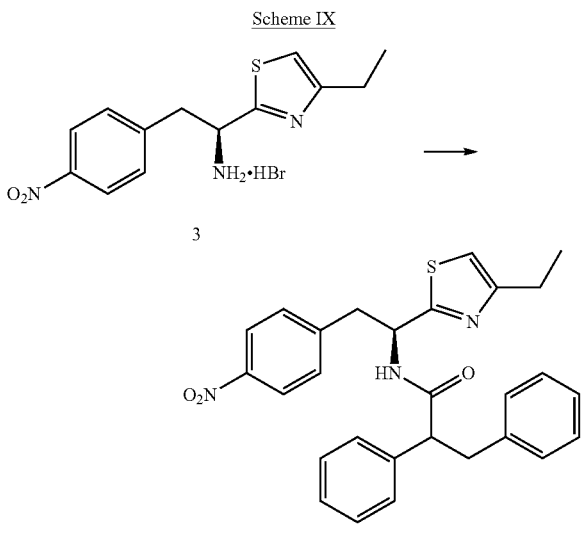

Reagents and conditions:
(a) diphenylpropionic acid, EDCI, HOBt, TEA, DMF; 0° C. to rt, 18 hr.

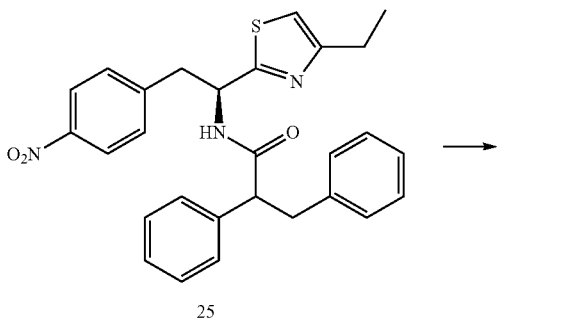

25

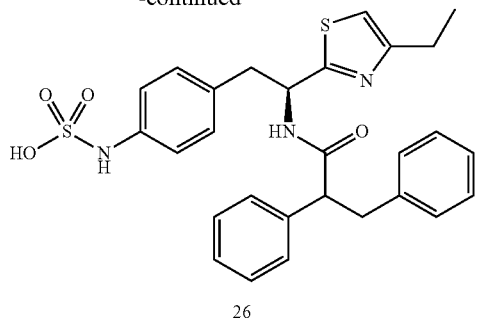

26

Reagents and conditions:
(b)(i) H₂:Pd/C, MeOH;
(ii) SO₃-pyridine, NH₄OH; rt, 18 hr.

EXAMPLE 10

(S)-4-(2-(2,3-Diphenylpropanamido)-2-(4-ethylthiazol-2-yl)ethyl)-phenylsulfamic acid (26)

Preparation of (S)—N-[1-(4-ethylthiazol-2-yl)-2-(4-nitrophenyl)ethyl]-2,3-diphenyl-propanamide (25): To a solution of 1-(S)-(4-ethylthiazol-2-yl)-2-(4-nitrophenyl)ethyl amine hydrobromide, 3, (0.95 g, 2.65 mmol), diphenylpropionic acid (0.60 g, 2.65 mmol) and 1-hydroxybenzotriazole (HOBt) (0.180 g, 1.33 mmol) in DMF (10 mL) at 0°, is added 1-(3-dimethylaminopropyl)-3-ethylcarbodiimide (EDCI) (0.502 g, 2.62 mmol) followed by triethylamine (1.1 mL, 7.95 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.903 g (70% yield) of the desired product which is used without further purification.

Preparation of (S)-4-(2-(2,3-diphenylpropanamido)-2-(4-ethylthiazol-2-yl)ethyl)phenylsulfamic acid (26) (S)—N-[1-(4-ethylthiazol-2-yl)-2-(4-nitrophenyl)ethyl]-2,3-diphenyl-propanamide, 25, (0.903 g) is dissolved in MeOH (10 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (30 mL) and treated with SO₃-pyridine (0.621 g). The reaction is stirred at room temperature for 5 minutes after which a 7% solution of NH₄OH is added. The mixture is then concentrated and the resulting residue is purified by reverse phase chromatography to afford 0.415 g of the desired product as the ammonium salt. ¹H NMR (CD₃OD) δ 8.59-8.52 (m, 1H), 7.37-7.04 (m, 9H), 6.97-6.93 (m, 1H), 6.89-6.85 (m, 2H), 5.36-5.32 (m, 1H), 3.91-3.83 (m, 1H), 3.29 (1H, A of ABX, obscured by solvent), 3.15 (1H, B of ABX, J=5.4, 33.8Hz), 2.99-2.88 (m, 2H), 2.81-2.69 (m, 2H), 1.32-1.25 (m, 3H).

The precursors of many of the Z units which comprise the third aspect of Category V are not readily available. The following procedure illustrates an example of the procedure which can be used to provide different $R^{5a}$ units according to the present disclosure. Using the procedure outlined in Scheme X and described in Example 11 the artisan can make modifications without undue experimentation to achieve the $R^{5a}$ units encompassed by the present disclosure.

Scheme X

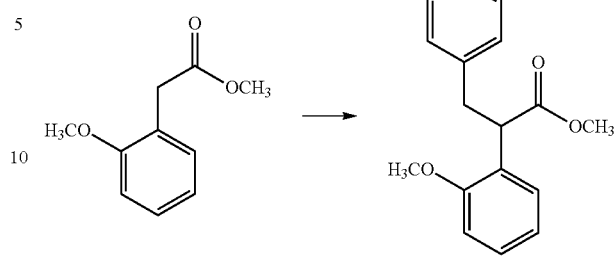

27

Reagents and conditions:
(a) benzyl bromide, LDA, THF; 0° C. to rt, 18 hr.

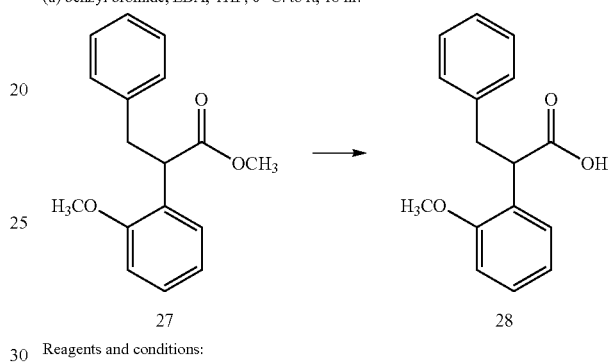

27                              28

Reagents and conditions:
(b) NaOH, THF/MeOH; rt, 18 hr.

EXAMPLE 11

2-(2-Methoxyphenyl)-3-phenylpropanoic acid (28)

Preparation of methyl 2-(2-methoxyphenyl)-3-phenylpropanoate (27): A 500 mL round-bottom flask is charged with methyl 2-(2-methoxyphenyl)acetate (8.496 g, 47 mmol, 1 eq) and THF (200 mL). The homogeneous mixture is cooled to 0° C. in an ice bath. Lithium diisopropyl amide (23.5 mL of a 2.0M solution in heptane/THF) is added, maintaining a temperature less than 3° C. The reaction is stirred 45 minutes at this reduced temperature. Benzyl bromide (5.6 mL, 47 mmol, 1 eq) is added dropwise. The reaction is allowed to gradually warm to room temperature and is stirred for 18 hours. The reaction is quenched with 1N HCl and extracted 3 times with equal portions of EtOAc. The combined extracts are washed with H₂O and brine, dried over Na₂SO₄, filtered, and concentrated. The residue is purified over silica to afford 4.433 g (35%) of the desired compound. ESI+ MS 293 (M+Na).

Preparation of 2-(2-methoxyphenyl)-3-phenylpropanoic acid (28): Methyl 2-(2-methoxyphenyl)-3-phenylpropanoate (4.433 g, 16 mmol, 1 eq) is dissolved in 100 mL of a 1:1 (v:v) mixture of THF and methanol. Sodium hydroxide (3.28 g, 82 mmol, 5 eq) is added and the reaction mixture is stirred 18 hours at room temperature. The reaction is then poured into H₂O and the pH is adjusted to 2 via addition of 1N HCl. A white precipitate forms which is removed by filtration. The resulting solution is extracted with 3 portion of diethyl ether. The extracts are pooled, washed with H₂O and brine, dried over Na₂SO₄, filtered, and concentrated in vacuo. The resulting residue is purified over silica to afford 2.107 g (51%) of the desired compound. ESI– MS 255 (M–1), 211 (M-CO₂H).

Intermediate 28 can be carried forward according to the procedure outlined in Scheme IX and described in Example 10 to produce the following compound according to the third aspect of Category V.

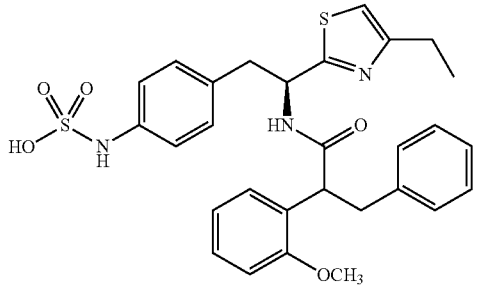 [SMILES: CCc1csc([C@H](Cc2ccc(NS(=O)(=O)O)cc2)NC(=O)C(Cc2ccccc2)c2ccccc2OC)n1]

(S)-4-{2-(4-Ethylthiazol-2-yl)-2-[2-(2-methoxyphenyl)-3-phenylpropanamido]-ethyl}phenylsulfamic acid: $^1$H NMR (CD$_3$OD) δ 7.32-7.12 (m, 7H), 7.05-7.02 (m, 1H), 6.99-6.83 (m, 4H), 6.80-6.75 (m, 2H), 5.35-5.31 (m, 1H), 4.31-4.26 (m, 1H), 3.75 (s, 3H), 3.20-2.90 (m, 4H), 2.79-2.74 (m, 2H), 1.32-1.25 (m, 3H).

The following are further non-limiting examples of compounds according to the third aspect of Category I of the present disclosure.

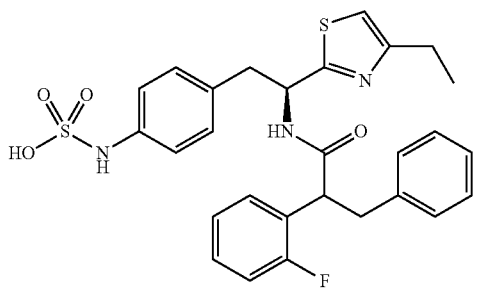 [SMILES: CCc1csc([C@H](Cc2ccc(NS(=O)(=O)O)cc2)NC(=O)C(Cc2ccccc2)c2ccccc2F)n1]

(S)-4-{2-(4-Ethylthiazol-2-yl)-2-[2-(3-fluorophenyl)-3-phenylpropanamido]-ethyl}phenylsulfamic acid: $^1$H NMR (CD$_3$OD) δ 7.33-6.87 (m, 14H), 5.39-5.25 (m, 1H), 3.95-3.83 (m, 1H), 3.31-3.10 (m, 1H), 3.05-2.88 (m, 2H), 2.80-2.70 (m, 2H), 1.32-1.23 (m, 3H). $^{19}$F NMR δ 47.59.

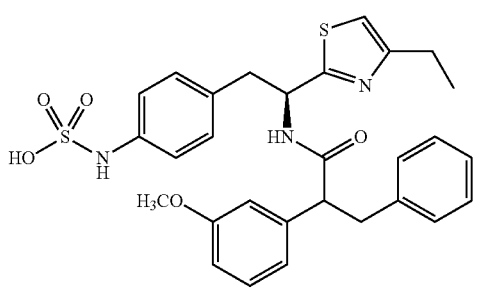 [SMILES: CCc1csc([C@H](Cc2ccc(NS(=O)(=O)O)cc2)NC(=O)C(Cc2ccccc2)c2cccc(OC)c2)n1]

(S)-4-{2-(4-Ethylthiazol-2-yl)-2-[2-(3-methoxyphenyl)-3-phenylpropanamido]-ethyl}phenylsulfamic acid: $^1$H NMR (CD$_3$OD) δ 7.85 (d, 1H, J=8.4Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

The fourth aspect of Category V of the present disclosure relates to compounds having the formula:

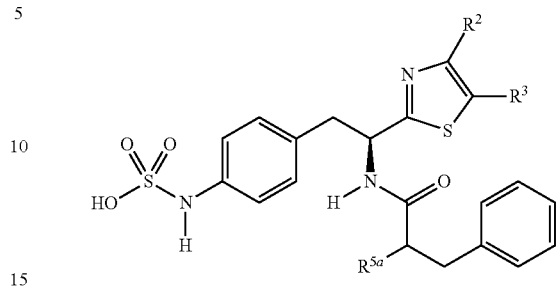

wherein the linking unit L comprises a phenyl unit, said linking group having the formula:

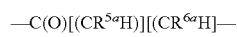

—C(O)[(CR$^{5a}$H)][(CR$^{6a}$H)]—

R$^1$ is hydrogen, R$^{6a}$ is phenyl, R$^{5a}$ is substituted or unsubstituted heteroaryl and the units R$^2$, R$^3$, and R$^{5a}$ are further exemplified herein below in Table XII.

TABLE XII

| No. | R$^2$ | R$^3$ | R$^{5a}$ |
|---|---|---|---|
| L496 | methyl | hydrogen | 3-methyl-1,2,4-oxadiazol-5-yl |
| L497 | methyl | hydrogen | thiophen-2-yl |
| L498 | methyl | hydrogen | thiazol-2-yl |
| L499 | methyl | hydrogen | oxazol-2-yl |
| L500 | methyl | hydrogen | isoxazol-3-yl |
| L501 | ethyl | hydrogen | 3-methyl-1,2,4-oxadiazol-5-yl |
| L502 | ethyl | hydrogen | thiophen-2-yl |
| L503 | ethyl | hydrogen | thiazol-2-yl |
| L504 | ethyl | hydrogen | oxazol-2-yl |
| L505 | ethyl | hydrogen | isoxazol-3-yl |
| L506 | ethyl | methyl | 3-methyl-1,2,4-oxadiazol-5-yl |
| L507 | ethyl | methyl | thiophen-2-yl |
| L508 | ethyl | methyl | thiazol-2-yl |
| L509 | ethyl | methyl | oxazol-2-yl |
| L510 | ethyl | methyl | isoxazol-3-yl |
| L511 | thiophen-2-yl | hydrogen | 3-methyl-1,2,4-oxadiazol-5-yl |
| L512 | thiophen-2-yl | hydrogen | thiophen-2-yl |
| L513 | thiophen-2-yl | hydrogen | thiazol-2-yl |
| L514 | thiophen-2-yl | hydrogen | oxazol-2-yl |
| L515 | thiophen-2-yl | hydrogen | isoxazol-3-yl |
| L516 | isoxazol-3-yl | hydrogen | 3-methyl-1,2,4-oxadiazol-5-yl |
| L517 | isoxazol-3-yl | hydrogen | thiophen-2-yl |
| L518 | isoxazol-3-yl | hydrogen | thiazol-2-yl |
| L519 | isoxazol-3-yl | hydrogen | oxazol-2-yl |
| L520 | isoxazol-3-yl | hydrogen | isoxazol-3-yl |

The compounds encompassed within the fourth aspect of Category V of the present disclosure can be prepared by the procedure outlined in Scheme V and described in Example 5 herein below.

Scheme XI

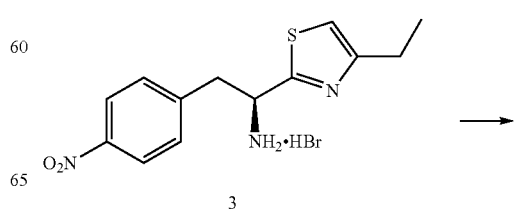

-continued

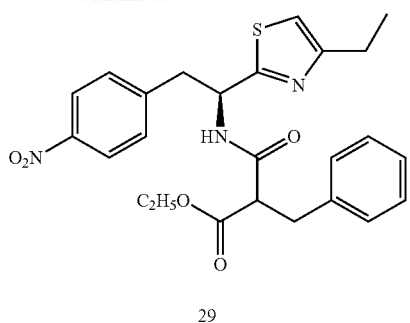

29

Reagents and conditions:
(a) 2-benzyl-3-ethoxy-3-oxopropanoic acid, EDCI, HOBt, DIPEA, DMF; rt, 18 hr.

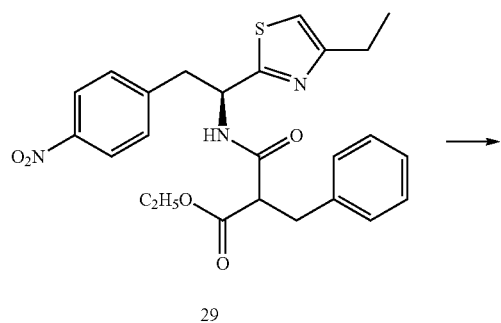

29

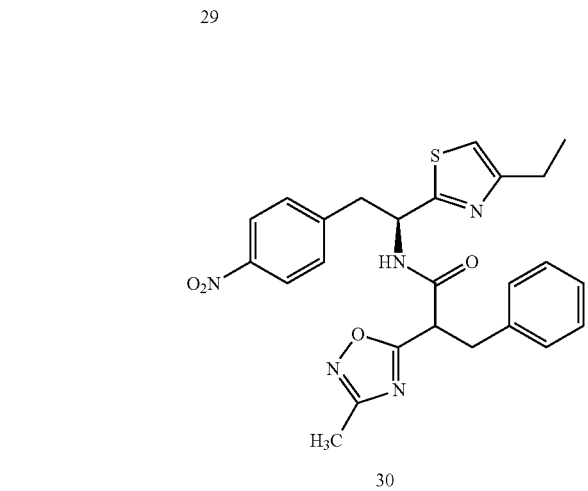

30

Reagents and conditions:
(b) CH₃C(=NOH)NH₂, K₂CO₃, toluene; reflux, 18 hr

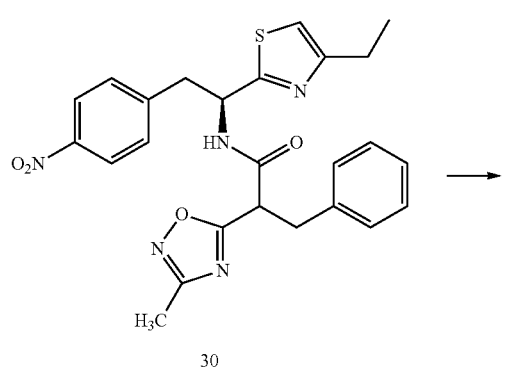

30

-continued

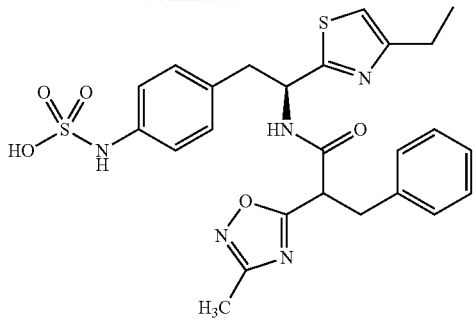

31

Reagents and conditions:
(c)(i) tin (II) chloride, EtOH; (ii) SO₃-pyridine, NH₄OH; rt, 18 hr.

EXAMPLE 12

4-{(S)-2-(4-Ethylthiazol-2-yl)-2-[2-(3-methyl-1,2,4-oxadiazol-5-yl)-3-phenylpropanamido]ethyl}phenylsulfamic acid (31)

Preparation of ethyl-2-benzyl-3-[(S)-1-(4-ethylthiazol-2-yl)-2-(4-nitrophenyl)-ethylamino]-3-oxopropanoate (29): To a solution of 1-(S)-(4-ethylthiazol-2-yl)-2-(4-nitrophenyl) ethyl amine hydrobromide, 3, (0.406 g, 1.13 mmol), 2-benzyl-3-ethoxy-3-oxopropanoic acid (0.277 g) and 1-hydroxybenzotriazole (HOBt) (0.191 g, 1.41 mmol) in DMF (10 mL) at 0°, is added 1-(3-dimethylaminopropyl)-3-ethylcarbodiimide (EDCI) (0.240 g, 1.25 mmol) followed by diisopropylethylamine (DIPEA) (0.306 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.169 g (31% yield) of the desired product which is used without further purification.

Preparation of N—[(S)-1-(4-ethylthiazol-2-yl)-2-(4-nitrophenyl)ethyl]-2-(3-methyl-1,2,4-oxadiazol-5-yl)-3-phenylpropanamide (30): Ethyl 2-benzyl-3-((S)-1-(4-ethylthiazol-2-yl)-2-(4-nitrophenyl)ethylamino)-3-oxopropanoate is dissolved in toluene (5 mL) and heated to reflux. Potassium carbonate (80 mg) and acetamide oxime (43 mg) are added. and treated with 80 mg potassium carbonate and 43 mg acetamide oxime at reflux. The reaction mixture is cooled to room temperature, filtered and concentrated. The residue is chromatographed over silica to afford 0.221 g (94%) of the desired product as a yellow oil.

Preparation of 4-{(S)-2-(4-ethylthiazol-2-yl)-2-[2-(3-methyl-1,2,4-oxadiazol-5-yl)-3-phenylpropanamido]ethyl}phenylsulfamic acid (31): N—[(S)-1-(4-ethylthiazol-2-yl)-2-(4-nitrophenyl)ethyl]-2-(3-methyl-1,2,4-oxadiazol-5-yl)-3-phenylpropanamide, 30, (0.221 g) and tin (II) chloride (507 mg, 2.2 mmol) are dissolved in EtOH (25 mL) and the solution is brought to reflux 4 hours. The solvent is removed in vacuo and the resulting residue is dissolved in EtOAc. A saturated solution of NaHCO₃ (50 mL) is added and the solution is stirred 1 hour. The organic layer is separated and the aqueous layer extracted twice with EtOAc. The combined organic layers are dried (Na₂SO₄), filtered and concentrated to a residue which is dissolved in pyridine (0.143 g) and treated with SO₃-pyridine (0.143 g). The reaction is stirred at room temperature for 5 minutes after which a 7% solution of NH$_4$OH is added. The mixture is then concentrated and the resulting residue is purified by reverse phase chromatography to afford 0.071 g of the desired product as the ammonium salt. $^1$H NMR (CD$_3$OD): δ 7.29-6.87 (m, 10H), 5.38-5.30 (m, 1H), 4.37-4.30 (m, 1H), 3.42-2.74 (m, 6H), 2.38-2.33 (m, 3H), 1.34-1.28 (m, 3H).

Category VI of the present disclosure relates to 2-(thiazol-2-yl) compounds having the formula:

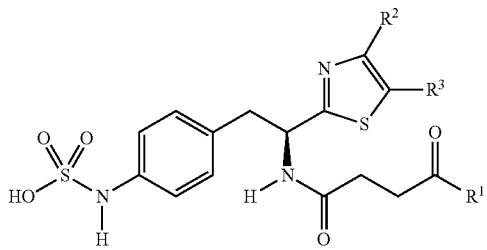

wherein R$^1$, R$^2$, R$^3$, and L are further defined herein in Table XIII herein below.

TABLE XIII

| No. | R$^2$ | R$^3$ | R$^1$ |
|---|---|---|---|
| M521 | ethyl | hydrogen | thiophen-2-yl |
| M522 | ethyl | hydrogen | thiazol-2-yl |
| M523 | ethyl | hydrogen | oxazol-2-yl |
| M524 | ethyl | hydrogen | isoxazol-3-yl |
| M525 | ethyl | hydrogen | imidazol-2-yl |
| M526 | ethyl | hydrogen | isoxazol-3-yl |
| M527 | ethyl | hydrogen | oxazol-4-yl |
| M528 | ethyl | hydrogen | isoxazol-4-yl |
| M529 | ethyl | hydrogen | thiophen-4-yl |
| M530 | ethyl | hydrogen | thiazol-4-yl |
| M531 | ethyl | methyl | methyl |
| M532 | ethyl | methyl | ethyl |
| M533 | ethyl | methyl | propyl |
| M534 | ethyl | methyl | iso-propyl |
| M535 | ethyl | methyl | butyl |
| M536 | ethyl | methyl | phenyl |
| M537 | ethyl | methyl | benzyl |
| M538 | ethyl | methyl | 2-fluorophenyl |
| M539 | ethyl | methyl | 3-fluorophenyl |
| M540 | ethyl | methyl | 4-fluorophenyl |
| M541 | phenyl | hydrogen | methyl |
| M542 | phenyl | hydrogen | ethyl |
| M543 | phenyl | hydrogen | propyl |
| M544 | phenyl | hydrogen | iso-propyl |
| M545 | phenyl | hydrogen | butyl |
| M546 | phenyl | hydrogen | phenyl |
| M547 | phenyl | hydrogen | benzyl |
| M548 | phenyl | hydrogen | 2-fluorophenyl |
| M549 | phenyl | hydrogen | 3-fluorophenyl |
| M550 | phenyl | hydrogen | 4-fluorophenyl |
| M551 | thiophen-2-yl | hydrogen | methyl |
| M552 | thiophen-2-yl | hydrogen | ethyl |
| M553 | thiophen-2-yl | hydrogen | propyl |
| M554 | thiophen-2-yl | hydrogen | iso-propyl |
| M555 | thiophen-2-yl | hydrogen | butyl |
| M556 | thiophen-2-yl | hydrogen | phenyl |
| M557 | thiophen-2-yl | hydrogen | benzyl |
| M558 | thiophen-2-yl | hydrogen | 2-fluorophenyl |
| M559 | thiophen-2-yl | hydrogen | 3-fluorophenyl |
| M560 | thiophen-2-yl | hydrogen | 4-fluorophenyl |

The compounds encompassed within Category VI of the present disclosure can be prepared by the procedure outlined in Scheme XII and described in Example 13 herein below.

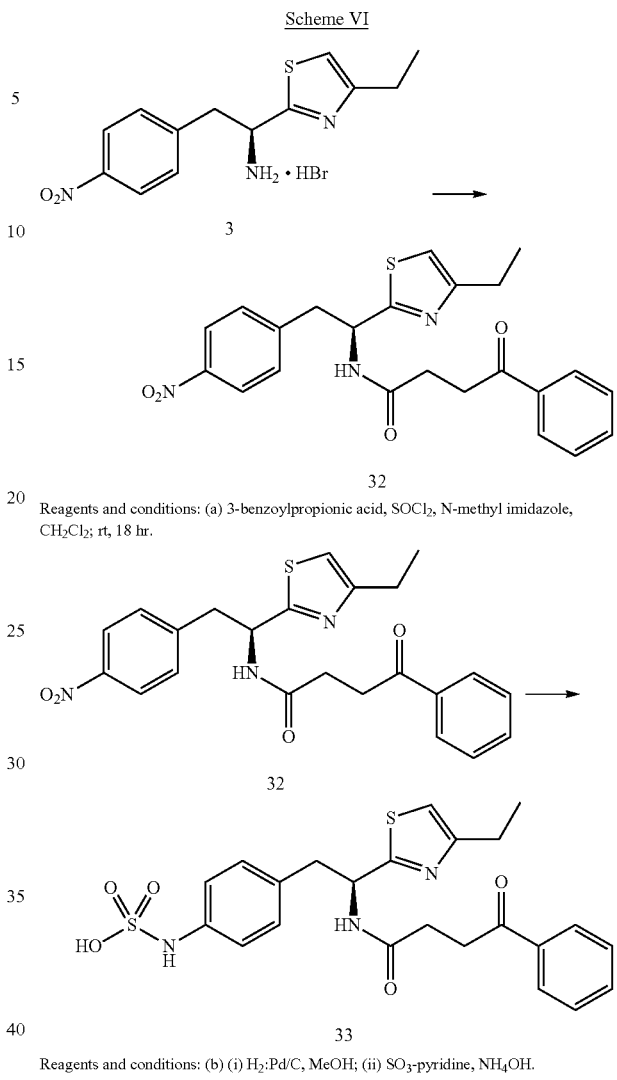

Scheme VI

Reagents and conditions: (a) 3-benzoylpropionic acid, SOCl$_2$, N-methyl imidazole, CH$_2$Cl$_2$; rt, 18 hr.

Reagents and conditions: (b) (i) H$_2$:Pd/C, MeOH; (ii) SO$_3$-pyridine, NH$_4$OH.

EXAMPLE 13

(S)-4-[2-(4-Ethylthiazol-2-yl)-2-(4-oxo-4-phenylbutanamido)ethyl]-phenylsulfamic acid (33)

Preparation of (S)—N-[1-(4-ethylthiazol-2-yl)-2-(4-nitrophenyl)ethyl]-4-oxo-4-phenylbutanamide (32): 3-Benzoylpropionic acid (0.250 g) is dissolved in CH$_2$Cl$_2$ (5 mL), N-methyl imidazole (0.333 mL) is added and the resulting solution is cooled to 0° C. after which a solution of thionyl chloride (0.320 g) in CH$_2$Cl$_2$ (2 mL) is added dropwise. After 0.5 hours (S)-1-(4-ethylthiazol-2-yl)-2-(4-nitrophenyl)ethanamine, 3, (0.388 g) is added. The reaction is stirred for 18 hours at room temperature and then concentrated in vacuo. The resulting residue is dissolved in EtOAc and washed with 1N HCl and brine. The solution is dried over Na$_2$SO$_4$, filtered, and concentrated and the crude material purified over silica to afford 0.415 g of the desired product.

Preparation of (S)-4-[2-(4-ethylthiazol-2-yl)-2-(4-oxo-4-phenylbutanamido)-ethyl]phenylsulfamic acid (33): (S)—N-[1-(4-ethylthiazol-2-yl)-2-(4-nitrophenyl)ethyl]-2,3-diphenyl-propanamide, 32, (0.2 g) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (5 mL) and treated with SO₃-pyridine (0.153 g). The reaction is stirred at room temperature for 5 minutes after which a 7% solution of NH₄OH is added. The mixture is then concentrated and the resulting residue is purified by reverse phase chromatography to afford 0.090 g of the desired product as the ammonium salt. ¹H NMR (CD₃OD) δ 8.68 (d, 1H, J=8.2 Hz), 8.00 (d, 2H, J=7.2 Hz), 7.80-7.50 (m, 3H), 7.12 (s, 4H), 7.03 (s, 1H), 5.46-5.38 (m, 1H), 3.29-3.14 (m, 2H), 3.06-2.99 (m, 2H), 2.83 (q, 2H, J=7.5 Hz), 2.69-2.54 (m, 2H), 1.33 (t, 3H, J=7.5 Hz).

The following are non-limiting examples of compounds encompassed within Category II of the present disclosure. The intermediate nitro compounds of the following can be prepared by coupling the appropriate 4-oxo-carboxylic acid with intermediate 3 under the conditions described herein above for the formation of intermediate 4 of scheme I.

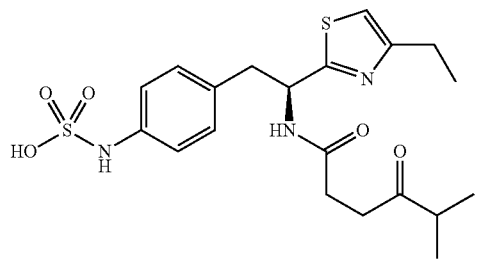 [SMILES: CCc1csc([C@H](Cc2ccc(NS(=O)(=O)O)cc2)NC(=O)CCC(=O)C(C)C)n1]

(S)-4-(2-(4-Ethylthiazol-2-yl)-2-(5-methyl-4-oxohexanamido)ethyl)phenylsulfamic acid: ¹H NMR (CD₃OD) δ 8.59 (d, 1H, J=8.1 Hz), 7.14 (s, 4H), 7.08 (t, 1H, J=13.0 Hz), 5.40-5.35 (m, 1H), 3.37-3.27 (m, 2H), 3.04-2.97 (m, 1H), 2.83-2.61 (m, 4H), 2.54-2.36 (m, 3H), 1.33 (t, 2H, J=7.3 Hz), 1.09 (dd, 6H, J=7.0, 2.2 Hz).

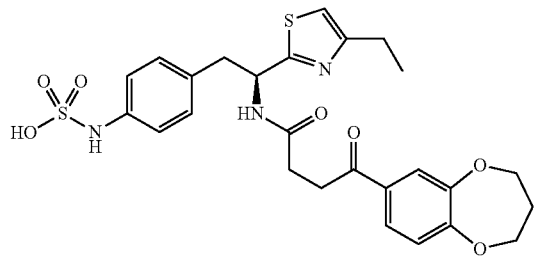 [SMILES: CCc1csc([C@H](Cc2ccc(NS(=O)(=O)O)cc2)NC(=O)CCC(=O)c2ccc3c(c2)OCCCO3)n1]

(S)-4-{2-[4-(3,4-Dihydro-2H-benzo[b][1,4]dioxepin-7-yl)-4-oxobutanamido]-2-(4-ethylthiazol-2-yl)ethyl}phenylsulfamic acid: ¹H NMR(CD₃OD) δ 8.64 (d, 1H, J=8.4 Hz), 7.60 (d, 2H, J=10.6 Hz), 7.11 (s, 3H), 7.04 (d, 2H, J=5.5 Hz), 5.42-5.40 (m, 1H), 4.30-4.22 (m, 4H), 3.20-2.98 (m, 4H), 2.82 (q, 2H, J=7.3 Hz), 2.67-2.48 (m, 2H), 2.23 (t, 2H, J=5.5 Hz), 1.32 (t, 3H, J=7.3 Hz).

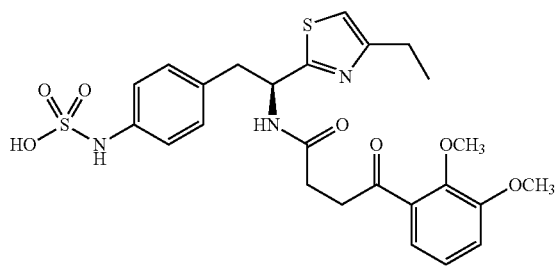 [SMILES: CCc1csc([C@H](Cc2ccc(NS(=O)(=O)O)cc2)NC(=O)CCC(=O)c2cccc(OC)c2OC)n1]

(S)-4-{2-[4-(2,3-Dimethoxyphenyl)-4-oxobutanamido]-2-(4-ethylthiazol-2-yl)ethyl}phenylsulfamic acid: ¹H NMR (CD₃OD), δ 8.64 (d, 1H, J=8.1 Hz), 7.21-7.11 (m, 7H), 7.02 (s, 1H), 5.42 (q, 1H, J=5.9 Hz), 3.90 (d, 3H, J=3.3 Hz), 3.88 (d, 3H, J=2.9 Hz), 3.22-3.18 (m, 2H), 3.07-2.99 (m, 2H), 2.83 (q, 2H, J=7.3 Hz), 2.63-2.54 (m, 2H), 1.34 (t, 3H, J=7.69 Hz).

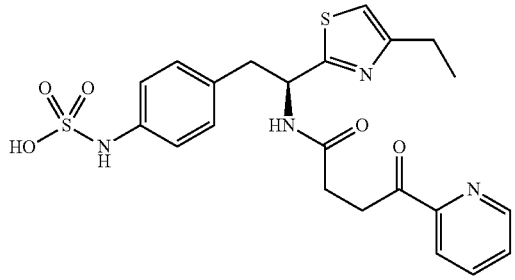 [SMILES: CCc1csc([C@H](Cc2ccc(NS(=O)(=O)O)cc2)NC(=O)CCC(=O)c2ccccn2)n1]

(S)-4-{2-(4-Ethylthiazol-2-yl)-2-[4-oxo-4-(pyridin-2-yl)butanamido]ethyl}-phenylsulfamic acid: ¹H NMR (CD₃OD) δ 8.60 (d, 1H, J=12.8 Hz), 7.91-7.81 (m, 2H), 7.48-7.44 (m, 1H), 7.22-7.21 (m, 1H), 6.99 (s, 3H), 6.91 (s, 1H), 5.30 (q, 1H, J=5.4 Hz), 3.36 (q, 2H, J=7.0 Hz), 3.21-3.15 (m, 1H), 2.91-2.85 (m, 1H), 2.74 (q, 2H, J=10.4 Hz), 2.57-2.50 (m, 2H), 1.20 (t, 3H, J=7.5 Hz).

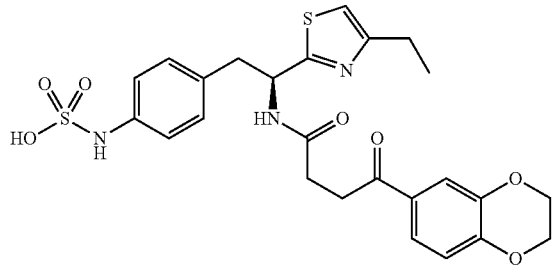 [SMILES: CCc1csc([C@H](Cc2ccc(NS(=O)(=O)O)cc2)NC(=O)CCC(=O)c2ccc3c(c2)OCCO3)n1]

(S)-4-{2-[4-(2,3-dihydrobenzo[b][1,4]dioxin-6-yl)-4-oxobutanamido]-2-(4-ethylthiazol-2-yl)ethyl}phenylsulfamic acid: ¹H NMR (CD₃OD) δ 7.52-7.47 (m, 2H), 7.11 (s, 4H), 7.03 (s, 1H), 6.95 (d, 1H, J=8.4 Hz), 5.41 (q, 1H, J=3.7 Hz), 4.31 (d, 4H, J=5.5 Hz), 3.24-3.12 (m, 2H), 3.06-2.98 (m, 2H), 2.83 (q, 2H, J=7.3 Hz), 2.62-2.53 (m, 2H), 1.33 (t, 3H, J=7.3 Hz).

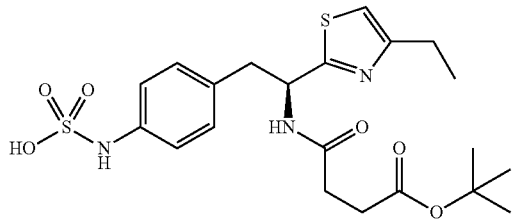 [SMILES: CCc1csc([C@H](Cc2ccc(NS(=O)(=O)O)cc2)NC(=O)CCC(=O)OC(C)(C)C)n1]

(S)-4-[2-(4-tert-butoxy-4-oxobutanamido)-2-(4-ethylthiazol-2-yl)ethyl]phenylsulfamic acid: ¹H NMR (CD₃OD), δ 7.10 (s 4H), 7.02 (s, 1H), 5.41 (q, 1H, J=3.7 Hz), 3.30-3.25 (m, 1H), 3.06-2.99 (m, 1H), 2.83 (q, 2H, J=7.3 Hz), 2.52-2.40 (m, 4H), 1.42 (s, 9H), 1.33 (t, 3H, J=7.3 Hz).

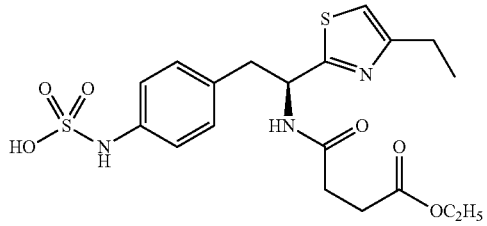 [SMILES: CCOC(=O)CCC(=O)N[C@@H](Cc1ccc(NS(=O)(=O)O)cc1)c1nc(CC)cs1]

(S)-4-[2-(4-ethoxy-4-oxobutanamido)-2-(4-ethylthiazol-2-yl)ethyl]phenylsulfamic acid: ¹H NMR (CD₃OD) δ 8.62

(d, 1H, J=8.4 Hz), 7.10 (s, 4H), 7.02 (s, 1H), 5.40 (q, 1H, 3.7 Hz), 4.15 (q, 2H, J=7.3 Hz), 3.28-3.25 (m, 1H), 3.05-3.02 (m, 1H), 2.82 (q, 2H, J=4.4 Hz), 2.54-2.48 (m, 2H), 1.33 (t, 3H, J=7.3 Hz), 1.24 (t, 3H, J=7.0 Hz).

The first aspect of Category VII of the present disclosure relates to 2-(thiazol-2-yl) compounds having the formula:

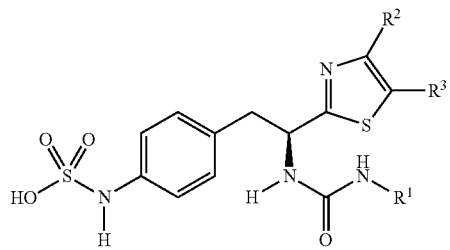

wherein non-limiting examples of $R^1$, $R^2$, and $R^3$ are further described herein below in Table XIV.

TABLE XIV

| No. | $R^2$ | $R^3$ | $R^1$ |
|---|---|---|---|
| N561 | methyl | hydrogen | phenyl |
| N562 | methyl | hydrogen | benzyl |
| N563 | methyl | hydrogen | 2-fluorophenyl |
| N564 | methyl | hydrogen | 3-fluorophenyl |
| N565 | methyl | hydrogen | 4-fluorophenyl |
| N566 | methyl | hydrogen | 2-chlorophenyl |
| N567 | methyl | hydrogen | 3-chlorophenyl |
| N568 | methyl | hydrogen | 4-chlorophenyl |
| N569 | ethyl | hydrogen | phenyl |
| N570 | ethyl | hydrogen | benzyl |
| N571 | ethyl | hydrogen | 2-fluorophenyl |
| N572 | ethyl | hydrogen | 3-fluorophenyl |
| N573 | ethyl | hydrogen | 4-fluorophenyl |
| N574 | ethyl | hydrogen | 2-chlorophenyl |
| N575 | ethyl | hydrogen | 3-chlorophenyl |
| N576 | ethyl | hydrogen | 4-chlorophenyl |
| N577 | thiene-2-yl | hydrogen | phenyl |
| N578 | thiene-2-yl | hydrogen | benzyl |
| N579 | thiene-2-yl | hydrogen | 2-fluorophenyl |
| N580 | thiene-2-yl | hydrogen | 3-fluorophenyl |
| N581 | thiene-2-yl | hydrogen | 4-fluorophenyl |
| N582 | thiene-2-yl | hydrogen | 2-chlorophenyl |
| N583 | thiene-2-yl | hydrogen | 3-chlorophenyl |
| N584 | thiene-2-yl | hydrogen | 4-chlorophenyl |

The compounds encompassed within Category VII of the present disclosure can be prepared by the procedure outlined in Scheme XIII and described in Example 14 herein below.

Scheme XIII

3

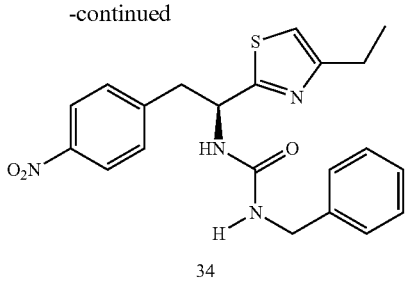

34

Reagents and conditions:
(a) benzyl isocyanate, TEA, CH$_2$Cl$_2$; rt, 18 hr.

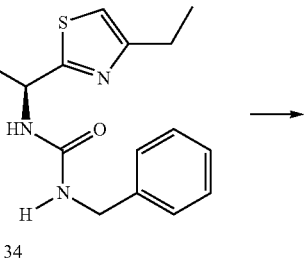

34

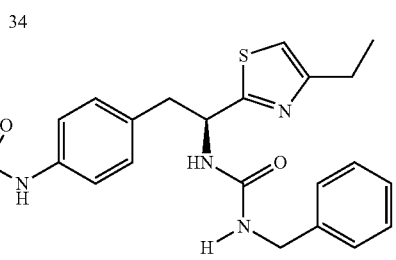

35

Reagents and conditions:
(b)(i) H$_2$:Pd/C, MeOH;
(ii) SO$_3$-pyridine, NH$_4$OH.

EXAMPLE 14

(S)-4-(2-(3-Benzylureido)-2-(4-ethylthiazol-2-yl) ethyl)phenylsulfamic acid (35)

Preparation of (S)-1-benzyl-3-[1-(4-ethylthiazol-2-yl)-2-(4-nitrophenyl)ethyl]urea (34): To a solution of 1-(S)-(4-ethylthiazol-2-yl)-2-(4-nitrophenyl)ethyl amine hydrobromide, 3, (0.360 g, 1 mmol) and Et$_3$N (0.42 mL, 3 mmol) in 10 mL CH$_2$Cl$_2$ is added benzyl isocyanate (0.12 mL, 1 mmol). The mixture is stirred at room temperature for 18 hours. The product is isolated by filtration to afford 0.425 g (96% yield) of the desired product which is used without further purification.

Preparation of (S)-4-(2-(3-benzylureido)-2-(4-ethylthiazol-2-yl)ethyl)phenylsulfamic acid (35): (S)-1-benzyl-3-[1-(4-ethylthiazol-2-yl)-2-(4-nitrophenyl)ethyl]urea, 34, (0.425 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.220 g). The reaction is stirred at room temperature for 5 minutes after which a 7% solution of NH$_4$OH is added. The mixture is then concentrated and the resulting residue is purified by reverse phase chromatography to afford 0.143 g of the desired product as the ammonium salt. $^1$H NMR (CD$_3$OD) δ 7.32-7.30 (m, 2H), 7.29-7.22 (m, 3H), 7.12-7.00 (m, 4H), 6.84 (d, 1H, J=8.1Hz), 5.35-5.30 (m, 1H), 4.29 (s, 2H), 3.27-3.22 (m, 3H), 3.11-3.04 (m, 3H), 2.81 (q, 2H, J=10.2, 13.0Hz), 1.31 (t, 3H, J=4.5Hz).

The following is a non-limiting examples of compounds encompassed within the first aspect of Category VII of the present disclosure.

4-{[(S)-2-(2-Ethylthiazol-4-yl)-2-(3-(R)-methoxy-1-oxo-3-phenylpropan-2-yl)ureido]ethyl}phenylsulfamic acid: $^1$H NMR (CD$_3$OD) δ 7.36-7.26 (m, 3H), 7.19-7.17 (m, 2H), 7.10-7.06 (m, 2H), 6.90-6.86 (m, 3H), 5.12-5.06 (m, 1H), 4.60-4.55 (m, 1H), 3.69 (s, 3H) 3.12-2.98 (m, 6H), 1.44-1.38 (m, 3H).

The second aspect of Category VII of the present disclosure relates to 2-(thiazol-4-yl) compounds having the formula:

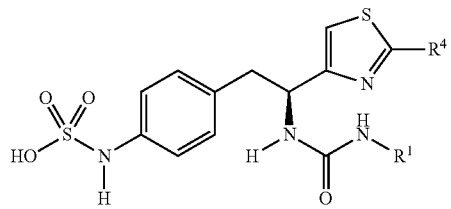

wherein non-limiting examples of $R^1$ and $R^4$ are further described herein below in Table XV.

TABLE XV

| No. | $R^1$ | $R^4$ |
| --- | --- | --- |
| O585 | methyl | methyl |
| O586 | ethyl | methyl |
| O587 | n-propyl | methyl |
| O588 | iso-propyl | methyl |
| O589 | phenyl | methyl |
| O590 | benzyl | methyl |
| O591 | 2-fluorophenyl | methyl |
| O592 | 2-chlorophenyl | methyl |
| O593 | thiophen-2-yl | methyl |
| O594 | thiazol-2-yl | methyl |
| O595 | oxazol-2-yl | methyl |
| O596 | isoxazol-3-yl | methyl |
| O597 | methyl | ethyl |
| O598 | ethyl | ethyl |
| O599 | n-propyl | ethyl |
| O600 | iso-propyl | ethyl |
| O601 | phenyl | ethyl |
| O602 | benzyl | ethyl |
| O603 | 2-fluorophenyl | ethyl |
| O604 | 2-chlorophenyl | ethyl |
| O605 | thiophen-2-yl | ethyl |
| O606 | thiazol-2-yl | ethyl |
| O607 | oxazol-2-yl | ethyl |
| O608 | isoxazol-3-yl | ethyl |
| O609 | methyl | thiophen-2-yl |
| O610 | ethyl | thiophen-2-yl |
| O611 | n-propyl | thiophen-2-yl |
| O612 | iso-propyl | thiophen-2-yl |
| O613 | phenyl | thiophen-2-yl |
| O614 | benzyl | thiophen-2-yl |
| O615 | 2-fluorophenyl | thiophen-2-yl |
| O616 | 2-chlorophenyl | thiophen-2-yl |
| O617 | thiophen-2-yl | thiophen-2-yl |
| O618 | thiazol-2-yl | thiophen-2-yl |
| O619 | oxazol-2-yl | thiophen-2-yl |
| O620 | isoxazol-3-yl | thiophen-2-yl |
| O621 | methyl | thiazol-2-yl |
| O622 | ethyl | thiazol-2-yl |
| O623 | n-propyl | thiazol-2-yl |
| O624 | iso-propyl | thiazol-2-yl |
| O625 | phenyl | thiazol-2-yl |
| O626 | benzyl | thiazol-2-yl |
| O627 | 2-fluorophenyl | thiazol-2-yl |
| O628 | 2-chlorophenyl | thiazol-2-yl |

TABLE XV-continued

| No. | $R^1$ | $R^4$ |
| --- | --- | --- |
| O629 | thiophen-2-yl | thiazol-2-yl |
| O630 | thiazol-2-yl | thiazol-2-yl |
| O631 | oxazol-2-yl | thiazol-2-yl |
| O632 | isoxazol-3-yl | thiazol-2-yl |
| O633 | methyl | oxazol-2-yl |
| O634 | ethyl | oxazol-2-yl |
| O635 | n-propyl | oxazol-2-yl |
| O636 | iso-propyl | oxazol-2-yl |
| O637 | phenyl | oxazol-2-yl |
| O638 | benzyl | oxazol-2-yl |
| O639 | 2-fluorophenyl | oxazol-2-yl |
| O640 | 2-chlorophenyl | oxazol-2-yl |
| O641 | thiophen-2-yl | oxazol-2-yl |
| O642 | thiazol-2-yl | oxazol-2-yl |
| O643 | oxazol-2-yl | oxazol-2-yl |
| O644 | isoxazol-3-yl | oxazol-2-yl |

The compounds encompassed within the second aspect of Category VII of the present disclosure can be prepared by the procedure outlined in Scheme XIV and described in Example 14 herein below.

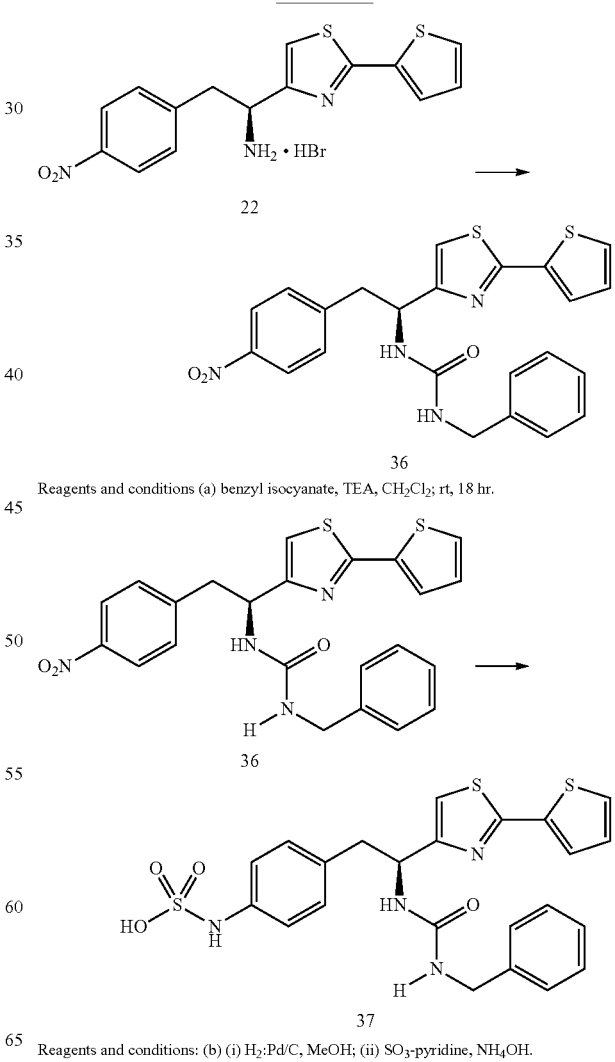

Scheme XIV

Reagents and conditions (a) benzyl isocyanate, TEA, CH$_2$Cl$_2$; rt, 18 hr.

Reagents and conditions: (b) (i) H$_2$:Pd/C, MeOH; (ii) SO$_3$-pyridine, NH$_4$OH.

EXAMPLE 15

4-{(S)-2-(3-Benzylureido)-2-[2-(thiophen-2-yl)thiazol-4-yl]ethyl}-phenylsulfamic acid (37)

Preparation of 1-benzyl-3-{(S)-2-(4-nitrophenyl)-1-[2-(thiophen-2-yl)thiazol-4-yl]ethyl}urea (36): To a solution of (S)-2-(4-nitrophenyl)-1-[(2-thiophen-2-yl)thiazol-4-yl) ethan-amine hydrobromide salt, 8, and Et$_3$N (0.42 mL, 3 mmol) in 10 mL DCM is added benzyl isocyanate (0.12 mL, 1 mmol). The mixture is stirred at room temperature for 18 hours. The product is isolated by filtration to afford 0.445 g (96% yield) of the desired product which is used without further purification.

Preparation of 4-{(S)-2-(3-benzylureido)-2-[2-(thiophen-2-yl)thiazol-4-yl]ethyl}phenylsulfamic acid (37): 1-Benzyl-3-{(S)-2-(4-nitrophenyl)-1-[2-(thiophen-2-yl)thiazol-4-yl]ethyl}urea, 36, (0.445 g) is dissolved in MeOH (10 mL) and CH$_2$Cl$_2$ (5 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.110 g). The reaction is stirred at room temperature for 5 minutes after which a 7% solution of NH$_4$OH is added. The mixture is then concentrated and the resulting residue is purified by reverse phase chromatography to afford 0.080 g of the desired product as the ammonium salt. $^1$H NMR (CD$_3$OD) δ 7.61 (d, 1H, J=2.1Hz), 7.58 (d, 1H, J=6Hz), 7.33-7.22 (m, 4H), 7.17-7.14 (m, 1H), 7.09-6.94 (m, 6H), 5.16 (t, 1H, J=6.6Hz), 4.13 (s, 2H), 3.14-3.11 (m, 2H).

Category VIII of the present disclosure relates to 2-(thiazol-4-yl) compounds having the formula:

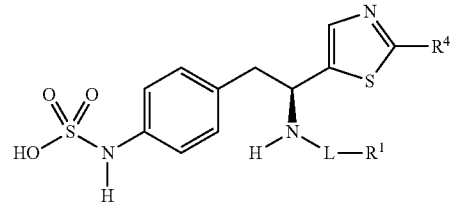

wherein R$^1$, R$^4$, and L are further defined herein in Table XVI herein below.

TABLE XVI

| No. | R$^4$ | L | R$^1$ |
|---|---|---|---|
| P645 | methyl | —SO$_2$— | methyl |
| P646 | ethyl | —SO$_2$— | methyl |
| P647 | phenyl | —SO$_2$— | methyl |
| P648 | thiophen-2-yl | —SO$_2$— | methyl |
| P649 | methyl | —SO$_2$— | trifluoromethyl |
| P650 | ethyl | —SO$_2$— | trifluoromethyl |
| P651 | phenyl | —SO$_2$— | trifluoromethyl |
| P652 | thiophen-2-yl | —SO$_2$— | trifluoromethyl |
| P653 | methyl | —SO$_2$— | ethyl |
| P654 | ethyl | —SO$_2$— | ethyl |
| P655 | phenyl | —SO$_2$— | ethyl |
| P656 | thiophen-2-yl | —SO$_2$— | ethyl |
| P657 | methyl | —SO$_2$— | 2,2,2-trifluoroethyl |
| P658 | ethyl | —SO$_2$— | 2,2,2-trifluoroethyl |
| P659 | phenyl | —SO$_2$— | 2,2,2-trifluoroethyl |
| P660 | thiophen-2-yl | —SO$_2$— | 2,2,2-trifluoroethyl |
| P661 | methyl | —SO$_2$— | phenyl |
| P662 | ethyl | —SO$_2$— | phenyl |
| P663 | phenyl | —SO$_2$— | phenyl |
| P664 | thiophen-2-yl | —SO$_2$— | phenyl |
| P665 | methyl | —SO$_2$— | 4-fluorophenyl |
| P666 | ethyl | —SO$_2$— | 4-fluorophenyl |
| P667 | phenyl | —SO$_2$— | 4-fluorophenyl |
| P668 | thiophen-2-yl | —SO$_2$— | 4-fluorophenyl |
| P669 | methyl | —SO$_2$— | 3,4-dihydro-2H-benzo[b][1,4]oxazin-7-yl |
| P670 | ethyl | —SO$_2$— | 3,4-dihydro-2H-benzo[b][1,4]oxazin-7-yl |
| P671 | phenyl | —SO$_2$— | 3,4-dihydro-2H-benzo[b][1,4]oxazin-7-yl |
| P672 | thiophen-2-yl | —SO$_2$— | 3,4-dihydro-2H-benzo[b][1,4]oxazin-7-yl |
| P673 | methyl | —SO$_2$— | 1-methyl-1H-imidazol-4-yl |
| P674 | ethyl | —SO$_2$— | 1-methyl-1H-imidazol-4-yl |
| P675 | phenyl | —SO$_2$— | 1-methyl-1H-imidazol-4-yl |
| P676 | thiophen-2-yl | —SO$_2$— | 1-methyl-1H-imidazol-4-yl |
| P678 | methyl | —SO$_2$— | 4-acetamidophenyl |
| P679 | ethyl | —SO$_2$— | 4-acetamidophenyl |
| P680 | phenyl | —SO$_2$— | 4-acetamidophenyl |
| P681 | thiophen-2-yl | —SO$_2$— | 4-acetamidophenyl |
| P682 | methyl | —SO$_2$CH$_2$— | phenyl |
| P683 | ethyl | —SO$_2$CH$_2$— | phenyl |
| P684 | phenyl | —SO$_2$CH$_2$— | phenyl |
| P685 | thiophen-2-yl | —SO$_2$CH$_2$— | phenyl |
| P686 | methyl | —SO$_2$CH$_2$— | (4-methylcarboxyphenyl)methyl |
| P687 | ethyl | —SO$_2$CH$_2$— | (4-methylcarboxyphenyl)methyl |
| P688 | phenyl | —SO$_2$CH$_2$— | (4-methylcarboxyphenyl)methyl |
| P689 | thiophen-2-yl | —SO$_2$CH$_2$— | (4-methylcarboxyphenyl)methyl |
| P690 | methyl | —SO$_2$CH$_2$— | (2-methylthiazol-4-yl)methyl |
| P691 | ethyl | —SO$_2$CH$_2$— | (2-methylthiazol-4-yl)methyl |
| P692 | phenyl | —SO$_2$CH$_2$— | (2-methylthiazol-4-yl)methyl |
| P693 | thiophen-2-yl | —SO$_2$CH$_2$— | (2-methylthiazol-4-yl)methyl |

TABLE XVI-continued

| No. | R⁴ | L | R¹ |
|---|---|---|---|
| P694 | methyl | —SO₂CH₂CH₂— | phenyl |
| P695 | ethyl | —SO₂CH₂CH₂— | phenyl |
| P696 | phenyl | —SO₂CH₂CH₂— | phenyl |
| P697 | thiophen-2-yl | —SO₂CH₂CH₂— | phenyl |

The compounds encompassed within Category VIII of the present disclosure can be prepared by the procedure outlined in Scheme XV and described in Example 16 herein below.

Scheme XV

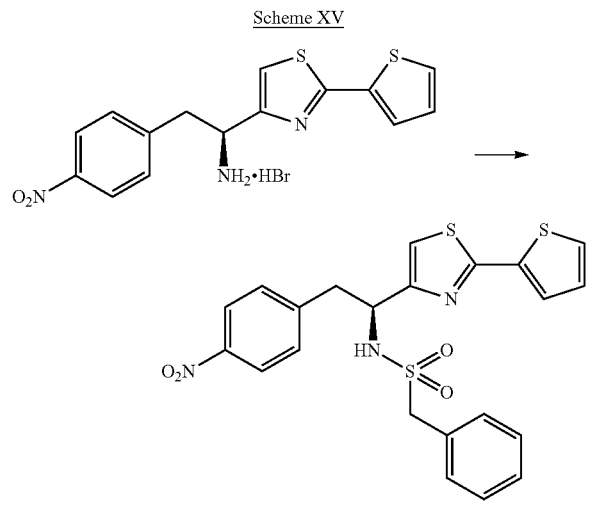

Reagents and conditions:
(a) C₆H₄CH₂SO₂Cl, DIPEA, CH₂Cl₂; 0° C. to rt, 14 hr.

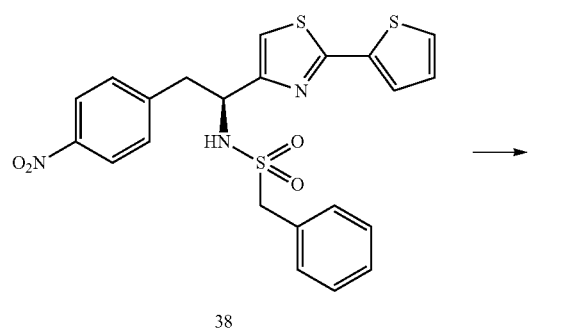

38

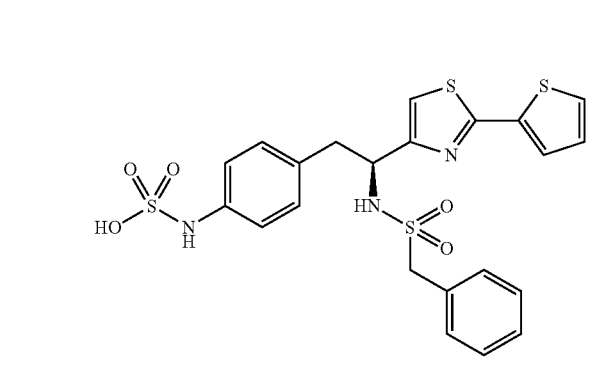

39

Reagents and conditions:
(b)(i) H₂:Pd/C, MeOH;
(ii) SO₃-pyridine, NH₄OH.

EXAMPLE 16

{4-(S)-[2-Phenylmethanesulfonylamino-2-(2-thiophen-2-ylthiazol-4-yl)ethyl]phenyl}sulfamic acid (39)

Preparation of (S)—N-{2-(4-nitrophenyl)-1-[2-(thiophen-2-yl)thiazol-4-yl]ethyl}-1-phenylmethanesulfonamide (38): To a suspension of 2-(4-nitrophenyl)-1-(2-thiophene2-ylthiazol-4-yl)ethylamine, 8, (330 mg, 0.80 mmol) in CH₂Cl₂ (6 mL) at 0° C. is added diisopropylethylamine (0.30 mL, 1.6 mmol) followed by phenylmethanesulfonyl chloride (167 mg, 0.88 mmol). The reaction mixture is stirred at room temperature for 14 hours. The mixture is diluted with CH₂Cl₂ and washed with sat. NaHCO₃ followed by brine, dried (Na₂SO₄), filtered and concentrated in vacuo. The resulting residue is purified over silica to afford 210 mg of the desired product as a white solid.

Preparation of {4-(S)-[2-phenylmethanesulfonylamino-2-(2-thiophen-2-ylthiazol-4-yl)ethyl]phenyl}sulfamic acid (39): (S)—N-{2-(4-nitrophenyl)-1-[2-(thiophen-2-yl)thiazol-4-yl]ethyl}-1-phenylmethanesulfonamide, 38, (210 mg, 0.41 mmol) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (197 mg, 1.23 mmol). The reaction is stirred at room temperature for 5 minutes after which a 7% solution of NH₄OH is added. The mixture is then concentrated and the resulting residue is purified by reverse phase chromatography to afford 0.060 g of the desired product as the ammonium salt. ¹H NMR (300 MHz, MeOH-d₄) δ 7.52-7.63 (m, 6.70-7.28 (m, 11H), 4.75 (t, J=7.2 Hz, 1H), 3.95-4.09 (m, 2H), 3.20 (dd, J=13.5 and 7.8 Hz, 1H), 3.05 (dd, J=13.5 and 7.8 Hz, 1H). 1013770

Intermediates for use in Step (a) of Scheme XV can be conveniently prepared by the procedure outlined herein below in Scheme XVI and described in Example 17.

Scheme XVI

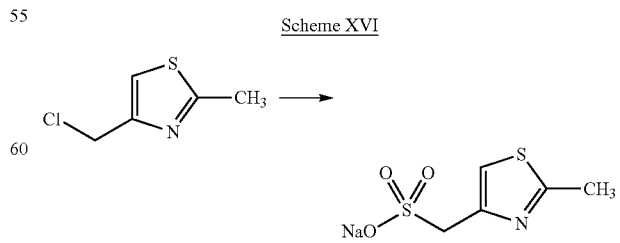

Reagents and conditions: (a) Na₂SO₃, H₂O; microwave @ 200° C., 20 min.

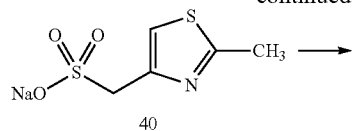

Reagents and conditions: (b) PCl$_5$, POCl$_3$; 50° C., 3 hrs.

EXAMPLE 17

(2-Methylthiazol-4-yl)methanesulfonyl chloride (41)

Preparation of sodium (2-methylthiazol-4-yl)methanesulfonate (40): 4-Chloromethyl-2-methylthiazole (250 mg, 1.69 mmol) is dissolved in H$_2$O (2 mL) and treated with sodium sulfite (224 mg, 1.78 mmol). The reaction mixture is subjected to microwave irradiation for 20 minutes at 200° C. The reaction mixture is diluted with H$_2$O (30 mL) and washed with EtOAc (2×25 mL). The aqueous layer is concentrated to afford 0.368 g of the desired product as a yellow solid. LC/MS ESI+ 194 (M+1, free acid).

Preparation of (2-methylthiazol-4-yl)methanesulfonyl chloride (41): Sodium (2-methylthiazol-4-yl)methanesulfonate, 40, (357 mg, 1.66 mmol) is dissolved in phosphorous oxychloride (6 mL) and is treated with phosphorous pentachloride (345 mg, 1.66 mmol). The reaction mixture is stirred at 50° C. for 3 hours, then allowed to cool to room temperature. The solvent is removed under reduced pressure and the residue is re-dissolved in CH$_2$Cl$_2$ (40 mL) and is washed with sat. NaHCO$_3$ and brine. The organic layer is dried over MgSO$_4$, filtered, and the solvent removed in vacuo to afford 0.095 g of the desired product as a brown oil. LC/MS ESI+ 211 (M+1). Intermediates are obtained in sufficient purity to be carried forward according to Scheme IX without the need for further purification.

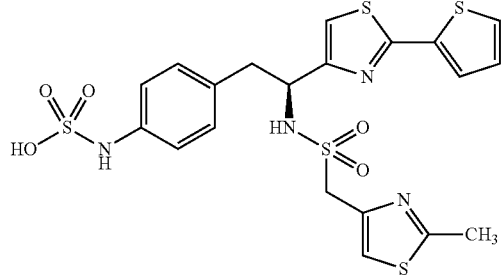 [SMILES: Cc1nc(CS(=O)(=O)N[C@@H](Cc2ccc(NS(=O)(=O)O)cc2)c2csc(-c3cccs3)n2)cs1]

4-{(S)-2-[(2-methylthiazol-4-yl)methylsulfonamido]-2-[2-(thiophen-2-yl)thiazol-4-yl]ethyl}phenylsulfamic acid: $^1$H NMR (CD$_3$OD): δ 7.71-7.66 (m, 2H), 7.27-7.10 (m, 7H), 4.87 (t, 1H, J=7.3 Hz), 4.30-4.16 (q, 2H, J=13.2 Hz), 3.34-3.13 (m, 2H), 2.70 (s, 3H).

The following are non-limiting examples of compounds encompassed within Category VIII of the present disclosure.

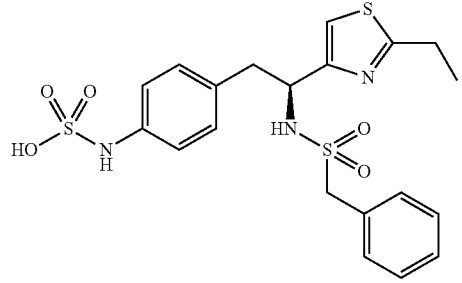 [SMILES: CCc1nc([C@H](Cc2ccc(NS(=O)(=O)O)cc2)NS(=O)(=O)Cc2ccccc2)cs1]

{4-(S)-[2-Phenylmethanesulfonylamino-2-(2-ethylthiazol-4-yl)ethyl]phenyl}-sulfamic acid: $^1$H NMR (300 MHz, MeOH-d$_4$) δ 7.27-7.32 (m, 3H), 7.16-7.20 (m, 3H), 7.05-7.6 (m, 2H), 6.96 (d, J=8.4 Hz, 2H), 4.70 (t, J=9.0 Hz, 1H), 3.91-4.02 (m, 2H), 2.95-3.18 (m, 4H), 1.41 (t, J=7.5 Hz, 3H).

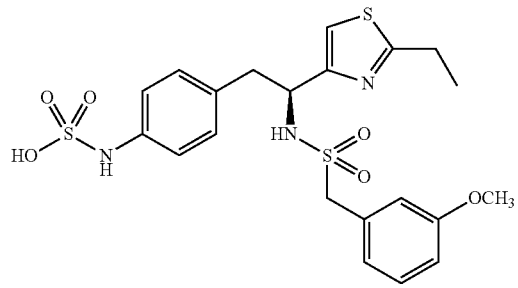 [SMILES: CCc1nc([C@H](Cc2ccc(NS(=O)(=O)O)cc2)NS(=O)(=O)Cc2cccc(OC)c2)cs1]

{4-(S)-[2-(3-Methoxyphenyl)methanesulfonylamino-2-(2-ethylthiazol-4-yl)ethyl]phenyl}sulfamic acid: $^1$H NMR (300 MHz, MeOH-d$_4$) δ 7.20 (t, J=8.1 Hz. 1H), 6.94-7.08 (m, 4H), 6.88-6.94 (m, 3H), 6.75-6.80 (m, 1H), 4.67 (t, J=7.2 Hz, 1H), 3.90-4.0 (m, 2H), 3.76 (s, 3H), 2.95-3.16 (m, 4H), 1.40 (t, J=7.5 HZ, 3H).

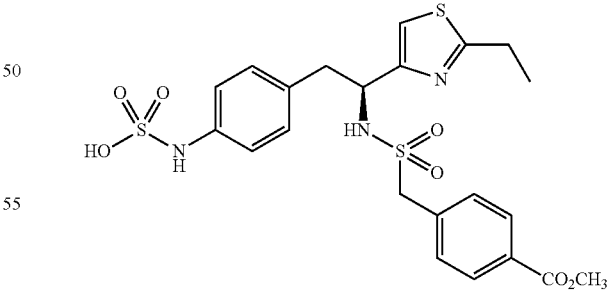

(S)-4-{[1-(2-Ethylthiazol-4-yl)-2-(4-sulfoaminophenyl)ethylsulfamoyl]methyl}-benzoic acid methyl ester: $^1$H NMR (300 MHz, MeOH-d$_4$) δ 7.90-7.94-(m, 2H), 7.27-7.30 (m, 2H), 7.06-7.11 (m, 3H), 6.97-7.00 (m, 2H), 4.71 (t, J=7.2 Hz, 1H), 3.95-4.08 (4, 2H), 3.92 (s, 3H), 2.80-3.50 (m, 4H), 1.38-1.44 (m, 3H).

103

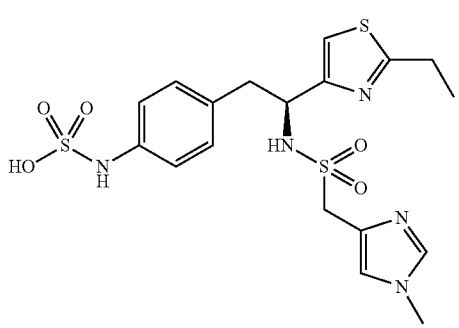 [SMILES: CCc1nc([C@H](Cc2ccc(NS(=O)(=O)O)cc2)NS(=O)(=O)Cc2cn(C)cn2)cs1]

(S)-4-[2-(2-Ethylthiazol-4-yl)-2-(1-methyl-1H-imidazol-4-sulfonamido)ethyl]-phenylsulfamic acid: $^1$H NMR (300 MHz, MeOH-d$_4$) δ 7.54 (s, 1H, 7.20 (s, 1H), 7.09 (s, 1H), 6.92-7.00 (m, 4H), 4.62 (t, J=5.4 Hz, 1H), 3.70 (s, 3H), 2.98-3.14 (m, 3H), 2.79 (dd, J=9.3 and 15.0 Hz, 1H), 1.39 (q, J=7.5 Hz, 3H).

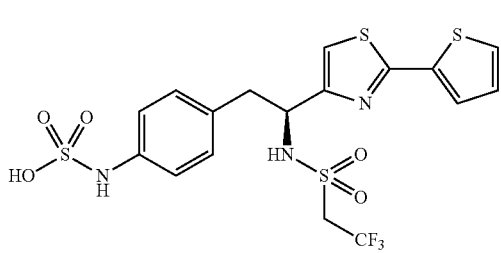 [SMILES: O=S(=O)(O)Nc1ccc(C[C@H](NS(=O)(=O)CC(F)(F)F)c2csc(-c3cccs3)n2)cc1]

4-{(S)-2-[2-(Thiophen-2-yl)thiazol-4-yl]-2-(2,2,2-trifluoroethylsulfonamido)-ethyl}phenylsulfamic acid: $^1$H NMR (CD$_3$OD): δ 7.62-7.56 (m, 2H), 7.22 (s, 1H), 7.16-7.06 (m, 5H), 4.84 (t, 1H, J=7.6 Hz), 3.71-3.62 (m, 2H), 3.32-3.03 (m, 2H).

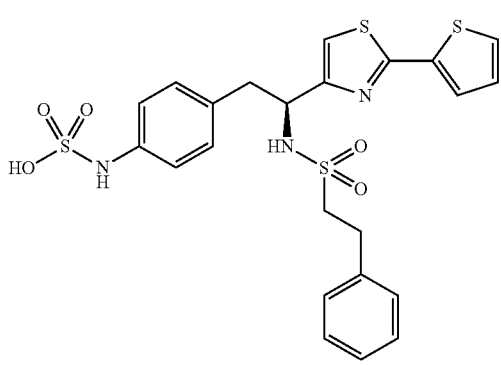 [SMILES: O=S(=O)(O)Nc1ccc(C[C@H](NS(=O)(=O)CCc2ccccc2)c2csc(-c3cccs3)n2)cc1]

{4-(S)-[2-(Phenylethanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 7.04-7.19 (m, 9H), 6.94-6.97 (m, 2H), 4.78 (t, J=7.8 Hz, 1H), 3.22-3.30 (m, 2H)), 3.11 (dd, J=13.5 and 7.8 Hz, 1H), 2.78-2.87 (m, 4H).

104

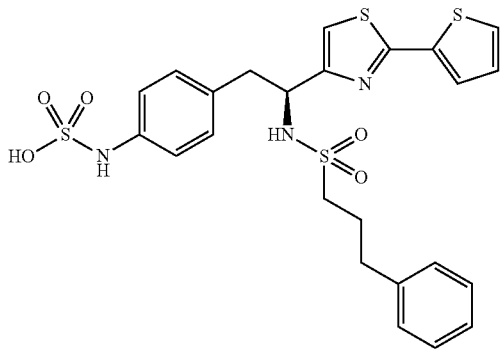 [SMILES: O=S(=O)(O)Nc1ccc(C[C@H](NS(=O)(=O)CCCc2ccccc2)c2csc(-c3cccs3)n2)cc1]

{4-(S)-[3-(Phenylpropanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 6.99-7.17 (m, 10H), 4.72 (t, J=7.8 Hz, 1H), 3.21 (dd, J=13.5 and 7.2 Hz, 1H), 3.02 (dd, J=13.5 and 7.2 Hz, 1H), 2.39-2.64 (m, 4H), 1.65-1.86 (m, 2H).

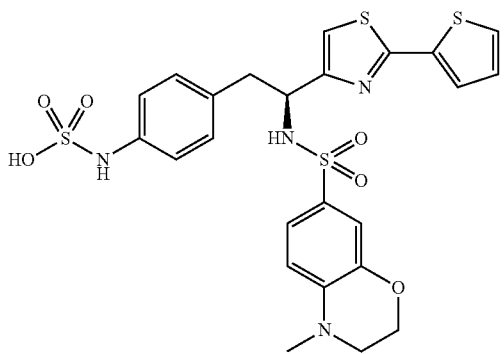 [SMILES: CN1CCOc2cc(S(=O)(=O)N[C@@H](Cc3ccc(NS(=O)(=O)O)cc3)c3csc(-c4cccs4)n3)ccc21]

(S)-{4-[2-(4-Methyl-3,4-dihydro-2H-benzo[1,4]oxazine-7-sulfonylamino)-2-(2-thiophen-2-ylthiazol-4-yl)ethyl]phenyl}sulfamic acid: $^1$H NMR (300 MHz, MeOH-d$_4$) δ 7.53 (d, J=5.1 Hz, 1H) 7.48 (d, J=5.1 Hz, 1H), 7.13-7.10 (m, 1H), 7.04 (d, J=8.4 Hz, 2H), 6.93-6.88 (m, 3H), 6.75 (d, J=8.1 Hz, 1H), 6.54 (d, J=8.1 Hz, 1H), 4.61 (t, J=7.5 Hz, 1H), 4.20-4.08 (m, 2H), 3.14-3.00 (m, 4H), 2.69 (s, 3H).

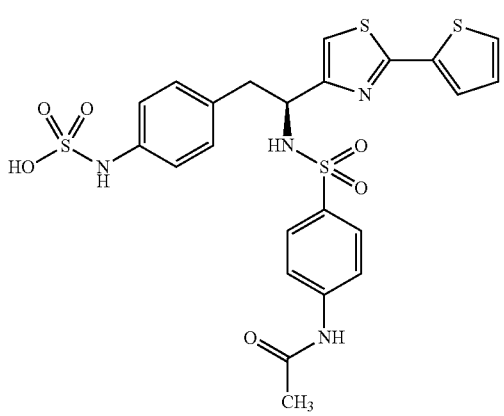 [SMILES: CC(=O)Nc1ccc(S(=O)(=O)N[C@@H](Cc2ccc(NS(=O)(=O)O)cc2)c2csc(-c3cccs3)n2)cc1]

4-{(S)-2-(4-acetamidophenylsulfonamido)-2-[2-(thiophen-2-yl)thiazol-4-yl]ethyl}phenylsulfamic acid: $^1$H NMR (CD$_3$OD): δ 7.67-7.52 (m, 6H), 7.24-7.23 (m, 1H), 7.12-7.09 (m, 3H), 7.02-6.99 (m, 2H), 4.70 (t, 1H, J=7.3 Hz), 3.25-3.00 (m, 2H), 2.24 (s, 3H).

The first aspect of Category IX of the present disclosure relates to compounds having the formula:

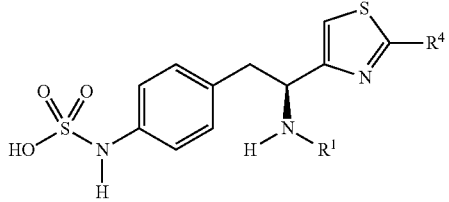

wherein R$^1$ is a substituted or unsubstituted heteroaryl and R$^4$ is C$_1$-C$_6$ linear, branched, or cyclic alkyl as further described herein below in Table XVII.

Compounds according to the first aspect of Category IX which comprise a substituted or unsubstituted thiazol-4-yl unit for R$^1$ can be prepared by the procedure outlined in Scheme XVII and described herein below in Example 18.

Scheme XVII

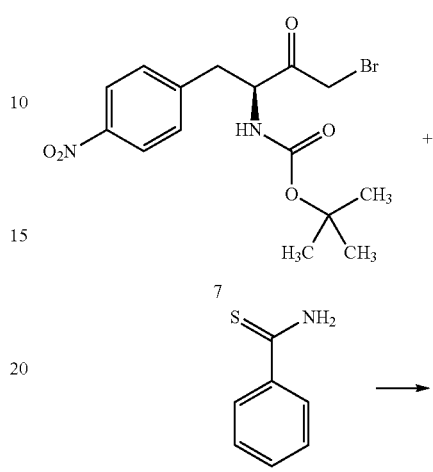

TABLE XVII

| No. | R$^4$ | R$^1$ |
|---|---|---|
| Q698 | —CH$_3$ | 4-(methoxycarbonyl)thiazol-5-yl |
| Q699 | —CH$_3$ | 4-[(2-methoxy-2-oxoethyl)carbamoyl]thiazol-5-yl |
| Q700 | —CH$_3$ | 5-[1-N-(2-methoxy-2-oxoethyl)-1-H-indol-3-yl]oxazol-2-yl |
| Q701 | —CH$_3$ | 5-(2-methoxyphenyl)oxazol-2-yl |
| Q702 | —CH$_3$ | 5-[(S)-1-(tert-butoxycarbonyl)-2-phenylethyl]oxazol-2-yl |
| Q703 | —CH$_3$ | 5-[4-(methylcarboxy)phenyl]oxazol-2-yl |
| Q704 | —CH$_3$ | 5-(3-methoxybenzyl)oxazol-2-yl |
| Q705 | —CH$_3$ | 5-(4-phenyl)oxazol-2-yl |
| Q706 | —CH$_3$ | 5-(2-methoxyphenyl)thiazol-2-yl |
| Q707 | —CH$_3$ | 5-(3-methoxyphenyl)thiazol-2-yl |
| Q708 | —CH$_3$ | 5-(4-fluorophenyl)thiazol-2-yl |
| Q709 | —CH$_3$ | 5-(2,4-difluorophenyl)thiazol-2-yl |
| Q710 | —CH$_3$ | 5-(3-methoxybenzyl)thiazol-2-yl |
| Q711 | —CH$_3$ | 4-(3-methoxyphenyl)thiazol-2-yl |
| Q712 | —CH$_3$ | 4-(4-fluorophenyl)thiazol-2-yl |
| Q713 | —CH$_2$CH$_3$ | 4-(methoxycarbonyl)thiazol-5-yl |
| Q714 | —CH$_2$CH$_3$ | 4-[(2-methoxy-2-oxoethyl)carbamoyl]thiazol-5-yl |
| Q715 | —CH$_2$CH$_3$ | 5-[1-N-(2-methoxy-2-oxoethyl)-1-H-indol-3-yl]oxazol-2-yl |
| Q716 | —CH$_2$CH$_3$ | 5-(2-methoxyphenyl)oxazol-2-yl |
| Q717 | —CH$_2$CH$_3$ | 5-[(S)-1-(tert-butoxycarbonyl)-2-phenylethyl]oxazol-2-yl |
| Q718 | —CH$_2$CH$_3$ | 5-[4-(methylcarboxy)phenyl]oxazol-2-yl |
| Q719 | —CH$_2$CH$_3$ | 5-(3-methoxybenzyl)oxazol-2-yl |
| Q720 | —CH$_2$CH$_3$ | 5-(4-phenyl)oxazol-2-yl |
| Q721 | —CH$_2$CH$_3$ | 5-(2-methoxyphenyl)thiazol-2-yl |
| Q722 | —CH$_2$CH$_3$ | 5-(3-methoxyphenyl)thiazol-2-yl |
| Q723 | —CH$_2$CH$_3$ | 5-(4-fluorophenyl)thiazol-2-yl |
| Q724 | —CH$_2$CH$_3$ | 5-(2,4-difluorophenyl)thiazol-2-yl |
| Q725 | —CH$_2$CH$_3$ | 5-(3-methoxybenzyl)thiazol-2-yl |
| Q726 | —CH$_2$CH$_3$ | 4-(3-methoxyphenyl)thiazol-2-yl |
| Q727 | —CH$_2$CH$_3$ | 4-(4-fluorophenyl)thiazol-2-yl |
| Q728 | cyclopropyl | 4-(methoxycarbonyl)thiazol-5-yl |
| Q729 | cyclopropyl | 4-[(2-methoxy-2-oxoethyl)carbamoyl]thiazol-5-yl |
| Q730 | cyclopropyl | 5-[1-N-(2-methoxy-2-oxoethyl)-1-H-indol-3-yl]oxazol-2-yl |
| Q731 | cyclopropyl | 5-(2-methoxyphenyl)oxazol-2-yl |
| Q732 | cyclopropyl | 5-[(S)-1-(tert-butoxycarbonyl)-2-phenylethyl]oxazol-2-yl |
| Q733 | cyclopropyl | 5-[4-(methylcarboxy)phenyl]oxazol-2-yl |
| Q734 | cyclopropyl | 5-(3-methoxybenzyl)oxazol-2-yl |
| Q735 | cyclopropyl | 5-(4-phenyl)oxazol-2-yl |
| Q736 | cyclopropyl | 5-(2-methoxyphenyl)thiazol-2-yl |
| Q737 | cyclopropyl | 5-(3-methoxyphenyl)thiazol-2-yl |
| Q738 | cyclopropyl | 5-(4-fluorophenyl)thiazol-2-yl |
| Q739 | cyclopropyl | 5-(2,4-difluorophenyl)thiazol-2-yl |
| Q740 | cyclopropyl | 5-(3-methoxybenzyl)thiazol-2-yl |
| Q741 | cyclopropyl | 4-(3-methoxyphenyl)thiazol-2-yl |
| Q742 | cyclopropyl | 4-(4-fluorophenyl)thiazol-2-yl |

-continued

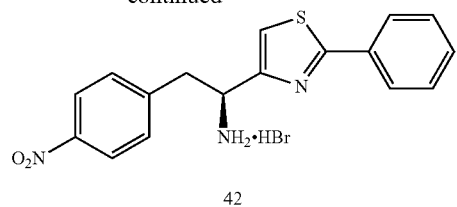

42

Reagents and conditions:
(a) CH$_3$CN, reflux; 24 hr.

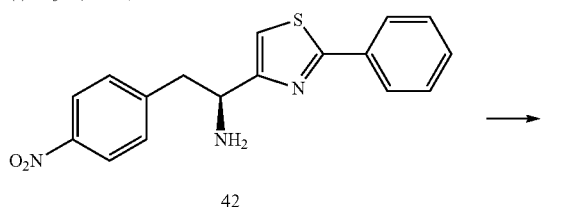

42

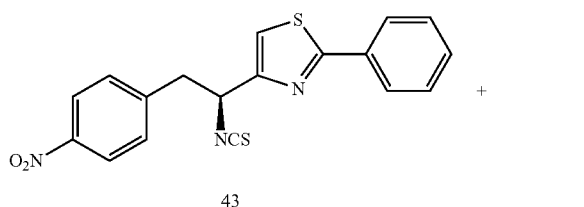

43

Reagents and conditions:
(b) thiophosgene, CaCO$_3$, CCl$_4$, H$_2$O; rt, 18 hr.

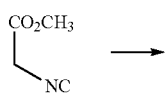

43

+

CO$_2$CH$_3$
|
NC

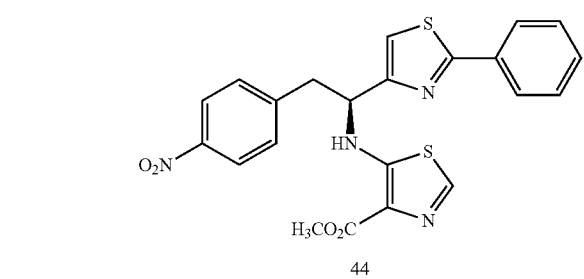

44

Reagents and conditions:
(c) KOtBu, THF; rt, 2 hr.

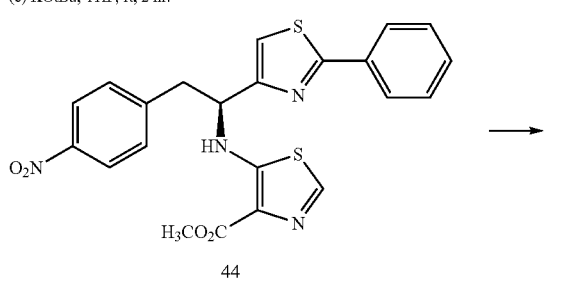

44

-continued

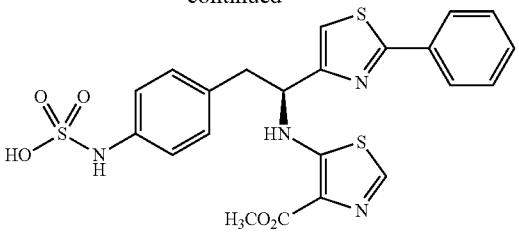

45

Reagents and conditions:
(d)(i) SnCl$_2$ — 2H$_2$O, EtOH; reflux, 4 hours (ii) SO$_3$-pyridine, NH$_4$OH.

EXAMPLE 18

(S)-4-(2-(2-Phenylthiazol-4-yl)2-(4-(methoxycarbonyl)thiazole-5-ylamino)ethyl)phenylsulfamic acid
(45)

Preparation of (S)-2-(4-nitrophenyl)-1-(2-phenylthiazol-4-yl)ethanamine hydrobromide salt (42): A mixture of (S)-tert-butyl 4-bromo-1-(4-nitrophenyl)-3-oxobutan-2-ylcarbamate, 7, (1.62 g, 4.17 mmol) and thiobenzamide (0.63 g, 4.60 mmol) in CH$_3$CN (5 mL) is refluxed for 24 hours. The reaction mixture is cooled to room temperature and diethyl ether (50 mL) is added to the solution. The precipitate which forms is collected by filtration. The solid is dried under vacuum to afford 1.2 g (67% yield) of the desired product. LC/MS ESI+ 326 (M+1).

Preparation of (S)-4-(1-isothiocyanato-2-(4-nitrophenyl)ethyl)-2-phenylthiazole (43): To a solution of (S)-2-(4-nitrophenyl)-1-(2-phenylthiazol-4-yl)ethanamine hydrobromide salt, 42, (726 mg, 1.79 mmol) and CaCO$_3$ (716 mg, 7.16 mmol) in H$_2$O (2 mL) is added CCl$_4$ (3 mL) followed by thiophosgene (0.28 mL, 3.58 mmol). The reaction is stirred at room temperature for 18 hours then diluted with CH$_2$Cl$_2$ and water. The layers are separated and the aqueous layer extracted with CH$_2$Cl$_2$. The combined organic layers are washed with brine, dried (Na$_2$SO$_4$) and concentrated in vacuo to a residue which is purified over silica (CH$_2$Cl$_2$) to afford 480 mg (73%) of the desired product as a yellow solid. $^1$H NMR (300 MHz, CDCl$_3$) δ 8.15 (d, J=8.7 Hz, 2H), 7.97-7.99 (m, 2H), 7.43-7.50 (m, 3H), 7.34 (d, J=8.7 Hz, 2H), 7.15 (d, J=0.9 Hz, 1H), 5.40-5.95 (m, 1H), 3.60 (dd, J=13.8 and 6.0 Hz, 1H), 3.46 (dd, J=13.8 and 6.0 Hz).

Preparation of (S)-methyl 5-[1-(2-phenylthiazol-4-yl)-2-(4-nitrophenyl)-ethylamino]thiazole-4-carboxylate (44): To a suspension of potassium tert-butoxide (89 mg, 0.75 mmol) in THF (3 mL) is added methyl isocyanoacetate (65 μL, 0.68 mmol) followed by (S)-2-phenyl-4-(1-isothiocyanato-2-(4-nitrophenyl)ethyl)thiazole, 43, (250 mg, 0.68 mmol). The reaction mixture is stirred at room temperature for 2 hours then poured into sat. NaHCO$_3$. The mixture is extracted with EtOAc (3×25 mL) and the combined organic layers are washed with brine and dried (Na$_2$SO$_4$) and concentrated in vacuo. The crude residue is purified over silica to afford 323 mg (~100% yield) of the desired product as a slightly yellow solid. $^1$H NMR (300 MHz, CDCl$_3$) δ 8.09-8.13 (m, 2H), 7.95-7.98 (m, 3H), 7.84 (d, J=1.2 Hz, 1H), 7.44-7.50 (m, 3H), 7.28-7.31 (m, 2H), 7.96 (d, J=0.6 Hz, 1H), 4.71-4.78 (m, 1H), 3.92 (s, 3H), 3.60 (dd, J=13.8 and 6.0 Hz, 1H), 3.45 (dd, J=13.8 and 6.0 Hz, 1H).

Preparation of (S)-4-(2-(2-phenylthiazol-4-yl)2-(4-(methoxycarbonyl)thiazole-5-ylamino)ethyl)phenylsulfamic acid (45): (S)-methyl 5-[1-(2-phenylthiazol-4-yl)-2-(4-nitrophenyl)-ethylamino]thiazole-4-carboxylate, 44, (323 mg, 0.68 mmol) and tin (II) chloride (612 mg, 2.72 mmol) are dissolved in EtOH and the solution is brought to reflux. The solvent is removed in vacuo and the resulting residue is dissolved in EtOAc. A saturated solution of NaHCO$_3$ is added and the solution is stirred 1 hour. The organic layer is separated and the aqueous layer extracted twice with EtOAc. The combined organic layers are dried (Na$_2$SO$_4$), filtered and concentrated to a residue which is dissolved in pyridine (10 mL) and treated with SO$_3$-pyridine (130 mg, 0.82 mmol). The reaction is stirred at room temperature for 5 minutes after which a 7% solution of NH$_4$OH is added. The mixture is then concentrated and the resulting residue is purified by reverse phase chromatography to afford 0.071 g of the desired product as the ammonium salt $^1$H NMR (300 MHz, MeOH-d$_4$) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

Compounds according to the first aspect of Category IX which comprise a substituted or unsubstituted thiazol-2-yl unit for R$^1$ can be prepared by the procedure outlined in Scheme XVIII and described herein below in Example 19. Intermediate 46 can be prepared according to Scheme II and Example 2 by substituting cyclopropane-carbothioic acid amide for thiophen-2-carbothioic acid amide.

Scheme XVIII

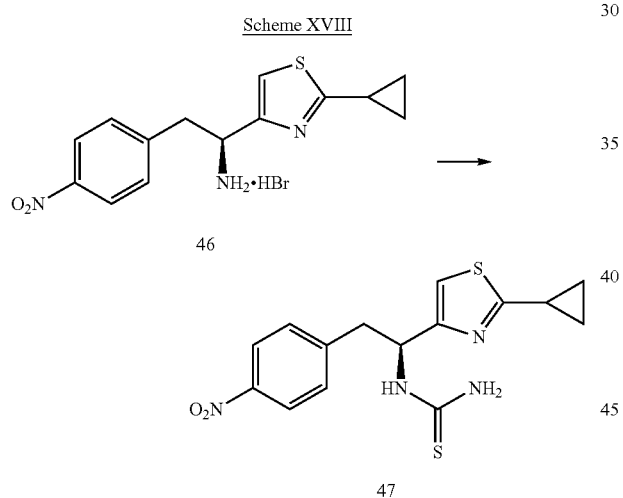

46

47

Reagents and conditions:
(a) thiophosgene, CaCO$_3$, CCl$_4$/H$_2$O; rt, 18 hr.

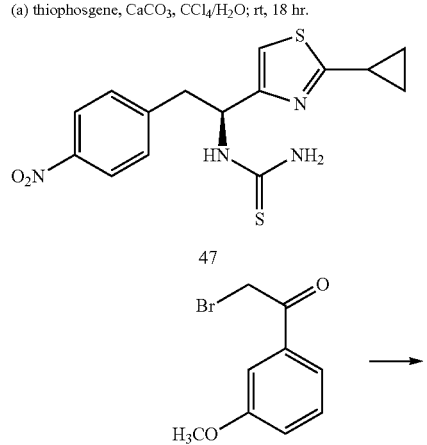

47

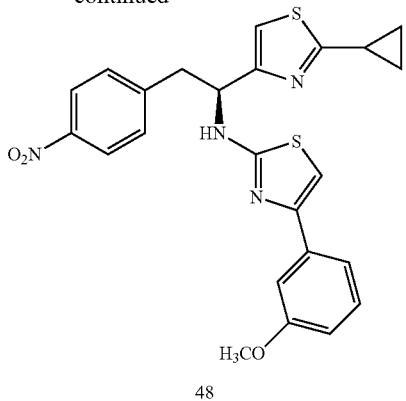

48

Reagents and conditions:
(b) CH$_3$CN, reflux, 24 hr.

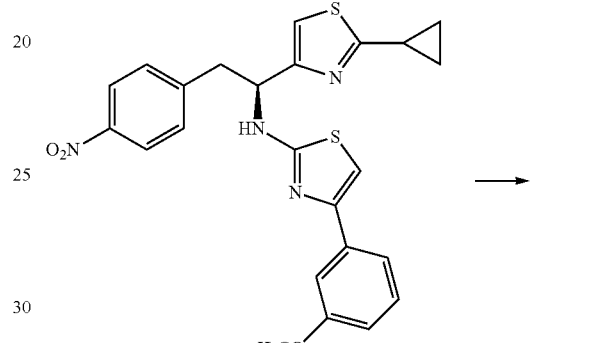

48

49

Reagents and conditions:
(c)(i) H$_2$:Pd/C, MeOH; (ii) SO$_3$-pyridine, NH$_4$OH.

EXAMPLE 19

4-{(S)-2-(2-Cyclopropylthiazol-4-yl)-2-[4-(3-methoxyphenyl)thiazol-2-ylamino]ethyl}phenylsulfamic acid (50)

Preparation of (S)-1-(1-(2-cyclopropylthiazol-4-yl)-2-(4-nitrophenyl)ethyl)-thiourea (47): To a solution of (S)-1-(2-cyclopropylthiazol-4-yl)-2-(4-nitrophenyl)ethan-amine hydrobromide hydrobromide salt, 32, (4.04 g, 10.9 mmol) and CaCO$_3$ (2.18 g, 21.8 mmol) in CCl$_4$/water (25 mL/20 mL) is added thiophosgene (1.5 g, 13.1 mmol). The reaction is stirred at room temperature for 18 hours then diluted with CH$_2$Cl$_2$ and water. The layers are separated and the aqueous layer extracted with CH$_2$Cl$_2$. The combined organic layers are washed with brine, dried (Na$_2$SO$_4$) and concentrated in vacuo to a residue which is subsequently treated with ammonia (0.5M in 1,4-dioxane, 120 mL) which is purified over silica to afford 2.90 g of the desired product as a red-brown solid. LC/MS ESI– 347 (M–1).

Preparation of (S)-4-(3-methoxybenzyl)-N-(1-(2-cyclopropylthiazol-4-yl)-2-(4-nitrophenyl)ethyl)thiazol-2-amine (48): (S)-1-(1-(2-Cyclopropylthiazol-4-yl)-2-(4-nitrophenyl)ethyl)-thiourea, 47, (350 mg, 1.00 mmol) and 2-bromo-3'-methoxy-acetophenone (253 mg, 1.10 mmol) are combined in 3 mL CH$_3$CN and heated to reflux for 24 hours. The mixture is concentrated and chromatographed to afford 0.172 g of the product as a yellow solid. LC/MS ESI+ 479 (M+1).

Preparation of 4-{(S)-2-(2-cyclopropylthiazol-4-yl)-2-[4-(3-methoxyphenyl)-thiazol-2-ylamino] ethyl}phenylsulfamic acid (49): (S)-4-(3-methoxybenzyl)-N-(1-(2-cyclopropylthiazol-4-yl)-2-(4-nitrophenyl)ethyl) thiazol-2-amine, 48, (0.172 g) is dissolved in 10 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 5 mL pyridine and treated with SO$_3$-pyridine (114 mg). The reaction is stirred at room temperature for 5 minutes after which 10 mL of a 7% solution of NH$_4$OH is added. The mixture is then concentrated and the resulting residue is purified by reverse-phase chromatography to afford 0.033 g of the desired product as the ammonium salt. $^1$H NMR (CD$_3$OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

The following are non-limiting examples of compounds encompassed within the first aspect of Category IX.

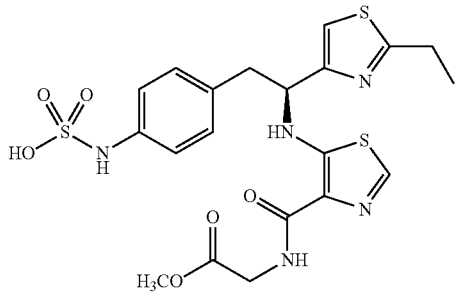 [SMILES: CCc1nc([C@H](Cc2ccc(NS(=O)(=O)O)cc2)Nc2scnc2C(=O)NCC(=O)OC)cs1]

(S)-4-(2-(4-((2-Methoxy-2-oxoethyl)carbamoyl)thiazole-5-ylamino)2-(2-ethylthiazole-4-yl)ethyl)phenylsulfamic acid: $^1$H NMR (300 MHz, MeOH-d$_4$) δ 7.91 (s, 1H), 7.08-7.10 (m, 3H), 6.99 (d, J=8.7 Hz, 2H), 4.58 (t, J=6.9 Hz, 1H), 4.11 (d, J=2.7 Hz, 2H), 3.78 (s, 3H), 3.14-3.28 (m, 2H), 3.06 (q, J=7.5 Hz, 2H), 1.41 (t, J=7.5 Hz, 3H).

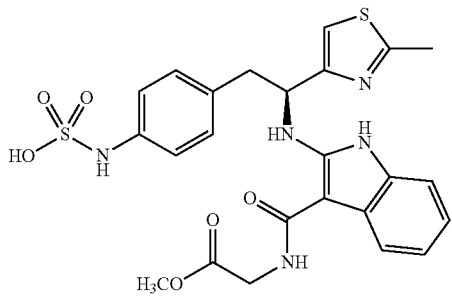 [SMILES: COC(=O)CNC(=O)c1c(N[C@@H](Cc2ccc(NS(=O)(=O)O)cc2)c2csc(C)n2)[nH]c2ccccc12]

(S)-4-(2-{5-[1-N-(2-Methoxy-2-oxoethylcarbamoyl)-1-H-indol-3-yl]oxazol-2-ylamino}-2-(2-methylthiazol-4-yl) ethyl)phenylsulfamic acid: $^1$H NMR (300 MHz, MeOH-d$_4$) δ 7.63 (d, J=7.8 Hz, 1H), 7.37 (s, 1H), 7.18-7.29 (m, 4H), 7.02-7.16 (m, 4H), 6.85 (s, 1H), 5.04-5.09 (m, 1H), 4.85 (s, 3H), 3.27 (dd, J=13.5 and 8.1 Hz, 1H), 3.10 (m, J=13.5 and 8.1 Hz, 1H), 2.69 (s, 3H).

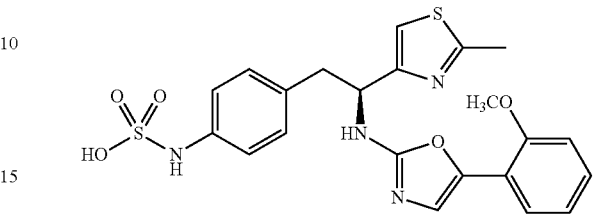

4-((S)-2-(5-(2-Methoxyphenyl)oxazol-2-ylamino)-2-(2-methylthiazol-4-yl)ethyl)phenylsulfamic acid: $^1$H NMR (300 MHz, MeOH-d$_4$) δ 7.52 (dd, J=7.5 and 1.2 Hz, 1H), 6.95-7.24 (m, 10H), 5.04-5.09 (m, 1H), 3.92 (s, 3H), 3.26 (dd, J=13.8 and 8.4 Hz, 1H), 3.10 (dd, J=13.8 and 8.4 Hz, 1H), 2.72 (s, 3H).

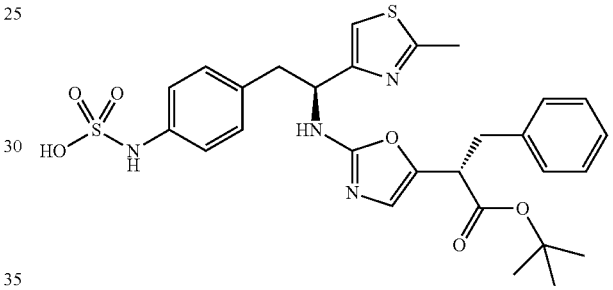

4-((S)-2-(5-((S)-1-(tert-Butoxycarbonyl)-2-phenylethyl) oxazole-2-ylamino)-2-(2-methylthiazole-4-yl)ethyl)phenylsulfamic acid: $^1$H NMR (300 MHz, MeOH-d$_4$) δ 7.03-7.27 (m, 10 H), 6.50 (s, 1H), 4.95-5.00 (m, 1H), 4.76 (t, J=6.9 Hz, 1H), 3.22 (dd, J=14.1 and 6.9 Hz, 1H), 3.00-3.10 (m, 2H), 2.90 (dd, J=14.1 and 6.9 Hz, 1H), 2.72 (s, 3H), 1.37 (s, 9H).

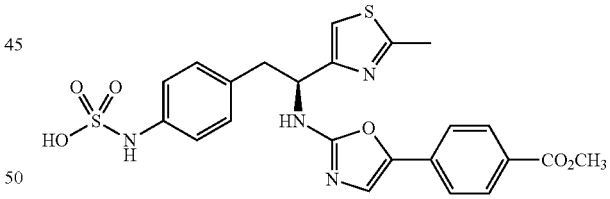

(S)-{4-{2-[5-(4-Methoxycarbonyl)phenyl]oxazol-2-ylamino}-2-(2-methylthiazol-4-yl)ethyl}phenylsulfamic acid: $^1$H NMR (300 MHz, MeOH-d$_4$) δ 7.99 (d, J=7.5 Hz, 2H), 7.56-7.59 (m, 2H), 7.23-7.24 (m, 1H), 7.08-7.14 (m, 4H), 6.83 (d, J=10.2 Hz, 1H), 5.08 (t, J=6.0 Hz, 1H), 3.91 (s, 3H), 3.25-3.35 (m, 1H), 3.09-3.13 (m, 1H), 2.73 (s, 3H).

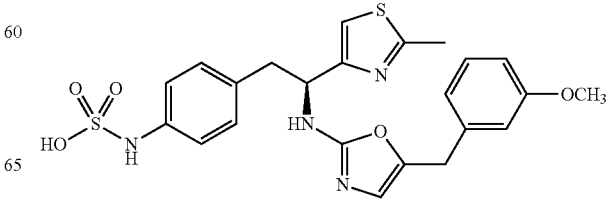

(S)-4-(2-(5-(3-Methoxybenzyl)oxazole-2-ylamino)-2-(2-methylthiazole-4-yl)ethyl)phenylsulfamic acid: $^1$H NMR (300 MHz, MeOH-d$_4$) δ 7.03-7.28 (m, 8H), 6.79-6.83 (m, 1H), 5.70 (s, 1H), 4.99-5.06 (m, 2H), 4.41 (d, J=2.1 Hz, 2H), 3.80 (s, 3H), 3.27-3.37 (m, 1H), 3.03-3.15 (m, 1H), 2.71 (s, 3H).

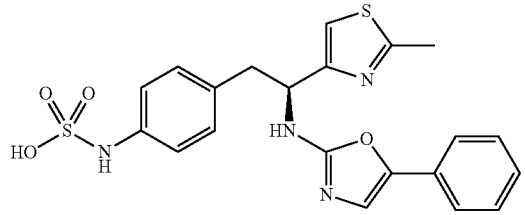 [SMILES: Cc1nc([C@H](Cc2ccc(NS(=O)(=O)O)cc2)Nc2ncc(-c3ccccc3)o2)cs1]

(S)-4-(2-(2-Methylthiazole-4-yl)2-(5-phenyloxazole-2-ylamino)ethyl)phenyl-sulfamic acid: $^1$H NMR (300 MHz, MeOH-d$_4$) δ 7.45 (d, J=8.7 Hz, 2H), 7.33 (t, J=7.8 Hz, 2H), 7.18-7.22 (m, 1H), 7.10-7.14 (m, 6H), 7.04 (s, 1H), 5.04-5.09 (m, 1H), 3.26 (dd, J=13.8 and 6.3 Hz, 1H), 3.10 (dd, J=13.8 and 6.3 Hz, 1H), 2.70 (s, 3H).

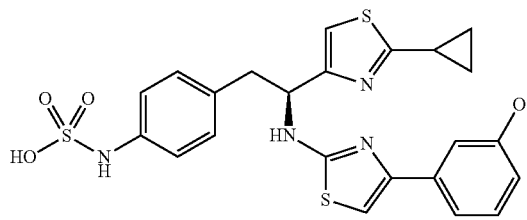

4-((S)-2-(2-Cyclopropylthiazol-4-yl)-2-(4-(3-methoxyphenyl)thiazol-2-ylamino)-ethyl)phenylsulfamic acid: $^1$H NMR (CD$_3$OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

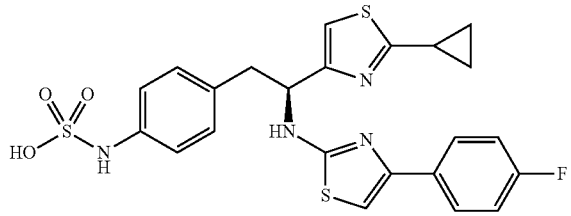 [SMILES: O=S(=O)(O)Nc1ccc(C[C@H](Nc2nc(-c3ccc(F)cc3)cs2)c2csc(C3CC3)n2)cc1]

(S)-4-(2-(2-cyclopropylthiazol-4-yl)-2-(4-(4-fluorophenyl)thiazol-2-ylamino)ethyl)-phenylsulfamic acid: $^1$H NMR (CD$_3$OD): δ 7.79-7.74 (m, 2H), 7.14-7.03 (m, 7H), 7.21 (s, 1H), 6.79 (s, 1H), 5.08 (t, 1H, J=6.6 Hz), 3.29-3.12 (m, 2H), 2.40 (q, 2.40, J=5.1 Hz), 1.23-1.18 (m, 2H), 1.08-1.02 (m, 2H).

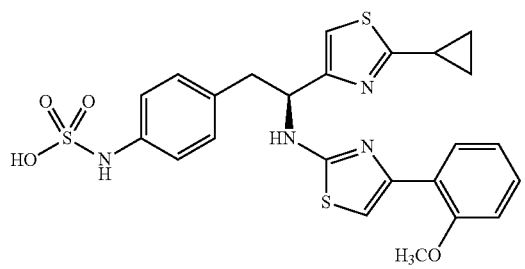 [SMILES: COc1ccccc1-c1csc(N[C@@H](Cc2ccc(NS(=O)(=O)O)cc2)c2csc(C3CC3)n2)n1]

4-((S)-2-(2-cyclopropylthiazol-4-yl)-2-(4-(2-methoxyphenyl)thiazol-2-ylamino)-ethyl)phenylsulfamic acid: $^1$H NMR (CD$_3$OD): δ 7.89-7.87 (d, 1H, J=7.6 Hz), 7.28 (t, 1H, J=7.0 Hz), 7.10-6.96 (m, 8H), 5.03 (t, 1H, J=6.9 Hz), 3.90 (s, 1H), 3.19 (q, 2H, J=6.6 Hz), 2.38 (q, 1H, J=4.8 Hz), 1.21-1.14 (m, 2H), 1.06-1.00 (m, 2H).

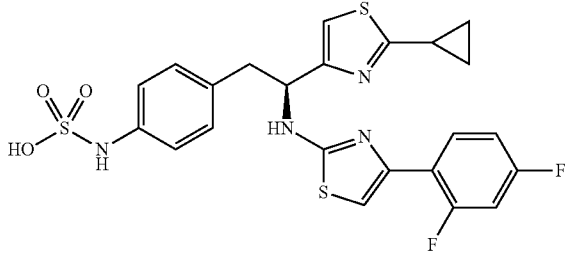 [SMILES: O=S(=O)(O)Nc1ccc(C[C@H](Nc2nc(-c3ccc(F)cc3F)cs2)c2csc(C3CC3)n2)cc1]

4-((S)-2-(2-cyclopropylthiazol-4-yl)-2-(4-(2,4-difluorophenyl)thiazol-2-ylamino)-ethyl)phenylsulfamic acid: $^1$H NMR (CD$_3$OD): δ 8.06-8.02 (q, 2H, J=6.9 Hz), 7.12-6.95 (m, 7H), 6.88 (s, 1H), 5.11 (t, 1H, J=6.9 Hz), 3.22-3.15 (m, 2H), 2.38 (q, 1H, J=4.8 Hz), 1.22-1.15 (m, 2H), 1.06-1.02 (m, 2H).

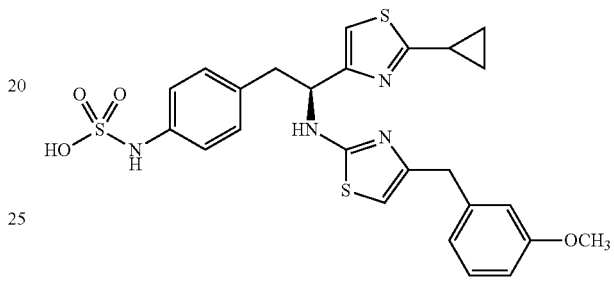

(S)-4-(2-(4-(3-methoxybenzyl)thiazol-2-ylamino)-2-(2-cyclopropylthiazol-4-yl)ethyl)phenylsulfamic acid: $^1$H NMR (CD$_3$OD): δ 7.22-7.17 (m, 3H), 7.09-6.97 (m, 5H), 6.78-6.66 (m, 3H), 3.77 (s, 2H), 3.75 (s, 3H), 3.20-3.07 (m, 2H), 2.35 (q, 1H, J=4.8 Hz), 1.19-1.13 (m, 2H), 1.03-1.00 (m, 2H).

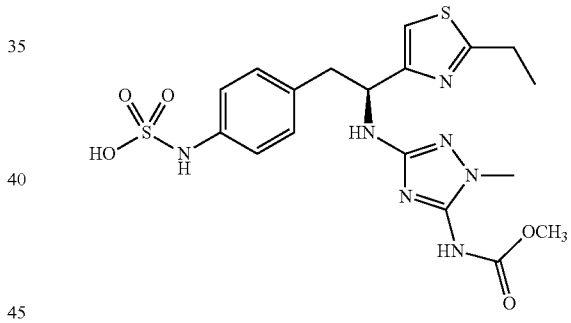

(S)-{5-[1-(2-Ethylthiazol-4-yl)-2-(4-sulfoaminophenyl)ethylamino]-2-methyl-2H-[1,2,4]triazole-3-yl}carbamic acid methyl ester: $^1$H NMR (300 MHz, MeOH-d$_4$) δ 6.97-7.08 (m, 5H), 3.71 (s, 3H), 3.51 (s, 3H), 3.15 (dd, J=13.5 and 6.3 Hz, 1H), 3.02-3.07 (m, 3H), 1.40 (t, J=6.6 Hz, 3H).

The second aspect of Category V of the present disclosure relates to compounds having the formula:

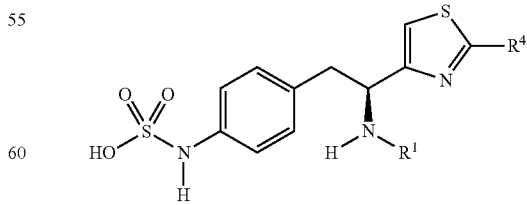

wherein R$^1$ is a substituted or unsubstituted heteroaryl and R$^4$ is substituted or unsubstituted phenyl and substituted or unsubstituted heteroaryl as further described herein below in Table XVIII.

TABLE XVIII

| No. | R⁴ | R¹ |
|---|---|---|
| R743 | phenyl | 4-(methoxycarbonyl)thiazol-5-yl |
| R744 | phenyl | 4-[(2-methoxy-2-oxoethyl)carbamoyl]thiazol-5-yl |
| R745 | phenyl | 5-[1-N-(2-methoxy-2-oxoethyl)-1-H-indol-3-yl]oxazol-2-yl |
| R746 | phenyl | 5-(2-methoxyphenyl)oxazol-2-yl |
| R747 | phenyl | 5-[(S)-1-(tert-butoxycarbonyl)-2-phenylethyl]oxazol-2-yl |
| R748 | phenyl | 5-[4-(methylcarboxy)phenyl]oxazol-2-yl |
| R749 | phenyl | 5-(3-methoxybenzyl)oxazol-2-yl |
| R750 | phenyl | 5-(4-phenyl)oxazol-2-yl |
| R751 | phenyl | 5-(2-methoxyphenyl)thiazol-2-yl |
| R752 | phenyl | 5-(3-methoxyphenyl)thiazol-2-yl |
| R753 | phenyl | 5-(4-fluorophenyl)thiazol-2-yl |
| R754 | phenyl | 5-(2,4-difluorophenyl)thiazol-2-yl |
| R755 | phenyl | 5-(3-methoxybenzyl)thiazol-2-yl |
| R756 | phenyl | 4-(3-methoxyphenyl)thiazol-2-yl |
| R757 | phenyl | 4-(4-fluorophenyl)thiazol-2-yl |
| R758 | thiophen-2-yl | 4-(methoxycarbonyl)thiazol-5-yl |
| R759 | thiophen-2-yl | 4-[(2-methoxy-2-oxoethyl)carbamoyl]thiazol-5-yl |
| R760 | thiophen-2-yl | 5-[1-N-(2-methoxy-2-oxoethyl)-1-H-indol-3-yl]oxazol-2-yl |
| R761 | thiophen-2-yl | 5-(2-methoxyphenyl)oxazol-2-yl |
| R762 | thiophen-2-yl | 5-[(S)-1-(tert-butoxycarbonyl)-2-phenylethyl]oxazol-2-yl |
| R763 | thiophen-2-yl | 5-[4-(methylcarboxy)phenyl]oxazol-2-yl |
| R764 | thiophen-2-yl | 5-(3-methoxybenzyl)oxazol-2-yl |
| R765 | thiophen-2-yl | 5-(4-phenyl)oxazol-2-yl |
| R766 | thiophen-2-yl | 5-(2-methoxyphenyl)thiazol-2-yl |
| R767 | thiophen-2-yl | 5-(3-methoxyphenyl)thiazol-2-yl |
| R768 | thiophen-2-yl | 5-(4-fluorophenyl)thiazol-2-yl |
| R769 | thiophen-2-yl | 5-(2,4-difluorophenyl)thiazol-2-yl |
| R770 | thiophen-2-yl | 5-(3-methoxybenzyl)thiazol-2-yl |
| R771 | thiophen-2-yl | 4-(3-methoxyphenyl)thiazol-2-yl |
| R772 | thiophen-2-yl | 4-(4-fluorophenyl)thiazol-2-yl |
| R773 | cyclopropyl | 4-(methoxycarbonyl)thiazol-5-yl |
| R774 | cyclopropyl | 4-[(2-methoxy-2-oxoethyl)carbamoyl]thiazol-5-yl |
| R775 | cyclopropyl | 5-[1-N-(2-methoxy-2-oxoethyl)-1-H-indol-3-yl]oxazol-2-yl |
| R776 | cyclopropyl | 5-(2-methoxyphenyl)oxazol-2-yl |
| R777 | cyclopropyl | 5-[(S)-1-(tert-butoxycarbonyl)-2-phenylethyl]oxazol-2-yl |
| R778 | cyclopropyl | 5-[4-(methylcarboxy)phenyl]oxazol-2-yl |
| R779 | cyclopropyl | 5-(3-methoxybenzyl)oxazol-2-yl |
| R780 | cyclopropyl | 5-(4-phenyl)oxazol-2-yl |
| R781 | cyclopropyl | 5-(2-methoxyphenyl)thiazol-2-yl |
| R782 | cyclopropyl | 5-(3-methoxyphenyl)thiazol-2-yl |
| R783 | cyclopropyl | 5-(4-fluorophenyl)thiazol-2-yl |
| R784 | cyclopropyl | 5-(2,4-difluorophenyl)thiazol-2-yl |
| R785 | cyclopropyl | 5-(3-methoxybenzyl)thiazol-2-yl |
| R786 | cyclopropyl | 4-(3-methoxyphenyl)thiazol-2-yl |
| R787 | cyclopropyl | 4-(4-fluorophenyl)thiazol-2-yl |

Compounds according to the second aspect of Category IX which comprise a substituted or unsubstituted thiazol-4-yl unit for R¹ can be prepared by the procedure outlined in Schemes XIX, XX, and XXI and described herein below in Examples 20, 21, and 22.

Scheme XIX

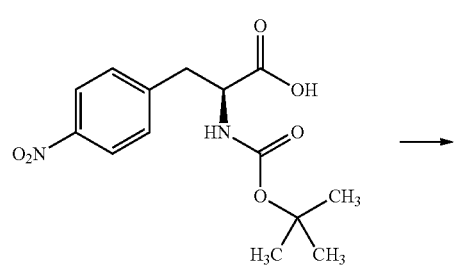

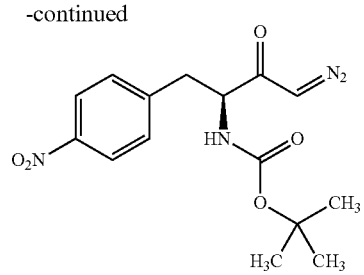

Reagents and conditions:
(a)(i) (iso-butyl)OCOCl, Et₃N, THF; 0° C., 20 min.
(ii) CH₂N₂; 0° C. to room temp for 3 hours.

117
-continued

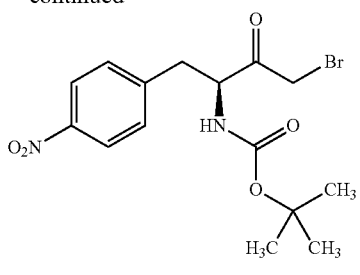
51

Reagents and conditions:
(b) 48% HBr, THF; 0° C., 1.5 hr.

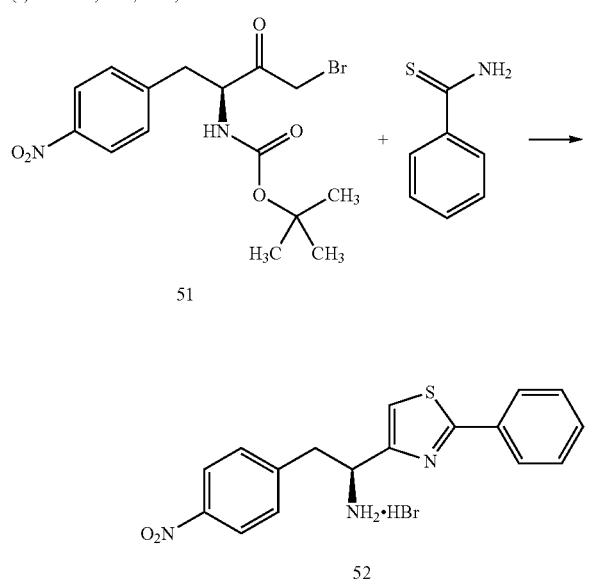
51

Reagents and conditions:
(c) CH₃CN; reflux 2 hr.

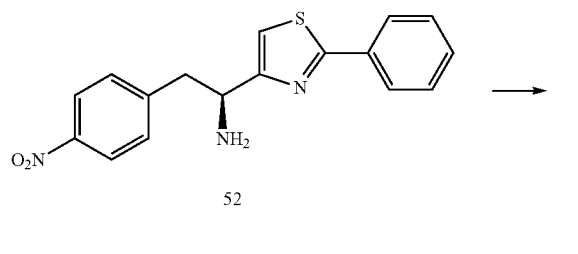
52

Reagents and conditions:
(d) thiophosgene, CaCO₃, CCl₄, H₂O; rt, 18 hr.

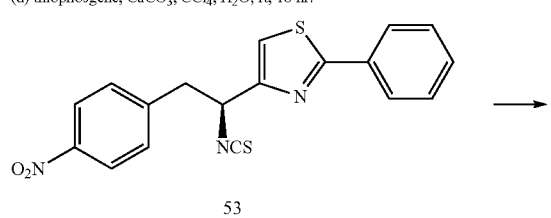
53

118
-continued

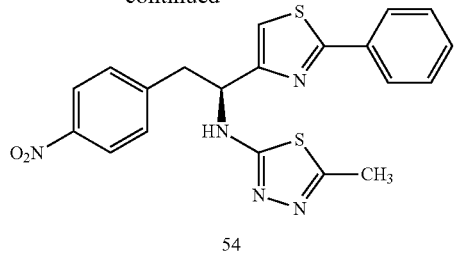
54

Reagents and conditions:
(e)(i) CH₃C(O)NHNH₂, EtOH; reflux, 2 hr.
(ii) POCl₃, rt 18 hr; 50° C. 2 hr.

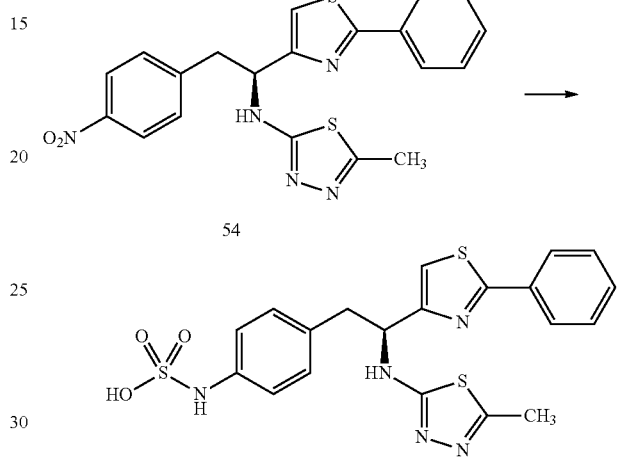
55

Reagents and conditions: (f)(i) H₂:Pd/C, MeOH; (ii) SO₃-pyridine, NH₄OH.

EXAMPLE 20

(S)-4-(2-(5-Methyl-1,3,4-thiadiazol-2-ylamino)-2-(2-phenylthiazol-4-yl)ethyl)phenylsulfamic acid (55)

Preparation of [3-diazo-1-(4-nitrobenzyl)-2-oxo-propyl]-carbamic acid tert-butyl ester (50): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 minutes then filtered. The filtrate is treated with an ether solution of diazomethane (~16 mmol) at 0° C. The reaction mixture is stirred at room temperature for 3 hours and concentrated. The residue is dissolved in EtOAc and washed successively with water and brine, dried (Na₂SO₄), filtered and concentrated in vacuo. The resulting residue is purified over silica (hexane/EtOAc 2:1) to afford 1.1 g (82% yield) of the desired product as a slightly yellow solid. $^1$H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of [3-bromo-1-(4-nitro-benzyl)-2-oxo-propyl]-carbamic acid tert-butyl ester (51): To a 0° C. solution of [3-diazo-1-(4-nitrobenzyl)-2-oxo-propyl]-carbamic acid tert-butyl ester, 50, (0.350 g, 1.04 mmol) in THF (5 mL) is added dropwise 48% aq. HBr (0.14 mL, 1.25 mmol). The reaction mixture is stirred at 0° C. for 1.5 hours and quenched at 0° C. with saturated aqueous Na₂CO₃. The mixture is extracted with EtOAc (3×25 mL) and the combined organic extracts are washed with brine, dried (Na$_2$SO$_4$), filtered and concentrated in vacuo to afford 0.400 g of the desired product that is used in the next step without further purification. $^1$H NMR (300 MHz, CDCl$_3$) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of (S)-2-(4-nitrophenyl)-1-(2-phenylthiazol-4-yl)ethanamine hydrobromide salt (52): A mixture of [3-bromo-1-(4-nitro-benzyl)-2-oxo-propyl]-carbamic acid tert-butyl ester, 51, (1.62 g, 4.17 mmol) and benzothioamide (0.630 g, 4.59 mmol), in CH$_3$CN (5 mL) is refluxed for 24 hours. The reaction mixture is cooled to room temperature and diethyl ether (50 mL) is added to the solution and the precipitate that forms is collected by filtration. The solid is dried under vacuum to afford 1.059 g (63%) of the desired product. ESI+ MS 326 (M+1).

Preparation of (S)-4-[1-isothiocyanato-2-(4-nitrophenyl)-ethyl]-2-phenylthiazole (53): To a solution of (S)-2-(4-nitrophenyl)-1-(2-phenylthiazol-4-yl)ethanamine hydrobromide salt, 52, (2.03 g, 5 mmol) and CaCO$_3$ (1 g, 10 mmol) in CCl$_4$/water (10:7.5 mL) is added thiophosgene (0.46 mL, 6 mmol). The reaction is stirred at room temperature for 18 hours then diluted with CH$_2$Cl$_2$ and water. The layers are separated and the aqueous layer extracted with CH$_2$Cl$_2$. The combined organic layers are washed with brine, dried (Na$_2$SO$_4$) and concentrated in vacuo to a residue that is purified over silica (CH$_2$Cl$_2$) to afford 1.71 g (93% yield) of the desired product. ESI+ MS 368 (M+1).

Preparation of (S)-5-methyl-N-[2-(4-nitrophenyl)-1-(2-phenylthiazol-4-yl)ethyl]-1,3,4-thiadiazol-2-amine (54): A solution of (S)-4-[1-isothiocyanato-2-(4-nitrophenyl)-ethyl]-2-phenylthiazole, 53, (332 mg, 0.876 mmol) and acetic hydrazide (65 mg, 0.876 mmol) in EtOH (5 mL) is refluxed for 2 hours. The solvent is removed under reduced pressure, the residue is dissolved in POCl$_3$ (3 mL) and the resulting solution is stirred at room temperature for 18 hours after which the solution is heated to 50° C. for 2 hours. The solvent is removed in vacuo and the residue is dissolved in EtOAc (40 mL) and the resulting solution is treated with 1N NaOH until the pH remains approximately 8. The solution is extracted with EtOAc. The combined aqueous layers are washed with EtOAc, the organic layers combined, washed with brine, dried over MgSO$_4$, filtered, and concentrated in vacuo to afford 0.345 g (93% yield) of the desired product as a yellow solid. $^1$H NMR (CDCl$_3$) 8.09 (d, J=8.4 Hz, 2H), 7.91 (m, 2H), 7.46 (m, 4H), 7.44 (s, 1H), 5.23 (m, 1H), 3.59 (m, 2H), 2.49 (s, 3H). ESI+ MS 424 (M+1).

Preparation of (S)-4-[2-(5-methyl-1,3,4-thiadiazol-2-ylamino)-2-(2-phenylthiazol-4-yl)ethyl]phenylsulfamic acid (55): (S)-5-Methyl-N-[2-(4-nitrophenyl)-1-(2-phenylthiazol-4-yl)ethyl]-1,3,4-thiadiazol-2-amine, 54, (0.404 g, 0.954 mmol) is dissolved in MeOH (5 mL). Pd/C (50 mg, 10% w/w) is added and the mixture is stirred under a hydrogen atmosphere until the reaction is judged to be complete. The reaction mixture is filtered through a bed of CELITE™ and the solvent removed under reduced pressure. The crude product is dissolved in pyridine (4 mL) and treated with SO$_3$-pyridine (0.304 g, 1.91 mmol). The reaction is stirred at room temperature for 5 minutes after which a 7% solution of NH$_4$OH (50 mL) is added. The mixture is then concentrated and the resulting residue is purified by reverse phase preparative HPLC to afford 0.052 g (11% yield) of the desired product as the ammonium salt. $^1$H NMR (CD$_3$OD): δ 8.00-7.97 (m, 2H), 7.51-7.47 (m, 3H), 7.23 (s, 1H), 7.11-7.04 (q, 4H, J=9.0 Hz), 5.18 (t, 1H, J=7.2 Hz), 3.34-3.22 (m, 2H), 2.50 (s, 3H). ESI– MS 472 (M–1).

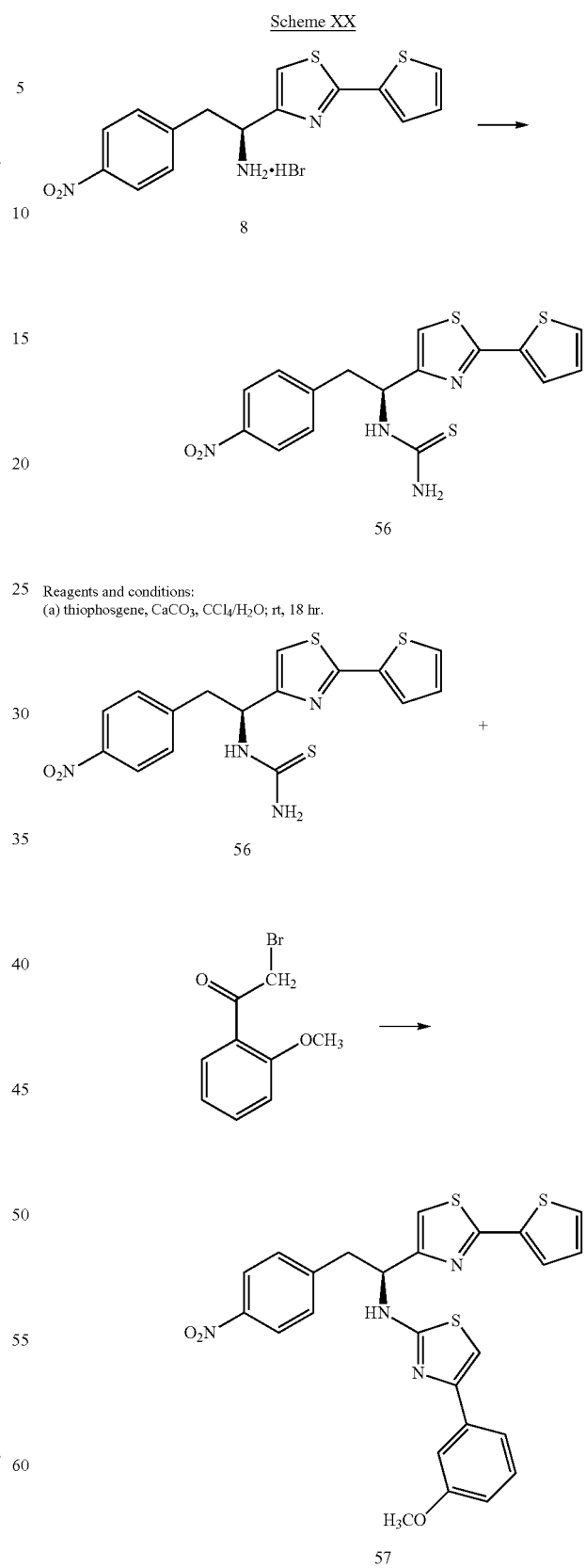

Scheme XX

Reagents and conditions:
(a) thiophosgene, CaCO$_3$, CCl$_4$/H$_2$O; rt, 18 hr.

Reagents and conditions:
(b) CH$_3$CN, reflux, 5 hours

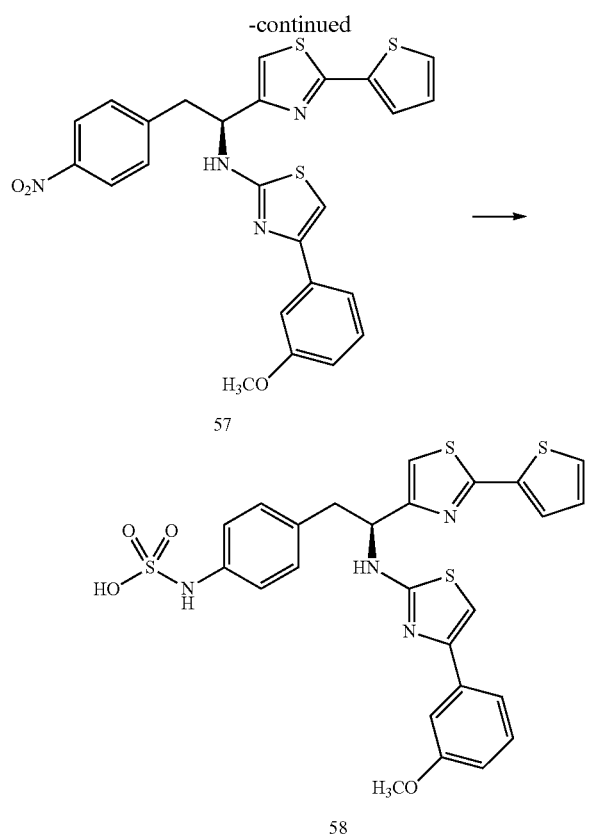

Reagents and conditions:
(c)(i) H₂:Pd/C, MeOH; (ii) SO₃-pyridine, NH₄OH; rt, 18 hr.

EXAMPLE 21

4-{(S)-2-[4-(2-Methoxyphenyl)thiazol-2-ylamino)-2-[2-(thiophen-2-yl)thiazol-4-yl]ethyl}phenylsulfamic acid (58)

Preparation of (S)-1-[1-(thiophen-2-ylthiazol-4-yl)-2-(4-nitrophenyl)ethyl]-thiourea (56): To a solution of (S)-2-(4-nitrophenyl)-1-(thiophen-2-ylthiazol-4-yl)ethanamine hydrobromide salt, 8, (1.23 g, 2.98 mmol) and CaCO₃ (0.597 g, 5.96 mmol) in CCl₄/water (10 mL/5 mL) is added thiophosgene (0.412 g, 3.58 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is subsequently treated with ammonia (0.5M in 1,4-dioxane, 29.4 mL, 14.7 mmol) which is purified over silica to afford 0.490 g of the desired product as a red-brown solid. ESI+ MS 399 (M+1).

Preparation of 4-(2-methoxyphenyl)-N-{(S)-2-(4-nitrophenyl)-1-[2-(thiophen-2-yl)thiazol-4-yl]ethyl}thiazol-2-amine (57): (S)-1-[1-(thiophen-2-ylthiazol-4-yl)-2-(4-nitrophenyl)ethyl]-thiourea, 56, (265 mg, 0.679 mmol) is treated with bromo-2'-methoxyacetophenone (171 mg, 0.746 mmol) to afford 0.221 g of the product as a yellow solid. ESI+ MS 521 (M+1).

Preparation on 4-{(S)-2-[4-(2-methoxyphenyl)thiazol-2-ylamino)-2-[2-(thiophen-2-yl)thiazol-4-yl]ethyl}phenylsulfamic acid (58): 4-(2-methoxyphenyl)-N-{(S)-2-(4-nitrophenyl)-1-[2-(thiophen-2-yl)thiazol-4-yl] ethyl}thiazol-2-amine, 57, (0.229 g) is dissolved in 12 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 6 mL pyridine and treated with SO₃-pyridine (140 mg). The reaction is stirred at room temperature for 5 minutes after which 10 mL of a 7% solution of NH₄OH is added. The mixture is then concentrated and the resulting residue is purified by reverse-phase chromatography to afford 0.033 g of the desired product as the ammonium salt. ¹H NMR (CD₃OD): δ 7.96-7.93 (m, 1H), 7.60-7.55 (m, 2H), 7.29-7.23 (m, 1H), 7.18-6.95 (m, 9H), 5.15 (t, 1H, J=6.9 Hz), 3.90 (s, 3H), 3.35-3.24 (m, 2H).

Compounds according to the second aspect of Category IX which comprise a substituted or unsubstituted oxazol-2-yl unit for R¹ can be prepared by the procedure outlined in Scheme XXI and described herein below in Example 22. Intermediate 39 can be prepared according to Scheme XVII and Example 18.

Scheme XXI

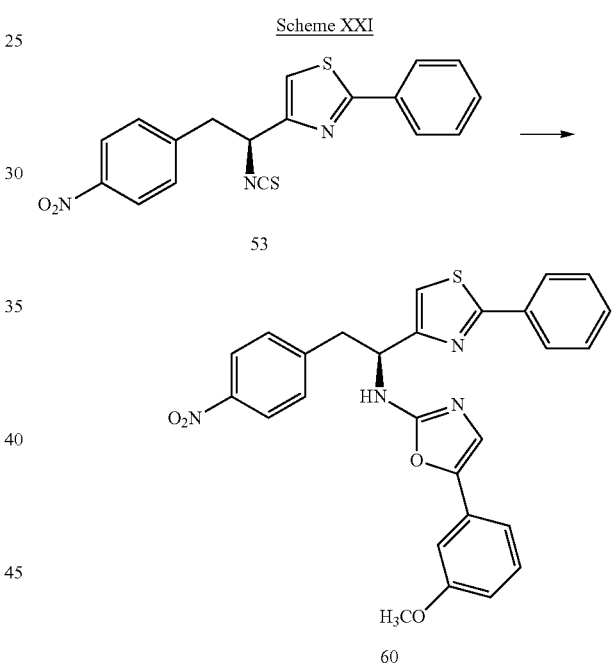

Reagents and conditions:
(a) 1-azido-1-(3-methoxyphenyl)ethanone, PPh₃, dioxane, 90° C. 20 minutes.

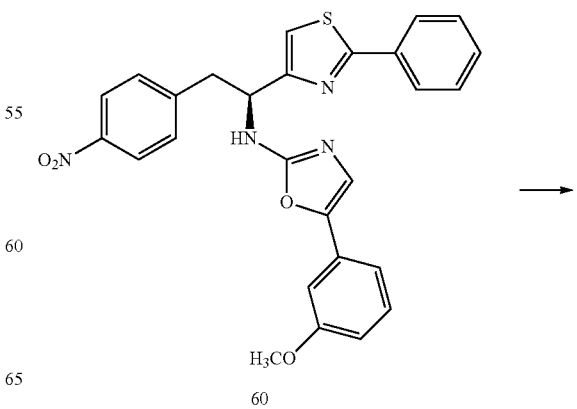

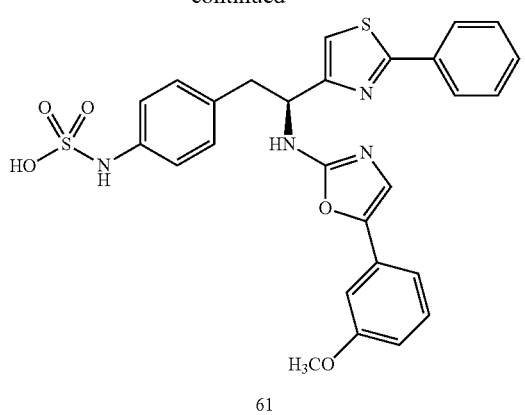

61

Reagents and conditions:
(b)(i) H₂:Pd/C, MeOH; (ii) SO₃-pyridine, NH₄OH; rt, 18 hr.

EXAMPLE 22

4-{(S)-2-[5-(3-Methoxyphenyl)oxazole-2-ylamino]-2-(2-phenylthiazol-4-yl)ethyl}phenylsulfamic acid (61)

Preparation of [5-(3-methoxyphenyl)oxazol-2-yl]-[2-(4-nitrophenyl)-1-(2-phenylthiazole-4-yl)ethyl]amine (60): A mixture of (S)-4-(isothiocyanato-2-(4-nitrophenyl)ethyl)-2-phenylthiazole, 53, (300 mg, 0.81 mmol), 1-azido-1-(3-methoxyphenyl)ethanone (382 mg, 2.0 mmol) and PPh₃ (0.8 g, polymer bound, ~3 mmol/g) in dioxane (6 mL) is heated at 90° C. for 20 minutes. The reaction solution is cooled to room temperature and the solvent removed in vacuo and the resulting residue is purified over silica to afford 300 mg (74% yield) of the desired product as a yellow solid. ¹H NMR (300 MHz, MeOH-d₄) δ 8.02 (d, J=7.2 Hz, 2H), 7.92-7.99 (m, 2H), 7.42-7.47 (m, 3H), 7.22-7.27 (m, 3H), 6.69-7.03 (m, 4H), 6.75-6.78 (m, 1H), 5.26 (t, J=6.3 Hz, 1H), 3.83 (s, 4H), 3.42-3.45 (m, 2H).

Preparation of 4-{(S)-2-[5-(3-methoxyphenyl)oxazole-2-ylamino]-2-(2-phenylthiazole-4-yl)ethyl}phenylsulfamic acid (61): [5-(3-methoxyphenyl)oxazol-2-yl]-[2-(4-nitrophenyl)-1-(2-phenylthiazole-4-yl)ethyl]amine, 60, (300 mg, 0.60 mmol) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (10 mL) and treated with SO₃-pyridine (190 mg, 1.2 mmol). The reaction is stirred at room temperature for 5 minutes after which a 7% solution of NH₄OH is added. The mixture is then concentrated and the resulting residue is purified by reverse-phase chromatography to afford 0.042 g of the desired product as the ammonium salt. ¹H NMR (300 MHz, MeOH-d₄) δ 7.99 (d, J=7.5 Hz, 2H), 7.46-7.50 (m, 3H), 7.23-7.29 (m, 3H), 7.04-7.12 (m, 6H), 6.78 (dd, J=8.4 and 2.4 Hz, 1H), 5.16 (t, J=6.6 Hz, 1H), 3.81 (s, 3H), 3.29-3.39 (m, 1H), 3.17 (dd, J=13.8 and 8.1 Hz, 1H).

The following are non-limiting examples of the second aspect of Category IX of the present disclosure.

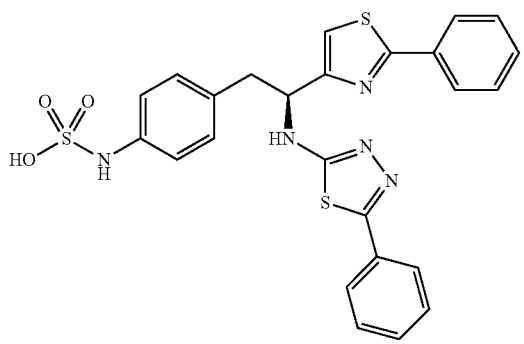 [SMILES: O=S(=O)(O)Nc1ccc(C[C@H](Nc2nnc(-c3ccccc3)s2)c2csc(-c3ccccc3)n2)cc1]

(S)-4-(2-(5-Phenyl-1,3,4-thiadiazol-2-ylamino)-2-(2-phenylthiazol-4-yl)ethyl)-phenylsulfamic acid: ¹H NMR (CD₃OD): δ 7.97-7.94 (m, 2H), 7.73-7.70 (m, 2H), 7.44-7.39 (m, 6H), 7.25 (s, 1H), 7.12 (s, 4H), 5.29 (t, 1H, J=6.9 Hz), 3.35-3.26 (m, 2H).

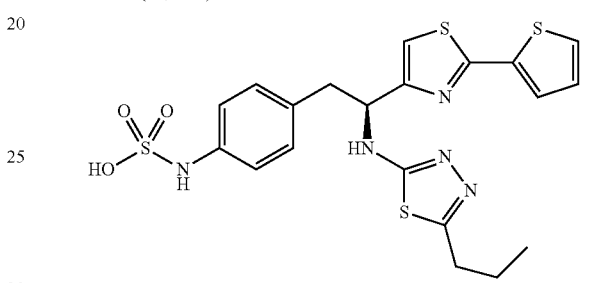

4-((S)-2-(5-Propyl-1,3,4-thiadiazol-2-ylamino)-2-(2-(thiophen-2-yl)thiazol-4-yl)ethyl)phenylsulfamic acid: ¹H NMR (CD₃OD): δ 7.59-7.54 (m, 2H), 7.17-7.03 (m, 6H), 5.13 (t, 1H, J=7.2 Hz), 3.32-3.13 (m, 2H), 2.81 (t, 2H, J=7.4 Hz), 1.76-1.63 (h, 6H, J=7.4 Hz), 0.97 (t, 3H, J=7.3 Hz).

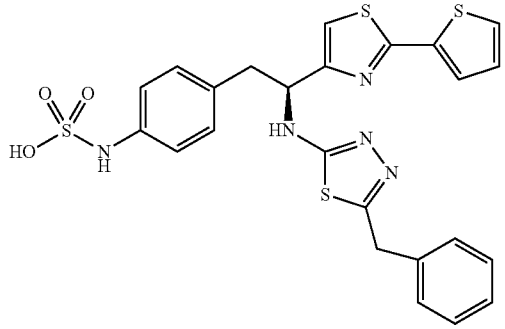 [SMILES: O=S(=O)(O)Nc1ccc(C[C@H](Nc2nnc(Cc3ccccc3)s2)c2csc(-c3cccs3)n2)cc1]

4-((S)-2-(5-Benzyl-1,3,4-thiadiazol-2-ylamino)-2-(2-(thiophen-2-yl)thiazol-4-yl)ethyl)phenylsulfamic acid: ¹H NMR (CD₃OD): δ (m, 2H), 7.49-7.45 (m, 2H), 7.26-7.16 (m, 5H), 7.05-6.94 (m, 6H), 5.04 (t, 1H, J=7.1 Hz), 4.07 (s, 2H), 3.22-3.04 (m, 2H).

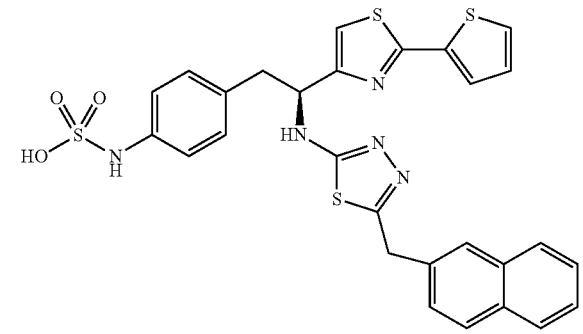 [SMILES: O=S(=O)(O)Nc1ccc(C[C@H](Nc2nnc(Cc3ccc4ccccc4c3)s2)c2csc(-c3cccs3)n2)cc1]

4-((S)-2-(5-(Naphthalen-1-ylmethyl)-1,3,4-thiadiazol-2-ylamino)-2-(2-(thiophen-2-yl)thiazol-4-yl)ethyl)phenylsulfamic acid: ¹H NMR (CD₃OD): δ 8.08-8.05 (m, 1H), 7.89-7.80 (m, 2H), 7.55-7.43 (m, 6H), 7.11-7.00 (m, 6H), 5.08 (t, 1H, J=7.1 Hz), 4.63 (s, 2H), 3.26-3.08 (m, 2H).

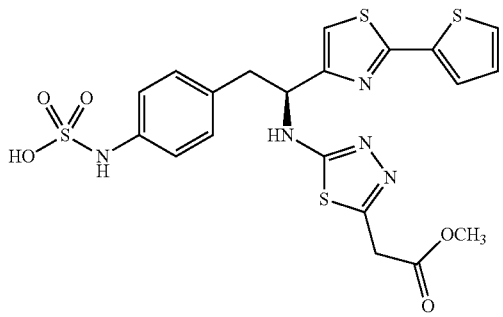 [SMILES: COC(=O)Cc1nnc(N[C@@H](Cc2ccc(NS(=O)(=O)O)cc2)c2csc(-c3cccs3)n2)s1]

4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid: ¹H NMR (CD₃OD): δ 7.48-7.44 (m, 2H), 7.03-6.92 (m, 6H), 5.02 (t, 1H, J=7.2 Hz), 4.30 (s, 2H), 3.55 (s, 3H), 3.22-3.02 (m, 2H).

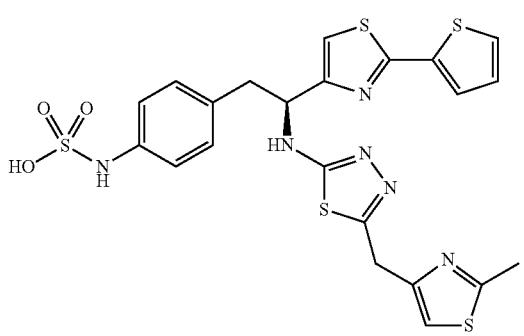 [SMILES: Cc1nc(Cc2nnc(N[C@@H](Cc3ccc(NS(=O)(=O)O)cc3)c3csc(-c4cccs4)n3)s2)cs1]

4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid: ¹H NMR (CD₃OD): δ 7.60-7.56 (m, 2H), 7.19 (s, 1H), 7.15-7.12 (m, 2H), 7.09-7.03 (q, 4H, J=8.7 Hz), 5.14 (t, 1H, J=7.2 Hz), 4.28 (s, 2H), 3.33-3.14 (m, 2H), 2.67 (s, 3H).

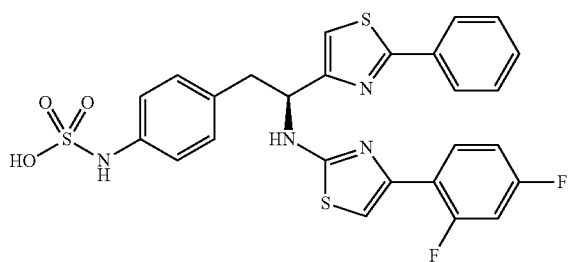 [SMILES: O=S(=O)(O)Nc1ccc(C[C@H](Nc2nc(-c3ccc(F)cc3F)cs2)c2csc(-c3ccccc3)n2)cc1]

4-{(S)-2-[4-(2,4-Difluorophenyl)thiazol-2-ylamino]-2-[2-(thiophen-2-yl)thiazol-4-yl]ethyl}phenylsulfamic acid: ¹H NMR (CD₃OD): δ 8.06-8.02 (q, 1H, J=6.8 Hz), 7.59-7.54 (m, 2H), 7.16-7.08 (m, 6H), 7.01-6.88 (m, 4H), 5.20 (t, 1H, J=7.0 Hz), 3.36-3.17 (m, 2H).

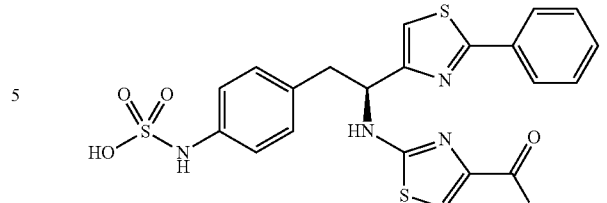

(S)-4-{2-[4-(Ethoxycarbonyl)thiazol-2-ylamino]-2-(2-phenylthiazol-4-yl)ethyl}phenylsulfamic acid: ¹H NMR (CD₃OD): δ 8.02-7.99 (m, 2H), 7.54-7.45 (m, 4H), 7.26 (s, 1H), 7.08 (s, 4H), 5.26 (t, 1H, J=6.9 Hz), 4.35-4.28 (q, 2H, J=6.9 Hz), 3.38-3.18 (m, 2H), 1.36 (t, 3H, J=7.2 Hz).

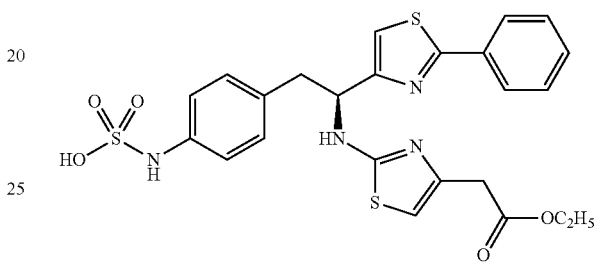

(S)-4-{2-[4-(2-Ethoxy-2-oxoethyl)thiazol-2-ylamino]-2-(2-phenylthiazol-4-yl)ethyl}phenylsulfamic acid: ¹H NMR (CD₃OD): δ 7.96 (m, 2H), 7.50-7.46 (m, 3H), 7.21 (s, 1H), 7.10-7.04 (m, 4H), 6.37 (s, 1H), 5.09 (t, 1H, J=6.9 Hz), 4.17-4.10 (q, 2H, J=7.1 Hz), 3.54 (s, 2H), 3.35-3.14 (m, 2H), 1.22 (t, 3H, J=7.1 Hz).

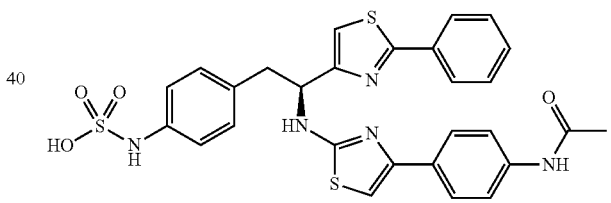

(S)-4-{2-[4-(4-acetamidophenyl)thiazol-2-ylamino]-2-(2-phenylthiazol-4-yl)ethyl}phenylsulfamic acid: ¹H NMR (CD₃OD): δ 8.11 (m, 2H), 7.82-7.80 (m, 2H), 7.71-7.61 (m, 6H), 7.40 (s, 1H), 7.23 (s, 4H), 5.32 (t, 1H, J=7.0 Hz), 3.51-3.35 (m, 2H), 2.28 (s, 3H).

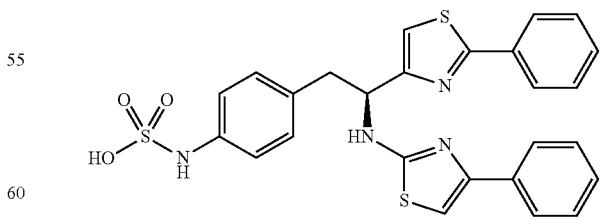

(S)-4-[2-(4-phenylthiazol-2-ylamino)-2-(2-phenylthiazol-4-yl)ethyl]phenylsulfamic acid: ¹H NMR (CD₃OD): δ 8.03-7.99 (m, 2H), 7.75-7.72 (d, 2H, J=8.4 Hz), 7.53-7.48 (m, 3H), 7.42 (m, 4H), 7.12 (s, 4H), 6.86 (s, 1H), 5.23 (t, 1H, J=7.2 Hz), 3.40-3.27 (m, 2H).

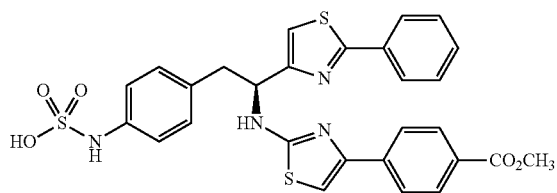 [SMILES: COC(=O)c1ccc(-c2csc(N[C@@H](Cc3ccc(NS(=O)(=O)O)cc3)c3csc(-c4ccccc4)n3)n2)cc1]

(S)-4-{2-[4-(4-(methoxycarbonyl)phenyl)thiazol-2-ylamino]-2-(2-phenylthiazol-4-yl)ethyl}phenylsulfamic acid: $^1$H NMR (CD$_3$OD): δ 8.04-8.00 (m, 4H), 7.92-7.89 (d, 2H, J=9.0 Hz), 7.53-7.49 (m, 3H), 7.30 (s, 1H), 7.15 (s, 4H), 7.05 (s, 1H), 5.28 (t, 1H, J=6.9 Hz), 3.93 (s, 3H), 3.35-3.24 (m, 2H).

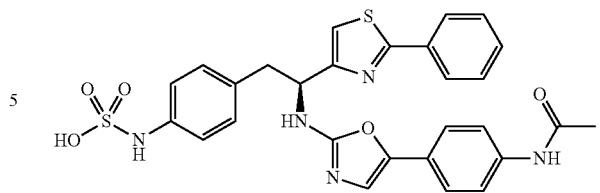

(S)-4-{2-[5-(4-Acetamidophenyl)oxazol-2-ylamino]-2-(2-phenylthiazol-4-yl)ethyl}phenylsulfamic acid: $^1$H NMR (300 MHz, MeOH-d$_4$) δ 7.92-7.94 (m, 2H), 7.55-7.58 (m, 2H), 7.39-7.50 (m, 5H), 7.26 (s, 1H), 7.12 (s, 4H), 7.02 (s, 1H0), 5.14 (t, J=7.8 Hz, 1H), 3.13-3.38 (m, 2H), 2.11 (s, 3H).

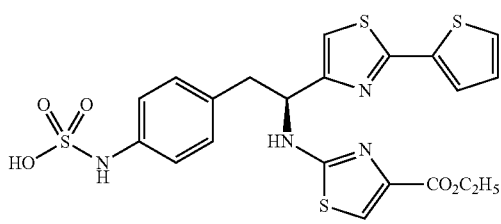 [SMILES: CCOC(=O)c1csc(N[C@@H](Cc2ccc(NS(=O)(=O)O)cc2)c2csc(-c3cccs3)n2)n1]

4-{(S)-2-[4-(Ethoxycarbonyl)thiazol-2-ylamino]-2-[2-(thiophen-2-yl)thiazol-4-yl]ethyl}phenylsulfamic acid: $^1$H NMR (CD$_3$OD): δ 7.43-7.38 (m, 2H), 7.26 (s, 1H), 7.00-6.94 (m, 3H), 6.89 (s, 4H), 5.02 (t, 1H, J=7.0 Hz), 4.16-4.09 (q, 2H, J=7.1 Hz), 3.14-2.94 (m, 2H), 1.17 (t, 3H, J=7.1 Hz).

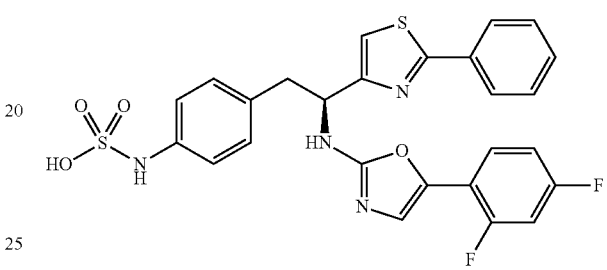

4-((S)-2-(5-(2,4-Difluorophenyl)oxazole-2-ylamino)-2-(2-phenylthiazole-4-yl)ethyl)phenylsulfamic acid: $^1$H NMR (300 MHz, MeOH-d$_4$) δ 7.97-7.99 (m, 2H), 7.54-7.62 (m, 1H), 7.45-7.50 (m, 3H), 7.28 (s, 1H), 7.12 (s, 4H), 6.97-7.06 (m, 3H), 5.15-5.20 (m, 1H), 3.28-3.40 (m, 1H), 3.20 (dd, J=13.8 and 8.4 Hz, 1H).

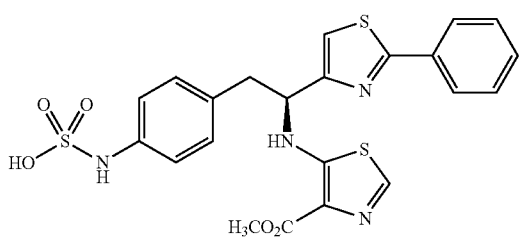 [SMILES: COC(=O)c1ncsc1N[C@@H](Cc1ccc(NS(=O)(=O)O)cc1)c1csc(-c2ccccc2)n1]

(S)-4-[2-(4-(Methoxycarbonyl)thiazol-5-ylamino)-2-(2-phenylthiazole-4-yl)ethyl]phenylsulfamic acid: $^1$H NMR (300 MHz, MeOH-d$_4$) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

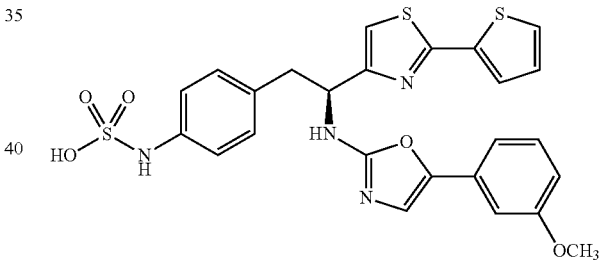

4-{(S)-2-[5-(3-Methoxyphenyl)oxazol-2-ylamino]-2-[(2-thiophen-2-yl)thiazole-4-yl]ethyl}phenylsulfamic acid: $^1$H NMR (300 MHz, MeOH-d$_4$) δ 7.55-7.60 (m, 2H), 7.26 (t, J=8.1 Hz, 1H), 7.21 (s, 1H), 7.04-7.15 (m, 8H), 6.77-6.81 (m, 1H), 5.10 (t, J=6.3 Hz, 1H), 3.81 (s, 3H), 3.29-3.36 (m, 1H), 3.15 (dd, J=14.1 and 8.4 Hz, 1H).

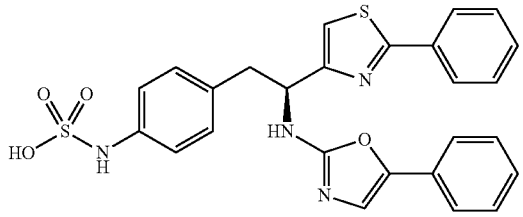 [SMILES: O=S(=O)(O)Nc1ccc(C[C@H](Nc2ncc(-c3ccccc3)o2)c2csc(-c3ccccc3)n2)cc1]

(S)-4-[2-(5-Phenyloxazol-2-ylamino)-2-(2-phenylthiazol-4-yl)ethyl]-phenylsulfamic acid: $^1$H NMR (300 MHz, MeOH-d$_4$) δ 7.94-7.96 (m, 2H), 7.45-7.49 (m, 5H), 7.32 (t, J=7.8 Hz, 2H), 7.12 (s, 1H), 7.19 (t, J=7.2 Hz, 1H), 7.12 (s, 4H), 7.05 (s, 1H), 5.15 (t, J=6.4 Hz, 1H), 3.34 (dd, J=14.1 and 8.4 Hz, 1H), 3.18 (dd, J=14.1 and 8.4 Hz, 1H).

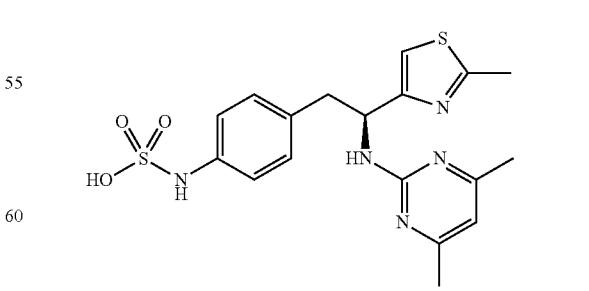

(S)-4-[2-(4,6-Dimethylpyrimidin-2-ylamino)-2-(2-methylthiazole-4-yl)ethyl]phenylsulfamic acid: $^1$H NMR (300 MHz, MeOH-d$_4$) δ 7.00-7.10 (m, 5H), 6.44 (s, 1H), 5.50 (t, J=7.2 Hz, 1H), 3.04-3.22 (m, 2H), 2.73 (s, 3H), 2.27 (s, 6H).

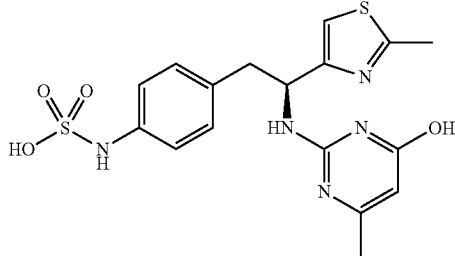 [SMILES: Cc1cc(O)nc(N[C@@H](Cc2ccc(NS(=O)(=O)O)cc2)c2csc(C)n2)n1]

(S)-4-[2-(4-Hydroxy-6-methylpyrimidine-2-ylamino)-2-(2-methylthiazole-4-yl)ethyl]phenylsulfamic acid: $^1$H NMR (300 MHz, MeOH-d4) δ 7.44 (d, J=8.4 Hz, 2H), 6.97-7.10 (m, 4H), 5.61 (s, 1H), 5.40-5.49 (m, 1H), 3.10-3.22 (m, 2H), 2.73 (s, 3H), 2.13 (s, 3H).

The first aspect of Category X of the present disclosure relates to compounds having the formula:

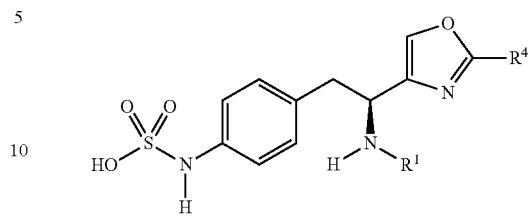

wherein $R^1$ is heteroaryl and $R^4$ is further described herein below in Table XIX.

TABLE XIX

| No.  | $R^4$        | $R^1$                                                         |
|------|--------------|---------------------------------------------------------------|
| S788 | phenyl       | 4-(methoxycarbonyl)thiazol-5-yl                               |
| S789 | phenyl       | 4-[(2-methoxy-2-oxoethyl)carbamoyl]thiazol-5-yl              |
| S790 | phenyl       | 5-[1-N-(2-methoxy-2-oxoethyl)-1-H-indol-3-yl]oxazol-2-yl     |
| S791 | phenyl       | 5-(2-methoxyphenyl)oxazol-2-yl                                |
| S792 | phenyl       | 5-[(S)-1-(tert-butoxycarbonyl)-2-phenylethyl]oxazol-2-yl     |
| S793 | phenyl       | 5-[4-(methylcarboxy)phenyl]oxazol-2-yl                        |
| S794 | phenyl       | 5-(3-methoxybenzyl)oxazol-2-yl                                |
| S795 | phenyl       | 5-(4-phenyl)oxazol-2-yl                                       |
| S796 | phenyl       | 5-(2-methoxyphenyl)thiazol-2-yl                               |
| S797 | phenyl       | 5-(3-methoxyphenyl)thiazol-2-yl                               |
| S798 | phenyl       | 5-(4-fluorophenyl)thiazol-2-yl                                |
| S799 | phenyl       | 5-(2,4-difluorophenyl)thiazol-2-yl                            |
| S800 | phenyl       | 5-(3-methoxybenzyl)thiazol-2-yl                               |
| S801 | phenyl       | 4-(3-methoxyphenyl)thiazol-2-yl                               |
| S802 | phenyl       | 4-(4-fluorophenyl)thiazol-2-yl                                |
| S803 | thiophen-2-yl| 4-(methoxycarbonyl)thiazol-5-yl                               |
| S804 | thiophen-2-yl| 4-[(2-methoxy-2-oxoethyl)carbamoyl]thiazol-5-yl              |
| S805 | thiophen-2-yl| 5-[1-N-(2-methoxy-2-oxoethyl)-1-H-indol-3-yl]oxazol-2-yl     |
| S806 | thiophen-2-yl| 5-(2-methoxyphenyl)oxazol-2-yl                                |
| S807 | thiophen-2-yl| 5-[(S)-1-(tert-butoxycarbonyl)-2-phenylethyl]oxazol-2-yl     |
| S808 | thiophen-2-yl| 5-[4-(methylcarboxy)phenyl]oxazol-2-yl                        |
| S809 | thiophen-2-yl| 5-(3-methoxybenzyl)oxazol-2-yl                                |
| S810 | thiophen-2-yl| 5-(4-phenyl)oxazol-2-yl                                       |
| S811 | thiophen-2-yl| 5-(2-methoxyphenyl)thiazol-2-yl                               |
| S812 | thiophen-2-yl| 5-(3-methoxyphenyl)thiazol-2-yl                               |
| S813 | thiophen-2-yl| 5-(4-fluorophenyl)thiazol-2-yl                                |
| S814 | thiophen-2-yl| 5-(2,4-difluorophenyl)thiazol-2-yl                            |
| S815 | thiophen-2-yl| 5-(3-methoxybenzyl)thiazol-2-yl                               |
| S816 | thiophen-2-yl| 4-(3-methoxyphenyl)thiazol-2-yl                               |
| S817 | thiophen-2-yl| 4-(4-fluorophenyl)thiazol-2-yl                                |
| S818 | cyclopropyl  | 4-(methoxycarbonyl)thiazol-5-yl                               |
| S819 | cyclopropyl  | 4-[(2-methoxy-2-oxoethyl)carbamoyl]thiazol-5-yl              |
| S820 | cyclopropyl  | 5-[1-N-(2-methoxy-2-oxoethyl)-1-H-indol-3-yl]oxazol-2-yl     |
| S821 | cyclopropyl  | 5-(2-methoxyphenyl)oxazol-2-yl                                |
| S822 | cyclopropyl  | 5-[(S)-1-(tert-butoxycarbonyl)-2-phenylethyl]oxazol-2-yl     |
| S823 | cyclopropyl  | 5-[4-(methylcarboxy)phenyl]oxazol-2-yl                        |
| S824 | cyclopropyl  | 5-(3-methoxybenzyl)oxazol-2-yl                                |
| S825 | cyclopropyl  | 5-(4-phenyl)oxazol-2-yl                                       |
| S826 | cyclopropyl  | 5-(2-methoxyphenyl)thiazol-2-yl                               |
| S827 | cyclopropyl  | 5-(3-methoxyphenyl)thiazol-2-yl                               |
| S828 | cyclopropyl  | 5-(4-fluorophenyl)thiazol-2-yl                                |
| S829 | cyclopropyl  | 5-(2,4-difluorophenyl)thiazol-2-yl                            |
| S830 | cyclopropyl  | 5-(3-methoxybenzyl)thiazol-2-yl                               |
| S831 | cyclopropyl  | 4-(3-methoxyphenyl)thiazol-2-yl                               |
| S832 | cyclopropyl  | 4-(4-fluorophenyl)thiazol-2-yl                                |

Compounds according to the first aspect of Category X can be prepared by the procedure outlined in Scheme XXII and described herein below in Example 23.

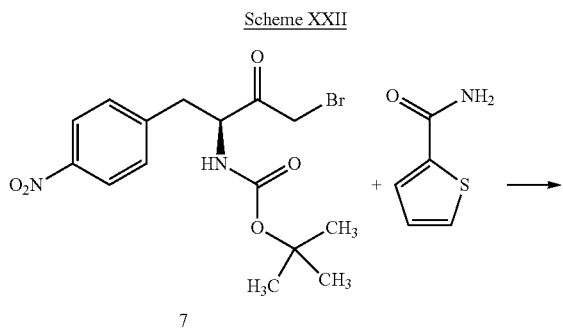

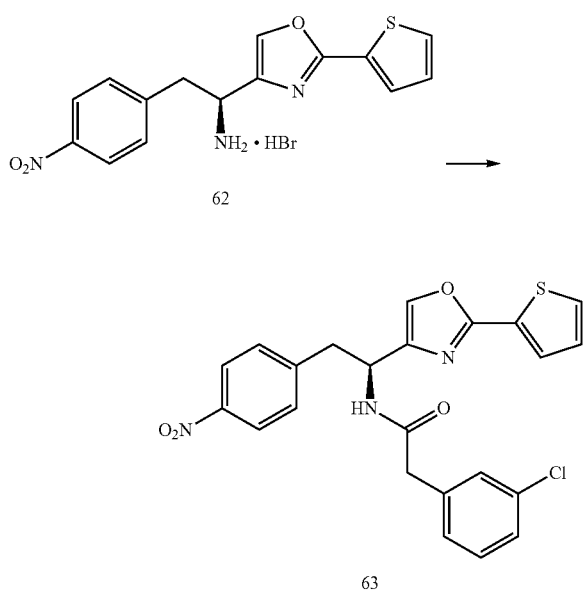

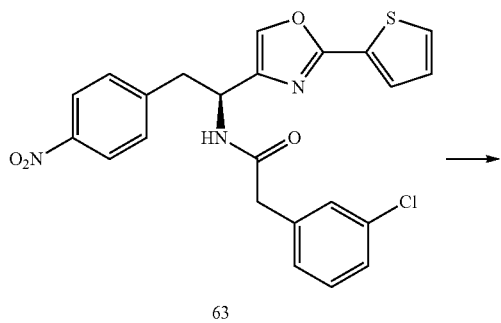

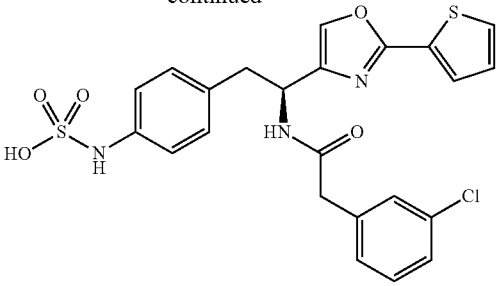

64

Reagents and conditions: (c) (i) H₂:Pd/C, MeOH; (ii) SO₃-pyridine, NH₄OH, rt, 18 hr.

EXAMPLE 23

4-((S)-2-(2-(3-Chlorophenyl)acetamido)-2-(2-(thiophen-2-yl)oxazol-4-yl)ethyl)phenylsulfamic acid (64)

Preparation of (S)-2-(4-nitrophenyl)-1-[(thiophen-2-yl)oxazol-4-yl]ethanamine hydrobromide salt (62): A mixture of (S)-tert-butyl 4-bromo-1-(4-nitrophenyl)-3-oxobutan-2-ylcarbamate, 7, (38.7 g, 100 mmol), and thiophen-2-carboxamide (14 g, 110 mmol) (available from Alfa Aesar) in CH₃CN (500 mL) is refluxed for 5 hours. The reaction mixture is cooled to room temperature and diethyl ether (200 mL) is added to the solution. The precipitate which forms is collected by filtration. The solid is dried under vacuum to afford the desired product which can be used for the next step without purification.

Preparation of 2-(3-chlorophenyl)-N-{(S)-2-(4-nitrophenyl)-1-[2-(thiophen-2-yl)oxazol-4-yl]ethyl}acetamide (63): To a solution of (S)-2-(4-nitrophenyl)-1-[(thiophen-2-yl)oxazol-4-yl]ethanamine HBr, 47, (3.15 g, 10 mmol) 3-chlorophenyl-acetic acid (1.70 g, 10 mmol) and 1-hydroxybenzotriazole (HOBt) (0.70 g, 5.0 mmol) in DMF (50 mL) at 0° C., is added 1-(3-dimethylaminopropyl)-3-ethylcarbodiimide (EDCI) (1.90 g, 10 mmol) followed by triethylamine (4.2 mL, 30 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of —((S)-2-(2-(3-chlorophenyl)acetamido)-2-(2-(thiophen-2-yl)oxazol-4-yl)ethyl)phenylsulfamic acid (64): 2-(3-chlorophenyl)-N-{(S)-2-(4-nitrophenyl)-1-[2-(thiophen-2-yl)oxazol-4-yl]ethyl}acetamide, 63, (3 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue can be purified by reverse phase chromatography to afford the desired product as the ammonium salt.

The second aspect of Category X of the present disclosure relates to compounds having the formula:

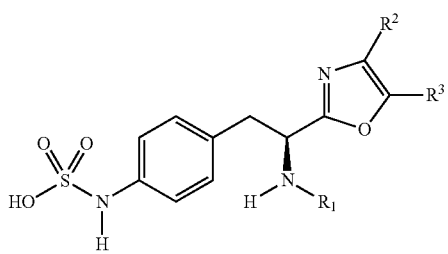

wherein R¹ is aryl and R² and R³ are further described herein below in Table XX.

TABLE XX

| No. | R² | R³ | R¹ |
|-----|------|----------|----------------|
| T833 | methyl | hydrogen | phenyl |
| T834 | methyl | hydrogen | benzyl |
| T835 | methyl | hydrogen | 2-fluorophenyl |
| T836 | methyl | hydrogen | 3-fluorophenyl |
| T837 | methyl | hydrogen | 4-fluorophenyl |
| T838 | methyl | hydrogen | 2-chlorophenyl |
| T839 | methyl | hydrogen | 3-chlorophenyl |
| T840 | methyl | hydrogen | 4-chlorophenyl |
| T841 | ethyl | hydrogen | phenyl |
| T842 | ethyl | hydrogen | benzyl |
| T843 | ethyl | hydrogen | 2-fluorophenyl |
| T844 | ethyl | hydrogen | 3-fluorophenyl |
| T845 | ethyl | hydrogen | 4-fluorophenyl |
| T846 | ethyl | hydrogen | 2-chlorophenyl |
| T847 | ethyl | hydrogen | 3-chlorophenyl |
| T848 | ethyl | hydrogen | 4-chlorophenyl |
| T849 | thien-2-yl | hydrogen | phenyl |
| T850 | thien-2-yl | hydrogen | benzyl |
| T851 | thien-2-yl | hydrogen | 2-fluorophenyl |
| T852 | thien-2-yl | hydrogen | 3-fluorophenyl |
| T853 | thien-2-yl | hydrogen | 4-fluorophenyl |
| T854 | thien-2-yl | hydrogen | 2-chlorophenyl |
| T855 | thien-2-yl | hydrogen | 3-chlorophenyl |
| T856 | thiene-2-yl | hydrogen | 4-chlorophenyl |

Compounds according to the second aspect of Category X can be prepared by the procedure outlined in Scheme XXIII and described herein below in Example 24.

Scheme XXIII

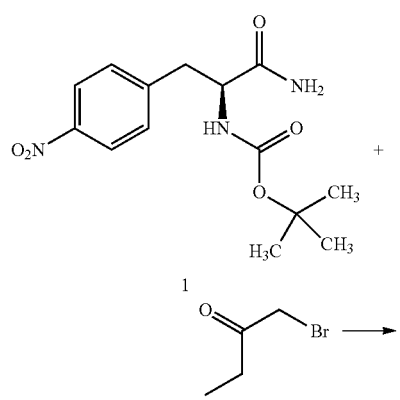

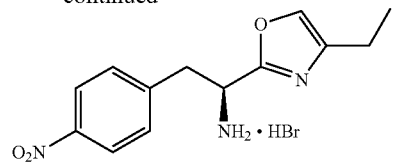

Reagents and conditions: (a) CH₃CN; reflux, 2 hr.

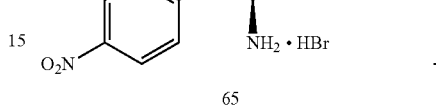

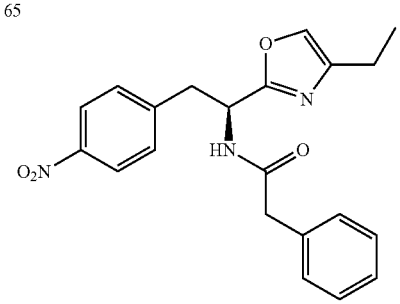

Reagents and conditions: (b) C₆H₄CO₂H, EDCI, HOBt, DIPEA, DMF; rt, 18 hr.

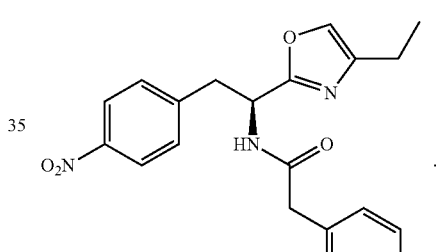

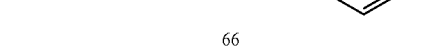

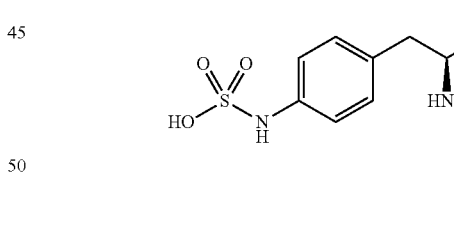

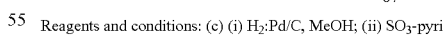

Reagents and conditions: (c) (i) H₂:Pd/C, MeOH; (ii) SO₃-pyridine, NH₄OH, rt, 18 hr.

EXAMPLE 24

{4-[2-(S)-(4-Ethyloxazol-2-yl)-2-phenylacetylaminoethyl]-phenyl}sulfamic acid (67)

Preparation of (S)-1-(4-ethyloxazol-2-yl)-2-(4-nitrophenyl)ethanamine (65): A mixture of [1-(S)-carbamoyl-2-(4-nitrophenyl)ethyl-carbamic acid tert-butyl ester, 1, (10 g, 32.3 mmol) and 1-bromo-2-butanone (90%, 4.1 mL, 36 mmol) in CH₃CN (500 mL) is refluxed for 18 hours. The reaction mixture is cooled to room temperature and diethyl ether is added to the solution and the precipitate which forms is removed by filtration and is used without further purification.

Preparation of N-[1-(4-ethyloxazol-2-yl)-2-(4-nitrophenyl)ethyl]-2-phenyl-acetamide (66): To a solution of (S)-1-(4-ethyloxazol-2-yl)-2-(4-nitrophenyl)ethanamine, 65, (2.9 g, 11 mmol), phenylacetic acid (1.90 g, 14 mmol) and 1-hydroxybenzotriazole (HOBt) (0.94 g, 7.0 mmol) in DMF (100 mL) at 0° C., is added 1-(3-dimethylamino-propyl)-3-ethylcarbodiimide (EDCI) (2.68 g, 14 mmol) followed by triethylamine (6.0 mL, 42 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of {4-[2-(S)-(4-ethyloxazol-2-yl)-2-phenylacetylaminoethyl]-phenyl}sulfamic acid (67): N-[1-(4-ethyloxazol-2-yl)-2-(4-nitrophenyl)ethyl]-2-phenyl-acetamide, 66, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.177 g, 1.23). The reaction is stirred at room temperature for 5 minutes after which a 7% solution of NH₄OH (10 mL) is added. The mixture is then concentrated and the resulting residue is purified by reverse phase chromatography to afford the desired product as the ammonium salt.

Methods

The vascular endothelium lines the inside of all blood vessels, forming a non-thrombogenic surface that controls the entry and exit of plasma and white blood cells to and from the bloodstream. The quiescent endothelium has turnover rates of months to years, and proliferates only following angiogenic activation. The loss of endothelial quiescence is a common feature of conditions such as inflammation, atherosclerosis, restenosis, angiogenesis and various types of vasculopathies.

Vasculogenesis and angiogenesis are down-regulated in the healthy adult and are, except for the organs of the female reproductive system, almost exclusively associated with pathology when angiogenesis is induced by microenvironmental factors such as hypoxia or inflammation. These pathological processes associated with, or induced by, angiogenesis include diseases as diverse as cancer, psoriasis, macular degeneration, diabetic retinopathy, thrombosis, and inflammatory disorders including arthritis and athrerosclerosis. However, in certain instances insufficient angiogenesis can lead to diseaeses such as ischemic heart disease and pre-eclampsia.

The quiescent vascular endothelium forms a tight barrier that controls the passage of plasma and cells from the bloodstream to the underlying tissues. Endothellial cells adhere to each other through junctional transmembrane proteins that are linked to specific intracelllar structural and signaling complexes. The endothelial layer can undergo a transition from the resting state to the active state wherein activation of the endothelium results in the expression of adhesion molecules. This endothelium activation is a prerequisite for initiating angiogensesis, inflammation and inflammation associated diseases.

Tie-2, a receptor-like tyrosine kinase exclusively expressed in endothelial cells that controls endothelial differentiation. Tie-2 binds and is activated by the stimulatory ligand angiopoeitin-1 (Ang-1) which promotes autophosphorylation of the Tie-2 receptor leading to a cascade of events that results in stabilization of vascular structures by promoting endothelial cell viability and preventing basement membrane dissolution. As such, Tie-2 activation is a method for attenuating leaking vasculature by maintaining a quiescent, intact vascular endothelium. Tie-2 activation is inhibited by Ang-2, which exhibits Ang-1 antagonism by competitively binding to Tie-2 and thus blocking phosphorylation of Tie-2. Elevated levels of Ang-2 have been found to be associated with inflammatory diseases, inter alia, sepsis, lupus, inflammatory bowel disease and metastatic diseases such as cancer.

During periods of high Ang-2 levels, fissures or breaks in the endothelium form which results in vascular leak syndrome. Vascular leak syndrome results in life-threatening effects such as tissue and pulmonary edema. For many disease states elevated Ang-2 levels are clear markers that a disease state or condition exists. Once a disease state has been resolved, the Ang-1/Ang-2 balance returns and the vascular endothelium is stabilized.

Amplification of Tie-2 Signaling

In conditions wherein the normal balance between Ang-1 and Ang-2 has been disrupted, the disclosed compounds have been found to amplify Tie-2 signaling by inhibiting dephosphorylation of phosphorylated Tie-2 via inhibition of Human Protein Tyrosine Phosphatase-β (HPTP-β). In addition, the disclosed compounds can be used in varying amounts to increase the Tie-2 signaling in a very controlled manner, and to therefore titrate the level of Tie-2 amplification.

IL-2 Induced Vascular Leak: Treatment of Metastatic Cancers

Immunotherapy is one method of treating cancer. Up-regulation of the body's own immune system is one aspect of immunotherapy. Among the many immune system signaling molecules is interleukin-2 (IL-2) which is instrumental in the body's natural response to microbial infection and in discriminating between foreign (non-self) and self High-dose interleukin-2 (HDIL-2) is an FDA approved treatment for patients with metastatic renal cell carcinoma (RCC) and metastatic melanoma. Although it has been reported that only 23% of those subjects given this therapy show a tumor response, the duration of this response can exceed 10 years (Elias L. et al., "A literature analysis of prognostic factors for response and quality of response of patients with renal cell carcinoma to interleukin-2-based therapy." *Oncology* (2001); 61: pp. 91-101). As such, IL-2 therapy is the only available treatment that offers the potential for cure.

Gallagher (Gallagher, D. C. et al., "Angiopoietin 2 Is a Potential Mediator of High-Dose Interleukin 2-Induced Vascular Leak" *Clin Cancer Res* (2007):13(7) 2115-2120) reports that elevated levels of angiopoietin-2 are found in patients treated with high doses of IL-2 and suggests that overcoming Ang-2 blockade of Tie-2 signaling might be curative for vascular leak syndrome which is a side effect of this therapy. As many as 65% of patients receiving this IL-2 therapy will necessarily interrupt or discontinue treatment due to VLS. VLS is typically characterized by 2 or more of the following 3 symptoms (hypotension, edema, hypoalbuminemia), although other manifestations include prerenal azotemia, metabolic acidosis, pleural effusions, and non-cardiogenic pulmonary edema.

IL-2 is known to cause endothelial cell activation, however, with loss of proper barrier function. Amplification of Tie-2 signaling during High Dose IL-2 immunotherapy would lead to attenuation of vascular leakage since Tie-2 stimulation promotes endothelial cell stability. As such, by administering an agent that can amplify Tie-2 signaling, vascular stability can be increased and, hence, the side effects of high IL-2 dosing mitigated. The disclosed compounds can amplify Tie-2 signaling under the conditions of low angiopoietin-1 concentrations or when high concentrations of angiopoietin-2 are present as in IL-2 treated patients.

By amplifying Tie-2 signaling without affecting Ang-2 levels, the use of elevated levels of Ang-2 as a potential pathology marker is retained. For example, a patient suffering from an inflammatory disease such as sepsis will normally have an elevated Ang-2 level that acts to suppress Ang-1 stimulation of Tie-2. This elevated Ang-2 results in edema which is a symptom of vascular leakage. The present methods, by amplifying Tie-2 signaling without affecting the Ang-2 level, provide a method for alleviating the symptoms that are associated with vascular leak while retaining the ability to use Ang-2 levels as a measure of disease progress and resolution.

Reduction of Vascular Leak Caused by an Anticancer Therapy

The following demonstrates the effectiveness of the disclosed compounds on Tie-2 signal amplification, and thus, the alleviation of vascular leakage due to administration of high doses of an anticancer treatment that induces vascular leak syndrome, i.e., IL-2.

Twenty-five mice were used for the following experiment. Five are selected as the control and received no treatment. The remaining twenty mice were divided into four groups of five mice each and dosed as follows over a period of 5 days:

Low dose of IL-2 was at 180,000 units per day
High dose of IL-2 was at 400,000 units per day
Tie-2 signal amplifier at 40 mg/kg for the first 2 days, then at 20 mg/kg for 3 days.

The animals were monitored for symptoms related to vascular leak syndrome seen in patients treated with high doses of IL-2, inter alia, blood pressure (hypertension/shock), viability (death), lung histology (VSL pathology) and serum cytokine etc. (VSL mechanistic analysis.

The disclosed compound, 4-{(S)-2-[(S)-2-(methoxycarbonylamino)-3-phenylpropanamido]-2-[2-(thiophen-2-yl)thiazol-4-yl]ethyl}phenylsulfamic acid, D91, having the formula:

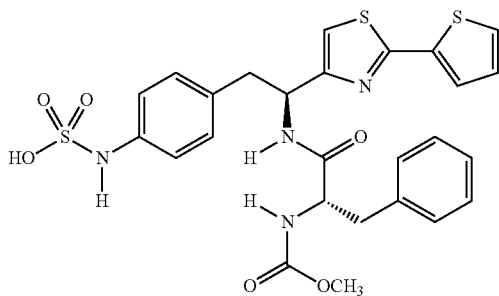 [SMILES: COC(=O)N[C@@H](Cc1ccccc1)C(=O)N[C@@H](Cc1ccc(NS(=O)(=O)O)cc1)c1csc(-c2cccs2)n1]

was used as the Tie-2 signal amplifier. As depicted in FIG. 1 the blood pressure of the animals treated with a high dose of IL-2 went to 0 mm Hg (death), whereas the animals treated with 4-{(S)-2-[(S)-2-(methoxycarbonylamino)-3-phenyl-propanamido]-2-[(2-(thiophen-2-yl)thiazol-4-yl]ethyl}phenylsulfamic acid ammonium salt showed little effect on blood pressure even in the case of those animals treated with the high dose of IL-2.

Figure 2:
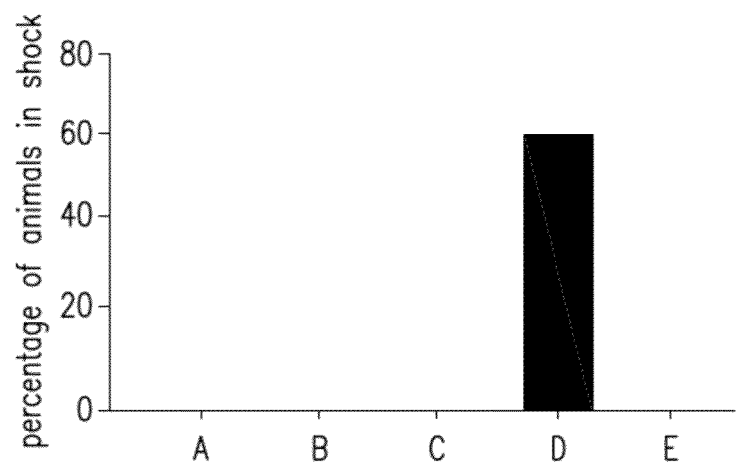
FIG. 2 depicts the effect of 4-{(S)-2-[(S)-2-(methoxycarbonylamino)-3-phenyl-propanamido]-2-[2-(thiophen-2-yl)thiazol-4-yl]ethyl}phenylsulfamic acid ammonium salt, a Tie-2 signal amplifier, on IL-2 induced shock in mice. A depicts the control sample; B depicts mice treated with 180,000 IU of IL-2 for 5 days; C depicts mice treated with 180,000 IU of IL-2 for 5 days and 40 mg/kg of D91 for the first 2 days, then at 20 mg/kg for 3 days; D depicts mice treated with 400,000 IU of IL-2 for 5 days; E depicts mice treated with 400,000 IU of IL-2 for 5 days and 40 mg/kg of D91 for the first 2 days, then at 20 mg/kg for 3 days.

As depicted in FIG. 2, of the animals receiving high doses of IL-2, 60% showed clinical symptoms of shock, whereas the animals receiving high doses of IL-2 and the Tie-2 signal amplifier 4-{(S)-2-[(S)-2-(methoxycarbonylamino)-3-phenyl-propanamido]-2-[2-(thiophen-2-yl)thiazol-4-yl]ethyl}phenylsulfamic acid ammonium salt showed no signs of shock.

Figure 3:
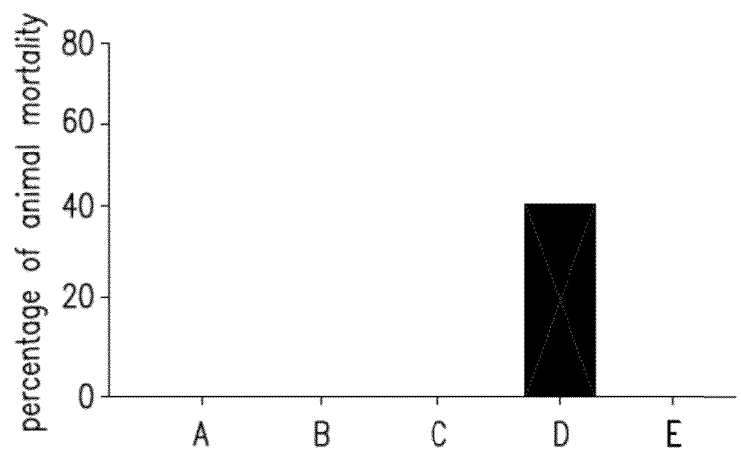
FIG. 3 depicts the effect of 4-{(S)-2-[(S)-2-(methoxycarbonylamino)-3-phenyl-propanamido]-2-[2-(thiophen-2-yl)thiazol-4-yl]ethyl}phenylsulfamic acid ammonium salt, a Tie-2 signal amplifier, on IL-2 induced murine mortality. A depicts the control sample; B depicts mice treated with 180,000 IU of IL-2 for 5 days; C depicts mice treated with 180,000 IU of IL-2 for 5 days and 40 mg/kg of D91 for the first 2 days, then at 20 mg/kg for 3 days; D depicts mice treated with 400,000 IU of IL-2 for 5 days; E depicts mice treated with 400,000 IU of IL-2 for 5 days and 40 mg/kg of D91 for the first 2 days, then at 20 mg/kg for 3 days.

As depicted in FIG. 3, of the animals receiving high doses of IL-2, 40% died, whereas the animals receiving high doses of IL-2 and the Tie-2 signal amplifier 4-{(S)-2-[(S)-2-(methoxycarbonylamino)-3-phenyl-propanamido]-2-[2-(thiophen-2-yl)thiazol-4-yl]ethyl}phenylsulfamic acid ammonium salt survived.

Figure 4:
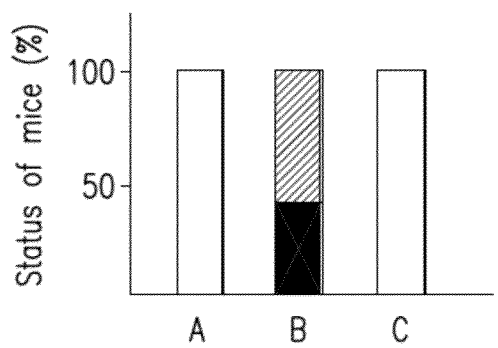
FIG. 4 depicts the status of the animals of each group after treatment with High IL-2 dosing with and without the Tie-2 signal amplifier, 4-{(S)-2-[(S)-2-(methoxycarbonylamino)-3-phenyl-propanamido]-2-[2-(thiophen-2-yl)thiazol-4-yl]ethyl}phenylsulfamic acid ammonium salt. A depicts the control sample; B depicts the status of mice treated with 400,000 IU of IL-2 for 5 days; C depicts status of mice treated with 400,000 IU of IL-2 for 5 days and 40 mg/kg of D91 for the first 2 days, then at 20 mg/kg for 3 days.
Figure 5:
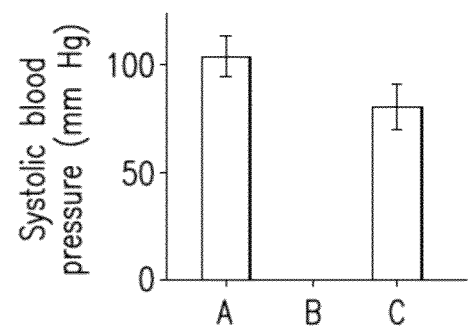
FIG. 5 depicts the rescue of mice from IL-2 induced hypotension and death. A represents the systolic blood pressure of C3H/HeN female mice treated with vehicle control. B represents the systolic blood pressure of C3H/HeN female mice treated with 400,000 IU of IL-2. C represents the systolic blood pressure of C3H/HeN female mice treated with 400,000 IU of IL-2 and 40 mg/kg of compound D91. Measurements were taken after 5 days of treatment.
Figure 6:
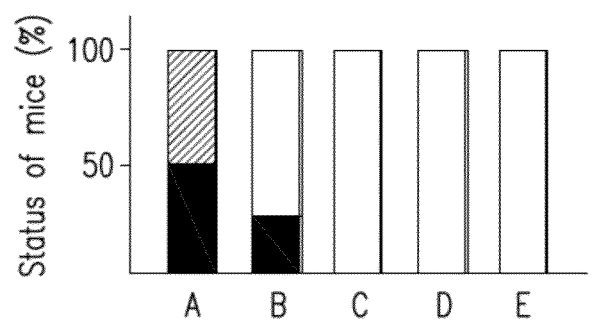
FIG. 6 depicts mice (4/group) that were treated with 400,000 IU of IL-2 in combination with various doses of D91 over 5 days. A represents 0 mg/kg D91, B represents 1 mg/kg D91, C represents 3 mg/kg D91, D represents 10 mg/kg D91, and E represents 30 mg/kg D91.

FIG. 4 depicts a summary of the status of the animals treated with high doses of IL-2, those treated with high doses of IL-2 and the Tie-2 signal amplifier 4-{(S)-2-[(S)-2-(methoxy-carbonylamino)-3-phenyl-propanamido]-2-[2-(thiophen-2-yl)thiazol-4-yl]ethyl}phenylsulfamic acid ammonium salt versus control.

The disclosed compounds can act as Tie-2 signaling amplifiers and, therefore can be used as an effective therapy to reduce vascular leak. The disclosed compounds can be co-administered with IL-2 or administered separately. As such, the IL-2 and Tie-2 signal amplifier can be administered in any order and by any method, for example, intravenously, orally, by patch, subcutaneous injection, and the like.

Disclosed herein is a method for treating renal cell carcinoma by administering to a patient in need of treatment a therapy that comprises:
 a) an effective amount of interleukin-2 such that an immune response is provided; and
 b) an effective amount of one or more of the disclosed compounds;
 wherein the interleukin-2 and the disclosed compounds can be administered together or in any order.

As such, disclosed herein is a method for treating renal cell carcinoma by contacting a patient with a composition comprising:
 a) a high dose of interleukin-2; and
 b) an effective amount of one or more of the compounds disclosed herein.

Disclosed herein is a method for treating metastatic melanoma by contacting a patient with a composition comprising:
 a) a high dose of interleukin-2; and
 b) an effective amount of one or more of the compounds disclosed herein.

Further disclosed is a method for treating metastatic melanoma by contacting a patient with a series of compositions, wherein the compositions can be administered in any order and at any effective amount, a first composition comprising, a high dose of interleukin-2 and the second composition comprising an effective amount of one or more of the disclosed compounds.

Still further disclosed is a method for treating renal cell carcinoma by contacting a patient with a series of compositions, wherein the compositions can be administered in any order and at any effective amount, a first composition comprising a high dose of interleukin-2 and the second composition comprising an effective amount of one or more of the disclosed compounds.

Disclosed herein is a method for treating metastatic melanoma by administering to a patient in need of treatment a therapy that comprises:
 a) an effective amount of interleukin-2 such that an immune response is provided; and
 b) an effective amount of one or more of the disclosed compounds;

wherein the interleukin-2 and the one or more disclosed compounds can be administered together or in any order.

Also disclosed herein is a method for treating metastatic melanoma by administering to a patient in need of treatment a therapy that comprises:
a) an effective amount of interleukin-2 such that an immune response is provided; and
b) an effective amount of one or more of the disclosed compounds;
wherein the interleukin-2 and the one or more disclosed compounds can be administered together or in any order.

Tumor growth is often a multi-step process that starts with the loss of control of cell proliferation. The cancerous cell then begins to divide rapidly, resulting in a microscopically small, spheroid tumor: an in situ carcinoma. As the tumor mass grows, the cells will find themselves further and further away from the nearest capillary. Finally the tumor stops growing and reaches a steady state, in which the number of proliferating cells counterbalances the number of dying cells. The restriction in size is caused by the lack of nutrients and oxygen. In tissues, the oxygen diffusion limit corresponds to a distance of 100 μm between the capillary and the cells, which is in the range of 3-5 lines of cells around a single vessel. In situ carcinomas may remain dormant and undetected for many years and metastases are rarely associated with these small (2 to 3 mm$^2$), avascular tumors.

When a tumor's growth is stopped due to a lack of nutrients and/or oxygen, this reduction in tumor vasculature also limits the ability of anti-tumor drugs to be delivered to the malignant cells. Moreover, if there is a slight increase in tumor vasculature, this will allow delivery of anti-tumor therapies to the malignant cells without initiating metastasis. As such, the disclosed compounds when used to slightly amplify Tie-2 signaling can be used to increase blood flow to the tumor cells without setting off metastasis or uncontrolled tumor cell proliferation while providing a method for delivering anti-cancer drugs to malignant cells.

Disclosed herein is a method for treating cancer comprising, administering to a patient in need an amount of one or more of the disclosed compounds that amplify Tie-2 signaling in conjunction with a chemotherapeutic compound or immunotherapeutic compound. By "chemotherapeutic compound" is meant any composition which comprises one or more compounds that can be administered to a patient for the purposes of attenuating or eliminating the presence of tumor cells. By "slightly amplify Tie-2 signaling" is meant that a sufficient amount of a disclosed compound is administered to a patient such that the amount of tumor cell vasculature is increased such that the increased circulation allows for delivery of the anti-tumor compound or therapy without instigating tumor growth wherein the rate of tumor cell growth is less than the rate of tumor cell death.

Disclosed herein is a method for treating a cancer wherein the cancer is medulloblastoma, ependymoma, ogliodendroglioma, pilocytic asrocytoma, diffuse astrocytoma, anaplasic astrocytoma, or glioblastoma. Further disclosed is a method for treating a tumor or invasive cancer chosen from medulloblastoma, ependymoma, ogliodendroglioma, pilocytic asrocytoma, diffuse astrocytoma, anaplasic astrocytoma, or glioblastoma wherein an effective amount of one or more disclosed Tie-2 signal amplifiers is administered to a subject. In addition, the method can comprise monitoring the Ang-2 level of the subject while the subject is undergoing treatment.

Angiopoietin-2 is significantly correlated to Gleason Score, metastases, and to cancer specific survival (Lind A. J. et al., "Angiopoietin-2 expression is related to histological grade, vascular density, metastases, and outcome in prostate cancer" Prostate (2005) 62:394-299). Angiopoietin-2 was found to be expressed in prostate cancer bone, liver and lymph node metastases, but with little to no angiopoietin-1 expression in prostate cancer tumor cells in bone, liver, and lymph nodes (Morrissey C. et al. "Differential expression of angiogenesis associated genes in prostate cancer bone, live and lymph node metastases" *Clin. Exp Metastasis* (2008) 25:377-388). As such, monitoring the level of Ang-2 provides a method for evaluating the presence of prostate cancer and the spread of prostate cancer cells throughout the body due to vascular leakage.

Vasculature Stabilization in Diseases Caused by Pathogens

Disclosed herein is a method for treating vascular leak syndrome caused by one or more pathogens, comprising administering to a human or other mammal in need of treatment an effective amount of one or more of the disclosed compounds.

Also disclosed herein is a method for treating vascular leak syndrome caused by one or more pathogens, comprising administering to a human or other mammal in need of treatment a composition comprising:
a) an effective amount of one or more compounds effective against a pathogen present in the human or mammal; and
b) an effective amount of one or more of the disclosed compounds;
wherein the of one or more compounds effective against a pathogen and the one or more of the disclosed compounds can be administered together or in any order.

Further disclosed herein is a method for preventing vascular leak syndrome in a human or other mammal diagnosed with an pathogen that can produce vascular leak syndrome in a human or mammal, comprising administering to a human or mammal a composition comprising:
a) an effective amount of one or more compounds effective against a pathogen present in the human or mammal; and
b) an effective amount of one or more of the disclosed compounds;
wherein the of one or more compounds effective against a pathogen and the one or more of the disclosed compounds can be administered together or in any order.

Increased amplification of Tie-2 signaling using the disclosed compounds provides a method for stabilizing vasculature without the need to affect Ang-1 and/or Ang-2 levels. Disclosed herein are methods for stabilizing vasculature, comprising administering to a patient in need an effective amount of one or more of the disclosed Tie-2 amplifiers.

Because the disclosed compounds can amplify Tie-2 signaling without increasing the amount of Ang-2, monitoring the amount of Ang-2 in blood serum of a subject while administering to a subject one or more of the disclosed compounds, serves as a method for determining the course of various illnesses or disease states associated with vascular leak syndrome, for example, sepsis as a result of infection. As such, disclosed is a method for stabilizing vasculature in a patient suffering from an inflammatory disease wherein the level of angiopoietin-2 is elevated, comprising:
a) administering to a subject an effective amount of one or more of the disclosed compounds as a treatment;
b) monitoring the level of angiopoietin-2 present in the subject; and
c) discontinuing treatment when the angiopoietin-2 level returns to a normal range.

What is meant herein by "normal angiopoietin-2 level" is an amount of Ang-2 in blood serum of from about 1 ng/mL to about 2 ng/mL. Alternatively, the level of Ang-2 can be determined for an individual suffering from a disease state, for example, severe sepsis and the level of Ang-2 can be monitored until the amount of Ang-2 in the subject's serum drop to a level that is nearer the normal range. In this case, the co-administration of a drug can be continued or discontinued. Therefore, disclosed herein is a method for stabilizing the vasculature of a subject during a course of treatment, comprising:

a) co-administering to a subject an effective amount of one or more of the disclosed compounds and one or more drugs as a treatment;
b) monitoring the level of angiopoietin-2 present in the subject; and
c) discontinuing the administration of the one or more drugs and selecting one or more other drugs for use as a treatment if the level of serum angiopoetin-2 does not decrease.

The disclosed compounds, while stabilizing the vasculature of a patient such that a course of treatment against a pathogen can be sustained, can also be used to stabilize a subject during a period wherein an effective treatment against a pathogen is being determined That is, the disclosed compounds by themselves can have a beneficial effect on the outcome of diseases caused by pathogens by reducing vascular leak and its complications.

Liposaccharide Induced Vascular Leak Model

The following liposaccharide induced vascular leakage model can be used to confirm the ability of the disclosed compounds to decrease the effects of vascular leak syndrome caused by pathogens. In the following example acute kidney injury (AKI) was studied to show the effect of D91 as a successful strategy that can preserve renal endothelial Tie2 phosphorylation in septic AKI.

Acute kidney injury is a frequent and serious problem in hospitalized patients, and is frequently a consequence of sepsis. The renal endothelium plays a key role in sepsis induced AKI. Activated Tie2, expressed mainly in endothelial cell surfaces, has many effects which are expected to be protective in sepsis-induced AKI, such as downregulation of adhesion molecule expression, inhibition of apoptosis, preservation of barrier function, and angiogenesis.

Male C57BL6 mice, 9 to 10 weeks old, were injected i.p. with 0.2 mg *E. Coli* lipopolysaccharide per 25 g body weight at time 0. Mice were injected with D91 at 50 mg/kg, 50 μL versus vehicle (50 μL) at the time 0, 8, and 16 hours. Mice were sacrifiecd at 24 hours after LPS injection. Vehicle control (saline) injected mice were studied in parallel as controls. Serum samples were analyzed for blood urea nitrogen (BUN) as a marker of kidney function.

Figure 7:
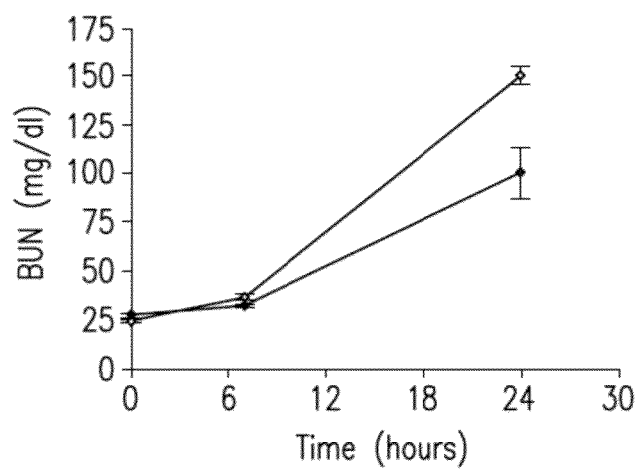
FIG. 7 depicts the level of blood urine nitrogen (BUN) in male C57BL6 mice injected i.p. with 0.2 mg *E. coli* lipopolysaccharides per 25 g body weight at 0 hours. Line (○) represents mice receiving only LPS and line (●) represents mice receiving LPS and 50 mg/kg of D91 at 0, 8, and 16 hours.

As shown in FIG. 7, the level of blood urine nitrogen (BUN) in the animals receiving only LPS (○) was approximately 150 mg/dL at 24 hours, whereas animals treated with 50 mg/kg of D91(●) had a blood urine nitrogen level of less than 80 mg/dL. These data show that D91 is capable of protecting mice against AKI in this model.

Figure 8:
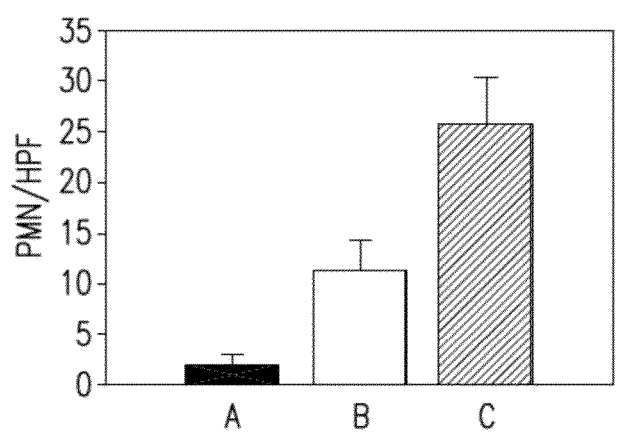
FIG. 8 depicts the level of LPS-induced renal neutrophil infiltration at 24 hours in male C57BL6 mice injected i.p. with 0.2 mg *E. coli* lipopolysaccharides per 25 g body weight at 0 hours. A depicts the neutrophil infiltration in sham (conrol), B depicts the neutrophil infiltration in male C57BL6 mice injected i.p. with 0.2 mg *E. coli* lipopolysaccharides per 25 g body weight and 50 mg/kg of D91, C depicts mice receiving only LPS.
Figure 9A:
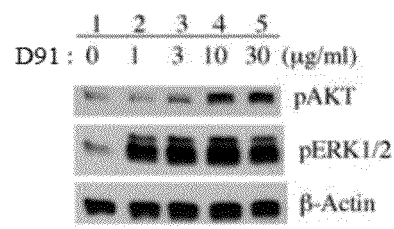
FIG. 9a depicts a Western blot analysis showing the increase in pAKT and pERK1/2 when EA.hy962 cells were cultured in the presence of varying amounts of D91 for 10 minutes.
Figure 9B:
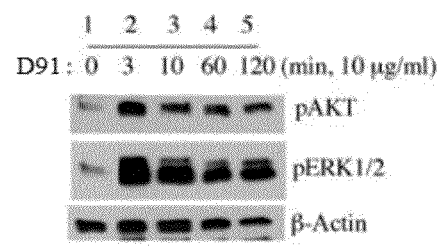
FIG. 9b depicts a Western blot analysis showing the levels of pAKT, pERK1/2 and β-Actin when EA.hy962 cells were cultured in the presence of 10 µg/mL D91 from start (T=0) to 120 minutes.

Tissue samples from the animals were analyzed by high powered field microscopy to determine the number of polymorphonuclear leukocytes present. As shown in FIG. 8, the number of PMN cells present in the LPS/vehicle animals was on average 26 whereas the number of PMN cells present in animals receiving D91 was on average 12. As such, this model demonstrates the effectiveness of D91 in preventing acute kidney injury due to pathogens, i.e., *E. coli*.

Figure 10A:
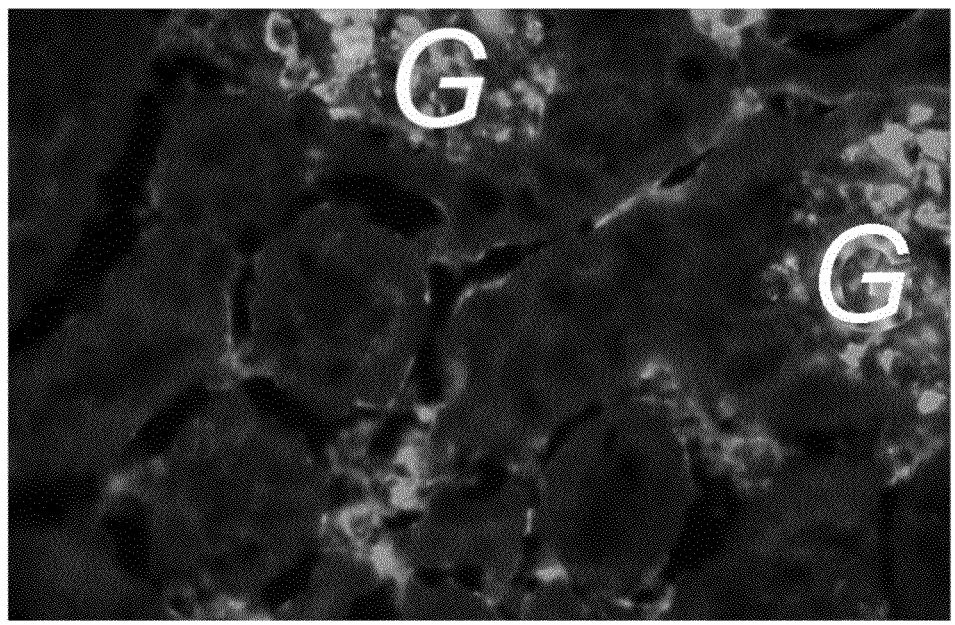
FIG. 10a is a micrograph of a renal section from a mouse treated with vehicle control that is subsequently injected with 70 kDa fluorescent fixable dextran by intravenous catheter 2 minutes prior to sacrifice. G indicates glomerular capillaries where the dye should normally be contained.
Figure 10B:
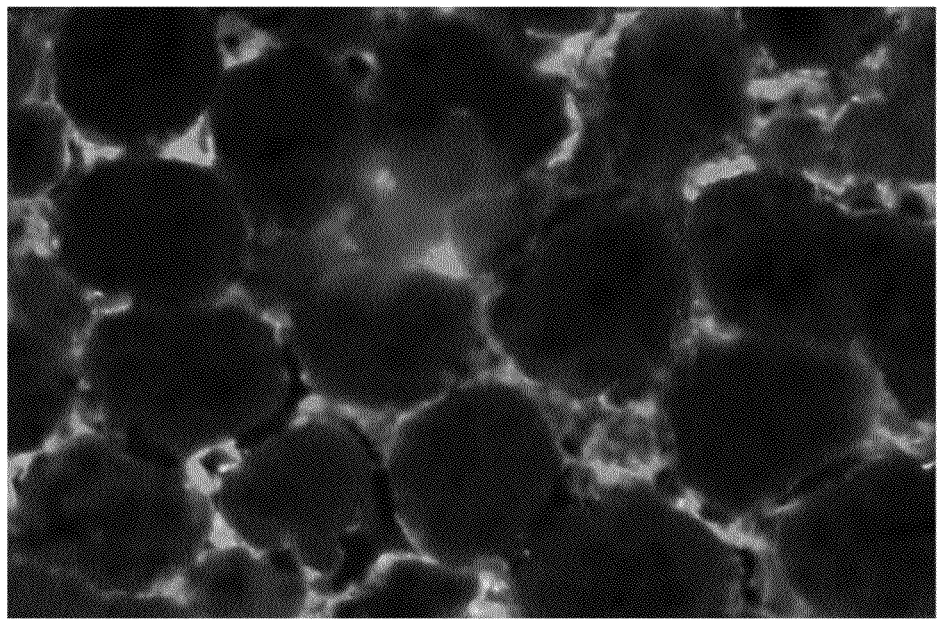
FIG. 10b is a micrograph showing the vascular leakage in cells of a renal section from a mouse treat with LPS that is subsequently injected with 70 kDa fluorescent fixable dextran by intravenous catheter 2 minutes prior to sacrifice. The 70 kDa fluorescent dextran is now significantly located in the interstitial space between the capillaries and the cells.
Figure 10C:
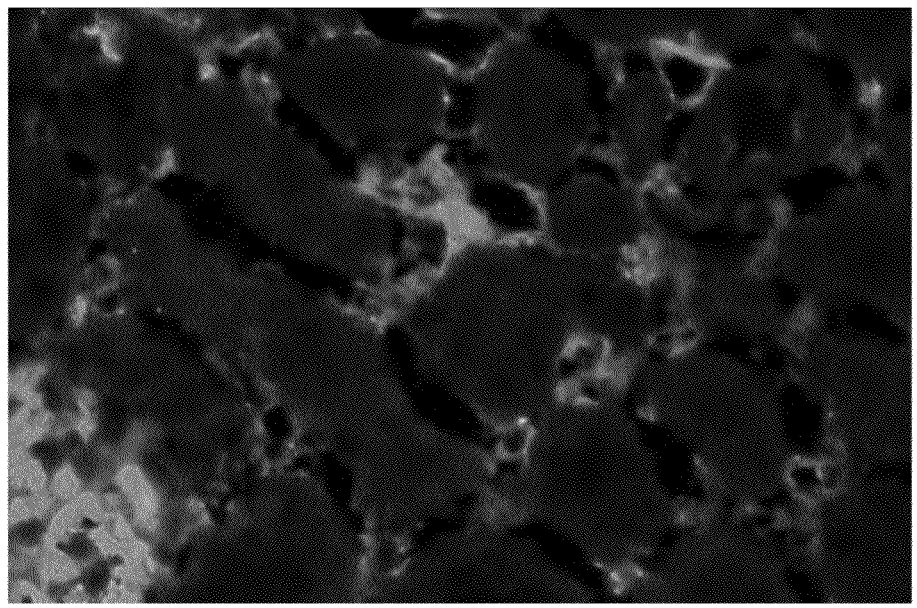

Phosphatase inhibition by the disclosed PTP-β inhibitors reduces LPS-induced renal vascular leak. Mice were injected with LPS at time 0 and D91 or vehicle at 1, 6, and 16 h. Two minutes prior to sacrifice at 24 hours 70 kDa fluorescent fixable dextrans were administered by intravenous catheter. Frozen sections showed extrusion of dye beyond the small peritubular capillaries was induced by LPS, but is reduced by D91. FIG. 10*a* is a micrograph of the control sample for the 70 kDa sample wherein the Letter "G" represents glomerular capillaries where the dye should normally be contained. FIG. 10*b* represents a renal section taken from an LPS treated animal and FIG. 10*c* represents a renal section taken from an animal treated with LPS and D91.

The following are non-limiting examples of virsus, bacteria, and other pathogens where virulence can be controlled by mitigating the degree of vascular leak that is induced by the organism. The following describe tests and assays that can be used to determine the effectiveness of the disclosed compounds, either alone, or a combination therapy.

Anthrax

Anthrax, the disease caused by *Bacillus anthracis*, was once a disease commonly spread among animals, but there is now a concern that this disease will be used as a part of bioterrorism. Inhalation anthrax is a deadly disease for which there is currently no effective treatment. Anthrax toxin, a major virulence factor of this organism, consists of three polypeptides: protective antigen (PA), lethal factor (LF), and edema factor (EF). PA is required for binding and translocation of EF and LF into target cells (Collier R. J. et al., (2003) Anthrax toxin. *Annu. Rev. Cell Dev. Biol.* 19:45-70). As such, lethal factor metalloproteinase is an integral component of the tripartite anthrax lethal toxin that is essential for the onset and progression of anthrax. The injection of lethal toxin (LT is LF plus PA) into animals is sufficient to induce some symptoms of anthrax infection, including pleural effusions indicative of vascular leak and lethality (Beall F. A. et al. (1966) The pathogenesis of the lethal effect of anthrax toxin in the rat. *J. Infect. Dis.* 116:377-389; Beall F. A. et al., (1962) Rapid lethal effect in rats of a third component found upon fractionating the toxin of *Bacillus anthracis*. *J. Bacteriol.* 83:1274-1280; Cui X. et al., (2004) Lethality during continuous anthrax lethal toxin infusion is associated with circulatory shock but not inflammatory cytokine or nitric oxide release in rats. *Am. J. Physiol. Regul. Integr. Comp. Physiol.* 286:R699-R709; Fish D. C. et al., (1968) Pathophysiological changes in the rat associated with anthrax toxin. *J. Infect. Dis.* 118:114-124; Klein F. et al., (1962) Anthrax toxin: causative agent in the death of rhesus monkeys. *Science* 138:1331-1333; Klein, F. et al., (1966) Pathophysiology of anthrax. *J. Infect. Dis.* 116:123-138; and Moayeri M. et al., (2003) *Bacillus anthracis* lethal toxin induces TNF-α-independent hypoxia-mediated toxicity in mice. *J. Clin. Investig.* 112:670-682). Early studies of anthrax suggested that lethal toxin kills animals by inducing nonspecific shock-like manifestations, and recent studies with mice and rats have confirmed an LT-mediated cytokine-independent vascular collapse. It has been reported that humans and primates exposed to spores via aerosol, present pleural effusions as the most common symptom of disease. Histopathological analyses of human subjects with inhalational anthrax infections display hemorrhaging in various organs resulting from destruction of both large and small vessels. Clearly, LT is an important virulence factor and contributes to some but not all the pathology observed with spore infection.

Recently, LT-mediated endothelial cell killing has been proposed to contribute to the vascular pathology observed during the course of anthrax (Kirby, J. E. (2004) Anthrax lethal toxin induces human endothelial cell apoptosis. *Infect. Immun.* 72:430-439). Since this LT-induced endothelial cytotoxicity occurs gradually (over 72 hours) and death from LT-mediated vascular collapse can occur in as little as 45 min (Ezzell J. W. et al., (1984) Immunoelectrophoretic analysis, toxicity, and kinetics of in vitro production of the protective antigen and lethal factor components of *Bacillus anthracis* toxin. *Infect. Immun.* 45:761-767), there is a need for a method for preventing increased vascular leakage due to anthrax lethal toxin.

In Vivo Vascular Leak

The Miles assay (Miles, A. A., and E. M. Miles (1952) Vascular reactions to histamine, histamine-liberator and leukotaxine in the skin of guinea-pigs. *J. Physiol.* 118:228-257 incorporated herein by reference in its entirety) can be used to directly investigate and quantify lethal toxin, as well as edema toxin (ET [PA plus EF])-mediated vascular leakage in the mouse model. The following is a modified Miles assay as described by Gozes Y. et al., Anthrax Lethal Toxin Induces Ketotifen-Sensitive Intradermal Vascular Leakage in Certain Inbred Mice *Infect Immun*. 2006 February; 74(2): 1266-1272 incorporated herein by reference in its entirety, that can be used to evaluate the disclosed compounds for their ability to prevent vascular leakage in humans and animals exposed to anthrax.

Highly pure PA, LF, and mutant LF E687C are purified as previously described (Varughese M. et al., (1998) Internalization of a *Bacillus anthracis* protective antigen-c-Myc fusion protein mediated by cell surface anti-c-Myc antibodies. *Mol. Med.* 4:87-95 included herein by reference in its entirety). Doses of ET or LT refer to the amount of each component (i.e., 100 µg LT is 100 µg PA plus 100 µg of LF). All drugs except for azelastine can be purchased from Sigma Aldrich (St. Louis, Mo.); azelastine can be purchased from LKT Laboratories (St. Paul, Minn.).

Animals.

BALB/cJ, DBA/2J, C3H/HeJ, C3H/HeOuJ, WBB6F1/J-$Kit^W/Kit^{W-v}$, and colony-matched wild-type homozygous control mice can be purchased from The Jackson Laboratory (Bar Harbor, Me.). BALB/c nude, C57BL/6J nude, and C3H hairless (C3.Cg/TifBomTac-hr) mice can be purchased from Taconic Farms (Germantown, N.Y.). C3H nude mice can be purchased from The National Cancer Institute Animal Production Area (Frederick, Md.). Mice are used when they are 8 to 12 weeks old. Except for C3H hairless and nude animals, all mice are shaved 24 hours prior to intradermal (i.d.) injections. In order to assess the susceptibility to systemic LT, mice are injected intraperitoneally (i.p.) with 100 µg LT and observed over 5 days for signs of malaise or death. Fischer 344 rats can be purchased from Taconic Farms (Germantown, N.Y.) and used at weights of 150 to 180 g. Rats are injected intravenously (i.v.) in the tail vein with 12 µg LT, with or without 250 µg of the mast cell stabilizer drug ketotifen and monitored for the exact time to death.

Miles Assay.

The Miles assay uses i.v. injection of Evans blue dye (which binds to endogenous serum albumin) as a tracer to assay macromolecular leakage from peripheral vessels after i.d. injection of test substances. Nude mice and normal shaved mice are injected i.v. with 200 µl of 0.1% Evans blue dye (Sigma Chemical Co., St. Louis, Mo.). After 10 min, 30 µl of test toxin or control samples (PA only, LF only, EF only, or phosphate-buffered saline) are injected i.d. in both left and right flanks, as well as at single or dual dorsal sites. To quantify the extents of leakage, equally sized (1.0- to 1.5-cm diameter) skin regions surrounding i.d. injection sites are removed 60 min after injection and placed in formamide (1 ml) at 41° C. for 48 h, allowing for dye extraction. The $A_{620}$ of samples is read, and the extent of leakage is calculated by comparison with phosphate-buffered saline-, PA-, or LF-treated controls.

In experiments wherein the effectiveness of the disclosed compounds are tested for LT-mediated leakage, mice are injected i.v. with Evans blue as described above, and the test compound introduced systemically through i.p. injection 10 min after dye injection. LT was introduced by i.d. injection 30 min after the injection of Evans blue. In another embodiment, the compound to be tested can be introduced locally by i.d. injection and LT injected in the same site after 10 min.

Cytotoxicity eExperiments.

MC/9 mast cells can be obtained from ATCC (Manassas, Va.) and grown in Dulbecco's modified Eagle's medium supplemented with 1-glutamine (2 mM), 2-mercaptoethanol (0.05 mM), Rat T-STIM (BD Biosciences-Discovery Labware, Bedford, Mass.) (10%), and fetal bovine serum (FBS, 10% final concentration; Invitrogen-GIBCO BRL, Gaithersburg, Md.). Cells are then seeded at a density of $10^4$/well in 96-well plates prior to treatment with various LT concentrations or PA-only controls. After 6, 12, and 24 hours, viability is assessed using Promega's CellTiter 96 $AQ_{ueous}$ One Solution cell proliferation assay (Promega, Madison, Wis.) per the manufacturer's protocol. Alternatively, toxicity assays can be performed in medium provided with all supplements except FBS (serum-free medium). In other embodiments, pooled human umbilical vein endothelial cells (HUVECs) at third to fifth passage can be obtained from Cambrex Corp. (Cambrex, Walkersville, Md.) and grown in an EGM-MV Bulletkit (Cambrex, Walkersville, Md.) in flasks pretreated with endothelial cell attachment factor (Sigma, St. Louis, Mo.). For cytotoxicity experiments, cells are typically seeded in 96-well plates in an EGM-MV Bulletkit. On the day of assays, this medium is then replaced with M199 medium (Sigma, St. Louis, Mo.) supplemented with 10% FBS or human serum (Sigma, St. Louis, Mo.), and cells are reseeded in 96-well plates at a density of $2\times10^3$/0.1 ml/well and treated with various concentrations of LT in triplicate. Cell viability is typically assessed as for MC/9 cells at 24, 48, and 72 hour time points.

HUVEC Permeability Assay

HUVEC monolayers can be effectively cultured on Transwell-Clear cell culture inserts (6.5-mm diameter, 0.4-µm pore size; Corning-Costar, Acton, Mass.) in 24-well plates, creating a two-chamber culturing system consisting of a luminal compartment (inside the insert) and a subluminal compartment (the tissue culture plate well). Prior to seeding cells, the inserts are coated with endothelial cell attachment factor (Sigma, St. Louis, Mo.). Prewarmed CS—C medium (Sigma, St. Louis, Mo.) containing 10% iron-supplemented calf serum and 1% endothelial cell growth factor (Sigma, St. Louis, Mo.) is added to wells prior to insert placement. A HUVEC cell suspension (200 µL of $5\times10^5$ cells/ml) is then added to each insert. Cells are cultured at 37° C. in 5% $CO_2$ for up to 21 days to ensure proper formation of a monolayer. For testing barrier function, medium can be changed to RPMI supplemented with 10% FBS or to RPMI without serum. To assess barrier function, horseradish peroxidase enzyme (Sigma, St. Louis, Mo.) is added to the inserts (10 mg/well). LT (1 µg/mL) or control treatments of PA alone (1 µg/mL) or LF alone (1 µg/mL) are added to duplicate wells, and every hour (for 12 hours), a sample of 10 µL was taken from the subluminal compartment and tested for the enzymatic activity of horseradish peroxidase by adding 100 µL substrate [2',2'-azino-bis(3-ethylbenzthizolin 6-sulfonic acid)] (A-3219; Sigma, St. Louis, Mo.) and reading at 405 nm.

Anthrax Combination Therapy

Increased stabilization of vascular tissue can increase the effectiveness of known antimicrobials against anthrax infection. As such, the disclosed compounds can be evaluated as a combination therapy for the treatment of anthrax. The following describes a series of assays that can be used to determine the effectiveness of the disclosed compounds as one part of a combination therapy useful for treating anthrax infections.

LF has been found to cleave mitogen-activated protein kinase kinases (MAPKK), disrupts signal transduction, and leads to macrophage lysis. As such, in addition to the Miles Assay, the following cell-based and peptide cleavage assay can be used to confirm the potency of the disclosed compounds to inhibit the effect of LT activity. For the following assay, MAPKKide can be purchased from List Biological Laboratories (Campbell, Calif. Fluorinated peptide substrate is available from Anaspec (San Jose, Calif.).

In Vivo Assays

One week before beginning an evaluation of a combination course of treatment for anthrax, test compounds (200 mg each) are dissolved in 800 μL of DMSO and stored at −20° C. Immediately before injection, each compound is diluted in PBS, resulting in a final concentration of 0.5 mg/mL in 2% DMSO. Test animal are challenged on day 0 with $2\times10^7$ spores per mouse in PBS through i.p. injection. Treatment was started 24 hours after challenge. One example of a suitable treatment regiment is the combination of ciprofloxacin (50 mg/kg) and one or more of the disclosed compounds (5 mg/kg). A control sample of untreated animals, ciprofloxacin alone, a disclosed compound alone, and ciprofloxacin in combination with a disclosed compound are given to the animals and they are monitored twice per day until day 14 after injection.

Ciprofloxacin and the compound to be tested can be conveniently administered through parenteral injection with a volume of 200 μL for each once per day for 10 days. All surviving animals are sacrificed on day 14. Sick animals that appear moribund (i.e., exhibiting a severely reduced or absent activity or locomotion level, an unresponsiveness to external stimuli, or an inability to obtain readily available food or water, along with any of the following accompanying signs: ruffled haircoat, hunched posture, inability to maintain normal body temperature, signs of hypothermia, respiratory distress, or other severely debilitating condition) should be sacrifice on the same day these symptoms are manifested.

Modulation of Bacterium-Induced Vascular Leak

Pathogenic bacteria are known to cause vascular leak. This induced vascular leakage inhibits the ability of antimicrobials and other pharmaceuticals from targeting the invading microorganism. As such, the disclosed compounds can be used alone or in combination with other pharmaceutical ingredients to boost the host immune system by preventing excess vascular leakage that occurs as a result of a bacterial infection.

*Staphylococcus aureus* is a major pathogen of gram-positive septic shock and is associated with consumption of plasma kininogen. The effect of the disclosed compounds on *S. aureus* induced vascular leakage activity can be determined by measuring the activity of these compounds with respect to two cysteine proteinases that are secreted by *S. aureus*. Proteolytically active staphopain A (ScpA) induces vascular leakage in a bradykinin (BK) $B_2$-receptor-dependent manner in guinea pig skin. This effect is augmented by staphopain B (SspB), which, by itself, had no vascular leakage activity. ScpA also produces vascular leakage activity from human plasma.

An important pathophysiologic mechanism of septic shock is hypovolemic hypotension that is caused by plasma leakage into the extravascular space. It has been found that ScpA induced vascular leakage at a concentration as low as 20 nM within 5 minute after injection into the guinea pig skin—with the reaction being augmented by coexisting SspB indicating that vascular leakage induction by these proteinases occurs efficiently in vivo (Imamura T. et al., Induction of vascular leakage through release of bradykinin and a novel kinin by cysteine proteinases from *Staphylococcus aureus* (2005) *J. Experimental Medicine* 201:10, 1669-1676).

Staphopains also can act on LK—whose plasma molar concentration has been found to be threefold greater than HK—they also have more opportunity to interact with substrate than proteinases that generate BK only from HK. Taken together, these results indicate that vascular leakage induction by staphopains is a mechanism of septic shock induction in severe *S. aureus* infection that provides an assay for determining the effectiveness of compounds to modulate vascular leakage.

Vascular Leakage Assay.

Animals can be evaluated for vascular leakage using the following procedure. 100 μL of a 1% solution of Evans blue dye (Sigma Aldrich) in saline is injected into the tail vein. Thirty minutes later, mice are sacrificed and perfused with saline via the right ventricle to remove intravascular Evans blue. Lungs are excised and extracted in 1 mL of formamide at 55° C. overnight. Evans blue content is determined as $OD_{620}$ minus $OD_{500}$ of the formamide extract.

Influenza

During the years following World War I, it is estimated that more that 50 million people were killed by a world-wide influenza pandemic. Recently, the spread of highly pathogenic avian influenza A (H5N1) viruses from Asia also poses a threat of becoming another influenza pandemic. It is thought that highly pathogenic (HP) influenza strains stimulate a stronger immune response than seasonal strains, causing severe vascular leakage and lung edema, and eventual death. A study of mouse immune cell responses following exposure to mouse-adapted influenza viruses that mimic either a seasonal flu or a HP flu strain (Aldridge J. R. et al., (2009). TNF/iNOS-producing dendritic cells are the necessary evil of lethal influenza virus infection. *Proc Natl Acad Sci USA* 106: 5306-5311).

The compounds disclosed herein can be used as a single pharmaceutical therapy to prevent the severity of influenza by mediating the effects of vascular leak caused by viruses, and, hence, allowing the body's own immune system to affect greater resistance to these pathogens. The following assays can be used to determine the effect of the disclosed compounds to inhibit viral severity because of improved vascular integrity.

The disclosed assays can utilize inhibition of viral plaques, viral cytopathic effect (CPE), and viral hemagglutitin.

Proteolytic Sensitivity Assay

The disclosed compounds can be determined to bind to hemagglutinin and thereby destabilize the protein assembly. The following procedure can be used to determine the increase in destabilization and therefore the increased sensitivity of hemagglutinin to proteolytic attack caused by the disclosed compounds. At the fusion conformation, HA becomes more sensitive to protease digestion. This property can be used to verify if a fusion inhibitor interacts with HA (Luo G. et al. "Molecular mechanism underlying the action of a novel fusion inhibitor of influenza A virus." *J Virol* (1997); 71(5):4062-70). Thus, the disclosed compounds, due to the control of vascular leakage, can be evaluated for their ability to indirectly effect HA digestion by enhancing the body's immune response.

The purified trimer of hemagglutinin ectodomain is incubated with the compound to be tested at a concentration of 5 μM. The trimers are subjected to trypsin digestion at pH 7.0 and pH 5.0 with controls of untreated HA and HA treated with DMSO which is the solvent used to dissolve the test compound. For the pH 5.0 sample, the HA trimers are treated with a pH 5.0 buffer for 15 minutes and neutralized to pH 7.0. Trypsin (20 ng) is added to the sample in 10 μL and the digestion allowed to proceed for 1 hour at 37° C., The amount of HA present is assessed by a western blot gel electrophoresis using anti-HA (H3) antisera. Samples containing effective inhibitors will provide an increase in digestion of HA by trypsin.

In addition, combination therapies can provide a method for treating influenza by providing an antiviral medication together with a compound that prevents the severity of vascular leakage due to influenza viruses.

An antiviral compound, for example, oseltamivir, can be used for an in vivo evaluation of the disclosed combination therapy and to evaluate the effectiveness of the disclosed compounds. The drug combination is administered in a single dose to mice infected with the influenza A/NWS/(H1N1) virus. In some instances, infection of the animals will include multiple passage of the virus through their lungs. One convenient protocol involves administering 20 mg/kg per day twice daily for 5 days beginning 4 hours prior to virus exposure. The animals are then challenged with different concentrations of virus, ranging 10-fold from $10^{-2}$ ($10^{5.75}$ cell culture 50% infectious doses ($CCID_{50}$) per mL). Four mice in each group are sacrificed on day 6 and their lungs removed, assigned a consolidation score ranging from 0 (normal) to 4 (maximal plum coloration), weighted, homogenized, the homogenates centrifuged at 2000×g for 10 minutes, and varying 10-fold dilutions of the supernata assayed for virus titer in MDCK cells using CPE produced after a 96-hour incubation at 37° C. as endpoint.

The serum taken from mice on day 6 is assayed for $a_1$-AG using single radial immunodiffusion kites. Eight additional mice in each group are continually observed daily for death for 21 days, and their arterial oxygen saturation ($SaO_2$) values determined by pulse oximetery (Sidwell R. et al., (1992) Utilization of pulse oximetry for the study of the inhibitory effects of antiviral agents on influenza virus in mice. *Antimicrob. Agents Chemother.* 36, 473-476) on day 3, when $SaO_2$ decline usually begins to occur, through day 11, when the values are seen to decline to the maximum degree of the animals otherwise die.

Vasogenic Edema 30 adult male Sprague-Dawley rats purchased from Charles River, Germany and weighing 250-330 g were used for the experiment. Animals were housed at a standard temperature (22±1° C.) and in a light-controlled environment (lights on from 7 am to 8 pm) with ad libitum access to food and water.

Animals were grouped as follows:

Group A: 15 rats treated with Vehicle (2 mL/kg, t.i.d., s.c.) starting 1 hour after stroke onset Group B: 15 rats treated with AKB-9778-AS (15 mg/kg, t.i.d., s.c.) starting 1 hour after stroke onset tMCAO Transient focal cerebral ischemia was produced by MCA occlusion in male Sprague-Dawley rats according to Koizumi with modifications (Koizumi et al., *Jpn. J. Stroke* 8:1-8, 1986). The rats were anesthetized with isoflurane in 70% $N_2O$ and 30% $O_2$; flow 300 mL/min. 2-3 min anesthesia induction with 5% isoflurane after which 1-2% isoflurane. The rectal temperature was maintained above 36.0° C. with a homeothermic blanket system. After a midline skin incision, the right common carotid artery (CCA) was exposed, and the external carotid artery (ECA) was ligated distal from the carotid bifurcation. A 0.25-mm diameter monofilament nylon thread, with tip blunted, was inserted 22-23 mm into the internal carotid artery (ICA) up to the origin of MCA. The wound was temporarily closed and the rats were allowed to recover. After 60 min of ischemia, the rats were re-anesthetized and MCA blood flow was restored by removal of the thread. The wounds were closed, disinfected, and the animals were allowed to recover from anesthesia. The rats were carefully monitored for possible post-surgical complications after the tMCAO. The rats were fed with standard laboratory diet suspended in tap water.

D91 or vehicle was administered s.c. three times a day. Treatment was given 1, 8, 16, 23, 32, 40 and 47 h after the onset of occlusion. Administration volume was 2 ml/kg and the vehicle is sterile saline. The body weight of each animal is measured daily. MRI at 24 and 48 hours: Absolute T2 and Spin Density for Vasogenic Edema and Infarct Volume T2-MRI was performed at 24 and 48 hours post-ischemia in a horizontal 7T magnet with bore size 160 mm (Magnex Scientific Ltd., Oxford, UK) equipped with Magnex gradient set (max. gradient strength 400 mT/m, bore 100 mm) interfaced to a Varian DirectDrive console (Varian, Inc., Palo Alto, Calif.) using a volume coil for transmission and surface phased array coil for receiving (Rapid Biomedical GmbH, Rimpar, Germany) Isoflurane-anesthetized (1% in 30/70 O2/N2) rats were fixed to a head holder and positioned in the magnet bore in a standard orientation relative to gradient coils. All MRI data were analyzed using in-house written Matlab software. Region of interest analysis was performed for ipsilateral hemisphere, lesion core and perifocal area. Values from contralateral hemisphere were used as a reference.

Tissue viability and vasogenic edema was determined using absolute T2 MRI. Multi-echo multi-slice sequence was used with following parameters; TR=3 s, 6 different echo times (12, 24, 36, 48, 60, 72 ms) and 4 averages. Seventeen (17) coronal slices of thickness 1 mm were acquired using field-of-view 30×30 mm2 and 256×128 imaging matrix (zero-filled to 256×256). In addition to absolute T2, spin density (amount of MRI visible protons, indicator of vasogenic edema) ratio of ipsi and contralateral ROI's was determined by extrapolating signal intensity at TE=0 from multiple TE data (intercept of T2 fitting).

For the determination of infarct volume, the same acquired T2-weighted images were analyzed using in-house written Matlab based software for morphometric measurement. The infarct volume analysis was done by an observer blinded to the treatment groups.

$D_{av}$ for Cytotoxic Edema

Cytotoxic edema (and its time course) was evaluated also at 24 and 48 hours as a control measure using diffusion MRI; the data for calculation of ⅓ of the trace of the diffusion tensor (which is an orientation independent measure of apparent water diffusion) were acquired using a diffusion weighted Fast Spin-Echo sequence. Following parameters were used: TR=1.5 s, ETL/TEeff=4/26 ms, b-values 0, 1000×10-3 s/mm2, NT=4. Imaging resolution, slice thickness and slice positioning were kept identical to absolute T2 MRI acquisition above. 5 slices were acquired and these were selected from absolute T2 images to best correspond to the center of lesion in antero-posterior direction.

Contrast Enhanced T1-weighted MRI for BBB Leakage

At 48 hours post-operation, Gadolinium based contrast enhanced T1-weighted MRI was applied to detect blood-brain barrier leakage. Femoral vein was cannulated before the rat was placed into the MRI. Contrast agent was injected as an i.v. bolus (0.5 M Gd-DTPA 0.4 ml/kg i.v. bolus). Pre- and post-contrast agent T1-weighted images were acquired with 15 min delay to allow proper uptake of the contrast agent. MRI was performed with conventional T1-weighted gradient echo sequence with identical imaging resolution and slice positioning and with following parameters; TR=0.16 s, TE=5 ms, 70 degree flip and NT=32. Subtraction images (deltaR, post-Gd minus pre-Gd) were produced to highlight and quantify BBB leakage. Gd-based contrast agents affect the T2 relaxation, thus this MRI component was performed at the very end of the MRI session.

Endpoint—Edema Evaluation

After the 48 hour MRI, the rats were decapitated. The brains were quickly removed, cut into ipsi- and contralateral hemispheres that were weighed for tissue wet weight (edema analysis). Edema % was calculated: [wet weight of ipsilateral hemisphere in mg/wet weight of contralateral hemisphere in mg]×100. Thereafter the brains were fresh-frozen on dry ice for possible PK or biochemical purposes. Bbrain tissue wet weight was found significantly lower in ischemic hemisphere in D91 treated rats, suggesting that D91 reduces the brain edema after tMCAO.

Inhibition of Protein Tyrosine Phosphatase Beta in a Cell

Disclosed herein are methods for inhibiting protein tyrosine phosphatase beta (PTP-β) activity in a cell, comprising contacting a cell with an effective amount of one or more of the disclosed compounds. The cell can be contacted in vivo, ex vivo, or in vitro.

Compositons

Disclosed herein are compositions which can be used to treat patients with cancer, wherein the patient having cancer is treated with one or more anticancer agents that induce vascular leak syndrome in the patient. As such, disclosed herein are compositions effective in reducing vascular leak resulting from an anticancer treatment, the compositions comprising an effective amount of one or more of the disclosed compounds.

In another aspect, disclosed herein are compositions effective for treating humans or other mammals having a medical condition or disease state wherein the treatment for the medical condition or disease state induces vascular leak syndrome, the composition comprising:
  a) an effective amount of one or more of the compounds disclosed herein; and
  b) one or more pharmaceutical drugs;
  wherein at least one of the pharmaceutical drugs induces vascular leak syndrome.

In a further aspect, disclosed herein are compositions comprising;
  a) an effective amount of one or more of the compounds disclosed herein: and
  b) one or more chemotherapeutic agents.

Also disclosed herein are compositions which can be used to control vascular leakage, the compositions comprising an effective amount of one or more of the compounds disclosed herein. Still further disclosed herein are compositions which can be used to treat patients with an inflammatory disease, non-limiting examples of which include sepsis, lupus, and inflammatory bowel disease, the compositions comprising an effective amount of one or more of the Tie-2 signaling amplifiers disclosed herein.

Disclosed herein are compositions which can be used to treat humans or other mammals having vascular leakage due to bacterial or viral infections, the compositions comprising an effective amount of one or more of the compounds disclosed herein.

Disclosed herein are compositions comprising one or more of the disclosed compounds wherein the compositions are useful for treatment of the disclosed conditions, illness, injuries, courses of treatment, cellular treatments, and the like.

One aspect relates to a composition comprising:
  a) an effective amount of one or more compounds disclosed herein; and
  b) one or more pharmaceutically acceptable ingredients.

Another aspect relates a composition comprising:
  a) an effective amount of one or more compounds disclosed herein; and
  b) an effective amount of one or more antiviral or antibacterial agents;
  wherein the disclosed compounds and the antiviral or antibacterial ingredients can be administered together or in any order.

A further aspect relates to a composition comprising:
  a) an effective amount of one or more compounds disclosed herein; and
  b) an effective amount of one or more antibacterial agents effective against anthrax;
  wherein the disclosed compounds and the antibacterial ingredients effective against anthrax can be administered together or in any order.

A yet further aspect relates to a composition comprising:
  a) an effective amount of one or more compounds disclosed herein; and
  b) an effective amount of one or more antiviral agents;
  wherein the disclosed compounds and the antiviral agents can be administered together or in any order.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

The term "effective amount" as used herein means "an amount of one or more PTP-β inhibitors, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present disclosure can be administered as frequently as necessary to achieve a therapeutic amount.

The disclosed PTP-β inhibitors can also be present in liquids, emulsions, or suspensions for delivery of active therapeutic agents in aerosol form to cavities of the body such as the nose, throat, or bronchial passages. The ratio of PTP-β inhibitors to the other compounding agents in these preparations will vary as the dosage form requires.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the PTP-β inhibitor in combination with a pharmaceutically acceptable carrier and, in addition, can include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, referenced above.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

Kits

Also disclosed are kits comprising the compounds be delivered into a human, mammal, or cell. The kits can comprise one or more packaged unit doses of a composition comprising one or more compounds to be delivered into a human, mammal, or cell. The unit dosage ampoules or multi-dose containers, in which the compounds to be delivered are packaged prior to use, can comprise an hermetically sealed container enclosing an amount of polynucleotide or solution containing a substance suitable for a pharmaceutically effective dose thereof, or multiples of an effective dose. The compounds can be packaged as a sterile formulation, and the hermetically sealed container is designed to preserve sterility of the formulation until use.

The disclosed compounds can also be present in liquids, emulsions, or suspensions for delivery of active therapeutic agents in aerosol form to cavities of the body such as the nose, throat, or bronchial passages. The ratio of compounds to the other compounding agents in these preparations will vary as the dosage form requires.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the compounds in combination with a pharmaceutically acceptable carrier and, in addition, can include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, referenced above.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

When the compounds are to be delivered into a mammal other than a human, the mammal can be a non-human primate, horse, pig, rabbit, dog, sheep, goat, cow, cat, guinea pig or rodent. The terms human and mammal do not denote a particular age or sex. Thus, adult and newborn subjects, as well as fetuses, whether male or female, are intended to be covered. A patient, subject, human or mammal refers to a subject afflicted with a disease or disorder. The term "patient" includes human and veterinary subjects.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for determining the course of treatment for a subject suffering from vascular leak syndrome, comprising:

a) administering to a subject an effective amount of one or more compounds having the formula:

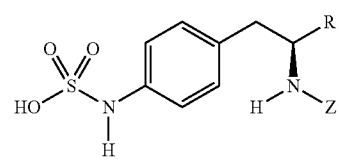

wherein R is a substituted or unsubstituted thiazolyl unit having the formula:

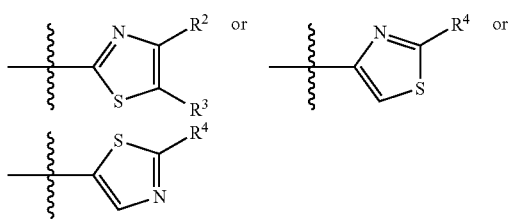

R², R³, and R⁴ are each independently:
i) hydrogen;
ii) substituted or unsubstituted $C_1$-$C_6$ linear, branched, or cyclic alkyl;
iii) substituted or unsubstituted $C_2$-$C_6$ linear, branched, or cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl;
vii) substituted or unsubstituted $C_1$-$C_9$ heterocyclic; or
viii) R² and R³ can be taken together to form a saturated or unsaturated ring having from 5 to 7 atoms; wherein from 1 to 3 atoms can optionally be heteroatoms chosen from oxygen, nitrogen, and sulfur;

Z is a unit having the formula:

-(L)$_n$-R¹

R¹ is chosen from:
i) hydrogen;
ii) hydroxyl;
iii) amino;
iv) substituted or unsubstituted $C_1$-$C_6$ linear, branched or cyclic alkyl;
v) substituted or unsubstituted $C_1$-$C_6$ linear, branched or cyclic alkoxy;
vi) substituted or unsubstituted $C_6$ or $C_{10}$ aryl;
vii) substituted or unsubstituted $C_1$-$C_9$ heterocyclic rings; or
viii) substituted or unsubstituted $C_1$-$C_9$ heteroaryl rings;

L is a linking unit having the formula:

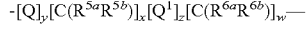
-[Q]$_y$[C(R$^{5a}$R$^{5b}$)]$_x$[Q¹]$_z$[C(R$^{6a}$R$^{6b}$)]$_w$—

Q and Q¹ are each independently:
i) —C(O)—;
ii) —NH—;
iii) —C(O)NH—;
iv) —NHC(O)—;
v) —NHC(O)NH—;
vi) —NHC(O)O—;
vii) —C(O)O—;
viii) —C(O)NHC(O)—;
ix) —O—;
x) —S—;
xi) —SO$_2$—;
xii) —C(=NH)—;
xiii) —C(=NH)NH—;
xiv) —NHC(=NH)—; or
xv) —NHC(=NH)NH—;

R$^{5a}$ and R$^{5b}$ are each independently:
i) hydrogen;
ii) hydroxy;
iii) halogen;
iv) $C_1$-$C_6$ substituted or unsubstituted linear or branched alkyl; or
v) a unit having the formula:

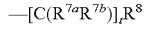
—[C(R$^{7a}$R$^{7b}$)]$_t$R⁸

R$^{7a}$ and R$^{7b}$ are each independently:
i) hydrogen; or
ii) substituted or unsubstituted $C_1$-$C_6$ linear, branched, or cyclic alkyl;

R⁸ is:
i) hydrogen;
ii) substituted or unsubstituted $C_1$-$C_6$ linear, branched, or cyclic alkyl;
iii) substituted or unsubstituted $C_6$ or $C_{10}$ aryl;
iv) substituted or unsubstituted $C_1$-$C_9$ heteroaryl; or
v) substituted or unsubstituted $C_1$-$C_9$ heterocyclic;

R$^{6a}$ and R$^{6b}$ are each independently:
i) hydrogen; or
ii) $C_1$-$C_4$ linear or branched alkyl;
the index n is 0 or 1; the indices t, w and x are each independently from 0 to 4; the indices y and z are each independently 0 or 1; or
a pharmaceutically acceptable salt thereof; and
b) monitoring the blood plasma level of angiopoietin-2 in the subject;
wherein administering of the one or more compounds stops when the level of angiopoietin-2 in the blood plasma of the subject is from about 1 ng/mL to about 2 ng/mL.

2. The method according to claim 1, wherein the compound has the formula:

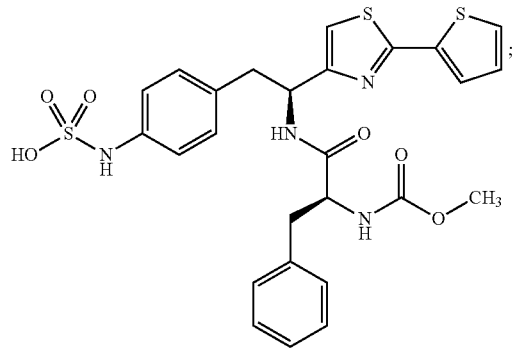 [SMILES: COC(=O)N[C@@H](Cc1ccccc1)C(=O)N[C@@H](Cc1ccc(NS(=O)(=O)O)cc1)c1csc(-c2cccs2)n1]

or
a pharmaceutically acceptable salts thereof.

* * * * *